US008097438B2

(12) United States Patent
Chang et al.

(10) Patent No.: US 8,097,438 B2
(45) Date of Patent: Jan. 17, 2012

(54) NUCLEIC ACIDS ENCODING MODIFIED CYTOCHROME P450 ENZYMES AND METHODS OF USE THEREOF

(75) Inventors: Michelle Chia-Yu Chang, Berkeley, CA (US); Rachel A. Krupa, San Francisco, CA (US); Dae-Kyun Ro, Calgary (CA); Yasuo Yoshikuni, Berkeley, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 671 days.

(21) Appl. No.: 12/067,441

(22) PCT Filed: Oct. 5, 2006

(86) PCT No.: PCT/US2006/039433

§ 371 (c)(1), (2), (4) Date: Nov. 13, 2008

(87) PCT Pub. No.: WO2007/044688

PCT Pub. Date: Apr. 19, 2007

(65) Prior Publication Data

US 2009/0098626 A1 Apr. 16, 2009

Related U.S. Application Data

(60) Provisional application No. 60/762,700, filed on Jan. 27, 2006, provisional application No. 60/724,525, filed on Oct. 7, 2005.

(51) Int. Cl.
*C12P 7/00* (2006.01)

(52) U.S. Cl. ........ 435/132; 435/183; 435/189; 435/195; 435/252.3; 536/23.2

(58) Field of Classification Search .................. 435/132, 435/183, 189, 252.3; 536/23.2
See application file for complete search history.

(56) References Cited

U.S. PATENT DOCUMENTS

| | | | | |
|---|---|---|---|---|
| 5,460,949 | A | 10/1995 | Saunders et al. | |
| 6,531,303 | B1 | 3/2003 | Millis et al. | |
| 6,689,593 | B2 | 2/2004 | Millis et al. | |
| 7,183,089 | B2 * | 2/2007 | Keasling et al. | 435/167 |
| 2003/0148479 | A1 | 8/2003 | Keasling et al. | |
| 2004/0005678 | A1 | 1/2004 | Keasling et al. | |
| 2004/0029239 | A1 | 2/2004 | Ohto et al. | |
| 2004/0063182 | A1 | 4/2004 | Ohto et al. | |
| 2004/0072323 | A1 | 4/2004 | Matsuda et al. | |
| 2004/0077039 | A1 | 4/2004 | Holtzman | |
| 2004/0110259 | A1 | 6/2004 | Baugh et al. | |
| 2004/0194162 | A1 | 9/2004 | Hahn et al. | |

OTHER PUBLICATIONS

Brock et al. On the mechanism of action of the antifungal agent propionate. (2004) Eur J. Biochem. 271: 3227-3241.

Choi et al. High-level production of poly(3-hydroxybutyrate-co-3-hydroxyvalerate) by fed-batch culture of recombinant *Escherichia coli*. (1999) Appl. Environ. Microbio. 65 4363-4368.

Carter et al. Monoterpene biosynthesis pathway construction in *Escherichia coli*. Phytochem. 2003, 64, 425-433.

Donald et al. Effects of overproduction of the catalytic domain of 3-hydroxy-3-methylglutaryl coenzyme a reductase on squalene synthesis in *Saccharomyces cerevisiae*. (1997) Appl. Env. Microbiol. 63:3341-3344.

T. Kazuhiko. Production of mevalonate by a metabolically-engineered *Escherichia coli*. (2004) Biotechnology Letters. 26: 1487-1491.

Jennewein et al. Cytochrome p450 taxadiene 5alpha-hydroxylase, a mechanistically unusual monooxygenase catalyzing the first oxygenation step of taxol biosynthesis.Chem. Biol. 2004, 11, 379-387.

Jackson et al. Metabolic engineering to produce sesquiterpenes in yeast. (2003) Organ. Lett. 5:1629-1632.

Luo et al. Molecular cloning and functional identification of (+)-delta-cadinene-8-hydroxylase, a cytochrome P450 mono-oxygenase (CYP706B1) of cotton sesquiterpene biosynthesis. Plant J. 2001, 28, 95-104.

Martin et al. Engineering a mevalonate pathway in *Escherichia coli* for production of terpenoids. (2003) Nat. Biotech. 21 (7):796-802.

Murli et al. Metabolic engineering of *Escherichia coli* for improved 6-deoxyerythronolide B production. (2003) J. Ind. Microbiol. Biotechnol. 30: 500-509.

Polakowski et al. Overexpression of a cytosolic hydroxymethylglutaryl-CoA reductase leads to squalene accumulation in yeast. (1998) Appl. Microbiol. Biotechnol. 49: 67-71.

Parke et al. Toxicity caused by hydroxycinnamoyl-coenzyme a thioester accumulation in mutants of *acinetobacter sp*. strain ADP1. (2004) Appl. Environ. Microbic. 70: 2974-2983.

Roosild et al. NMR structure of Mistic, a membrane-integrating protein for membrane protein expression. Science 2005, 307, 1317-1321.

Starai et al. Identification of the protein acetyltransferase (Pat) enzyme that acetylates acetyl-CoA synthetase in *Salmonella enterica*. (2004) J. Mol. Biol. 340:1005-1012.

Sowden et al. Biotransformation of the sesquiterpene (+)-valencene by cytochrome P450cam and P450BM-3. Org. Biomol. Chem. 2005, 3, 57-64.

Barnes et al. Expression and enzymatic activity of recombinant cytochrome P450 17 alpha-hydroxylase in *Escherichia coli*. Proc. Natl. Acad. Sci. USA 1991, 88, 5597-5601.

Craft et al. Identification and characterization of the CYP52 family of *Candida tropicalis* ATCC 20336, important for the conversion of fatty acids and alkanes to alpha,omega-dicarboxylic acids. Appl. Environ. Microbiol. 2003, 69, 5983-5991.

(Continued)

*Primary Examiner* — Tekchand Saidha

(74) *Attorney, Agent, or Firm* — Paula A. Borden; Bozicevic Field & Francis LLP

(57) ABSTRACT

The present invention provides nucleic acids comprising nucleotide sequences encoding modified cytochrome P450 enzymes; as well as recombinant vectors and host cells comprising the nucleic acids. The present invention further provides methods of producing a functionalized compound in a host cell genetically modified with a nucleic acid comprising nucleotide sequences encoding a modified cytochrome P450 enzyme.

13 Claims, 44 Drawing Sheets

OTHER PUBLICATIONS

Hamano et al. Cloning of a gene cluster encoding enzymes responsible for the mevalonate pathway from a terpenoid-antibiotic-producing *Streptomyces* strain. (2001) Biosci. Biotechnol. Biochem. 65:1627-1635.

T. Kuzuyama. Heterologous mevalonate production in *Streptomyces lividans* TK23. (2004) Biosci. Biotechnol. Biochem. 68(4): 931-934.

Schoch et al. Engineering of a water-soluble plant cytochrome P450, CYP73A1, and NMR-based orientation of natural and alternate substrates in the active site.Plant Physiol. 2003, 133, 1198-1208.

Subrahmanyam et al. Overproduction of a functional fatty acid biosynthetic enzyme blocks fatty acid synthesis in *Escherichia coli*. (1998) J. Bact. 180: 4596-4602.

Starai et al. Residue Leu-641 of Acetyl-CoA synthetase is critical for the acetylation of residue Lys-609 by the Protein acetyltransferase enzyme of *Salmonella enterica*. (2005) J. Biol. Chem. 280:26200-26205.

Wilding et al. Identification, evolution, and essentiality of the mevalonate pathway for isopentenyl diphosphate biosynthesis in gram-positive cocci. (2000) J Bacteriol 182(15): 4319-27.

Facchini, et al. Can arabidopsis make complex alkaloids? (2004) Trends in Plant Science, vol. 9, No. 3: 116-122.

Hwang, et al. Production of plant-specific flavanones by *Escherichia coli* containing an artificial gene cluster. (2003) Applied and Environmental Microbiology, vol. 69, No. 5, 2699-2706.

Sono, et al. Heme-containing oxygenases. (1996) Chem. Rev. vol. 96, pp. 2841-2887.

* cited by examiner

FIG. 4A

| | |
|---|---|
| wild-type (TM domain) | MLFPVALSFLVAILGISLWHVWT (SEQ ID NO:23) |
| CYP52A13 (*C. tropicalis*, A13) | MTVHDIIATYFTKWYVIVPLALIAYRVLDYFY(SEQ ID NO:14) |
| CYP52A17 (*C. tropicalis*, A17) | MIEQLLEYWYVVVPVLYIIKQLLAYTK(SEQ ID NO:5) |
| P45017α (*Bos taurus*, bovine) | MALLLAVFLGLSCLLLLSLW(SEQ ID NO:2) |
| truncated | |
| OmpA-A17 | MKKTAIAIAVALAGFATVAQA-A17 TM domain(SEQ ID NO:6) |
| Peptitergent (PD1) | EELLKQALQQAQQLLQQAQELAKK(SEQ ID NO:13) |
| mistic | fusion protein |

FIG. 4B

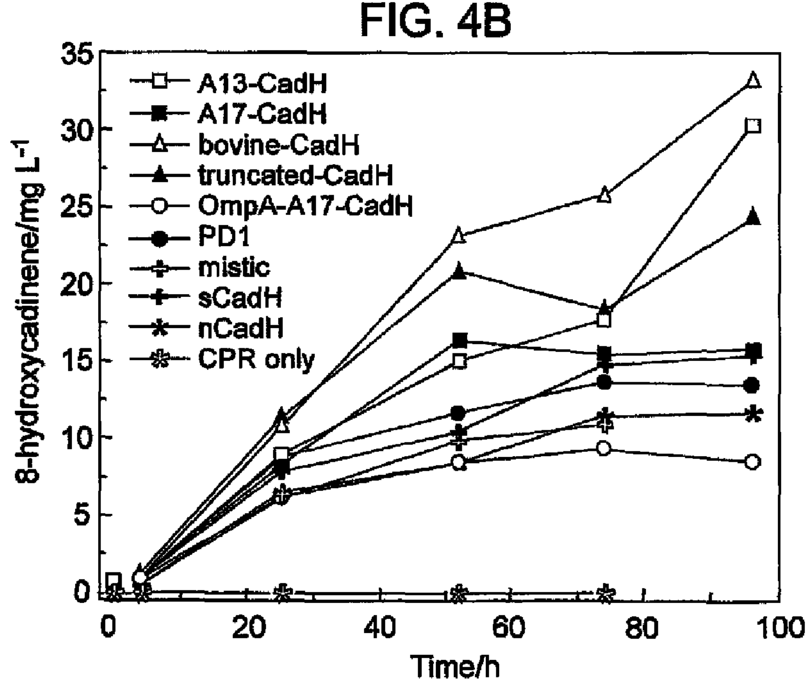

FIG. 5

GenBank Accession No. AAX20121 (AY874162)

MFCTFFEKHHRKWDILLEKSTGVMEAMKVTSEEKEQLSTAIDRMNEGLDAFIQLYNESE
IDEPLIQLDDDTAELMKQARDMYGQEKLNEKLNTIIKQILSISVSEEGEKE (SEQ ID
NO:24)

FIG. 6

*Mentha x gracilis* Limonene-6-Hydroxylase (GenBank Accession Nos. AAQ18706; and AY281025)

```
MELDLLSAIIIILVATYIVSLLINQWRKSKSQQNLPPSPPKLPVIGHLHFLWGGLPQHVFRSIAQKYGPVAH
VQLGEVYSVVLSSAEAAKQAMKVLDPNFADRFDGIGSRTMWYDKDDIIFSPYNDHWRQMRRICVTELLSPK
NVRSFGYIRQEEIERLIRLLGSSGGAPVDVTEEVSKMSCVVVCRAAFGSVLKDQGSLAELVKESLALASGF
ELADLYPSSWLLNLLSLNKYRLQRMRRRLDHILDGFLEEHREKKSGEFGGEDIVDVLFRMQKGSDIKIPIT
SNCIKGFIFDTFSAGAETSSTTISWALSELMRNPAKMAKVQAEVREALKGKTVVDLSEVQELKYLRSVLKE
TLRLHPPFPLIPRQSREECEVNGYTIPAKTRIFINVWAIGRDPQYWEDPDTFRPERFDEVSRDFMGNDFEF
IPFGAGRRICPGLHFGLANVEIPLAQLLYHFDWKLPQGMTDADLDMTETPGLSGPKKKNVCLVPTLYKSP
```

(SEQ ID NO:25)

FIG. 7

*Nicotiana tabacum* 5-*epi*-aristolochene dihydroxylase (GenBank Accession Nos. AAK62342; and AF368376)

*MQFFS*LVSIFLFLAFLFLLRKWKNSNSQSKKLPPGPWKIPILGSMLHMIGGEPHHVLRD
LAKKYGPLMHLQLGEISAVVVTSRDMAKEVLKTHDVVFASRPKIVAMDIICYNQSDIAF
SPYGDHWRQMRKICVMELLNAKNVRSFSSIRRDEVVRLIDSIRSDSSSGELVNFTQRII
WFASSMTCRSAFGQVLKGQDIFAKKIREVIGLAEGFDVVDIFPTYKFLHVLSGMKRKLL
NAHLKVDAIVEDVINEHKKNLAAGKSNGALEDMFAAGTETSSTTTVWAMAEMMKNPSVF
TKAQAEVREAFRDKVSFDENDVEELKYLKLVIKETLRLHPPSPLLVPRECREDTDINGY
TIPAKTKVMVNVWALGRDPKYWDDAESFKPERFEQCSVDFFGNNFEFLPFGGGRRICPG
MSFGLANLYLPLAQLLYHFDWKLPTGIMPRDLDLTELSGITIARKGDLYLNATPYQPSR
E (SEQ ID NO:26)

FIG. 8A

*Gossypium arboreum* native (wild-type) P450 monooxygenase (δ-cadinene-8-hydroxylase; CadH); GenBank AF332974 and AAK60517

*MLQIAFSSYSWLLTASNQKDG*MLFPVALSFLVAILGISLWHVWTIRKPKKDIAPLPPGP
RGLPIVGYLPYLGTDNLHLVFTDLAAAYGPIYKLWLGNKLCVVISSAPLAKEVVRDNDI
TFSERDPPVCAKIITFGLNDIVFDSYSSPDWRMKRKVLVREMLSHSSIKACYGLRREQV
LKGVQNVAQSAGKPIDFGETAFLTSINAMMSMLWGGKQGGERKGADVWGQFRDLITELM
VILGKPNVSDIFPVLARFDIQGLEKEMTKIVNSFDKLFNSMIEERENFSNKLSKEDGNT
ETKDFLQLLLDLKQKNDSGISITMNQVKALLMDIVVGGTDTTSTMMEWTMAELIANPEA
MKKVKQEIDDVVGSDGAVDETHLPKLRYLDAAVKETFRLHPPMPLLVPRCPGDSSNVGG
YSVPKGTRVFLNIWCIQRDPQLWENPLEFKPERFLTDHEKLDYLGNDSRYMPFGSGRRM
CAGVSLGEKMLYSSLAAMIHAYDWNLADGEENDLIGLFGIIMKKKKPLILVPTPRPSNL
QHYMK (SEQ ID NO:27)

FIG. 8B

MALLLAVFLGLSCLLLLSLWIRKPKKDIAPLPPGPRGLPIVGYLPYLGTDNLHLVFTDL
AAAYGPIYKLWLGNKLCVVISSAPLAKEVVRDNDITFSERDPPVCAKIITFGLNDIVFD
SYSSPDWRMKRKVLVREMLSHSSIKACYGLRREQVLKGVQNVAQSAGKPIDFGETAFLT
SINAMMSMLWGGKQGGERKGADVWGQFRDLITELMVILGKPNVSDIFPVLARFDIQGLE
KEMTKIVNSFDKLFNSMIEERENFSNKLSKEDGNTETKDFLQLLLDLKQKNDSGISITM
NQVKALLMDIVVGGTDTTSTMMEWTMAELIANPEAMKKVKQEIDDVVGSDGAVDETHLP
KLRYLDAAVKETFRLHPPMPLLVPRCPGDSSNVGGYSVPKGTRVFLNIWCIQRDPQLWE
NPLEFKPERFLTDHEKLDYLGNDSRYMPFGSGRRMCAGVSLGEKMLYSSLAAMIHAYDW
NLADGEENDLIGLFGIIMKKKKPLILVPTPRPSNLQHYMK (SEQ ID NO:28)

FIG. 8C

EELLKQALQQAQQLLQQAQELAKKIRKPKKDIAPLPPGPRGLPIVGYLPYLGTDNLHLV
FTDLAAAYGPIYKLWLGNKLCVVISSAPLAKEVVRDNDITFSERDPPVCAKIITFGLND
IVFDSYSSPDWRMKRKVLVREMLSHSSIKACYGLRREQVLKGVQNVAQSAGKPIDFGET
AFLTSINAMMSMLWGGKQGGERKGADVWGQFRDLITELMVILGKPNVSDIFPVLARFDI
QGLEKEMTKIVNSFDKLFNSMIEERENFSNKLSKEDGNTETKDFLQLLLDLKQKNDSGI
SITMNQVKALLMDIVVGGTDTTSTMMEWTMAELIANPEAMKKVKQEIDDVVGSDGAVDE
THLPKLRYLDAAVKETFRLHPPMPLLVPRCPGDSSNVGGYSVPKGTRVFLNIWCIQRDP
QLWENPLEFKPERFLTDHEKLDYLGNDSRYMPFGSGRRMCAGVSLGEKMLYSSLAAMIH
AYDWNLADGEENDLIGLFGIIMKKKKPLILVPTPRPSNLQHYMK (SEQ ID NO:29)

FIG. 8D

MKKTAIAIAVALAGFATVAQALLEYWYVVVPVLYIIKQLLAYTKIRKPKKDIAPLPPGP
RGLPIVGYLPYLGTDNLHLVFTDLAAAYGPIYKLWLGNKLCVVISSAPLAKEVVRDNDI
TFSERDPPVCAKIITFGLNDIVFDSYSSPDWRMKRKVLVREMLSHSSIKACYGLRREQV
LKGVQNVAQSAGKPIDFGETAFLTSINAMMSMLWGGKQGGERKGADVWGQFRDLITELM
VILGKPNVSDIFPVLARFDIQGLEKEMTKIVNSFDKLFNSMIEERENFSNKLSKEDGNT
ETKDFLQLLLDLKQKNDSGISITMNQVKALLMDIVVGGTDTTSTMMEWTMAELIANPEA
MKKVKQEIDDVVGSDGAVDETHLPKLRYLDAAVKETFRLHPPMPLLVPRCPGDSSNVGG
YSVPKGTRVFLNIWCIQRDPQLWENPLEFKPERFLTDHEKLDYLGNDSRYMPFGSGRRM
CAGVSLGEKMLYSSLAAMIHAYDWNLADGEENDLIGLFGIIMKKKKPLILVPTPRPSNL
QHYMK (SEQ ID NO:30)

FIG. 9A

*Taxus cuspidata* taxadiene-5α-hydroxylase (GenBank Accession Nos. AY289209 and AAQ56240)

```
MDALYKSTVAKFNEVTQLDCSTESFSIALSAIAGILLLLLLFRSKRHSSLKLPPGKLGI
PFIGESFIFLRALRSNSLEQFFDERVKKFGLVFKTSLIGHPTVVLCGPAGNRLILSNEE
KLVQMSWPAQFMKLMGENSVATRRGEDHIVMRSALAGFFGPGALQSYIGKMNTEIQSHI
NEKWKGKDEVNVLPLVRELVFNISAILFFNIYDKQEQDRLHKLLETILVGSFALPIDLP
GFGFHRALQGRAKLNKIMLSLIKKRKEDLQSGSATATQDLLSVLLTFRDDKGTPLTNDE
ILDNFSSLLHASYDTTTSPMALIFKLLSSNPECYQKVVQEQLEILSNKEEGEEITWKDL
KAMKYTWQVAQETLRMFPPVFGTFRKAITDIQYDGYTIPKGWKLLWTTYSTHPKDLYFN
EPEKFMPSRFDQEGKHVAPYTFLPFGGGQRSCVGWEFSKMEILLFVHHFVKTFSSYTPV
DPDEKISGDPLPPLPSKGFSIKLFPETIVN (SEQ ID NO:31)
```

FIG. 9B

*Taxus canadensis* taxadiene-5α-hydroxylase (GenBank Accession No. AY364469)

```
MDALYKSTVAKFNEVTQLDCSTESFSIALSSIAGILLLLLLFRSKRHSSLKLPPGKLGI
PFIGESFIFLRALRSNSLEQFFDERVKKFGLVFKTSLIGHPTVVLCGPAGNRLILSNEE
KLVQMSWPAQFMKLMGENSVATRRGEDHIVMRSALAGFFGPGALQSYIGKMNTEIQNHI
NEKWKGKDEVNVLPLVRELVFNISAILFFNIYDKQEQDRLHKLLETILVGSFALPIDLP
GFGFHRALQGRATLNKIMLSLIKKRKEDLQSGSATATQDLLSVLLTFRDDKGTPLTNDE
ILDNFSSLLHASYDTTTSPMALIFKLLSSNPECYQKVVQEQLEILSNKEEGEEITWKDL
KAMKYTWQVAQETLRMFPPVFGTFRKAITDIQYDGYTIPKGWKLLWTTYSTHPKDLYFS
EPEKFMPSRFDQEGKHVAPYTFLPFGGGQRSCVGWEFSKMEILLFVHHFVKTFSSYTPV
DPDEKISGDPLPPLPSKGFSIKLFPETIVN (SEQ ID NO:32)
```

FIG. 10

*Arabidopsis thaliana ent*-kaurene oxidase (GenBank Accession Nos. AAC39505 and AF047719)

MAFFSMISILLGFVISSFIFIFFFKKLLSFSRKNMSEVSTLPSV
PVVPGFPVIGNLLQLKEKKPHKTFTRWSEIYGPIYSIKMGSSSLIVLNSTETAKEAMV
TRFSSISTRKLSNALTVLTCDKSMVATSDYDDFHKLVKRCLLNGLLGANAQKRKRHYR
DALIENVSSKLHAHARDHPQEPVNFRAIFEHELFGVALKQAFGKDVESIYVKELGVTL
SKDEIFKVLVHDMMEGAIDVDWRDFFPYLKWIPNKSFEARIQQKHKRRLAVMNALIQD
RLKQNGSESDDDCYLNFLMSEAKTLTKEQIAILVWETIIETADTTLVTTEWAIYELAK
HPSVQDRLCKEIQNVCGGEKFKEEQLSQVPYLNGVFHETLRKYSPAPLVPIRYAHEDT
QIGGYHVPAGSEIAINIYGCNMDKKRWERPEDWWPERFLDDGKYETSDLHKTMAFGAG
KRVCAGALQASLMAGIAIGRLVQEFEWKLRDGEEENVDTYGLTSQKLYPLMAIINPRR
S (SEQ ID NO:33)

FIG. 11A

*Gossypium arboreum* native (wild-type) P450 monooxygenase (δ-cadinene-8-hydroxylase; CadH); GenBank AF332974

```
   1 ccacttcgca gcaatattat tgcagttcct ggttggctac ctctgagttt tcaacttaaa
  61 atttcttggt tttcctcaag aaggaagaag atgttgcaaa tagctttcag ctcgtattca
 121 tggctgttga ctgctagcaa ccagaaagat ggaatgttgt tcccagtagc tttgtcattt
 181 ttggtagcca tattgggaat ttcactgtgg cacgtatgga ccataaggaa gccaaagaaa
 241 gacatcgccc cattaccgcc gggtccccgt gggttgccaa tagtgggata tcttccatat
 301 cttggaactg ataatcttca cttggtgttt acagatttgg ctgcagctta cggtcccatc
 361 tacaagcttt ggctaggaaa caaattatgc gtagtcatta gctcggcacc actggcgaaa
 421 gaagtggttc gtgacaacga catcacattt tctgaaaggg atcctcccgt ttgtgcaaag
 481 attattacct ttggcctcaa tgatattgta tttgattctt acagtagtcc agattggaga
 541 atgaagagaa aagtgctggt acgtgaaatg cttagccata gtagcattaa agcttgttat
 601 ggtctaagga gggaacaagt gcttaaaggc gtacaaaatg ttgctcaaag tgctggcaag
 661 ccaattgatt ttggtgaaac ggcattttta acatcaatca atgcgatgat gagcatgctg
 721 tggggtggca aacagggagg agagcggaaa ggggccgacg tttggggcca atttcgagat
 781 ctcataaccg aactaatggt gatacttgga aaaccaaacg tttctgatat tttcccggtg
 841 cttgcaaggt ttgacataca gggattggag aaggaaatga ctaaaatcgt taattctttc
 901 gataagcttt tcaactccat gattgaagaa agagagaact ttagcaacaa attgagcaaa
 961 gaagatggaa acactgaaac aaaagacttc ttgcagcttc tgttggacct caagcagaag
1021 aacgatagcg gaatatcgat aacaatgaat caagtcaagg ccttgctcat ggacattgtg
1081 gtcggtggaa ctgatacaac atcaaccatg atggaatgga caatggctga actaattgca
1141 aatcctgaag caatgaaaaa ggtgaagcaa gaaatagacg atgttgtcgg ttcggatggc
1201 gccgtcgatg agactcactt gcctaagttg cgctatctag atgctgcagt aaaggagacc
1261 ttccgattgc acccaccgat gccactcctt gtaccccgtt gcccgggcga ctcaagcaac
1321 gttggtggct atagcgtacc aaagggcacc agggtcttct taaacatttg gtgtattcag
1381 agggatccac agctttggga aaatccttta gaattcaagc ctgagaggtt cttgactgat
1441 catgagaagc tcgattattt aggaaacgat tcccggtaca tgccgtttgg ttctggaagg
1501 agaatgtgtg ccggagtatc tctcggtgaa aagatgttgt attcctcctt ggcagcaatg
1561 atccatgctt atgattggaa cttggccgac ggtgaagaaa atgacttgat tggcttattt
1621 ggaattatta tgaagaaaaa gaagccttta attcttgttc ctacaccaag accatcaaat
1681 ctccagcact atatgaagta actttactat tgtatttctt ttataccact ttattgcctc
1741 tttgtcatgt ttaggcaaca attctaagta ataagtttgg ctatatggtg aacaataatg
1801 tgtttattat acatcataag caatgagctc ttcccgaccc tagggcaata caatgatact
1861 gtgtattaag tgaaatcaac aaatctttta ttctaa (SEQ ID NO:34)
```

FIG. 11B

Nucleotide sequence of codon-optimized cadinene hydroxylase

```
atgctgcagattgctttttcttcttattcttggctgctgaccgcttctaaccagaaagacggcatgctgtt
cccggtggcgctgagcttcctggtggcaatcctgggcattagcctgtggcacgtgtggactatccgtaaac
cgaagaaagatatcgcaccgctgccaccgggtccgcgtggcctgccgatcgttggctacctgccgtatctg
ggcaccgacaacctgcacctggtgttcaccgacctggcagccgcgtacggtccgatctacaaactgtggct
gggcaataaactgtgcgtagttatctcctctgctcctctggcgaaggaggtggttcgcgacaacgacatca
ccttctccgaacgtgacccaccggtctgtgctaaaatcatcaccttcggcctgaacgacatcgtattcgac
tcctatagctctcctgactggcgtatgaaacgtaaggttctggtacgcgagatgctgtcccacagctccat
taaggcatgctacggcctgcgtcgcgaacaggtactgaaaggcgtacaaaacgtagcgcagtccgcgggca
aaccgatcgatttcggcgaaacggccttcctgactagcatcaacgctatgatgtccatgctgtggggtggt
aaacagggcggcgagcgtaaaggcgccgacgtatggggccagtttcgtgacctgatcaccgaactgatggt
gattctgggcaaaccgaacgtcagcgacatcttcccggttctggctcgcttcgacatccagggcctggaaa
aagaaatgaccaagatcgtcaactctttcgacaaactgtttaactccatgatcgaagaacgcgaaaatttc
tctaacaaactgagcaaagaagatggcaacaccgaaactaaagatttcctgcagctgctgctggacctgaa
acaaaagaacgattctggtatctccattaccatgaaccaagtgaaagcgctgctgatggacattgttgtgg
gtggtactgacaccacttctaccatgatggaatggacgatggcagaactgattgctaatccggaagcgatg
aagaaagtgaaacaagaaattgatgatgtagtgggctctgatggtgcggtagacgagacgcacctgcctaa
gctgcgttatctggacgcagccgtgaaagaaaccttccgtctgcatccgcctatgccgctgctggttccac
gttgcccaggcgattccagcaacgttggtggctatagcgtaccgaagggtacccgtgtgttcctgaatatc
tggtgcattcagcgcgacccgcagctgtgggaaaacccgctggagttcaaacctgaacgcttcctgaccga
ccatgaaaagctggactacctgggcaacgattcccgttacatgccgttcggttctggccgtcgtatgtgcg
caggcgtctccctgggcgagaaaatgctgtactctagcctggctgccatgatccacgcttacgactggaac
ctggcagatggtgaagagaacgacctgatcggcctgttcggcatcattatgaaaaagaaaaagccgctgat
cctggtgccgactccgcgtccaagcaacctgcagcactacatgaaactggtgccgcgtggctctaaagaaa
ccgctgctgcaaaattcgaacgtcagcacatggacagctaataa (SEQ ID NO:35)
```

FIG. 12A

GenBank AY571340
SOURCE CPR *Taxus cuspidata*
MQANSNTVEGASQGKSLLDISRLDHIFALLLNGKGGDLGAMTGS
ALILTENSQNLMILTTALAVLVACVFFFVWRRGGSDTQKPAVRPTPLVKEEDEEEEDD
SAKKKVTIFFGTQTGTAEGFAKALAEEAKARYEKAVFKVVDLDNYAADDEQYEEKLKK
EKLAFFMLATYGDGEPTDNAARFYKWFLEGKEREPWLSDLTYGVFGLGNRQYEHFNKV
AKAVDEVLIEQGAKRLVPVGLGDDDQCIEDDFTAWREQVWPELDQLLRDEDDEPTSAT
PYTAAIPEYRVEIYDSVVSVYEETHALKQNGQAVYDIHHPCRSNVAVRRELHTPLSDR
SCIHLEFDISDTGLIYETGDHVGVHTENSIETVEEAAKLLGYQLDTIFSVHGDKEDGT
PLGGSSLPPPFPGPCTLRTALARYADLLNPPRKAAFLALAAHASDPAEAERLKFLSSP
AGKDEYSQWVTASQRSLLEIMAEFPSAKPPLGVFFAAIAPRLQPRYYSISSSPRFAPS
RIHVTCALVYGPSPTGRIHKGVCSNWMKNSLPSEETHDCSWAPVFVRQSNFKLPADST
TPIVMVGPGTGFAPFRGFLQERAKLQEAGEKLGPAVLFFGCRNRQMDYIYEDELKGYV
EKGILTNLIVAFSREGATKEYVQHKMLEKASDTWSLIAQGGYLYVCGDAKGMARDVHR
TLHTIVQEQESVDSSKAEFLVKKLQMDGRYLRDIW (SEQ ID NO:36)

FIG. 12B

CPR from *Candida tropicalis*. (GenBank accession M35199)
MALDKLDLYVIITLVVAIAAYFAKNQFLDQQQDTGFLNTDSGDG
NSRDILQALKKNNKNTLLLFGSQTGTAEDYANKLSRELHSRFGLKTMVADFADYDFEN
FGDITEDILVFFIVATYGEGEPTDNADEFHTWLTEEADTLSTLKYTVFGLGNSTYEFF
NAIGRKFDRLLGEKGGDRFAEYGEGDDGTGTLDEDFLAWKDNVFDSLKNDLNFEEKEL
KYEPNVKLTERDDLSGNDPDVSLGEPNVKYIKSEGVDLTKGPFDHTHPFLARIVKTKE
LFTSEDRHCVHVEFDISESNLKYTTGDHLAIWPSNSDENIKQFAKCFGLEDKLDTVIE
LKALDSTYSIPFPNPITYGAVIRHHLEISGPVSRQFFLSIAGFAPDEETKKSFTRIGG
DKQEFASKVTRRKFNIADALLFASNNRPWSDVPFEFLIENVQHLTPRYYSISSSSLSE
KQTINVTAVVEAEEEADGRPVTGVVTNLLKNIEIEQNKTGETPMVHYDLNGPRGKFSK
FRLPVHVRRSNFKLPKNSTTPVILIGPGTGVAPLRGFVRERVQQVKNGVNVGKTVLFY
GCRNSEQDFLYKQEWSEYASVLGENFEMFNAFSRQDPTKKVYVQDKILENSALVDELL
SSGAIIYVCGDASRMARDVQAAIAKIVAKSRDIHEDKAAELVKSWKVQNRYQEDVW (SEQ ID NO:37)

FIG. 12C

ATR1
>gi|6088150|emb|CAB58575.1| NADPH CYTOCHROME P450 REDUCTASE [*Arabidopsis thaliana*] (GenBank Accession No. X66016)

MTSALYASDLFKQLKSIMGTDSLSDDVVLVIATTSLALVAGFVVLLWKKTTADRSGELKPLMIPKSLMAK
DEDDDLDLGSGKTRVSIFFGTQTGTAEGFAKALSEEIKARYEKAAVKVIDLDDYAADDDQYEEKLKKETL
AFFCVATYGDGEPTDNAARFSKWFTEENERDIKLQQLAYGVFALGNRQYEHFNKIGIVLDEELCKKGAKR
LIEVGLGDDDQSIEDDFNAWKESLWSELDKLLKDEDDKSVATPYTAVIPEYRVVTHDPRFTTQKSMESNV
ANGNTTIDIHHPCRVDVAVQKELHTHESDRSCIHLEFDISRTGITYETGDHVGVYAENHVEIVEEAGKLL
GHSLDLVFSIHADKEDGSPLESAVPPPFPGPCTLGTGLARYADLLNPPRKSALVALAAYATEPSEAEKLK
HLTSPDGKDEYSQWIVASQRSLLEVMAAFPSAKPPLGVFFAAIAPRLQPRYYSISSCQDWAPSRVHVTSA
LVYGPTPTGRIHKGVCSTWMKNAVPAEKSHECSGAPIFIRASNFKLPSNPSTPIVMVGPGTGLAPFRGFL
QERMALKEDGEELGSSLLFFGCRNRQMDFIYEDELNNFVDQGVISELIMAFSREGAQKEYVQHKMMEKAA
QVWDLIKEEGYLYVCGDAKGMARDVHRTLHTIVQEQEGVSSSEAEAIVKKLQTEGRYLRDVW (SEQ ID NO:38)

FIG. 12D

*Arabidopsis thaliana* cytochrome P450 reductase ATR2 (GenBank Accession No. X66017

MSSSSSSSTSMIDLMAAIIKGEPVIVSDPANASAYESVAAELSS
MLIENRQFAMIVTTSIAVLIGCIVMLVWRRSGSGNSKRVEPLKPLVIKPREEEIDDGR
KKVTIFFGTQTGTAEGFAKALGEEAKARYEKTRFKIVDLDDYAADDDEYEEKLKKEDV
AFFFLATYGDGEPTDNAARFYKWFTEGNDRGEWLKNLKYGVFGLGNRQYEHFNKVAKV
VDDILVEQGAQRLVQVGLGDDDQCIEDDFTAWREALWPELDTILREEGDTAVATPYTA
AVLEYRVSIHDSEDAKFNDITLANGNGYTVFDAQHPYKANVAVKRELHTPESDRSCIH
LEFDIAGSGLTMKLGDHVGVLCDNLSETVDEALRLLDMSPDTYFSLHAEKEDGTPISS
SLPPPFPPCNLRTALTRYACLLSSPKKSALVALAAHASDPTEAERLKHLASPAGKDEY
SKWVVESQRSLLEVMAEFPSAKPPLGVFFAGVAPRLQPRFYSISSSPKIAETRIHVTC
ALVYEKMPTGRIHKGVCSTWMKNAVPYEKSEKLFLGRPIFVRQSNFKLPSDSKVPIIM
IGPGTGLAPFRGFLQERLALVESGVELGPSVLFFGCRNRRMDFIYEEELQRFVESGAL
AELSVAFSREGPTKEYVQHKMMDKASDIWNMISQGAYLYVCGDAKGMARDVHRSLHTI
AQEQGSMDSTKAEGFVKNLQTSGRYLRDVW (SEQ ID NO:39)

FIG. 12E

ATR2mod
>gi|13272461|gb|AAK17169.1|AF325101_1 NADPH-ferrihemoprotein reductase (ATR2) [Arabidopsis thaliana]
MLIENRQFAMIVTTSIAVLIGCIVMLVWRRSGSGNSKRVEPLKPLVIKPREEEIDDGRKKVTIFFGTQTGT
AEGFAKALGEEAKARYEKTRFKIVDLDDYAADDDEYEEKLKKEDVAFFFLATYGDGEPTDNAARFYKWFTE
GNDRGEWLKNLKYGVFGLGNRQYEHFNKVAKVVDDILVEQGAQRLVQVGLGDDDQCIEDDFTAWREALWPE
LDTILREEGDTAVATPYTAAVLEYRVSIHDSEDAKFNDINMANGNGYTVFDAQHPYKANVAVKRELHTPES
DRSCIHLEFDIAGSGLTYETGDHVGVLCDNLSETVDEALRLLDMSPDTYFSLHAEKEDGTPISSSLPPPFP
PCNLRTALTRYACLLSSPKKSALVALAAHASDPTEAERLKHLASPAGKDEYSKWVVESQRSLLEVMAEFPS
AKPPLGVFFAGVAPRLQPRFYSISSSPKIAETRIHVTCALVYEKMPTGRIHKGVCSTWMKNAVPYEKSENC
SSAPIFVRQSNFKLPSDSKVPIIMIGPGTGLAPFRGFLQERLALVESGVELGPSVLFFGCRNRRMDFIYEE
ELQRFVESGALAELSVAFSREGPTKEYVQHKMMDKASDIWNMISQGAYLYVCGDAKGMARDVHRSLHTIAQ
EQGSMDSTKAEGFVKNLQTSGRYLRDVW (SEQ ID NO:40)

Isoprenoid metabolic pathways
OPO(OH)OP(OH)2O
Isopentenyl diphosphate (IPP)
OPO(OH)OP(OH)2O
Dimethylallyl diphosphate (DMAPP)
OPO(OH)OP(OH)2O
Geranyl diphosphate (GPP)
Monoterpenes
OPO(OH)OP(OH)2O
Farnesyl diphosphate (FPP)
Sesquiterpenes
OPO(OH)OP(OH)2O
Geranylgeranyl diphosphate (GGPP)
Diterpenes
Carotenoids

DXP pathway

FIG. 19A

*Eschscholzia stolonifera* Methylcoclaurine 3'-Hydroxylase (Accession: AF014802)

MEKPILLQLQAGILGLLALICFLYYVIKVSLSTRNCNQLVKHPPEAAGSWPIVGHLPQL
VGSGKPLFRVLGDMADKFGPIFMVRFGVYPTLVVSTWEMAKECFTSNDKFLASRPPSAA
SSYMTYDHAMFGFSFYGPYWREIRKISTLHLLSHRRLELLKHVPHTEIHNFIKGLFGIW
KDHQKQQQPTGREDRDSVMLEMSQLFGYLTLNVVLSLVVGKRVCNYHADGHLDDGEEAG
QGQKLHQTITDFFKLSGVSVASDALPLLGLFDLGGKKESMKRVAKEMDFFAERWLQDKK
LSLSLSSETNNKQNDAGEGDGDDFMDVLMSILPDDDDSLFTKYSRDTVIKATSLSMVVA
ASDTTSVSLTWALSLLLNNIQVLRKAQDELDTKVGRDRHVEEKDIDNLVYLQAIVKETL
RMYPAGPLSVPHEAIEDCNVGGYHIKTGTRLLVNIWKLQRDPRVWSNPSEFRPERFLDN
QSNGTLLDFRGQHFEYIPFGSGRRMCPGVNFATLILHMTLARLLQAFDLSTPSSSPVDM
TEGSGLTMPKVTPLKVLLTPRLPLPLYDY (SEQ ID NO:41)

FIG. 19B

*Catharanthus roseus* Geraniol-10-hydroxylase (Accession: AJ251269)

MDYLTIILTLLFALTLYEAFSYLSRRTKNLPPGPSPLPFIGSLHLLGDQPHKSLAKLSK
KHGPIMSLKLGQITTIVISSSTMAKEVLQKQDLAFSSRSVPNALHAHNQFKFSVVWLPV
ASRWRSLRKVLNSNIFSGNRLDANQHLRTRKVQELIAYCRKNSQSGEAVDVGRAAFRTS
LNLLSNLIFSKDLTDPYSDSAKEFKDLVWNIMVEAGKPNLVDFFPLLEKVDPQGIRHRM
TIHFGEVLKLFGGLVNERLEQRRSKGEKNDVLDVLLTTSQESPEEIDRTHIERMCLDLF
VAGTDTTSSTLEWAMSEMLKNPDKMKKTQDELAQVIGRGKTIEESDINRLPYLRCVMKE
TLRIHPPVPFLIPRKVEQSVEVCGYNVPKGSQVLVNAWAIGRDETVWDDALAFKPERFM
ESELDIRGRDFELIPFGAGRRICPGLPLALRTVPLMLGSLLNSFNWKLEGGMAPKDLDM
EEKFGITLQKAHPLRAVPSTL (SEQ ID NO:42)

FIG. 19C

*Catharanthus roseus* Tabersonine-16-hydroxylase (Accession: AJ238612)

MLLFCFILSKTTKKFGQNSQYSNHDELPPGPPQIPILGNAHQLSGGHTHHILRDLAKKY
GPLMHLKIGEVSTIVASSPQIAEEIFRTHDILFADRPSNLESFKIVSYDFSDMVVSPYG
NYWRQLRKISMMELLSQKSVQSFRSIREEEVLNFIKSIGSKEGTRINLSKEISLLIYGI
TTRAAFGEKNKNTEEFIRLLDQLTKAVAEPNIADMFPSLKFLQLISTSKYKIEKIHKQF
DVIVETILKGHKEKINKPLSQENGEKKEDLVDVLLNIQRRNDFEAPLGDKNIKAIIFNI
FSAGTETSSTTVDWAMCEMIKNPTVMKKAQEEVRKVFNEEGNVDETKLHQLKYLQAVIK
ETLRLHPPVPLLLPRECREQCKIKGYTIPSKSRVIVNAWAIGRDPNYWIEPEKFNPDRF
LESKVDFKGNSFEYLPFGGGRRICPGITFALANIELPLAQLLFHFDWQSNTEKLNMKES
RGVTVRREDDLYLTPVNFSSSSPA (SEQ ID NO:43)

FIG. 20A

*Arabidopsis thaliana* cinnamate-4-hydroxylase (Accession NM 128601)

MDLLLLEKSLIAVFVAVILATVISKLRGKKLKLPPGPIPIPIFGNWLQVGDDLNHRNL
VDYAKKFGDLFLLRMGQRNLVVVSSPDLTKEVLLTQGVEFGSRTRNVVFDIFTGKGQDM
VFTVYGEHWRKMRRIMTVPFFTNKVVQQNREGWEFEAASVVEDVKKNPDSATKGIVLRK
RLQLMMYNNMFRIMFDRRFESEDDPLFLRLKALNGERSRLAQSFEYNYGDFIPILRPFL
RGYLKICQDVKDRRIALFKKYFVDERKQIASSKPTGSEGLKCAIDHILEAEQKGEINED
NVLYIVENINVAAIETTLWSIEWGIAELVNHPEIQSKLRNELDTVLGPGVQVTEPDLHK
LPYLQAVVKETLRLRMAIPLLVPHMNLHDAKLAGYDIPAESKILVNAWWLANNPNSWKK
PEEFRPERFFEEESHVEANGNDFRYVPFGVGRRSCPGIILALPILGITIGRMVQNFELL
PPPGQSKVDTSEKGGQFSLHILNHSIIVMKPRNC (SEQ ID NO:44)

FIG. 20B

*Ocimum basilicum p*-coumaroyl shikimate-3'-hydroxylase (Accession AY082611)

MAALLLLLLLPLLLPAIFLLHHLYYRLRFRLPPGPRPLPIVGNLYDVKPVRFRCFADWA
QSYGPIISVWFGSTLNVIVSNTELAKEVLKEKDQQLADRHRSRSAAKFSRDGQDLIWAD
YGPHYVKVRKVCTLELFSPKRLEALRPIREDEVTAMVESIYHDCTAPDNAGKSLLVKKY
LGAVAFNNITRLAFGKRFVNSEGIIDKQGLEFKAIVSNGLKLGASLAMAEHIPSLRWMF
PLDEDAFAKHGARRDQLTREIMEEHTRAREESGGAKQHFFDALLTLKDKYDLSEDTIIG
LLWDMITAGMDTTAISVEWAMAELIKNPRVQQKAQEELDRVIGYERVMTELDFSNLPYL
QCVAKEALRLHPPTPLMLPHRSNSNVKIGGYDIPKGSNVHVNVWAVARDPAVWKNPCEF
RPERFLEEDVDMKGHDFRLLPFGAGRRVCPGAQLGINLVTSMIGHLLHHFNWAPPSGVS
SDELDMGENPGLVTYMRTPLEAVPTPRLPSDLYKRIAVDL (SEQ ID NO:45)

FIG. 20C

*Glycine max* Isoflavone Synthase (Accession AF195798)

MLLELALGLFVLALFLHLRPTPSAKSKALRHLPNPPSPKPRLPFIGHLHLLKDKLLHYA
LIDLSKKHGPLFSLSFGSMPTVVASTPELFKLFLQTHEATSFNTRFQTSAIRRLTYDNS
VAMVPFGPYWKFVRKLIMNDLLNATTVNKLRPLRTQQIRKFLRVMAQSAEAQKPLDVTE
ELLKWTNSTISMMMLGEAEEIRDIAREVLKIFGEYSLTDFIWPLKYLKVGKYEKRIDDI
LNKFDPVVERVIKKRREIVRRRKNGEVVEGEASGVFLDTLLEFAEDETMEIKITKEQIK
GLVVDFFSAGTDSTAVATEWALAELINNPRVLQKAREEVYSVVGKDRLVDEVDTQNLPY
IRAIVKETFRMHPPLPVVKRKCTEECEINGYVIPEGALVLFNVWQVGRDPKYWDRPSEF
RPERFLETGAEGEAGPLDLRGQHFQLLPFGSGRRMCPGVNLATSGMATLLASLIQCFDL
QVLGPQGQILKGDDAKVSMEERAGLTVPRAHSLVCVPLARIGVASKLLS (SEQ ID NO:46)

FIG. 21A

*Streptomyces avermitilis* aveE (Accession: AB032367)

MMSQSTSSIPEAPGAWPVVGHVPPLMRQPLEFLRSAADHGDLLKLRLGPKTAYLATHPD
LVRTMLVSSGSGDFTRSKGAQGASRFIGPILVAVSGETHRRQRRRMQPGFHRQRLESYV
ATMAAAAQETADSWSAGQVVDVEQAACDLSLAMITKTLFFSDLGAKAEAALRKTGHDIL
KVARLSALAPTLYEVLPTAGKRSVGRTSATIREAITAYRADGRDHGDLLSTMLRATDAE
GASMTDQEVHDEVMGIAVAGIGGPAAITAWIFHELGQNAEIESRLHAELDTVLGGRLPT
HEDLPRLPYTQNLVKEALRKYPGWVGSRRTVRPVRLGGHDLPADVEVMYSAYAIQRDPR
WYPEPERLDPGRWETKGSSRGVPKGAWVPFALGTYKCIGDNFALLETAVTVAVVASHWR
LHALPGDEVRPKTKATHVFPNRLRMIAEPRSVVRLEEPAAMGA (SEQ ID NO:47)

FIG. 21B

MGLPLTSTKTAPVSYPFGRPEGLDLDEAYEQARKSEGLLWVHMPYGEPGWLVSRYDDAR
FVLGDRRFSHAAEAENDAPRMRELRTPNGIIGMDAPDHTRLRGLVTKAFTPRRVEAMRP
HVRRMTASLLRDMTALGSPVDLVDHYAVPLPVAVICGLLGVPEEDRDLFRGWCEIAMST
SSLTAEDHVRLAGELTGYLADLITARRAAPRDDLVSALVEARDAQGRLSQEELVDLIVF
LLFAGHETTASQISNFVLVLLEQPDQLALLRDRPDLLDNAVEELTRFVPLGSQAGFPRY
ATEDVEVGGTLVRAGDPVLVQMNAANRDALRFRSPGVLDITRDDAGRHLGYGHGPEHCL
GASLARLELQEALRTLLDELPGLHLAQPVEWKTEMVVRGPRTMLVGW (SEQ ID NO:48)

FIG. 24A

Wild type Amorphadiene oxidase

CATATGAAGTCTATTCTGAAAGCAATGGCTCTGTCTCTGACCACTAGCATCGCCCTGGCGACTATCCTGCTGTTTGTGT
ACAAATTCGCGACCCGTTCTAAAAGCACTAAGAAATCTCTGCCGGAACCGTGGCGTCTGCCAATCATCGGTCACATGCA
CCACCTGATCGGCACCACCCCGCACCGTGGCGTACGCGACCTGGCGCGTAAGTACGGCTCTCTGATGCATCTGCAGCTG
GGCGAGGTACCTACTATCGTCGTTTCCTCCCCGAAGTGGGCCAAAGAAATCCTGACTACCTATGACATCACTTTCGCCA
ACCGCCCGGAAACGCTGACCGGCGAAATTGTCCTGTACCATAACACGGATGTGGTTCTGGCCCCGTACGGTGAGTACTG
GCGCCAGCTGCGCAAAATTTGTACTCTGGAACTGCTGAGCGTTAAAAAGGTTAAATCCTTCCAGAGCCTGCGTGAAGAG
GAATGCTGGAACCTGGTGCAGGAGATTAAAGCGTCTGGCAGCGGTCGTCCAGTTAACCTGTCTGAGAATGTTTTTAAAC
TGATCGCTACTATCCTGTCTCGCGCGGCATTCGGTAAAGGTATCAAAGATCAGAAAGAACTGACCGAAATCGTTAAGGA
AATCCTGCGCCAGACTGGTGGCTTCGACGTTGCGGACATCTTCCCGTCCAAAAAGTTCCTGCACCATCTGTCTGGCAAA
CGCGCTCGTCTGACCTCCCTGCGTAAGAAAATTGATAACCTGATTGACAACCTGGTCGCTGAGCACACTGTGAACACCT
CTTCTAAAACCAACGAAACCCTGCTGGACGTACTGCTGCGCCTGAAGGACTCTGCCGAATTTCCACTGACTAGCGACAA
TATCAAAGCAATCATCCTGGACATGTTCGGCGCCGGTACCGATACGTCCTCTTCCACGATTGAGTGGGCTATTTCCGAA
CTGATCAAATGCCCGAAGGCGATGGAAAAAGTGCAGGCGGAACTGCGTAAAGCGCTGAACGGTAAAGAGAAAATTCATG
AAGAGGACATCCAGGAACTGTCCTACCTGAATATGGTAATCAAAGAAACTCTGCGTCTGCATCCGCCGCTGCCACTGGT
TCTGCCGCGTGAATGCCGTCAGCCGGTTAACCTGGCCGGCTACAACATTCCGAACAAAACGAAGCTGATCGTCAACGTT
TTCGCGATCAACCGCGATCCTGAATACTGGAAAGACGCGGAAGCGTTCATTCCGGAACGCTTTGAGAACTCCTCTGCCA
CCGTTATGGGCGCTGAATACGAGTACCTGCCGTTCGGTGCGGGTCGCCGTATGTGCCCGGGTGCTGCACTGGGCCTGGC
GAACGTTCAACTGCCACTGGCGAACATCCTGTACCACTTCAACTGGAAACTGCCTAACGGCGTATCTTATGATCAAATC
GACATGACCGAAAGCTCCGGCGCGACCATGCAGCGTAAAACCGAACTGCTGCTGGTTCCGTCCTTTTAACCTAGG
(SEQ ID NO:49)

FIG. 24B

Nde←Leader→←→Transmembrane

CATATGAAGTCTATTCTGAAAGCAATGGCTCTGTCTCTGACCACTAGCATCGCCCTGGCGACTATCCTGCTGTTTGTGT

→ >Amorphadiene Oxidase

ACAAATTCGCGACCCGTTCTAAAAGCACTAAGAAATCTCTGCCGGAACCGTGGCGTCTGCCAATCATCGGTCACATGCA
CCACCTGATCGGCACCACCCCGCACCGTGGCGTACGCGACCTGGCGCGTAAGTACGGCTCTCTGATGCATCTGCAGCTG
GGCGAGGTACCTACTATCGTCGTTTCCTCCCCGAAGTGGGCCAAAGAAATCCTGACTACCTATGACATCACTTTCGCCA
ACCGCCCGGAAACGCTGACCGGCGAAATTGTCCTGTACCATAACACGGATGTGGTTCTGGCCCCGTACGGTGAGTACTG
GCGCCAGCTGCGCAAAATTTGTACTCTGGAACTGCTGAGCGTTAAAAAGGTTAAATCCTTCCAGAGCCTGCGTGAAGAG
GAATGCTGGAACCTGGTGCAGGAGATTAAAGCGTCTGGCAGCGGTCGTCCAGTTAACCTGTCTGAGAATGTTTTTAAAC
TGATCGCTACTATCCTGTCTCGCGCGGCATTCGGTAAAGGTATCAAAGATCAGAAAGAACTGACCGAAATCGTTAAGGA
AATCCTGCGCCAGACTGGTGGCTTCGACGTTGCGGACATCTTCCCGTCCAAAAAGTTCCTGCACCATCTGTCTGGCAAA
CGCGCTCGTCTGACCTCCCTGCGTAAGAAAATTGATAACCTGATTGACAACCTGGTCGCTGAGCACACTGTGAACACCT
CTTCTAAAACCAACGAAACCCTGCTGGACGTACTGCTGCGCCTGAAGGACTCTGCCGAATTTCCACTGACTAGCGACAA
TATCAAAGCAATCATCCTGGACATGTTCGGCGCCGGTACCGATACGTCCTCTTCCACGATTGAGTGGGCTATTTCCGAA
CTGATCAAATGCCCGAAGGCGATGGAAAAAGTGCAGGCGGAACTGCGTAAAGCGCTGAACGGTAAAGAGAAAATTCATG
AAGAGGACATCCAGGAACTGTCCTACCTGAATATGGTAATCAAAGAAACTCTGCGTCTGCATCCGCCGCTGCCACTGGT
TCTGCCGCGTGAATGCCGTCAGCCGGTTAACCTGGCCGGCTACAACATTCCGAACAAAACGAAGCTGATCGTCAACGTT
TTCGCGATCAACCGCGATCCTGAATACTGGAAAGACGCGGAAGCGTTCATTCCGGAACGCTTTGAGAACTCCTCTGCCA
CCGTTATGGGCGCTGAATACGAGTACCTGCCGTTCGGTGCGGGTCGCCGTATGTGCCCGGGTGCTGCACTGGGCCTGGC
GAACGTTCAACTGCCACTGGCGAACATCCTGTACCACTTCAACTGGAAACTGCCTAACGGCGTATCTTATGATCAAATC

Stop

GACATGACCGAAAGCTCCGGCGCGACCATGCAGCGTAAAACCGAACTGCTGCTGGTTCCGTCCTTTTAACCTAGG

>AvrII (SEQ ID NO:50)

FIG. 25

```
Translation Map
Leader
     1 ATGAAGTCTATTCTG
     1 M K S I L
Transmembrane
     1 AAAGCAATGGCTCTGTCTCTGACCACTAGCATCGCCCTGGCGACTATCCTGCTGTTTGTG
     1 K A M A L S L T T S I A L A T I L L F V
    61 TACAAATTC
    21 Y K F
Amorphadiene Oxidase
     1 GCGACCCGTTCTAAAAGCACTAAGAAATCTCTGCCGGAACCGTGGCGTCTGCCAATCATC
     1 A T R S K S T K K S L P E P W R L P I I
    61 GGTCACATGCACCACCTGATCGGCACCACCCCGCACCGTGGCGTACGCGACCTGGCGCGT
    21 G H M H H L I G T T P H R G V R D L A R
   121 AAGTACGGCTCTCTGATGCATCTGCAGCTGGGCGAGGTACCTACTATCGTCGTTTCCTCC
    41 K Y G S L M H L Q L G E V P T I V V S S
   181 CCGAAGTGGGCCAAAGAAATCCTGACTACCTATGACATCACTTTCGCCAACCGCCCGGAA
    61 P K W A K E I L T T Y D I T F A N R P E
   241 ACGCTGACCGGCGAAATTGTCCTGTACCATAACACGGATGTGGTTCTGGCCCCGTACGGT
    81 T L T G E I V L Y H N T D V V L A P Y G
   301 GAGTACTGGCGCCAGCTGCGCAAAATTTGTACTCTGGAACTGCTGAGCGTTAAAAAGGTT
   101 E Y W R Q L R K I C T L E L L S V K K V
   361 AAATCCTTCCAGAGCCTGCGTGAAGAGGAATGCTGGAACCTGGTGCAGGAGATTAAAGCG
   121 K S F Q S L R E E E C W N L V Q E I K A
   421 TCTGGCAGCGGTCGTCCAGTTAACCTGTCTGAGAATGTTTTTAAACTGATCGCTACTATC
   141 S G S G R P V N L S E N V F K L I A T I
   481 CTGTCTCGCGCGGCATTCGGTAAAGGTATCAAAGATCAGAAAGAACTGACCGAAATCGTT
   161 L S R A A F G K G I K D Q K E L T E I V
   541 AAGGAAATCCTGCGCCAGACTGGTGGCTTCGACGTTGCGGACATCTTCCCGTCCAAAAAG
   181 K E I L R Q T G G F D V A D I F P S K K
   601 TTCCTGCACCATCTGTCTGGCAAACGCGCTCGTCTGACCTCCCTGCGTAAGAAAATTGAT
   201 F L H H L S G K R A R L T S L R K K I D
   661 AACCTGATTGACAACCTGGTCGCTGAGCACACTGTGAACACCTCTTCTAAAACCAACGAA
   221 N L I D N L V A E H T V N T S S K T N E
   721 ACCCTGCTGGACGTACTGCTGCGCCTGAAGGACTCTGCCGAATTTCCACTGACTAGCGAC
   241 T L L D V L L R L K D S A E F P L T S D
   781 AATATCAAAGCAATCATCCTGGACATGTTCGGCGCCGGTACCGATACGTCCTCTTCCACG
   261 N I K A I I L D M F G A G T D T S S S T
   841 ATTGAGTGGGCTATTTCCGAACTGATCAAATGCCCGAAGGCGATGGAAAAAGTGCAGGCG
   281 I E W A I S E L I K C P K A M E K V Q A
   901 GAACTGCGTAAAGCGCTGAACGGTAAAGAGAAAATTCATGAAGAGGACATCCAGGAACTG
   301 E L R K A L N G K E K I H E E D I Q E L
   961 TCCTACCTGAATATGGTAATCAAAGAAACTCTGCGTCTGCATCCGCCGCTGCCACTGGTT
   321 S Y L N M V I K E T L R L H P P L P L V
  1021 CTGCCGCGTGAATGCCGTCAGCCGGTTAACCTGGCCGGCTACAACATTCCGAACAAAACG
   341 L P R E C R Q P V N L A G Y N I P N K T
  1081 AAGCTGATCGTCAACGTTTTCGCGATCAACCGCGATCCTGAATACTGGAAAGACGCGGAA
   361 K L I V N V F A I N R D P E Y W K D A E
  1141 GCGTTCATTCCGGAACGCTTTGAGAACTCCTCTGCCACCGTTATGGGCGCTGAATACGAG
   381 A F I P E R F E N S S A T V M G A E Y E
  1201 TACCTGCCGTTCGGTGCGGGTCGCCGTATGTGCCCGGGTGCTGCACTGGGCCTGGCGAAC
   401 Y L P F G A G R R M C P G A A L G L A N
  1261 GTTCAACTGCCACTGGCGAACATCCTGTACCACTTCAACTGGAAACTGCCTAACGGCGTA
   421 V Q L P L A N I L Y H F N W K L P N G V
  1321 TCTTATGATCAAATCGACATGACCGAAAGCTCCGGCGCGACCATGCAGCGTAAAACCGAA
   441 S Y D Q I D M T E S S G A T M Q R K T E
  1381 CTGCTGCTGGTTCCGTCCTTT TAA (SEQ ID NO:51)
   461 L L L V P S F (SEQ ID NO:52)
```

FIG. 26

A13 Leader

```
CATATGACCGTACACGACATCATCGCAACGTACTTCACTAAATGGTACGTAATTGTGCCGCTGGCACTGATTGCGTATC
GCGTGCTGGATTATTTCTACGCGACCCGTTCTAAAAGCACTAAGAAATCTCTGCCGGAACCGTGGCGTCTGCCAATCAT
CGGTCACATGCACCACCTGATCGGCACCACCCCGCACCGTGGCGTACGCGACCTGGCGCGTAAGTACGGCTCTCTGATG
CATCTGCAGCTGGGCGAGGTACCTACTATCGTCGTTTCCTCCCCGAAGTGGGCCAAAGAAATCCTGACTACCTATGACA
TCACTTTCGCCAACCGCCCGGAAACGCTGACCGGCGAAATTGTCCTGTACCATAACACGGATGTGGTTCTGGCCCCGTA
CGGTGAGTACTGGCGCCAGCTGCGCAAAATTTGTACTCTGGAACTGCTGAGCGTTAAAAAGGTTAAATCCTTCCAGAGC
CTGCGTGAAGAGGAATGCTGGAACCTGGTGCAGGAGATTAAAGCGTCTGGCAGCGGTCGTCCAGTTAACCTGTCTGAGA
ATGTTTTTAAACTGATCGCTACTATCCTGTCTCGCGCGGCATTCGGTAAAGGTATCAAAGATCAGAAAGAACTGACCGA
AATCGTTAAGGAAATCCTGCGCCAGACTGGTGGCTTCGACGTTGCGGACATCTTCCCGTCCAAAAAGTTCCTGCACCAT
CTGTCTGGCAAACGCGCTCGTCTGACCTCCCTGCGTAAGAAAATTGATAACCTGATTGACAACCTGGTCGCTGAGCACA
CTGTGAACACCTCTTCTAAAACCAACGAAACCCTGCTGGACGTACTGCTGCGCCTGAAGGACTCTGCCGAATTTCCACT
GACTAGCGACAATATCAAAGCAATCATCCTGGACATGTTCGGCGCCGGTACCGATACGTCCTCTTCCACGATTGAGTGG
GCTATTTCCGAACTGATCAAATGCCCGAAGGCGATGGAAAAAGTGCAGGCGGAACTGCGTAAAGCGCTGAACGGTAAAG
AGAAAATTCATGAAGAGGACATCCAGGAACTGTCCTACCTGAATATGGTAATCAAAGAAACTCTGCGTCTGCATCCGCC
GCTGCCACTGGTTCTGCCGCGTGAATGCCGTCAGCCGGTTAACCTGGCCGGCTACAACATTCCGAACAAAACGAAGCTG
ATCGTCAACGTTTTCGCGATCAACCGCGATCCTGAATACTGGAAAGACGCGGAAGCGTTCATTCCGGAACGCTTTGAGA
ACTCCTCTGCCACCGTTATGGGCGCTGAATACGAGTACCTGCCGTTCGGTGCGGGTCGCCGTATGTGCCCGGGTGCTGC
ACTGGGCCTGGCGAACGTTCAACTGCCACTGGCGAACATCCTGTACCACTTCAACTGGAAACTGCCTAACGGCGTATCT
TATGATCAAATCGACATGACCGAAAGCTCCGGCGCGACCATGCAGCGTAAAACCGAACTGCTGCTGGTTCCGTCCTTTT
```

```
        >Nde     <-----------A13N-term-------------------------------------------
AACCTAGGCATATGACCGTACACGACATCATCGCAACGTACTTCACTAAATGGTACGTAATTGTGCCGCTGGCACTGAT
           Start

------------------------------------>          >Amorphadiene Oxidase
TGCGTATCGCGTGCTGGATTATTTCTACGCGACCCGTTCTAAAAGCACTAAGAAATCTCTGCCGGAACCGTGGCGTCTG
CCAATCATCGGTCACATGCACCACCTGATCGGCACCACCCCGCACCGTGGCGTACGCGACCTGGCGCGTAAGTACGGCT
CTCTGATGCATCTGCAGCTGGGCGAGGTACCTACTATCGTCGTTTCCTCCCCGAAGTGGGCCAAAGAAATCCTGACTAC
CTATGACATCACTTTCGCCAACCGCCCGGAAACGCTGACCGGCGAAATTGTCCTGTACCATAACACGGATGTGGTTCTG
GCCCCGTACGGTGAGTACTGGCGCCAGCTGCGCAAAATTTGTACTCTGGAACTGCTGAGCGTTAAAAAGGTTAAATCCT
TCCAGAGCCTGCGTGAAGAGGAATGCTGGAACCTGGTGCAGGAGATTAAAGCGTCTGGCAGCGGTCGTCCAGTTAACCT
GTCTGAGAATGTTTTTAAACTGATCGCTACTATCCTGTCTCGCGCGGCATTCGGTAAAGGTATCAAAGATCAGAAAGAA
CTGACCGAAATCGTTAAGGAAATCCTGCGCCAGACTGGTGGCTTCGACGTTGCGGACATCTTCCCGTCCAAAAAGTTCC
TGCACCATCTGTCTGGCAAACGCGCTCGTCTGACCTCCCTGCGTAAGAAAATTGATAACCTGATTGACAACCTGGTCGC
TGAGCACACTGTGAACACCTCTTCTAAAACCAACGAAACCCTGCTGGACGTACTGCTGCGCCTGAAGGACTCTGCCGAA
TTTCCACTGACTAGCGACAATATCAAAGCAATCATCCTGGACATGTTCGGCGCCGGTACCGATACGTCCTCTTCCACGA
TTGAGTGGGCTATTTCCGAACTGATCAAATGCCCGAAGGCGATGGAAAAAGTGCAGGCGGAACTGCGTAAAGCGCTGAA
CGGTAAAGAGAAAATTCATGAAGAGGACATCCAGGAACTGTCCTACCTGAATATGGTAATCAAAGAAACTCTGCGTCTG
CATCCGCCGCTGCCACTGGTTCTGCCGCGTGAATGCCGTCAGCCGGTTAACCTGGCCGGCTACAACATTCCGAACAAAA
CGAAGCTGATCGTCAACGTTTTCGCGATCAACCGCGATCCTGAATACTGGAAAGACGCGGAAGCGTTCATTCCGGAACG
CTTTGAGAACTCCTCTGCCACCGTTATGGGCGCTGAATACGAGTACCTGCCGTTCGGTGCGGGTCGCCGTATGTGCCCG
GGTGCTGCACTGGGCCTGGCGAACGTTCAACTGCCACTGGCGAACATCCTGTACCACTTCAACTGGAAACTGCCTAACG
GCGTATCTTATGATCAAATCGACATGACCGAAAGCTCCGGCGCGACCATGCAGCGTAAAACCGAACTGCTGCTGGTTCC

       >Stop
GTCCTTTTAA CCTAGG (SEQ ID NO:53)
           >AvrII
```

FIG. 27

```
Translation Map
Start
     1 ATG
     1  M
A13N-term
     1 ACCGTACACGACATCATCGCAACGTACTTCACTAAATGGTACGTAATTGTGCCGCTGGCA
     1  T  V  H  D  I  I  A  T  Y  F  T  K  W  Y  V  I  V  P  L  A
    61 CTGATTGCGTATCGCGTGCTGGATTATTTCTAC
    21  L  I  A  Y  R  V  L  D  Y  F  Y
Amorphadiene Oxidase
     1 GCGACCCGTTCTAAAAGCACTAAGAAATCTCTGCCGGAACCGTGGCGTCTGCCAATCATC
     1  A  T  R  S  K  S  T  K  K  S  L  P  E  P  W  R  L  P  I  I
    61 GGTCACATGCACCACCTGATCGGCACCACCCCGCACCGTGGCGTACGCGACCTGGCGCGT
    21  G  H  M  H  H  L  I  G  T  T  P  H  R  G  V  R  D  L  A  R
   121 AAGTACGGCTCTCTGATGCATCTGCAGCTGGGCGAGGTACCTACTATCGTCGTTTCCTCC
    41  K  Y  G  S  L  M  H  L  Q  L  G  E  V  P  T  I  V  V  S  S
   181 CCGAAGTGGGCCAAAGAAATCCTGACTACCTATGACATCACTTTCGCCAACCGCCCGGAA
    61  P  K  W  A  K  E  I  L  T  T  Y  D  I  T  F  A  N  R  P  E
   241 ACGCTGACCGGCGAAATTGTCCTGTACCATAACACGGATGTGGTTCTGGCCCCGTACGGT
    81  T  L  T  G  E  I  V  L  Y  H  N  T  D  V  V  L  A  P  Y  G
   301 GAGTACTGGCGCCAGCTGCGCAAAATTTGTACTCTGGAACTGCTGAGCGTTAAAAAGGTT
   101  E  Y  W  R  Q  L  R  K  I  C  T  L  E  L  L  S  V  K  K  V
   361 AAATCCTTCCAGAGCCTGCGTGAAGAGGAATGCTGGAACCTGGTGCAGGAGATTAAAGCG
   121  K  S  F  Q  S  L  R  E  E  E  C  W  N  L  V  Q  E  I  K  A
   421 TCTGGCAGCGGTCGTCCAGTTAACCTGTCTGAGAATGTTTTTAAACTGATCGCTACTATC
   141  S  G  S  G  R  P  V  N  L  S  E  N  V  F  K  L  I  A  T  I
   481 CTGTCTCGCGCGGCATTCGGTAAAGGTATCAAAGATCAGAAAGAACTGACCGAAATCGTT
   161  L  S  R  A  A  F  G  K  G  I  K  D  Q  K  E  L  T  E  I  V
   541 AAGGAAATCCTGCGCCAGACTGGTGGCTTCGACGTTGCGGACATCTTCCCGTCCAAAAAG
   181  K  E  I  L  R  Q  T  G  G  F  D  V  A  D  I  F  P  S  K  K
   601 TTCCTGCACCATCTGTCTGGCAAACGCGCTCGTCTGACCTCCCTGCGTAAGAAAATTGAT
   201  F  L  H  H  L  S  G  K  R  A  R  L  T  S  L  R  K  K  I  D
   661 AACCTGATTGACAACCTGGTCGCTGAGCACACTGTGAACACCTCTTCTAAAACCAACGAA
   221  N  L  I  D  N  L  V  A  E  H  T  V  N  T  S  S  K  T  N  E
   721 ACCCTGCTGGACGTACTGCTGCGCCTGAAGGACTCTGCCGAATTTCCACTGACTAGCGAC
   241  T  L  L  D  V  L  L  R  L  K  D  S  A  E  F  P  L  T  S  D
   781 AATATCAAAGCAATCATCCTGGACATGTTCGGCGCCGGTACCGATACGTCCTCTTCCACG
   261  N  I  K  A  I  I  L  D  M  F  G  A  G  T  D  T  S  S  S  T
   841 ATTGAGTGGGCTATTTCCGAACTGATCAAATGCCCGAAGGCGATGGAAAAAGTGCAGGCG
   281  I  E  W  A  I  S  E  L  I  K  C  P  K  A  M  E  K  V  Q  A
   901 GAACTGCGTAAAGCGCTGAACGGTAAAGAGAAAATTCATGAAGAGGACATCCAGGAACTG
   301  E  L  R  K  A  L  N  G  K  E  K  I  H  E  E  D  I  Q  E  L
   961 TCCTACCTGAATATGGTAATCAAAGAAACTCTGCGTCTGCATCCGCCGCTGCCACTGGTT
   321  S  Y  L  N  M  V  I  K  E  T  L  R  L  H  P  P  L  P  L  V
  1021 CTGCCGCGTGAATGCCGTCAGCCGGTTAACCTGGCCGGCTACAACATTCCGAACAAAACG
   341  L  P  R  E  C  R  Q  P  V  N  L  A  G  Y  N  I  P  N  K  T
  1081 AAGCTGATCGTCAACGTTTTCGCGATCAACCGCGATCCTGAATACTGGAAAGACGCGGAA
   361  K  L  I  V  N  V  F  A  I  N  R  D  P  E  Y  W  K  D  A  E
  1141 GCGTTCATTCCGGAACGCTTTGAGAACTCCTCTGCCACCGTTATGGGCGCTGAATACGAG
   381  A  F  I  P  E  R  F  E  N  S  S  A  T  V  M  G  A  E  Y  E
  1201 TACCTGCCGTTCGGTGCGGGTCGCCGTATGTGCCCGGGTGCTGCACTGGGCCTGGCGAAC
   401  Y  L  P  F  G  A  G  R  R  M  C  P  G  A  A  L  G  L  A  N
  1261 GTTCAACTGCCACTGGCGAACATCCTGTACCACTTCAACTGGAAACTGCCTAACGGCGTA
   421  V  Q  L  P  L  A  N  I  L  Y  H  F  N  W  K  L  P  N  G  V
  1321 TCTTATGATCAAATCGACATGACCGAAAGCTCCGGCGCGACCATGCAGCGTAAAACCGAA
   441  S  Y  D  Q  I  D  M  T  E  S  S  G  A  T  M  Q  R  K  T  E
  1381 CTGCTGCTGGTTCCGTCCTTTTAA (SEQ ID NO:54)
   461  L  L  L  V  P  S  F   (SEQ ID NO:55)
```

FIG. 28

A17 Leader

CATATGATCGAACAACTGCTGGAATACTGGTACGTGGTTGTGCCTGTTCTGTATATTATCAAACAGCTGCTGGCGTACA
CTAAAGCGACCCGTTCTAAAAGCACTAAGAAATCTCTGCCGGAACCGTGGCGTCTGCCAATCATCGGTCACATGCACCA
CCTGATCGGCACCACCCCGCACCGTGGCGTACGCGACCTGGCGCGTAAGTACGGCTCTCTGATGCATCTGCAGCTGGGC
GAGGTACCTACTATCGTCGTTTCCTCCCCGAAGTGGGCCAAAGAAATCCTGACTACCTATGACATCACTTTCGCCAACC
GCCCGGAAACGCTGACCGGCGAAATTGTCCTGTACCATAACACGGATGTGGTTCTGGCCCCGTACGGTGAGTACTGGCG
CCAGCTGCGCAAAATTTGTACTCTGGAACTGCTGAGCGTTAAAAAGGTTAAATCCTTCCAGAGCCTGCGTGAAGAGGAA
TGCTGGAACCTGGTGCAGGAGATTAAAGCGTCTGGCAGCGGTCGTCCAGTTAACCTGTCTGAGAATGTTTTTAAACTGA
TCGCTACTATCCTGTCTCGCGCGGCATTCGGTAAAGGTATCAAAGATCAGAAAGAACTGACCGAAATCGTTAAGGAAAT
CCTGCGCCAGACTGGTGGCTTCGACGTTGCGGACATCTTCCCGTCCAAAAAGTTCCTGCACCATCTGTCTGGCAAACGC
GCTCGTCTGACCTCCCTGCGTAAGAAAATTGATAACCTGATTGACAACCTGGTCGCTGAGCACACTGTGAACACCTCTT
CTAAAACCAACGAAACCCTGCTGGACGTACTGCTGCGCCTGAAGGACTCTGCCGAATTTCCACTGACTAGCGACAATAT
CAAAGCAATCATCCTGGACATGTTCGGCGCCGGTACCGATACGTCCTCTTCCACGATTGAGTGGGCTATTTCCGAACTG
ATCAAATGCCCGAAGGCGATGGAAAAAGTGCAGGCGGAACTGCGTAAAGCGCTGAACGGTAAAGAGAAAATTCATGAAG
AGGACATCCAGGAACTGTCCTACCTGAATATGGTAATCAAAGAAACTCTGCGTCTGCATCCGCCGCTGCCACTGGTTCT
GCCGCGTGAATGCCGTCAGCCGGTTAACCTGGCCGGCTACAACATTCCGAACAAAACGAAGCTGATCGTCAACGTTTTC
GCGATCAACCGCGATCCTGAATACTGGAAAGACGCGGAAGCGTTCATTCCGGAACGCTTTGAGAACTCCTCTGCCACCG
TTATGGGCGCTGAATACGAGTACCTGCCGTTCGGTGCGGGTCGCCGTATGTGCCCGGGTGCTGCACTGGGCCTGGCGAA
CGTTCAACTGCCACTGGCGAACATCCTGTACCACTTCAACTGGAAACTGCCTAACGGCGTATCTTATGATCAAATCGAC

>Nde

ATGACCGAAAGCTCCGGCGCGACCATGCAGCGTAAAACCGAACTGCTGCTGGTTCCGTCCTTTTAACCTAGGCATATG

>Start

A17

ATCGAACAACTGCTGGAATACTGGTACGTGGTTGTGCCTGTTCTGTATATTATCAAACAGCTGCTGGCGTACACTAAA

>Amorphadiene Oxidase

GCGACCCGTTCTAAAAGCACTAAGAAATCTCTGCCGGAACCGTGGCGTCTGCCAATCATCGGTCACATGCACCACCTGA
TCGGCACCACCCCGCACCGTGGCGTACGCGACCTGGCGCGTAAGTACGGCTCTCTGATGCATCTGCAGCTGGGCGAGGT
ACCTACTATCGTCGTTTCCTCCCCGAAGTGGGCCAAAGAAATCCTGACTACCTATGACATCACTTTCGCCAACCGCCCG
GAAACGCTGACCGGCGAAATTGTCCTGTACCATAACACGGATGTGGTTCTGGCCCCGTACGGTGAGTACTGGCGCCAGC
TGCGCAAAATTTGTACTCTGGAACTGCTGAGCGTTAAAAAGGTTAAATCCTTCCAGAGCCTGCGTGAAGAGGAATGCTG
GAACCTGGTGCAGGAGATTAAAGCGTCTGGCAGCGGTCGTCCAGTTAACCTGTCTGAGAATGTTTTTAAACTGATCGCT
ACTATCCTGTCTCGCGCGGCATTCGGTAAAGGTATCAAAGATCAGAAAGAACTGACCGAAATCGTTAAGGAAATCCTGC
GCCAGACTGGTGGCTTCGACGTTGCGGACATCTTCCCGTCCAAAAAGTTCCTGCACCATCTGTCTGGCAAACGCGCTCG
TCTGACCTCCCTGCGTAAGAAAATTGATAACCTGATTGACAACCTGGTCGCTGAGCACACTGTGAACACCTCTTCTAAA
ACCAACGAAACCCTGCTGGACGTACTGCTGCGCCTGAAGGACTCTGCCGAATTTCCACTGACTAGCGACAATATCAAAG
CAATCATCCTGGACATGTTCGGCGCCGGTACCGATACGTCCTCTTCCACGATTGAGTGGGCTATTTCCGAACTGATCAA
ATGCCCGAAGGCGATGGAAAAAGTGCAGGCGGAACTGCGTAAAGCGCTGAACGGTAAAGAGAAAATTCATGAAGAGGAC
ATCCAGGAACTGTCCTACCTGAATATGGTAATCAAAGAAACTCTGCGTCTGCATCCGCCGCTGCCACTGGTTCTGCCGC
GTGAATGCCGTCAGCCGGTTAACCTGGCCGGCTACAACATTCCGAACAAAACGAAGCTGATCGTCAACGTTTTCGCGAT
CAACCGCGATCCTGAATACTGGAAAGACGCGGAAGCGTTCATTCCGGAACGCTTTGAGAACTCCTCTGCCACCGTTATG
GGCGCTGAATACGAGTACCTGCCGTTCGGTGCGGGTCGCCGTATGTGCCCGGGTGCTGCACTGGGCCTGGCGAACGTTC
AACTGCCACTGGCGAACATCCTGTACCACTTCAACTGGAAACTGCCTAACGGCGTATCTTATGATCAAATCGACATGAC

Stop

CGAAAGCTCCGGCGCGACCATGCAGCGTAAAACCGAACTGCTGCTGGTTCCGTCCTTTTAACCTAGG

>AvrII (SEQ ID NO:56)

FIG. 29

```
Translation Map
Start
     1 ATG
     1  M
A17
     1 ATCGAACAACTGCTGGAATACTGGTACGTGGTTGTGCCTGTTCTGTATATTATCAAACAG
     1  I  E  Q  L  L  E  Y  W  Y  V  V  V  P  V  L  Y  I  I  K  Q
    61 CTGCTGGCGTACACTAAA
    21  L  L  A  Y  T  K
Amorphadiene Oxidase
     1 GCGACCCGTTCTAAAAGCACTAAGAAATCTCTGCCGGAACCGTGGCGTCTGCCAATCATC
     1  A  T  R  S  K  S  T  K  K  S  L  P  E  P  W  R  L  P  I  I
    61 GGTCACATGCACCACCTGATCGGCACCACCCCGCACCGTGGCGTACGCGACCTGGCGCGT
    21  G  H  M  H  H  L  I  G  T  T  P  H  R  G  V  R  D  L  A  R
   121 AAGTACGGCTCTCTGATGCATCTGCAGCTGGGCGAGGTACCTACTATCGTCGTTTCCTCC
    41  K  Y  G  S  L  M  H  L  Q  L  G  E  V  P  T  I  V  V  S  S
   181 CCGAAGTGGGCCAAAGAAATCCTGACTACCTATGACATCACTTTCGCCAACCGCCCGGAA
    61  P  K  W  A  K  E  I  L  T  T  Y  D  I  T  F  A  N  R  P  E
   241 ACGCTGACCGGCGAAATTGTCCTGTACCATAACACGGATGTGGTTCTGGCCCCGTACGGT
    81  T  L  T  G  E  I  V  L  Y  H  N  T  D  V  V  L  A  P  Y  G
   301 GAGTACTGGCGCCAGCTGCGCAAAATTTGTACTCTGGAACTGCTGAGCGTTAAAAAGGTT
   101  E  Y  W  R  Q  L  R  K  I  C  T  L  E  L  L  S  V  K  K  V
   361 AAATCCTTCCAGAGCCTGCGTGAAGAGGAATGCTGGAACCTGGTGCAGGAGATTAAAGCG
   121  K  S  F  Q  S  L  R  E  E  E  C  W  N  L  V  Q  E  I  K  A
   421 TCTGGCAGCGGTCGTCCAGTTAACCTGTCTGAGAATGTTTTTAAACTGATCGCTACTATC
   141  S  G  S  G  R  P  V  N  L  S  E  N  V  F  K  L  I  A  T  I
   481 CTGTCTCGCGCGGCATTCGGTAAAGGTATCAAAGATCAGAAAGAACTGACCGAAATCGTT
   161  L  S  R  A  A  F  G  K  G  I  K  D  Q  K  E  L  T  E  I  V
   541 AAGGAAATCCTGCGCCAGACTGGTGGCTTCGACGTTGCGGACATCTTCCCGTCCAAAAAG
   181  K  E  I  L  R  Q  T  G  G  F  D  V  A  D  I  F  P  S  K  K
   601 TTCCTGCACCATCTGTCTGGCAAACGCGCTCGTCTGACCTCCCTGCGTAAGAAAATTGAT
   201  F  L  H  H  L  S  G  K  R  A  R  L  T  S  L  R  K  K  I  D
   661 AACCTGATTGACAACCTGGTCGCTGAGCACACTGTGAACACCTCTTCTAAAACCAACGAA
   221  N  L  I  D  N  L  V  A  E  H  T  V  N  T  S  S  K  T  N  E
   721 ACCCTGCTGGACGTACTGCTGCGCCTGAAGGACTCTGCCGAATTTCCACTGACTAGCGAC
   241  T  L  L  D  V  L  L  R  L  K  D  S  A  E  F  P  L  T  S  D
   781 AATATCAAAGCAATCATCCTGGACATGTTCGGCGCCGGTACCGATACGTCCTCTTCCACG
   261  N  I  K  A  I  I  L  D  M  F  G  A  G  T  D  T  S  S  S  T
   841 ATTGAGTGGGCTATTTCCGAACTGATCAAATGCCCGAAGGCGATGGAAAAAGTGCAGGCG
   281  I  E  W  A  I  S  E  L  I  K  C  P  K  A  M  E  K  V  Q  A
   901 GAACTGCGTAAAGCGCTGAACGGTAAAGAGAAAATTCATGAAGAGGACATCCAGGAACTG
   301  E  L  R  K  A  L  N  G  K  E  K  I  H  E  E  D  I  Q  E  L
   961 TCCTACCTGAATATGGTAATCAAAGAAACTCTGCGTCTGCATCCGCCGCTGCCACTGGTT
   321  S  Y  L  N  M  V  I  K  E  T  L  R  L  H  P  P  L  P  L  V
  1021 CTGCCGCGTGAATGCCGTCAGCCGGTTAACCTGGCCGGCTACAACATTCCGAACAAAACG
   341  L  P  R  E  C  R  Q  P  V  N  L  A  G  Y  N  I  P  N  K  T
  1081 AAGCTGATCGTCAACGTTTTCGCGATCAACCGCGATCCTGAATACTGGAAAGACGCGGAA
   361  K  L  I  V  N  V  F  A  I  N  R  D  P  E  Y  W  K  D  A  E
  1141 GCGTTCATTCCGGAACGCTTTGAGAACTCCTCTGCCACCGTTATGGGCGCTGAATACGAG
   381  A  F  I  P  E  R  F  E  N  S  S  A  T  V  M  G  A  E  Y  E
  1201 TACCTGCCGTTCGGTGCGGGTCGCCGTATGTGCCCGGGTGCTGCACTGGGCCTGGCGAAC
   401  Y  L  P  F  G  A  G  R  R  M  C  P  G  A  A  L  G  L  A  N
  1261 GTTCAACTGCCACTGGCGAACATCCTGTACCACTTCAACTGGAAACTGCCTAACGGCGTA
   421  V  Q  L  P  L  A  N  I  L  Y  H  F  N  W  K  L  P  N  G  V
  1321 TCTTATGATCAAATCGACATGACCGAAAGCTCCGGCGCGACCATGCAGCGTAAAACCGAA
   441  S  Y  D  Q  I  D  M  T  E  S  S  G  A  T  M  Q  R  K  T  E
  1381 CTGCTGCTGGTTCCGTCCTTTTAA (SEQ ID NO:57)
   461  L  L  L  V  P  S  F   (SEQ ID NO:58)
```

FIG. 30

Bovine Leader

```
CATATGGCTCTGCTGCTGGCTGTCTTCCTGGGTCTGTCCTGCCTGCTGCTGCTGTCCCTGTGGGCGACCCGTTCTAAAA
GCACTAAGAAATCTCTGCCGGAACCGTGGCGTCTGCCAATCATCGGTCACATGCACCACCTGATCGGCACCACCCCGCA
CCGTGGCGTACGCGACCTGGCGCGTAAGTACGGCTCTCTGATGCATCTGCAGCTGGGCGAGGTACCTACTATCGTCGTT
TCCTCCCCGAAGTGGGCCAAAGAAATCCTGACTACCTATGACATCACTTTCGCCAACCGCCCGGAAACGCTGACCGGCG
AAATTGTCCTGTACCATAACACGGATGTGGTTCTGGCCCCGTACGGTGAGTACTGGCGCCAGCTGCGCAAAATTTGTAC
TCTGGAACTGCTGAGCGTTAAAAAGGTTAAATCCTTCCAGAGCCTGCGTGAAGAGGAATGCTGGAACCTGGTGCAGGAG
ATTAAAGCGTCTGGCAGCGGTCGTCCAGTTAACCTGTCTGAGAATGTTTTTAAACTGATCGCTACTATCCTGTCTCGCG
CGGCATTCGGTAAAGGTATCAAAGATCAGAAAGAACTGACCGAAATCGTTAAGGAAATCCTGCGCCAGACTGGTGGCTT
CGACGTTGCGGACATCTTCCCGTCCAAAAAGTTCCTGCACCATCTGTCTGGCAAACGCGCTCGTCTGACCTCCCTGCGT
AAGAAAATTGATAACCTGATTGACAACCTGGTCGCTGAGCACACTGTGAACACCTCTTCTAAAACCAACGAAACCCTGC
TGGACGTACTGCTGCGCCTGAAGGACTCTGCCGAATTTCCACTGACTAGCGACAATATCAAAGCAATCATCCTGGACAT
GTTCGGCGCCGGTACCGATACGTCCTCTTCCACGATTGAGTGGGCTATTTCCGAACTGATCAAATGCCCGAAGGCGATG
GAAAAAGTGCAGGCGGAACTGCGTAAAGCGCTGAACGGTAAAGAGAAAATTCATGAAGAGGACATCCAGGAACTGTCCT
ACCTGAATATGGTAATCAAAGAAACTCTGCGTCTGCATCCGCCGCTGCCACTGGTTCTGCCGCGTGAATGCCGTCAGCC
GGTTAACCTGGCCGGCTACAACATTCCGAACAAAACGAAGCTGATCGTCAACGTTTTCGCGATCAACCGCGATCCTGAA
TACTGGAAAGACGCGGAAGCGTTCATTCCGGAACGCTTTGAGAACTCCTCTGCCACCGTTATGGGCGCTGAATACGAGT
ACCTGCCGTTCGGTGCGGGTCGCCGTATGTGCCCGGGTGCTGCACTGGGCCTGGCGAACGTTCAACTGCCACTGGCGAA
CATCCTGTACCACTTCAACTGGAAACTGCCTAACGGCGTATCTTATGATCAAATCGACATGACCGAAAGCTCCGGCGCG

                                                             Nde  <-----------------
ACCATGCAGCGTAAAACCGAACTGCTGCTGGTTCCGTCCTTTTGACCTAGGCATATGGCTCTGCTGCTGGCTGTCTTCC
                                                               >Start

>Bovine ------------------------->        >Amorphadiene Oxidase
TGGGTCTGTCCTGCCTGCTGCTGCTGTCCCTGTGGGCGACCCGTTCTAAAAGCACTAAGAAATCTCTGCCGGAACCGTG
GCGTCTGCCAATCATCGGTCACATGCACCACCTGATCGGCACCACCCCGCACCGTGGCGTACGCGACCTGGCGCGTAAG
TACGGCTCTCTGATGCATCTGCAGCTGGGCGAGGTACCTACTATCGTCGTTTCCTCCCCGAAGTGGGCCAAAGAAATCC
TGACTACCTATGACATCACTTTCGCCAACCGCCCGGAAACGCTGACCGGCGAAATTGTCCTGTACCATAACACGGATGT
GGTTCTGGCCCCGTACGGTGAGTACTGGCGCCAGCTGCGCAAAATTTGTACTCTGGAACTGCTGAGCGTTAAAAAGGTT
AAATCCTTCCAGAGCCTGCGTGAAGAGGAATGCTGGAACCTGGTGCAGGAGATTAAAGCGTCTGGCAGCGGTCGTCCAG
TTAACCTGTCTGAGAATGTTTTTAAACTGATCGCTACTATCCTGTCTCGCGCGGCATTCGGTAAAGGTATCAAAGATCA
GAAAGAACTGACCGAAATCGTTAAGGAAATCCTGCGCCAGACTGGTGGCTTCGACGTTGCGGACATCTTCCCGTCCAAA
AAGTTCCTGCACCATCTGTCTGGCAAACGCGCTCGTCTGACCTCCCTGCGTAAGAAAATTGATAACCTGATTGACAACC
TGGTCGCTGAGCACACTGTGAACACCTCTTCTAAAACCAACGAAACCCTGCTGGACGTACTGCTGCGCCTGAAGGACTC
TGCCGAATTTCCACTGACTAGCGACAATATCAAAGCAATCATCCTGGACATGTTCGGCGCCGGTACCGATACGTCCTCT
TCCACGATTGAGTGGGCTATTTCCGAACTGATCAAATGCCCGAAGGCGATGGAAAAAGTGCAGGCGGAACTGCGTAAAG
CGCTGAACGGTAAAGAGAAAATTCATGAAGAGGACATCCAGGAACTGTCCTACCTGAATATGGTAATCAAAGAAACTCT
GCGTCTGCATCCGCCGCTGCCACTGGTTCTGCCGCGTGAATGCCGTCAGCCGGTTAACCTGGCCGGCTACAACATTCCG
AACAAAACGAAGCTGATCGTCAACGTTTTCGCGATCAACCGCGATCCTGAATACTGGAAAGACGCGGAAGCGTTCATTC
CGGAACGCTTTGAGAACTCCTCTGCCACCGTTATGGGCGCTGAATACGAGTACCTGCCGTTCGGTGCGGGTCGCCGTAT
GTGCCCGGGTGCTGCACTGGGCCTGGCGAACGTTCAACTGCCACTGGCGAACATCCTGTACCACTTCAACTGGAAACTG
CCTAACGGCGTATCTTATGATCAAATCGACATGACCGAAAGCTCCGGCGCGACCATGCAGCGTAAAACCGAACTGCTGC

                >Stop
TGGTTCCGTCCTTTTAACCTAGG  (SEQ ID NO:59)
                  >AvrII
```

FIG. 31

```
Translation Map
Start
     1 ATG
     1  M
Bovine
     1 GCTCTGCTGCTGGCTGTCTTCCTGGGTCTGTCCTGCCTGCTGCTGCTGTCCCTGTGG
     1  A  L  L  L  A  V  F  L  G  L  S  C  L  L  L  L  S  L  W
Amorphadiene Oxidase
     1 GCGACCCGTTCTAAAAGCACTAAGAAATCTCTGCCGGAACCGTGGCGTCTGCCAATCATC
     1  A  T  R  S  K  S  T  K  K  S  L  P  E  P  W  R  L  P  I  I
    61 GGTCACATGCACCACCTGATCGGCACCACCCCGCACCGTGGCGTACGCGACCTGGCGCGT
    21  G  H  M  H  H  L  I  G  T  T  P  H  R  G  V  R  D  L  A  R
   121 AAGTACGGCTCTCTGATGCATCTGCAGCTGGGCGAGGTACCTACTATCGTCGTTTCCTCC
    41  K  Y  G  S  L  M  H  L  Q  L  G  E  V  P  T  I  V  V  S  S
   181 CCGAAGTGGGCCAAAGAAATCCTGACTACCTATGACATCACTTTCGCCAACCGCCCGGAA
    61  P  K  W  A  K  E  I  L  T  T  Y  D  I  T  F  A  N  R  P  E
   241 ACGCTGACCGGCGAAATTGTCCTGTACCATAACACGGATGTGGTTCTGGCCCCGTACGGT
    81  T  L  T  G  E  I  V  L  Y  H  N  T  D  V  V  L  A  P  Y  G
   301 GAGTACTGGCGCCAGCTGCGCAAAATTTGTACTCTGGAACTGCTGAGCGTTAAAAAGGTT
   101  E  Y  W  R  Q  L  R  K  I  C  T  L  E  L  L  S  V  K  K  V
   361 AAATCCTTCCAGAGCCTGCGTGAAGAGGAATGCTGGAACCTGGTGCAGGAGATTAAAGCG
   121  K  S  F  Q  S  L  R  E  E  E  C  W  N  L  V  Q  E  I  K  A
   421 TCTGGCAGCGGTCGTCCAGTTAACCTGTCTGAGAATGTTTTTAAACTGATCGCTACTATC
   141  S  G  S  G  R  P  V  N  L  S  E  N  V  F  K  L  I  A  T  I
   481 CTGTCTCGCGCGGCATTCGGTAAAGGTATCAAAGATCAGAAAGAACTGACCGAAATCGTT
   161  L  S  R  A  A  F  G  K  G  I  K  D  Q  K  E  L  T  E  I  V
   541 AAGGAAATCCTGCGCCAGACTGGTGGCTTCGACGTTGCGGACATCTTCCCGTCCAAAAAG
   181  K  E  I  L  R  Q  T  G  G  F  D  V  A  D  I  F  P  S  K  K
   601 TTCCTGCACCATCTGTCTGGCAAACGCGCTCGTCTGACCTCCCTGCGTAAGAAAATTGAT
   201  F  L  H  H  L  S  G  K  R  A  R  L  T  S  L  R  K  K  I  D
   661 AACCTGATTGACAACCTGGTCGCTGAGCACACTGTGAACACCTCTTCTAAAACCAACGAA
   221  N  L  I  D  N  L  V  A  E  H  T  V  N  T  S  S  K  T  N  E
   721 ACCCTGCTGGACGTACTGCTGCGCCTGAAGGACTCTGCCGAATTTCCACTGACTAGCGAC
   241  T  L  L  D  V  L  L  R  L  K  D  S  A  E  F  P  L  T  S  D
   781 AATATCAAAGCAATCATCCTGGACATGTTCGGCGCCGGTACCGATACGTCCTCTTCCACG
   261  N  I  K  A  I  I  L  D  M  F  G  A  G  T  D  T  S  S  S  T
   841 ATTGAGTGGGCTATTTCCGAACTGATCAAATGCCCGAAGGCGATGGAAAAAGTGCAGGCG
   281  I  E  W  A  I  S  E  L  I  K  C  P  K  A  M  E  K  V  Q  A
   901 GAACTGCGTAAAGCGCTGAACGGTAAAGAGAAAATTCATGAAGAGGACATCCAGGAACTG
   301  E  L  R  K  A  L  N  G  K  E  K  I  H  E  E  D  I  Q  E  L
   961 TCCTACCTGAATATGGTAATCAAAGAAACTCTGCGTCTGCATCCGCCGCTGCCACTGGTT
   321  S  Y  L  N  M  V  I  K  E  T  L  R  L  H  P  P  L  P  L  V
  1021 CTGCCGCGTGAATGCCGTCAGCCGGTTAACCTGGCCGGCTACAACATTCCGAACAAAACG
   341  L  P  R  E  C  R  Q  P  V  N  L  A  G  Y  N  I  P  N  K  T
  1081 AAGCTGATCGTCAACGTTTTCGCGATCAACCGCGATCCTGAATACTGGAAAGACGCGGAA
   361  K  L  I  V  N  V  F  A  I  N  R  D  P  E  Y  W  K  D  A  E
  1141 GCGTTCATTCCGGAACGCTTTGAGAACTCCTCTGCCACCGTTATGGGCGCTGAATACGAG
   381  A  F  I  P  E  R  F  E  N  S  S  A  T  V  M  G  A  E  Y  E
  1201 TACCTGCCGTTCGGTGCGGGTCGCCGTATGTGCCCGGGTGCTGCACTGGGCCTGGCGAAC
   401  Y  L  P  F  G  A  G  R  R  M  C  P  G  A  A  L  G  L  A  N
  1261 GTTCAACTGCCACTGGCGAACATCCTGTACCACTTCAACTGGAAACTGCCTAACGGCGTA
   421  V  Q  L  P  L  A  N  I  L  Y  H  F  N  W  K  L  P  N  G  V
  1321 TCTTATGATCAAATCGACATGACCGAAAGCTCCGGCGCGACCATGCAGCGTAAAACCGAA
   441  S  Y  D  Q  I  D  M  T  E  S  S  G  A  T  M  Q  R  K  T  E
  1381 CTGCTGCTGGTTCCGTCCTTTTAA (SEQ ID NO:60)
   461  L  L  L  V  P  S  F   (SEQ ID NO:61)
```

FIG. 35A

MevT atoB

CTTGATATCGAATTCCTGCAGCCCGGGGATCCTCTAGAGTCGACTAGGAGGAATATAAAATGAAAAATTGTGTCA
TCGTCAGTGCGGTACGTACTGCTATCGGTAGTTTTAACGGTTCACTCGCTTCCACCAGCGCCATCGACCTGGGGG
CGACAGTAATTAAAGCCGCCATTGAACGTGCAAAAATCGATTCACAACACGTTGATGAAGTGATTATGGGTAACG
TGTTACAAGCCGGGCTGGGGCAAAATCCGGCGCGTCAGGCACTGTTAAAAAGCGGGCTGGCAGAAACGGTGTGCG
GATTCACGGTCAATAAAGTATGTGGTTCGGGTCTTAAAAGTGTGGCGCTTGCCGCCCAGGCCATTCAGGCAGGTC
AGGCGCAGAGCATTGTGGCGGGGGGTATGGAAAATATGAGTTTAGCCCCCTACTTACTCGATGCAAAAGCACGCT
CTGGTTATCGTCTTGGAGACGGACAGGTTTATGACGTAATCCTGCGCGATGGCCTGATGTGCGCCACCCATGGTT
ATCATATGGGGATTACCGCCGAAAACGTGGCTAAAGAGTACGGAATTACCCGTGAAATGCAGGATGAACTGGCGC
TACATTCACAGCGTAAAGCGGCAGCCGCAATTGAGTCCGGTGCTTTTACAGCCGAAATCGTCCCGGTAAATGTTG
TCACTCGAAAGAAAACCTTCGTCTTCAGTCAAGACGAATTCCCGAAAGCGAATTCAACGGCTGAAGCGTTAGGTG
CATTGCGCCCGGCCTTCGATAAAGCAGGAACAGTCACCGCTGGGAACGCGTCTGGTATTAACGACGGTGCTGCCG
CTCTGGTGATTATGGAAGAATCTGCGGCGCTGGCAGCAGGCCTTACCCCCCTGGCTCGCATTAAAAGTTATGCCA
GCGGTGGCGTGCCCCCCGCATTGATGGGTATGGGGCCAGTACCTGCCACGCAAAAAGCGTTACAACTGGCGGGGC
TGCAACTGGCGGATATTGATCTCATTGAGGCTAATGAAGCATTTGCTGCACAGTTCCTTGCCGTTGGGAAAAACC
TGGGCTTTGATTCTGAGAAAGTGAATGTCAACGGCGGGGCCATCGCGCTCGGGCATCCTATCGGTGCCAGTGGTG
CTCGTATTCTGGTCACACTATTACATGCCATGCAGGCACGCGATAAAACGCTGGGGCTGGCAACACTGTGCATTG atoB HMGS GCGGCGGTCAGGGAATTGCGATGGTGATTGAACGGTTGAATTAAGGAGGACAGCTAAATGAAACTCTCAACTAAA
CTTTGTTGGTGTGGTATTAAAGGAAGACTTAGGCCGCAAAAGCAACAACAATTACACAATACAAACTTGCAAATG
ACTGAACTAAAAAAACAAAAGACCGCTGAACAAAAAACCAGACCTCAAAATGTCGGTATTAAAGGTATCCAAATT
TACATCCCAACTCAATGTGTCAACCAATCTGAGCTAGAGAAATTTGATGGCGTTTCTCAAGGTAAATACACAATT
GGTCTGGGCCAAACCAACATGTCTTTTGTCAATGACAGAGAAGATATCTACTCGATGTCCCTAACTGTTTTGTCT
AAGTTGATCAAGAGTTACAACATCGACACCAACAAAATTGGTAGATTAGAAGTCGGTACTGAAACTCTGATTGAC
AAGTCCAAGTCTGTCAAGTCTGTCTTGATGCAATTGTTTGGTGAAAACACTGACGTCGAAGGTATTGACACGCTT
AATGCCTGTTACGGTGGTACCAACGCGTTGTTCAACTCTTTGAACTGGATTGAATCTAACGCATGGGATGGTAGA
GACGCCATTGTAGTTTGCGGTGATATTGCCATCTACGATAAGGGTGCCGCAAGACCAACCGGTGGTGCCGGTACT
GTTGCTATGTGGATCGGTCCTGATGCTCCAATTGTATTTGACTCTGTAAGAGCTTCTTACATGGAACACGCCTAC
GATTTTTACAAGCCAGATTTCACCAGCGAATATCCTTACGTCGATGGTCATTTTTCATTAACTTGTTACGTCAAG
GCTCTTGATCAAGTTTACAAGAGTTATTCCAAGAAGGCTATTTCTAAAGGGTTGGTTAGCGATCCCGCTGGTTCG
GATGCTTTGAACGTTTTGAAATATTTCGACTACAACGTTTTCCATGTTCCAACCTGTAAATTGGTCACAAAATCA
TACGGTAGATTACTATATAACGATTTCAGAGCCAATCCTCAATTGTTCCCAGAAGTTGACGCCGAATTAGCTACT
CGCGATTATGACGAATCTTTAACCGATAAGAACATTGAAAAAACTTTTGTTAATGTTGCTAAGCCATTCCACAAA
GAGAGAGTTGCCCAATCTTTGATTGTTCCAACAAACACAGGTAACATGTACACCGCATCTGTTTATGCCGCCTTT
GCATCTCTATTAAACTATGTTGGATCTGACGACTTACAAGGCAAGCGTGTTGGTTTATTTTCTTACGGTTCCGGT
TTAGCTGCATCTCTATATTCTTGCAAAATTGTTGGTGACGTCCAACATATTATCAAGGAATTAGATATTACTAAC
AAATTAGCCAAGAGAATCACCGAAACTCCAAAGGATTACGAAGCTGCCATCGAATTGAGAGAAAATGCCCATTTG
AAGAAGAACTTCAAACCTCAAGGTTCCATTGAGCATTTGCAAAGTGGTGTTTACTACTTGACCAACATCGATGAC
AAATTTAGAAGATCTTACGA HMGS truncated HMGR TGTTAAAAAATAAGGAGGATTACACTATGGTTTTAACCAATAAAACAGTCATTTCTGGATCGAAAGTCAAAAGTT
TATCATCTGCGCAATCGAGCTCATCAGGACCTTCATCATCTAGTGAGGAAGATGATTCCCGCGATATTGAAAGCT
TGGATAAGAAAATACGTCCTTTAGAAGAATTAGAAGCATTATTAAGTAGTGGAAATACAAAACAATTGAAGAACA
AAGAGGTCGCTGCCT

FIG. 35B

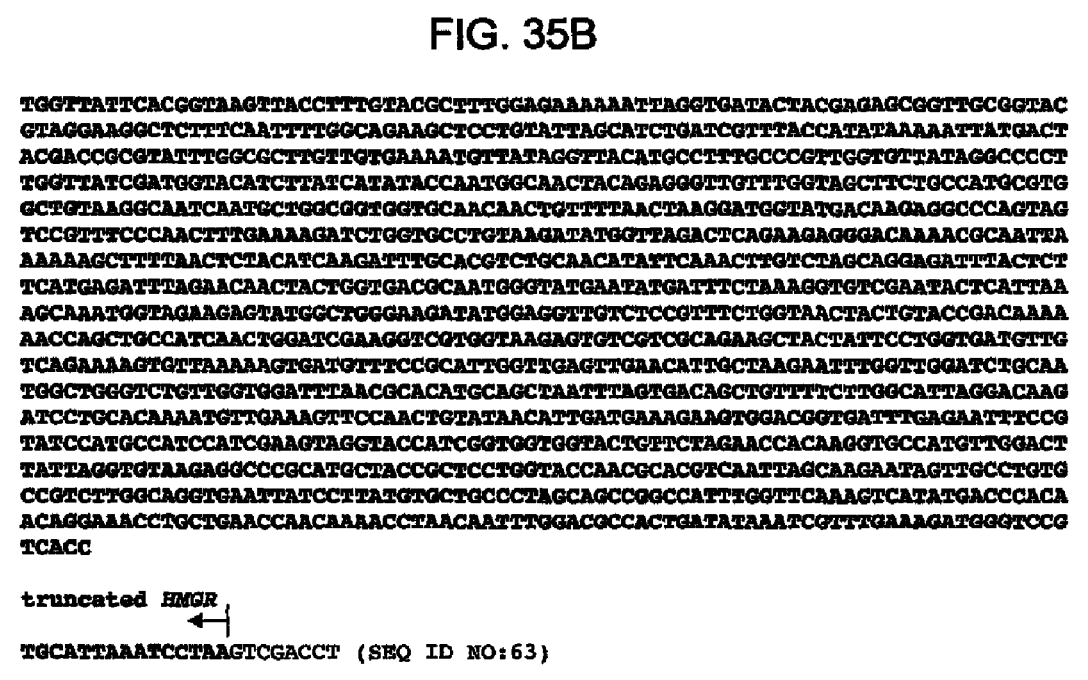

**TGGTTATTCACGGTAAGTTACCTTTGTACGCTTTGGAGAAAAAATTAGGTGATACTACGAGAGCGGTTGCGGTAC
GTAGGAAGGCTCTTTCAATTTTGGCAGAAGCTCCTGTATTAGCATCTGATCGTTTACCATATAAAAATTATGACT
ACGACCGCGTATTTGGCGCTTGTTGTGAAAATGTTATAGGTTACATGCCTTTGCCCGTTGGTGTTATAGGCCCCT
TGGTTATCGATGGTACATCTTATCATATACCAATGGCAACTACAGAGGGTTGTTTGGTAGCTTCTGCCATGCGTG
GCTGTAAGGCAATCAATGCTGGCGGTGGTGCAACAACTGTTTTAACTAAGGATGGTATGACAAGAGGCCCAGTAG
TCCGTTTCCCAACTTTGAAAAGATCTGGTGCCTGTAAGATATGGTTAGACTCAGAAGAGGGACAAAACGCAATTA
AAAAAGCTTTTAACTCTACATCAAGATTTGCACGTCTGCAACATATTCAAACTTGTCTAGCAGGAGATTTACTCT
TCATGAGATTTAGAACAACTACTGGTGACGCAATGGGTATGAATATGATTTCTAAAGGTGTCGAATACTCATTAA
AGCAAATGGTAGAAGAGTATGGCTGGGAAGATATGGAGGTTGTCTCCGTTTCTGGTAACTACTGTACCGACAAAA
AACCAGCTGCCATCAACTGGATCGAAGGTCGTGGTAAGAGTGTCGTCGCAGAAGCTACTATTCCTGGTGATGTTG
TCAGAAAAGTGTTAAAAAGTGATGTTTCCGCATTGGTTGAGTTGAACATTGCTAAGAATTTGGTTGGATCTGCAA
TGGCTGGGTCTGTTGGTGGATTTAACGCACATGCAGCTAATTTAGTGACAGCTGTTTTCTTGGCATTAGGACAAG
ATCCTGCACAAAATGTTGAAAGTTCCAACTGTATAACATTGATGAAAGAAGTGGACGGTGATTTGAGAATTTCCG
TATCCATGCCATCCATCGAAGTAGGTACCATCGGTGGTGGTACTGTTCTAGAACCACAAGGTGCCATGTTGGACT
TATTAGGTGTAAGAGGCCCGCATGCTACCGCTCCTGGTACCAACGCACGTCAATTAGCAAGAATAGTTGCCTGTG
CCGTCTTGGCAGGTGAATTATCCTTATGTGCTGCCCTAGCAGCCGGCCATTTGGTTCAAAGTCATATGACCCACA
ACAGGAAACCTGCTGAACCAACAAAACCTAACAATTTGGACGCCACTGATATAAATCGTTTGAAAGATGGGTCCG
TCACC**

**truncated *HMGR***

TGCATTAAATCCTAAGTCGACCT (SEQ ID NO:63)

FIG. 36A pMBIS plasmid sequence

ACCTTCGGGAGCGCCTGAAGCCCGTTCTGGACGCCCTGGGGCCGTTGAATCGGGATATGCAGGCCAAGGCCGCCG
CGATCATCAAGGCCGTGGGCGAAAAGCTGCTGACGGAACAGCGGGAAGTCCAGCGCCAGAAACAGGCCCAGCGCC
AGCAGGAACGCGGGCGCGCACATTTCCCCGAAAAGTGCCACCTGACGTCTAAGAAACCATTATTATCATGACATT
AACCTATAAAAATAGGCGTATCACGAGGCCCTTTCGTCTTCAAGAATTCTCATGTTTGACAGCTTATCATCGATA
AGCTTTAATGCGGTAGTTTA

Tetracycline resistance gene

TCACAGTTAAATTGCTAACGCAGTCAGGCACCGTGTATGAAATCTAACAATGCGCTCATCGTCATCCTCGGCACC
GTCACCCTGGATGCTGTAGGCATAGGCTTGGTTATGCCGGTACTGCCGGGCCTCTTGCGGGATATCGTCCATTCC
GACAGCATCGCCAGTCACTATGGCGTGCTGCTAGCGCTATATGCGTTGATGCAATTTCTATGCGCACCCGTTCTC
GGAGCACTGTCCGACCGCTTTGGCCGCCGCCCAGTCCTGCTCGCTTCGCTACTTGGAGCCACTATCGACTACGCG
ATCATGGCGACCACACCCGTCCTGTGGATCCTCTACGCCGGACGCATCGTGGCCGGCATCACCGGCGCCACAGGT
GCGGTTGCTGGCGCCTATATCGCCGACATCACCGATGGGGAAGATCGGGCTCGCCACTTCGGGCTCATGAGCGCT
TGTTTCGGCGTGGGTATGGTGGCAGGCCCCGTGGCCGGGGGACTGTTGGGCGCCATCTCCTTGCATGCACCATTC
CTTGCGGCGGCGGTGCTCAACGGCCTCAACCTACTACTGGGCTGCTTCCTAATGCAGGAGTCGCATAAGGGAGAG
CGTCGACCGATGCCCTTGAGAGCCTTCAACCCAGTCAGCTCCTTCCGGTGGGCGCGGGGCATGACTATCGTCGCC
GCACTTATGACTGTCTTCTTTATCATGCAACTCGTAGGACAGGTGCCGGCAGCGCTCTGGGTCATTTTCGGCGAG
GACCGCTTTCGCTGGAGCGCGACGATGATCGGCCTGTCGCTTGCGGTATTCGGAATCTTGCACGCCCTCGCTCAA
GCCTTCGTCACTGGTCCCGCCACCAAACGTTTCGGCGAGAAGCAGGCCATTATCGCCGGCATGGCGGCCGACGCG
CTGGGCTACGTCTTGCTGGCGTTCGCGACGCGAGGCTGGATGGCCTTCCCCATTATGATTCTTCTCGCTTCCGGC
GGCATCGGGATGCCCGCGTTGCAGGCCATGCTGTCCAGGCAGGTAGATGACGACCATCAGGGACAGCTTCAAGGA
TCGCTCGCGGCTCTTACCAGCCTAACTTCGATCACTGGACCGCTGATCGTCACGGCGATTTATGCCGCCTCGGCG
AGCACATGGAACGGGTTGGCATGGATTGTAGGCGCCGCCCTATACCTTGTCTGCCTCCCCGCGTTGCGTCGCGGT
GCATGGAGCCGGGCCACCTCGACCTGAATGGAAGCCGGCGGCACCTCGCTAACGGATTCACCACTCCAAGAATTG
GAGCCAATCAATTCTTGCGGAGAACTGTGAATGCGCAAATGCGCCCAATACGCAAACCGCCTCTCCCCGCGCGTT
GGCCGATTCA

Modified $P_{LAC}$ promoter

TTAATGCAGCTGGCACGACAGGTTTCCCGACTGGAAAGCGGGCAGTGAGCGCAACGCAATTAATGTGAGTTAGCT
CACTCATTAGGCACCCCAGGCTTTACACTTTATGCTTCCGGCTCGTATGTTGTGTGGAATTGTGAGCGGATAACA
ATTTCACACAGGAAACAGCTATGACCATGATTACGCCAAGCGCGCAATTAACCCTCACTAAAGGGAACAAAAGCT
GGGTACCGGGCCCCC

*MK*

CCTCGAGGTCGACGGTATCGATAAGCTTGATATCGAATTCCTGCAGTAGGAGGAATTAACCATGTCATTACCGTT
CTTAACTTCTGCACCGGGAAAGGTTATTATTTTTGGTGAACACTCTGCTGTGTACAACAAGCCTGCCGTCGCTGC
TAGTGTGTCTGCGTTGAGAACCTACCTGCTAATAAGCGAGTCATCTGCACCAGATACTATTGAATTGGACTTCCC
GGACATTAGCTTTAATCATAAGTGGTCCATCAATGATTTCAATGCCATCACCGAGGATCAAGTAAACTCCCAAAA
ATTGGCCAAGGCTCAACAAGCCACCGATGGCTTGTCTCAGGAACTCGTTAGTCTTTTGGATCCGTTGTTAGCTCA
ACTATCCGAATCCTTCCACTACCATGCAGCGTTTTGTTTCCTGTATATGTTTGTTTGCCTATGCCCCCATGCCAA
GAATATTAAGTTTTCTTTAAAGTCTACTTTACCCATCGGTGCTGGGTTGGGCTCAAGCGCCTCTATTTCTGTATC
ACTGGCCTTAGCTATGGCCTACTTGGGGGGGTTAATAGGATCTAATGACTTGGAAAAGCTGTCAGAAAACGATAA
GCATATAGTGAATCAATGGGCCTTCATAGGTGAAAAGTGTATTCACGGTACCCCTTCAGGAATAGATAACGCTGT
GGCCACTTATGGTAATGCCCTGCTATTTGAAAAAGACTCACATAATGGAACAATAAACACAAACAATTTTAAGTT
CTTAGATGATTTCCCAGCCATTCCAATGATCCTAACCTATACTAGAATTCCAAGGTCTACAAAAGATCTTGTTGC
TCGCGTTCGTGTGTTGGTCACCGAGAAATTTCCTGAAGTTATGAAGCCAATTCTAGATGCCATGGGTGAATGTGC
CCTACAAGGCTTAGAGATCATGACTAAGTTAAGTAAATGTAAAGGCACCGATGACGAGGCTGTAGAAACTAATAA
TGAACTGTATGAACAACTATTGGAATTGATAAGAATAAATCATGGACTGCTTGTCTCAATCGGTGTTTCTCATCC
TGGATTAGAACTTATTAAAAATCTGAGCGATGATTTGAGAATTGGCTCCACAAAACTTACCGGTGCTGGTGGCGG
CGGTTGCTCTTTGACTTTGTTACGAAGAGACATTACTCAAGAGCAAATTGACAGCTTCAAAAAGAAATTGCAAGA
TGATTTTAGTTACGAGACATTTGAAACAGACTTGGGTGGGACTGGCTGCTGTTTGTTAAGCGCAAAAAATTTGAA
TAAAGATCTTAAAATCAAATCCCTAGTATTCCAATTATTTGAAAATAAAACTACCACAAAGCAACAAATTGACGA
TCTATTATTG

FIG. 36B

MK ← → PMK

CCAGGAAACACGAATTTACCATGGACTTCATAGGAGGCAGATCAAATGTCAGAGTTGAGAGCCTTCAGTGCCCCA
GGGAAAGCGTTACTAGCTGGTGGATATTTAGTTTTAGATACAAAATATGAAGCATTTGTAGTCGGATTATCGGCA
AGAATGCATGCTGTAGCCCATCCTTACGGTTCATTGCAAGGGTCTGATAAGTTTGAAGTGCGTGTGAAAAGTAAA
CAATTTAAAGATGGGGAGTGGCTGTACCATATAAGTCCTAAAAGTGGCTTCATTCCTGTTTCGATAGGCGGATCT
AAGAACCCTTTCATTGAAAAAGTTATCGCTAACGTATTTAGCTACTTTAAACCTAACATGGACGACTACTGCAAT
AGAAACTTGTTCGTTATTGATATTTTCTCTGATGATGCCTACCATTCTCAGGAGGATAGCGTTACCGAACATCGT
GGCAACAGAAGATTGAGTTTTCATTCGCACAGAATTGAAGAAGTTCCCAAAACAGGGCTGGGCTCCTCGGCAGGT
TTAGTCACAGTTTTAACTACAGCTTTGGCCTCCTTTTTTGTATCGGACCTGGAAAATAATGTAGACAAATATAGA
GAAGTTATTCATAATTTAGCACAAGTTGCTCATTGTCAAGCTCAGGGTAAAATTGGAAGCGGGTTTGATGTAGCG
GCGGCAGCATATGGATCTATCAGATATAGAAGATTCCCACCCGCATTAATCTCTAATTTGCCAGATATTGGAAGT
GCTACTTACGGCAGTAAACTGGCGCATTTGGTTGATGAAGAAGACTGGAATATTACGATTAAAAGTAACCATTTA
CCTTCGGGATTAACTTTATGGATGGGCGATATTAAGAATGGTTCAGAAACAGTAAAACTGGTCCAGAAGGTAAAA
AATTGGTATGATTCGCATATGCCAGAAAGCTTGAAAATATATACAGAACTCGATCATGCAAATTCTAGATTTATG
GATGGACTATCTAAACTAGATCGCTTACACGAGACTCATGACGATTACAGCGATCAGATATTTGAGTCTCTTGAG
AGGAATGACTGTACCTGTCAAAAGTATCCTGAAATCACAGAAGTTAGAGATGCAGTTGCCACAATTAGACGTTCC
TTTAGAAAAATAACTAAAGAATCTGGTGCCGATATCGAACCTCCCGTACAAACTAGCTTATTGGATGATTGCCAG
ACCTTAAAAGGAGTTCTTACTTGCTTAATACCTGGTGCTGGTGGTTATGACGCCATTGCAGTGATTACTAAGCAA
GATGTTGATCTTAGGGCTCAAACCGCTAATGACAAAAGATTTTCTAAGGTTCAATGGCTGGATGTAACTCAGGCT
GACTGGGGTG

PMK ← → MPD

TTAGGAAAGAAAAAGATCCGGAAACTTATCTTGATAAATAGGAGGTAATACTCATGACCGTTTACACAGCATCCG
TTACCGCACCCGTCAACATCGCAACCCTTAAGTATTGGGGGAAAAGGACACGAAGTTGAATCTGCCCACCAATT
CGTCCATATCAGTGACTTTATCGCAAGATGACCTCAGAACGTTGACCTCTGCGGCTACTGCACCTGAGTTTGAAC
GCGACACTTTGTGGTTAAATGGAGAACCACACAGCATCGACAATGAAAGAACTCAAAATTGTCTGCGCGACCTAC
GCCAATTAAGAAAGGAAATGGAATCGAAGGACGCCTCATTGCCCACATTATCTCAATGGAAACTCCACATTGTCT
CCGAAAATAACTTTCCTACAGCAGCTGGTTTAGCTTCCTCCGCTGCTGGCTTTGCTGCATTGGTCTCTGCAATTG
CTAAGTTATACCAATTACCACAGTCAACTTCAGAAATATCTAGAATAGCAAGAAAGGGGTCTGGTTCAGCTTGTA
GATCGTTGTTTGGCGGATACGTGGCCTGGAAATGGAAAAGCTGAAGATGGTCATGATTCCATGGCAGTACAAA
TCGCAGACAGCTCTGACTGGCCTCAGATGAAAGCTTGTGTCCTAGTTGTCAGCGATATTAAAAAGGATGTGAGTT
CCACTCAGGGTATGCAATTGACCGTGGCAACCTCCGAACTATTTAAAGAAAGAATTGAACATGTCGTACCAAAGA
GATTTGAAGTCATGCGTAAAGCCATTGTTGAAAAAGATTTCGCCACCTTTGCAAAGGAAACAATGATGGATTCCA
ACTCTTTCCATGCCACATGTTTGGACTCTTTCCCTCCAATATTCTACATGAATGACACTTCCAAGCGTATCATCA
GTTGGTGCCACACCATTAATCAGTTTTACGGAGAAACAATCGTTGCATACACGTTTGATGCAGGTCCAAATGCTG
TGTTGTACTACTTAGCTGAAAATGAGTCGAAACTCTTTGCATTTATCTATAAATTGTTTGGCTCTGTTCCTGGAT
GGGACAAGAAATTTACTACTGAGCAGCTTGAGGCTTTCAACCATCAATTTGAATCATCTAACTTTACTGCACGTG
AATTGGATCTTGAGTTGCAAAAGGATGTTGCCAGAGTGATTTTAACTCAAGTCGGTTCAGGCCCACAAGAAACAA

MPD ← → idi

ACGAATCTTTGATTGACGCAAAGACTGGTCTACCAAAGGAATAACTGCAGCCCGGGAGGAGGATTACTATATGCA
AACGGAACACGTCATTTTATTGAATGCACAGGGAGTTCCCACGGGTACGCTGGAAAAGTATGCCGCACACACGGC
AGACACCCGCTTACATCTCGCGTTCTCCAGTTGGCTGTTTAATGCCAAAGGACAATTATTAGTTACCCGCCGCGC
ACTGAGCAAAAAAGCATGGCCTGGCGTGTGGACTAACTCGGTTTGTGGGCACCCACAACTGGGAGAAAGCAACGA
AGACGCAGTGATCCGCCGTTGCCGTTATGAGCTTGGCGTGGAAATTACGCCTCCTGAATCTATCTATCCTGACTT
TCGCTACCGCGCCACCGATCCGAGTGGCATTGTGGAAAATGAAGTGTGTCCGGTATTTGCCGCACGCACCACTAG
TGCGTTACAGATCAATGATGATGAAGTGATGGATTATCAATGGTGTGATTTAGCAGATGTATTACACGGTATTGA
TGCCACGCCGTGGGCGTTCAGTCCGTGGATGGTGATGCAGGCGACAAATCGCGAAGCCAGAAAACGATTATCTGC
ATTTACCCAGCTTAAATAACCCGGGGGATCCACTAGTTCT
←

FIG. 36C ispA

AGAGCGGCCGCCACCGCGGAGGAGGAATGAGTAATGGACTTTCCGCAGCAACTCGAAGCCTGCGTTAAGCAGGCC
AACCAGGCGCTGAGCCGTTTTATCGCCCCACTGCCCTTTCAGAACACTCCCGTGGTCGAAACCATGCAGTATGGC
GCATTATTAGGTGGTAAGCGCCTGCGACCTTTCCTGGTTTATGCCACCGGTCATATGTTCGGCGTTAGCACAAAC
ACGCTGGACGCACCCGCTGCCGCCGTTGAGTGTATCCACGCTTACTCATTAATTCATGATGATTTACCGGCAATG
GATGATGACGATCTGCGTCGCGGTTTGCCAACCTGCCATGTGAAGTTTGGCGAAGCAAACGCGATTCTCGCTGGC
GACGCTTTACAAACGCTGGCGTTCTCGATTTTAAGCGATGCCGATATGCCGGAAGTGTCGGACCGCGACAGAATT
TCGATGATTTCTGAACTGGCGAGCGCCAGTGGTATTGCCGGAATGTGCGGTGGTCAGGCATTAGATTTAGACGCG
GAAGGCAAACACGTACCTCTGGACGCGCTTGAGCGTATTCATCGTCATAAAACCGGCGCATTGATTCGCGCCGCC
GTTCGCCTTGGTGCATTAAGCGCCGGAGATAAAGGACGTCGTGCTCTGCCGGTACTCGACAAGTATGCAGAGAGC
ATCGGCCTTGCCTTCCAGGTTCAGGATGACATCCTGGATGTGGTGGGAGATACTGCAACGTTGGGAAAACGCCAG
GGTGCCGACCAGCAACTTGGTAAAAGTACCTACCCTGCACTTCTGGGTCTTGAGCAAGCCCGGAAGAAAGCCCGG
GATCTGATCGACGATGCCCGTCAGTCGCTGAAACAACTGGCTGAACAGTCACTCGATACCTCGGCACTGGAAGCG
CTAGCGGACTACATCATCCAGCGTAATAAATAA

GAGCTCCAATTCGCCCTATAGTGAGTCGTATTACGCGCGCTCACTGGCCGTCGTTTTACAACGTCGTGACTGGGA
AAACCCTGGCGTTACCCAACTTAATCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGAAATTGTAAGCGTTAATATTTTGTTA
AAATTCGCGTTAAATTTTTGTTAAATCAGCTCATTTTTTAACCAATAGGCCGACTGCGATGAGTGGCAGGGCGGG
GCGTAATTTTTTTAAGGCAGTTATTGGTGCCCTTAAACGCCTGGTGCTACGCCTGAATAAGTGATAATAAGCGGA
TGAATGGCAGAAATTCGAAAGCAAATTCGACCCGGTCGTCGGTTCAGGGCAGGGTCGTTAAATAGCCGCTTATGT
CTATTGCTGGTTTACCGGTTTATTGACTACCGGAAGCAGTGTGACCGTGTGCTTCTCAAATGCCTGAGGCCAGTT
TGCTCAGGCTCTCCCCGTGGAGGTAATAATTGACGATATGATCATTTATTCTGCCTCCCAGAGCCTGATAAAAAC
GGTGAATCCGTTAGCGAGGTGCCGCCGGCTTCCATTCAGGTCGAGGTGGCCCGGCTCCATGCACCGCGACGCAAC
GCGGGGAGGCAGACAAGGTATAGGGCGGCGAGGCGGCTACAGCCGATAGTCTGGAACAGCGCACTTACGGGT

Origin of replication

TGCTGCGCAACCCAAGTGCTACCGGCGCGGCAGCGTGACCCGTGTCGGCGGCTCCAACGGCTCGCCATCGTCCAG
AAAACACGGCTCATCGGGCATCGGCAGGCGCTGCTGCCCGCGCCGTTCCCATTCCTCCGTTTCGGTCAAGGCTGG
CAGGTCTGGTTCCATGCCCGGAATGCCGGGCTGGCTGGGCGGCTCCTCGCCGGGGCCGGTCGGTAGTTGCTGCTC
GCCCGGATACAGGGTCGGGATGCGGCGCAGGTCGCCATGCCCCAACAGCGATTCGTCCTGGTCGTCGTGATCAAC
CACCACGGCGGCACTGAACACCGACAGGCGCAACTGGTCGCGGGGCTGGCCCCACGCCACGCGGTCATTGACCAC
GTAGGCCGACACGGTGCCGGGGCCGTTGAGCTTCACGACGGAGATCCAGCGCTCGGCCACCAAGTCCTTGACTGC
GTATTGGACCGTCCGCAAAGAACGTCCGATGAGCTTGGAAAGTGTCTTCTGGCTGACCACCACGGCGTTCTGGTG
GCCCATCTGCGCCACGAGGTGATGCAGCAGCATTGCCGCCGTGGGTTTCCTCGCAATAAGCCCGGCCCACGCCTC
ATGCGCTTTGCGTTCCGTTTGCACCCAGTGACCGGGCTTGTTCTTGGCTTGAATGCCGATTTCTCTGGACTGCGT
GGCCATGCTTATCTCCATGCGGTAGGGTGCCGCACGGTTGCGGCACCATGCGCAATCAGCTGCAACTTTTCGGCA
GCGCGACAACAATTATGCGTTGCGTAAAAGTGGCAGTCAATTACAGATTTTCTTTAACCTACGCAATGAGCTATT
GCGGGGGGTGCCGCAATGAGCTGTTGCGTACCCCCCTTTTTTAAGTTGTTGATTTTTAAGTCTTTCGCATTTCGC
CCTATATCTAGTTCTTTGGTGCCCAAAGAAGGGCACCCCTGCGGGGTTCCCCCACGCCTTCGGCGCGGCTCCCCC
TCCGGCAAAAAGTGGCCCCTCCGGGGCTTGTTGATCGACTGCGCGGCCTTCGGCCTTGCCCAAGGTGGCGCTGCC
CCCTTGGAACCCCCGCACTCGCCGCCGTGAGGCTCGGGGGGCAGGCGGGCGGGCTTCGCCTTCGACTGCCCCCAC
TCGCATAGGCTTGGGTCGTTCCAGGCGCGTCAAGGCCAAGCCGCTGCGCGGTCGCTGCGCGAGCCTTGACCCGCC
TTCCACTTGGTGTCCAACCGGCAAGCGAAGCGCGCAGGCCGCAGGCCGGAGGCTTTTCCCCAGAGAAAATTAAAA
AAATTGATGGGGCAAGGCCGCAGGCCGCGCAGTTGGAGCCGGTGGGTATGTGGTCGAAGGCTGGGTAGCCGGTGG
GCAATCCCTGTGGTCAAGCTCGTGGGCAGGCGCAGCCTGTCCATCAGCTTGTCCAGCAGGGTTGTCCACGGGCCG
AGCGAAGCGAGCCAGCCGGTGGCCGCTCGCGGCCATCGTCCACATATCCACGGGCTGGCAAGGGAGCGCAGCGAC
CGCGCAGGGCGAAGCCCGGAGAGCAAGCCCGTAGGGCGCCGCAGCCGCCGTAGGCGGTCACGACTTTGCGAAGCA
AAGTCTAGTGAGTATACTCAAGCATTGAGTGGCCCGCCGGAGGCACCGCCTTGCGCTGCCCCCGTCGAGCCGGTT
GGACACCAAAAGGGAGGGGCAGGCATGGCGGCATACGCGATCATGCGATGCAAGAAGCTGGCGAAAATGGGCAAC
GTGGCGGCCAGTCTCAAGCACGCCTACCGCGAGCGCGAGACGCCCAACGCTGACGCCAGCAGGACGCCAGAGAAC
GAGCACTGGGCGGCCAGCAGCACCGATGAAGCGATGGGCCGACTGCGCGAGTTGCTGCCAGAGAAGCGGCGCAAG
GACGCTGTGTTGGCGGTCGAGTACGTCATGACGGCCAGCCCGGAATGGTGGAAGTCGGCCAGCCAAGAACAGCAG
GCGGCGTTCTTCGAGAAGGCGCACAAGTGGCTGGCGGACAAGTACGGGGCGGATCGCATCGTGACGGCCAGCATC
CACCGTGACGAAACCAGCCCGCACATGACCGCGTTCGTGGTGCCGCTGACGCAGGACGGCAGGCTGTCGGCCAAG

FIG. 36D

GAGTTCATCGGCAACAAAGCGCAGATGACCCGCGACCAGACCACGTTTGCGGCCGCTGTGGCCGATCTAGGGCTG
CAACGGGGCATCGAGGGCAGCAAGGCACGTCACACGCGCATTCAGGCGTTCTACGAGGCCCTGGAGCGGCCACCA
GTGGGCCACGTCACCATCAGCCCGCAAGCGGTCGAGCCACGCGCCTATGCACCGCAGGGATTGGCCGAAAAGCTG
GGAATCTCAAAGCGCGTTGAGACGCCGGAAGCCGTGGCCGACCGGCTGACAAAAGCGGTTCGGCAGGGGTATGAG
CCTGCCCTACAGGCCGCCGCAGGAGCGCGTGAGATGCGCAAGAAGGCCGATCAAGCCCAAGAGACGGCCCGAG
(SEQ ID NO:62)

SEQUENCE LISTING

```
<160> NUMBER OF SEQ ID NOS: 63

<210> SEQ ID NO 1
<211> LENGTH: 19
<212> TYPE: PRT
<213> ORGANISM: Artificial Sequence
<220> FEATURE:
<223> OTHER INFORMATION: synthetic peptide

<400> SEQUENCE: 1

Met Trp Leu Leu Leu Ile Ala Val Phe Leu Leu Thr Leu Ala Tyr Leu
 1               5                  10                  15

Phe Trp Pro


<210> SEQ ID NO 2
<211> LENGTH: 20
<212> TYPE: PRT
<213> ORGANISM: Artificial Sequence
<220> FEATURE:
<223> OTHER INFORMATION: synthetic peptide

<400> SEQUENCE: 2

Met Ala Leu Leu Leu Ala Val Phe Leu Gly Leu Ser Cys Leu Leu Leu
 1               5                  10                  15

Leu Ser Leu Trp
        20


<210> SEQ ID NO 3
<211> LENGTH: 18
```

```
<212> TYPE: PRT
<213> ORGANISM: Artificial Sequence
<220> FEATURE:
<223> OTHER INFORMATION: synthetic peptide

<400> SEQUENCE: 3

Met Ala Ile Leu Ala Ala Ile Phe Ala Leu Val Val Ala Thr Ala Thr
 1               5                   10                  15

Arg Val


<210> SEQ ID NO 4
<211> LENGTH: 24
<212> TYPE: PRT
<213> ORGANISM: Artificial Sequence
<220> FEATURE:
<223> OTHER INFORMATION: synthetic peptide

<400> SEQUENCE: 4

Met Asp Ala Ser Leu Leu Leu Ser Val Ala Leu Ala Val Val Leu Ile
 1               5                   10                  15

Pro Leu Ser Leu Ala Leu Leu Asn
            20


<210> SEQ ID NO 5
<211> LENGTH: 27
<212> TYPE: PRT
<213> ORGANISM: Artificial Sequence
<220> FEATURE:
<223> OTHER INFORMATION: synthetic peptide

<400> SEQUENCE: 5

Met Ile Glu Gln Leu Leu Glu Tyr Trp Tyr Val Val Val Pro Val Leu
 1               5                   10                  15

Tyr Ile Ile Lys Gln Leu Leu Ala Tyr Thr Lys
            20                  25


<210> SEQ ID NO 6
<211> LENGTH: 21
<212> TYPE: PRT
<213> ORGANISM: Artificial Sequence
<220> FEATURE:
<223> OTHER INFORMATION: synthetic peptide

<400> SEQUENCE: 6

Met Lys Lys Thr Ala Ile Ala Ile Ala Val Ala Leu Ala Gly Phe Ala
 1               5                   10                  15

Thr Val Ala Gln Ala
            20


<210> SEQ ID NO 7
<211> LENGTH: 21
<212> TYPE: PRT
<213> ORGANISM: Artificial Sequence
<220> FEATURE:
<223> OTHER INFORMATION: synthetic peptide

<400> SEQUENCE: 7

Met Lys Lys Thr Ala Ile Ala Ile Val Val Ala Leu Ala Gly Phe Ala
 1               5                   10                  15

Thr Val Ala Gln Ala
            20


<210> SEQ ID NO 8
<211> LENGTH: 21
<212> TYPE: PRT
```

```
<213> ORGANISM: Artificial Sequence
<220> FEATURE:
<223> OTHER INFORMATION: synthetic peptide

<400> SEQUENCE: 8

Met Lys Lys Thr Ala Leu Ala Leu Ala Val Ala Leu Ala Gly Phe Ala
 1               5                  10                  15

Thr Val Ala Gln Ala
            20


<210> SEQ ID NO 9
<211> LENGTH: 26
<212> TYPE: PRT
<213> ORGANISM: Artificial Sequence
<220> FEATURE:
<223> OTHER INFORMATION: synthetic peptide

<400> SEQUENCE: 9

Met Lys Ile Lys Thr Gly Ala Arg Ile Leu Ala Leu Ser Ala Leu Thr
 1               5                  10                  15

Thr Met Met Phe Ser Ala Ser Ala Leu Ala
            20                  25


<210> SEQ ID NO 10
<211> LENGTH: 25
<212> TYPE: PRT
<213> ORGANISM: Artificial Sequence
<220> FEATURE:
<223> OTHER INFORMATION: synthetic peptide

<400> SEQUENCE: 10

Met Asn Met Lys Lys Leu Ala Thr Leu Val Ser Ala Val Ala Leu Ser
 1               5                  10                  15

Ala Thr Val Ser Ala Asn Ala Met Ala
            20                  25


<210> SEQ ID NO 11
<211> LENGTH: 21
<212> TYPE: PRT
<213> ORGANISM: Artificial Sequence
<220> FEATURE:
<223> OTHER INFORMATION: synthetic peptide

<400> SEQUENCE: 11

Met Lys Gln Ser Thr Ile Ala Leu Ala Leu Leu Pro Leu Leu Phe Thr
 1               5                  10                  15

Pro Val Thr Lys Ala
            20


<210> SEQ ID NO 12
<211> LENGTH: 44
<212> TYPE: PRT
<213> ORGANISM: Artificial Sequence
<220> FEATURE:
<223> OTHER INFORMATION: synthetic peptide

<400> SEQUENCE: 12

Met Lys Lys Thr Ala Ile Ala Ile Ala Val Ala Leu Ala Gly Phe Ala
 1               5                  10                  15

Thr Val Ala Gln Ala Leu Leu Glu Tyr Trp Tyr Val Val Val Pro Val
            20                  25                  30

Leu Tyr Ile Ile Lys Gln Leu Leu Ala Tyr Thr Lys
        35                  40
```

```
<210> SEQ ID NO 13
<211> LENGTH: 24
<212> TYPE: PRT
<213> ORGANISM: Artificial Sequence
<220> FEATURE:
<223> OTHER INFORMATION: synthetic peptide

<400> SEQUENCE: 13

Glu Glu Leu Leu Lys Gln Ala Leu Gln Gln Ala Gln Gln Leu Leu Gln
 1               5                  10                  15

Gln Ala Gln Glu Leu Ala Lys Lys
            20


<210> SEQ ID NO 14
<211> LENGTH: 32
<212> TYPE: PRT
<213> ORGANISM: Artificial Sequence
<220> FEATURE:
<223> OTHER INFORMATION: synthetic peptide

<400> SEQUENCE: 14

Met Thr Val His Asp Ile Ile Ala Thr Tyr Phe Thr Lys Trp Tyr Val
 1               5                  10                  15

Ile Val Pro Leu Ala Leu Ile Ala Tyr Arg Val Leu Asp Tyr Phe Tyr
            20                  25                  30


<210> SEQ ID NO 15
<211> LENGTH: 29
<212> TYPE: PRT
<213> ORGANISM: Artificial Sequence
<220> FEATURE:
<223> OTHER INFORMATION: synthetic peptide

<400> SEQUENCE: 15

Gly Leu Phe Gly Ala Ile Ala Gly Phe Ile Glu Gly Gly Trp Thr Gly
 1               5                  10                  15

Met Ile Asp Gly Trp Tyr Gly Tyr Gly Gly Gly Lys Lys
            20                  25


<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

Met Ala Lys Lys Thr Ser Ser Lys Gly
 1               5


<210> SEQ ID NO 17
<211> LENGTH: 6
<212> TYPE: PRT
<213> ORGANISM: Artificial Sequence
<220> FEATURE:
<223> OTHER INFORMATION: synthetic peptide

<400> SEQUENCE: 17

Ala Ala Ala Gly Gly Met
 1               5


<210> SEQ ID NO 18
<211> LENGTH: 14
<212> TYPE: PRT
<213> ORGANISM: Artificial Sequence
<220> FEATURE:
<223> OTHER INFORMATION: synthetic peptide
```

<400> SEQUENCE: 18

```
Ala Ala Ala Gly Gly Met Pro Pro Ala Ala Ala Gly Gly Met
 1               5                   10
```

<210> SEQ ID NO 19
<211> LENGTH: 6
<212> TYPE: PRT
<213> ORGANISM: Artificial Sequence
<220> FEATURE:
<223> OTHER INFORMATION: linker peptide

<400> SEQUENCE: 19

```
Ala Ala Ala Gly Gly Met
 1               5
```

<210> SEQ ID NO 20
<211> LENGTH: 8
<212> TYPE: PRT
<213> ORGANISM: Artificial Sequence
<220> FEATURE:
<223> OTHER INFORMATION: linker peptide

<400> SEQUENCE: 20

```
Pro Pro Ala Ala Ala Gly Gly Met
 1               5
```

<210> SEQ ID NO 21
<211> LENGTH: 4
<212> TYPE: PRT
<213> ORGANISM: Artificial Sequence
<220> FEATURE:
<223> OTHER INFORMATION: linker peptide

<400> SEQUENCE: 21

```
Ile Glu Gly Arg
 1
```

<210> SEQ ID NO 22
<211> LENGTH: 6
<212> TYPE: PRT
<213> ORGANISM: Artificial Sequence
<220> FEATURE:
<223> OTHER INFORMATION: linker peptide

<400> SEQUENCE: 22

```
Gly Gly Lys Gly Gly Lys
 1               5
```

<210> SEQ ID NO 23
<211> LENGTH: 23
<212> TYPE: PRT
<213> ORGANISM: Artificial Sequence
<220> FEATURE:
<223> OTHER INFORMATION: synthetic peptide

<400> SEQUENCE: 23

```
Met Leu Phe Pro Val Ala Leu Ser Phe Leu Val Ala Ile Leu Gly Ile
 1               5                   10                  15

Ser Leu Trp His Val Trp Thr
            20
```

<210> SEQ ID NO 24
<211> LENGTH: 110
<212> TYPE: PRT
<213> ORGANISM: Bacillus subtilis

<400> SEQUENCE: 24

Met Phe Cys Thr Phe Phe Glu Lys His His Arg Lys Trp Asp Ile Leu
1 5 10 15

Leu Glu Lys Ser Thr Gly Val Met Glu Ala Met Lys Val Thr Ser Glu
20 25 30

Glu Lys Glu Gln Leu Ser Thr Ala Ile Asp Arg Met Asn Glu Gly Leu
35 40 45

Asp Ala Phe Ile Gln Leu Tyr Asn Glu Ser Glu Ile Asp Glu Pro Leu
50 55 60

Ile Gln Leu Asp Asp Asp Thr Ala Glu Leu Met Lys Gln Ala Arg Asp
65 70 75 80

Met Tyr Gly Gln Glu Lys Leu Asn Glu Lys Leu Asn Thr Ile Ile Lys
85 90 95

Gln Ile Leu Ser Ile Ser Val Ser Glu Glu Gly Glu Lys Glu
100 105 110

<210> SEQ ID NO 25
<211> LENGTH: 496
<212> TYPE: PRT
<213> ORGANISM: Mentha x gracilis

<400> SEQUENCE: 25

Met Glu Leu Asp Leu Leu Ser Ala Ile Ile Ile Leu Val Ala Thr Tyr
1 5 10 15

Ile Val Ser Leu Leu Ile Asn Gln Trp Arg Lys Ser Lys Ser Gln Gln
20 25 30

Asn Leu Pro Pro Ser Pro Pro Lys Leu Pro Val Ile Gly His Leu His
35 40 45

Phe Leu Trp Gly Gly Leu Pro Gln His Val Phe Arg Ser Ile Ala Gln
50 55 60

Lys Tyr Gly Pro Val Ala His Val Gln Leu Gly Glu Val Tyr Ser Val
65 70 75 80

Val Leu Ser Ser Ala Glu Ala Ala Lys Gln Ala Met Lys Val Leu Asp
85 90 95

Pro Asn Phe Ala Asp Arg Phe Asp Gly Ile Gly Ser Arg Thr Met Trp
100 105 110

Tyr Asp Lys Asp Asp Ile Ile Phe Ser Pro Tyr Asn Asp His Trp Arg
115 120 125

Gln Met Arg Arg Ile Cys Val Thr Glu Leu Leu Ser Pro Lys Asn Val
130 135 140

Arg Ser Phe Gly Tyr Ile Arg Gln Glu Glu Ile Glu Arg Leu Ile Arg
145 150 155 160

Leu Leu Gly Ser Ser Gly Gly Ala Pro Val Asp Val Thr Glu Glu Val
165 170 175

Ser Lys Met Ser Cys Val Val Val Cys Arg Ala Ala Phe Gly Ser Val
180 185 190

Leu Lys Asp Gln Gly Ser Leu Ala Glu Leu Val Lys Glu Ser Leu Ala
195 200 205

Leu Ala Ser Gly Phe Glu Leu Ala Asp Leu Tyr Pro Ser Ser Trp Leu
210 215 220

Leu Asn Leu Leu Ser Leu Asn Lys Tyr Arg Leu Gln Arg Met Arg Arg
225 230 235 240

Arg Leu Asp His Ile Leu Asp Gly Phe Leu Glu Glu His Arg Glu Lys
245 250 255

Lys Ser Gly Glu Phe Gly Gly Glu Asp Ile Val Asp Val Leu Phe Arg

```
            260                 265                 270

Met Gln Lys Gly Ser Asp Ile Lys Ile Pro Ile Thr Ser Asn Cys Ile
        275                 280                 285

Lys Gly Phe Ile Phe Asp Thr Phe Ser Ala Gly Ala Glu Thr Ser Ser
    290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
        355                 360                 365

Gln Ser Arg Glu Glu Cys Glu Val Asn Gly Tyr Thr Ile Pro Ala Lys
    370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
            420                 425                 430

Arg Arg Ile Cys Pro Gly Leu His Phe Gly Leu Ala Asn Val Glu Ile
        435                 440                 445

Pro Leu Ala Gln Leu Leu Tyr His Phe Asp Trp Lys Leu Pro Gln Gly
    450                 455                 460

Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
                485                 490                 495


<210> SEQ ID NO 26
<211> LENGTH: 473
<212> TYPE: PRT
<213> ORGANISM: Nicotiana tabacum

<400> SEQUENCE: 26

Met Gln Phe Phe Ser Leu Val Ser Ile Phe Leu Phe Leu Ala Phe Leu
 1               5                  10                  15

Phe Leu Leu Arg Lys Trp Lys Asn Ser Asn Ser Gln Ser Lys Lys Leu
            20                  25                  30

Pro Pro Gly Pro Trp Lys Ile Pro Ile Leu Gly Ser Met Leu His Met
        35                  40                  45

Ile Gly Gly Glu Pro His His Val Leu Arg Asp Leu Ala Lys Lys Tyr
    50                  55                  60

Gly Pro Leu Met His Leu Gln Leu Gly Glu Ile Ser Ala Val Val Val
65                  70                  75                  80

Thr Ser Arg Asp Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140

Phe Ser Ser Ile Arg Arg Asp Glu Val Val Arg Leu Ile Asp Ser Ile
```

```
145                 150                 155                 160

Arg Ser Asp Ser Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Ile Phe Ala Lys Lys Ile Arg Glu Val Ile Gly
        195                 200                 205

Leu Ala Glu Gly Phe Asp Val Val Asp Ile Phe Pro Thr Tyr Lys Phe
    210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
                245                 250                 255

Leu Ala Ala Gly Lys Ser Asn Gly Ala Leu Glu Asp Met Phe Ala Ala
            260                 265                 270

Gly Thr Glu Thr Ser Ser Thr Thr Thr Val Trp Ala Met Ala Glu Met
        275                 280                 285

Met Lys Asn Pro Ser Val Phe Thr Lys Ala Gln Ala Glu Val Arg Glu
    290                 295                 300

Ala Phe Arg Asp Lys Val Ser Phe Asp Glu Asn Asp Val Glu Glu Leu
305                 310                 315                 320

Lys Tyr Leu Lys Leu Val Ile Lys Glu Thr Leu Arg Leu His Pro Pro
                325                 330                 335

Ser Pro Leu Leu Val Pro Arg Glu Cys Arg Glu Asp Thr Asp Ile Asn
            340                 345                 350

Gly Tyr Thr Ile Pro Ala Lys Thr Lys Val Met Val Asn Val Trp Ala
        355                 360                 365

Leu Gly Arg Asp Pro Lys Tyr Trp Asp Asp Ala Glu Ser Phe Lys Pro
    370                 375                 380

Glu Arg Phe Glu Gln Cys Ser Val Asp Phe Phe Gly Asn Asn Phe Glu
385                 390                 395                 400

Phe Leu Pro Phe Gly Gly Gly Arg Arg Ile Cys Pro Gly Met Ser Phe
                405                 410                 415

Gly Leu Ala Asn Leu Tyr Leu Pro Leu Ala Gln Leu Leu Tyr His Phe
            420                 425                 430

Asp Trp Lys Leu Pro Thr Gly Ile Met Pro Arg Asp Leu Asp Leu Thr
        435                 440                 445

Glu Leu Ser Gly Ile Thr Ile Ala Arg Lys Gly Asp Leu Tyr Leu Asn
    450                 455                 460

Ala Thr Pro Tyr Gln Pro Ser Arg Glu
465                 470


<210> SEQ ID NO 27
<211> LENGTH: 536
<212> TYPE: PRT
<213> ORGANISM: Gossypium arboreum

<400> SEQUENCE: 27

Met Leu Gln Ile Ala Phe Ser Ser Tyr Ser Trp Leu Leu Thr Ala Ser
 1               5                  10                  15

Asn Gln Lys Asp Gly Met Leu Phe Pro Val Ala Leu Ser Phe Leu Val
            20                  25                  30

Ala Ile Leu Gly Ile Ser Leu Trp His Val Trp Thr Ile Arg Lys Pro
        35                  40                  45

Lys Lys Asp Ile Ala Pro Leu Pro Pro Gly Pro Arg Gly Leu Pro Ile
```

```
    50                  55                  60

Val Gly Tyr Leu Pro Tyr Leu Gly Thr Asp Asn Leu His Leu Val Phe
65                  70                  75                  80

Thr Asp Leu Ala Ala Ala Tyr Gly Pro Ile Tyr Lys Leu Trp Leu Gly
                85                  90                  95

Asn Lys Leu Cys Val Val Ile Ser Ser Ala Pro Leu Ala Lys Glu Val
            100                 105                 110

Val Arg Asp Asn Asp Ile Thr Phe Ser Glu Arg Asp Pro Pro Val Cys
        115                 120                 125

Ala Lys Ile Ile Thr Phe Gly Leu Asn Asp Ile Val Phe Asp Ser Tyr
    130                 135                 140

Ser Ser Pro Asp Trp Arg Met Lys Arg Lys Val Leu Val Arg Glu Met
145                 150                 155                 160

Leu Ser His Ser Ser Ile Lys Ala Cys Tyr Gly Leu Arg Arg Glu Gln
                165                 170                 175

Val Leu Lys Gly Val Gln Asn Val Ala Gln Ser Ala Gly Lys Pro Ile
            180                 185                 190

Asp Phe Gly Glu Thr Ala Phe Leu Thr Ser Ile Asn Ala Met Met Ser
        195                 200                 205

Met Leu Trp Gly Gly Lys Gln Gly Gly Glu Arg Lys Gly Ala Asp Val
    210                 215                 220

Trp Gly Gln Phe Arg Asp Leu Ile Thr Glu Leu Met Val Ile Leu Gly
225                 230                 235                 240

Lys Pro Asn Val Ser Asp Ile Phe Pro Val Leu Ala Arg Phe Asp Ile
                245                 250                 255

Gln Gly Leu Glu Lys Glu Met Thr Lys Ile Val Asn Ser Phe Asp Lys
            260                 265                 270

Leu Phe Asn Ser Met Ile Glu Glu Arg Glu Asn Phe Ser Asn Lys Leu
        275                 280                 285

Ser Lys Glu Asp Gly Asn Thr Glu Thr Lys Asp Phe Leu Gln Leu Leu
    290                 295                 300

Leu Asp Leu Lys Gln Lys Asn Asp Ser Gly Ile Ser Ile Thr Met Asn
305                 310                 315                 320

Gln Val Lys Ala Leu Leu Met Asp Ile Val Val Gly Gly Thr Asp Thr
                325                 330                 335

Thr Ser Thr Met Met Glu Trp Thr Met Ala Glu Leu Ile Ala Asn Pro
            340                 345                 350

Glu Ala Met Lys Lys Val Lys Gln Glu Ile Asp Asp Val Val Gly Ser
        355                 360                 365

Asp Gly Ala Val Asp Glu Thr His Leu Pro Lys Leu Arg Tyr Leu Asp
    370                 375                 380

Ala Ala Val Lys Glu Thr Phe Arg Leu His Pro Pro Met Pro Leu Leu
385                 390                 395                 400

Val Pro Arg Cys Pro Gly Asp Ser Ser Asn Val Gly Gly Tyr Ser Val
                405                 410                 415

Pro Lys Gly Thr Arg Val Phe Leu Asn Ile Trp Cys Ile Gln Arg Asp
            420                 425                 430

Pro Gln Leu Trp Glu Asn Pro Leu Glu Phe Lys Pro Glu Arg Phe Leu
        435                 440                 445

Thr Asp His Glu Lys Leu Asp Tyr Leu Gly Asn Asp Ser Arg Tyr Met
    450                 455                 460

Pro Phe Gly Ser Gly Arg Arg Met Cys Ala Gly Val Ser Leu Gly Glu
465                 470                 475                 480
```

```
Lys Met Leu Tyr Ser Ser Leu Ala Ala Met Ile His Ala Tyr Asp Trp
                485                 490                 495

Asn Leu Ala Asp Gly Glu Glu Asn Asp Leu Ile Gly Leu Phe Gly Ile
            500                 505                 510

Ile Met Lys Lys Lys Lys Pro Leu Ile Leu Val Pro Thr Pro Arg Pro
        515                 520                 525

Ser Asn Leu Gln His Tyr Met Lys
    530                 535


<210> SEQ ID NO 28
<211> LENGTH: 512
<212> TYPE: PRT
<213> ORGANISM: Artificial Sequence
<220> FEATURE:
<223> OTHER INFORMATION: Modified P450 monooxygenase

<400> SEQUENCE: 28

Met Ala Leu Leu Leu Ala Val Phe Leu Gly Leu Ser Cys Leu Leu Leu
 1               5                  10                  15

Leu Ser Leu Trp Ile Arg Lys Pro Lys Lys Asp Ile Ala Pro Leu Pro
            20                  25                  30

Pro Gly Pro Arg Gly Leu Pro Ile Val Gly Tyr Leu Pro Tyr Leu Gly
        35                  40                  45

Thr Asp Asn Leu His Leu Val Phe Thr Asp Leu Ala Ala Ala Tyr Gly
    50                  55                  60

Pro Ile Tyr Lys Leu Trp Leu Gly Asn Lys Leu Cys Val Val Ile Ser
65                  70                  75                  80

Ser Ala Pro Leu Ala Lys Glu Val Val Arg Asp Asn Asp Ile Thr Phe
                85                  90                  95

Ser Glu Arg Asp Pro Pro Val Cys Ala Lys Ile Ile Thr Phe Gly Leu
            100                 105                 110

Asn Asp Ile Val Phe Asp Ser Tyr Ser Ser Pro Asp Trp Arg Met Lys
        115                 120                 125

Arg Lys Val Leu Val Arg Glu Met Leu Ser His Ser Ser Ile Lys Ala
    130                 135                 140

Cys Tyr Gly Leu Arg Arg Glu Gln Val Leu Lys Gly Val Gln Asn Val
145                 150                 155                 160

Ala Gln Ser Ala Gly Lys Pro Ile Asp Phe Gly Glu Thr Ala Phe Leu
                165                 170                 175

Thr Ser Ile Asn Ala Met Met Ser Met Leu Trp Gly Gly Lys Gln Gly
            180                 185                 190

Gly Glu Arg Lys Gly Ala Asp Val Trp Gly Gln Phe Arg Asp Leu Ile
        195                 200                 205

Thr Glu Leu Met Val Ile Leu Gly Lys Pro Asn Val Ser Asp Ile Phe
    210                 215                 220

Pro Val Leu Ala Arg Phe Asp Ile Gln Gly Leu Glu Lys Glu Met Thr
225                 230                 235                 240

Lys Ile Val Asn Ser Phe Asp Lys Leu Phe Asn Ser Met Ile Glu Glu
                245                 250                 255

Arg Glu Asn Phe Ser Asn Lys Leu Ser Lys Glu Asp Gly Asn Thr Glu
            260                 265                 270

Thr Lys Asp Phe Leu Gln Leu Leu Leu Asp Leu Lys Gln Lys Asn Asp
        275                 280                 285

Ser Gly Ile Ser Ile Thr Met Asn Gln Val Lys Ala Leu Leu Met Asp
    290                 295                 300

Ile Val Val Gly Gly Thr Asp Thr Thr Ser Thr Met Met Glu Trp Thr
```

```
305                 310                 315                 320

Met Ala Glu Leu Ile Ala Asn Pro Glu Ala Met Lys Lys Val Lys Gln
                325                 330                 335

Glu Ile Asp Asp Val Val Gly Ser Asp Gly Ala Val Asp Glu Thr His
            340                 345                 350

Leu Pro Lys Leu Arg Tyr Leu Asp Ala Ala Val Lys Glu Thr Phe Arg
        355                 360                 365

Leu His Pro Pro Met Pro Leu Leu Val Pro Arg Cys Pro Gly Asp Ser
    370                 375                 380

Ser Asn Val Gly Gly Tyr Ser Val Pro Lys Gly Thr Arg Val Phe Leu
385                 390                 395                 400

Asn Ile Trp Cys Ile Gln Arg Asp Pro Gln Leu Trp Glu Asn Pro Leu
                405                 410                 415

Glu Phe Lys Pro Glu Arg Phe Leu Thr Asp His Glu Lys Leu Asp Tyr
            420                 425                 430

Leu Gly Asn Asp Ser Arg Tyr Met Pro Phe Gly Ser Gly Arg Arg Met
        435                 440                 445

Cys Ala Gly Val Ser Leu Gly Glu Lys Met Leu Tyr Ser Ser Leu Ala
    450                 455                 460

Ala Met Ile His Ala Tyr Asp Trp Asn Leu Ala Asp Gly Glu Glu Asn
465                 470                 475                 480

Asp Leu Ile Gly Leu Phe Gly Ile Ile Met Lys Lys Lys Lys Pro Leu
                485                 490                 495

Ile Leu Val Pro Thr Pro Arg Pro Ser Asn Leu Gln His Tyr Met Lys
            500                 505                 510


<210> SEQ ID NO 29
<211> LENGTH: 516
<212> TYPE: PRT
<213> ORGANISM: Artificial Sequence
<220> FEATURE:
<223> OTHER INFORMATION: Modified P450 monooxygenase

<400> SEQUENCE: 29

Glu Glu Leu Leu Lys Gln Ala Leu Gln Gln Ala Gln Gln Leu Leu Gln
 1               5                  10                  15

Gln Ala Gln Glu Leu Ala Lys Lys Ile Arg Lys Pro Lys Lys Asp Ile
            20                  25                  30

Ala Pro Leu Pro Pro Gly Pro Arg Gly Leu Pro Ile Val Gly Tyr Leu
        35                  40                  45

Pro Tyr Leu Gly Thr Asp Asn Leu His Leu Val Phe Thr Asp Leu Ala
    50                  55                  60

Ala Ala Tyr Gly Pro Ile Tyr Lys Leu Trp Leu Gly Asn Lys Leu Cys
65                  70                  75                  80

Val Val Ile Ser Ser Ala Pro Leu Ala Lys Glu Val Val Arg Asp Asn
                85                  90                  95

Asp Ile Thr Phe Ser Glu Arg Asp Pro Pro Val Cys Ala Lys Ile Ile
            100                 105                 110

Thr Phe Gly Leu Asn Asp Ile Val Phe Asp Ser Tyr Ser Ser Pro Asp
        115                 120                 125

Trp Arg Met Lys Arg Lys Val Leu Val Arg Glu Met Leu Ser His Ser
    130                 135                 140

Ser Ile Lys Ala Cys Tyr Gly Leu Arg Arg Glu Gln Val Leu Lys Gly
145                 150                 155                 160

Val Gln Asn Val Ala Gln Ser Ala Gly Lys Pro Ile Asp Phe Gly Glu
                165                 170                 175
```

```
Thr Ala Phe Leu Thr Ser Ile Asn Ala Met Met Ser Met Leu Trp Gly
            180                 185                 190

Gly Lys Gln Gly Gly Glu Arg Lys Gly Ala Asp Val Trp Gly Gln Phe
        195                 200                 205

Arg Asp Leu Ile Thr Glu Leu Met Val Ile Leu Gly Lys Pro Asn Val
    210                 215                 220

Ser Asp Ile Phe Pro Val Leu Ala Arg Phe Asp Ile Gln Gly Leu Glu
225                 230                 235                 240

Lys Glu Met Thr Lys Ile Val Asn Ser Phe Asp Lys Leu Phe Asn Ser
                245                 250                 255

Met Ile Glu Glu Arg Glu Asn Phe Ser Asn Lys Leu Ser Lys Glu Asp
            260                 265                 270

Gly Asn Thr Glu Thr Lys Asp Phe Leu Gln Leu Leu Leu Asp Leu Lys
        275                 280                 285

Gln Lys Asn Asp Ser Gly Ile Ser Ile Thr Met Asn Gln Val Lys Ala
    290                 295                 300

Leu Leu Met Asp Ile Val Val Gly Gly Thr Asp Thr Thr Ser Thr Met
305                 310                 315                 320

Met Glu Trp Thr Met Ala Glu Leu Ile Ala Asn Pro Glu Ala Met Lys
                325                 330                 335

Lys Val Lys Gln Glu Ile Asp Asp Val Val Gly Ser Asp Gly Ala Val
            340                 345                 350

Asp Glu Thr His Leu Pro Lys Leu Arg Tyr Leu Asp Ala Ala Val Lys
        355                 360                 365

Glu Thr Phe Arg Leu His Pro Pro Met Pro Leu Leu Val Pro Arg Cys
    370                 375                 380

Pro Gly Asp Ser Ser Asn Val Gly Gly Tyr Ser Val Pro Lys Gly Thr
385                 390                 395                 400

Arg Val Phe Leu Asn Ile Trp Cys Ile Gln Arg Asp Pro Gln Leu Trp
                405                 410                 415

Glu Asn Pro Leu Glu Phe Lys Pro Glu Arg Phe Leu Thr Asp His Glu
            420                 425                 430

Lys Leu Asp Tyr Leu Gly Asn Asp Ser Arg Tyr Met Pro Phe Gly Ser
        435                 440                 445

Gly Arg Arg Met Cys Ala Gly Val Ser Leu Gly Glu Lys Met Leu Tyr
    450                 455                 460

Ser Ser Leu Ala Ala Met Ile His Ala Tyr Asp Trp Asn Leu Ala Asp
465                 470                 475                 480

Gly Glu Glu Asn Asp Leu Ile Gly Leu Phe Gly Ile Ile Met Lys Lys
                485                 490                 495

Lys Lys Pro Leu Ile Leu Val Pro Thr Pro Arg Pro Ser Asn Leu Gln
            500                 505                 510

His Tyr Met Lys
        515
```

<210> SEQ ID NO 30
<211> LENGTH: 536
<212> TYPE: PRT
<213> ORGANISM: Artificial Sequence
<220> FEATURE:
<223> OTHER INFORMATION: Modified P450 monooxygenase

<400> SEQUENCE: 30

```
Met Lys Lys Thr Ala Ile Ala Ile Ala Val Ala Leu Ala Gly Phe Ala
 1               5                  10                  15
```

```
Thr Val Ala Gln Ala Leu Leu Glu Tyr Trp Tyr Val Val Val Pro Val
            20                  25                  30

Leu Tyr Ile Ile Lys Gln Leu Leu Ala Tyr Thr Lys Ile Arg Lys Pro
        35                  40                  45

Lys Lys Asp Ile Ala Pro Leu Pro Pro Gly Pro Arg Gly Leu Pro Ile
    50                  55                  60

Val Gly Tyr Leu Pro Tyr Leu Gly Thr Asp Asn Leu His Leu Val Phe
65                  70                  75                  80

Thr Asp Leu Ala Ala Ala Tyr Gly Pro Ile Tyr Lys Leu Trp Leu Gly
                85                  90                  95

Asn Lys Leu Cys Val Val Ile Ser Ser Ala Pro Leu Ala Lys Glu Val
            100                 105                 110

Val Arg Asp Asn Asp Ile Thr Phe Ser Glu Arg Asp Pro Pro Val Cys
        115                 120                 125

Ala Lys Ile Ile Thr Phe Gly Leu Asn Asp Ile Val Phe Asp Ser Tyr
    130                 135                 140

Ser Ser Pro Asp Trp Arg Met Lys Arg Lys Val Leu Val Arg Glu Met
145                 150                 155                 160

Leu Ser His Ser Ser Ile Lys Ala Cys Tyr Gly Leu Arg Arg Glu Gln
                165                 170                 175

Val Leu Lys Gly Val Gln Asn Val Ala Gln Ser Ala Gly Lys Pro Ile
            180                 185                 190

Asp Phe Gly Glu Thr Ala Phe Leu Thr Ser Ile Asn Ala Met Met Ser
        195                 200                 205

Met Leu Trp Gly Gly Lys Gln Gly Gly Glu Arg Lys Gly Ala Asp Val
    210                 215                 220

Trp Gly Gln Phe Arg Asp Leu Ile Thr Glu Leu Met Val Ile Leu Gly
225                 230                 235                 240

Lys Pro Asn Val Ser Asp Ile Phe Pro Val Leu Ala Arg Phe Asp Ile
                245                 250                 255

Gln Gly Leu Glu Lys Glu Met Thr Lys Ile Val Asn Ser Phe Asp Lys
            260                 265                 270

Leu Phe Asn Ser Met Ile Glu Glu Arg Glu Asn Phe Ser Asn Lys Leu
        275                 280                 285

Ser Lys Glu Asp Gly Asn Thr Glu Thr Lys Asp Phe Leu Gln Leu Leu
    290                 295                 300

Leu Asp Leu Lys Gln Lys Asn Asp Ser Gly Ile Ser Ile Thr Met Asn
305                 310                 315                 320

Gln Val Lys Ala Leu Leu Met Asp Ile Val Val Gly Gly Thr Asp Thr
                325                 330                 335

Thr Ser Thr Met Met Glu Trp Thr Met Ala Glu Leu Ile Ala Asn Pro
            340                 345                 350

Glu Ala Met Lys Lys Val Lys Gln Glu Ile Asp Asp Val Val Gly Ser
        355                 360                 365

Asp Gly Ala Val Asp Glu Thr His Leu Pro Lys Leu Arg Tyr Leu Asp
    370                 375                 380

Ala Ala Val Lys Glu Thr Phe Arg Leu His Pro Pro Met Pro Leu Leu
385                 390                 395                 400

Val Pro Arg Cys Pro Gly Asp Ser Ser Asn Val Gly Gly Tyr Ser Val
                405                 410                 415

Pro Lys Gly Thr Arg Val Phe Leu Asn Ile Trp Cys Ile Gln Arg Asp
            420                 425                 430

Pro Gln Leu Trp Glu Asn Pro Leu Glu Phe Lys Pro Glu Arg Phe Leu
        435                 440                 445
```

```
Thr Asp His Glu Lys Leu Asp Tyr Leu Gly Asn Asp Ser Arg Tyr Met
    450                 455                 460

Pro Phe Gly Ser Gly Arg Arg Met Cys Ala Gly Val Ser Leu Gly Glu
465                 470                 475                 480

Lys Met Leu Tyr Ser Ser Leu Ala Ala Met Ile His Ala Tyr Asp Trp
                485                 490                 495

Asn Leu Ala Asp Gly Glu Glu Asn Asp Leu Ile Gly Leu Phe Gly Ile
            500                 505                 510

Ile Met Lys Lys Lys Lys Pro Leu Ile Leu Val Pro Thr Pro Arg Pro
        515                 520                 525

Ser Asn Leu Gln His Tyr Met Lys
    530                 535


<210> SEQ ID NO 31
<211> LENGTH: 502
<212> TYPE: PRT
<213> ORGANISM: Taxus cuspidata

<400> SEQUENCE: 31

Met Asp Ala Leu Tyr Lys Ser Thr Val Ala Lys Phe Asn Glu Val Thr
 1               5                  10                  15

Gln Leu Asp Cys Ser Thr Glu Ser Phe Ser Ile Ala Leu Ser Ala Ile
            20                  25                  30

Ala Gly Ile Leu Leu Leu Leu Leu Leu Phe Arg Ser Lys Arg His Ser
        35                  40                  45

Ser Leu Lys Leu Pro Pro Gly Lys Leu Gly Ile Pro Phe Ile Gly Glu
    50                  55                  60

Ser Phe Ile Phe Leu Arg Ala Leu Arg Ser Asn Ser Leu Glu Gln Phe
65                  70                  75                  80

Phe Asp Glu Arg Val Lys Lys Phe Gly Leu Val Phe Lys Thr Ser Leu
                85                  90                  95

Ile Gly His Pro Thr Val Val Leu Cys Gly Pro Ala Gly Asn Arg Leu
            100                 105                 110

Ile Leu Ser Asn Glu Glu Lys Leu Val Gln Met Ser Trp Pro Ala Gln
        115                 120                 125

Phe Met Lys Leu Met Gly Glu Asn Ser Val Ala Thr Arg Arg Gly Glu
    130                 135                 140

Asp His Ile Val Met Arg Ser Ala Leu Ala Gly Phe Phe Gly Pro Gly
145                 150                 155                 160

Ala Leu Gln Ser Tyr Ile Gly Lys Met Asn Thr Glu Ile Gln Ser His
                165                 170                 175

Ile Asn Glu Lys Trp Lys Gly Lys Asp Glu Val Asn Val Leu Pro Leu
            180                 185                 190

Val Arg Glu Leu Val Phe Asn Ile Ser Ala Ile Leu Phe Phe Asn Ile
        195                 200                 205

Tyr Asp Lys Gln Glu Gln Asp Arg Leu His Lys Leu Leu Glu Thr Ile
    210                 215                 220

Leu Val Gly Ser Phe Ala Leu Pro Ile Asp Leu Pro Gly Phe Gly Phe
225                 230                 235                 240

His Arg Ala Leu Gln Gly Arg Ala Lys Leu Asn Lys Ile Met Leu Ser
                245                 250                 255

Leu Ile Lys Lys Arg Lys Glu Asp Leu Gln Ser Gly Ser Ala Thr Ala
            260                 265                 270

Thr Gln Asp Leu Leu Ser Val Leu Leu Thr Phe Arg Asp Asp Lys Gly
        275                 280                 285
```

```
Thr Pro Leu Thr Asn Asp Glu Ile Leu Asp Asn Phe Ser Ser Leu Leu
    290                 295                 300

His Ala Ser Tyr Asp Thr Thr Thr Ser Pro Met Ala Leu Ile Phe Lys
305                 310                 315                 320

Leu Leu Ser Ser Asn Pro Glu Cys Tyr Gln Lys Val Val Gln Glu Gln
                325                 330                 335

Leu Glu Ile Leu Ser Asn Lys Glu Glu Gly Glu Glu Ile Thr Trp Lys
            340                 345                 350

Asp Leu Lys Ala Met Lys Tyr Thr Trp Gln Val Ala Gln Glu Thr Leu
        355                 360                 365

Arg Met Phe Pro Pro Val Phe Gly Thr Phe Arg Lys Ala Ile Thr Asp
    370                 375                 380

Ile Gln Tyr Asp Gly Tyr Thr Ile Pro Lys Gly Trp Lys Leu Leu Trp
385                 390                 395                 400

Thr Thr Tyr Ser Thr His Pro Lys Asp Leu Tyr Phe Asn Glu Pro Glu
                405                 410                 415

Lys Phe Met Pro Ser Arg Phe Asp Gln Glu Gly Lys His Val Ala Pro
            420                 425                 430

Tyr Thr Phe Leu Pro Phe Gly Gly Gly Gln Arg Ser Cys Val Gly Trp
        435                 440                 445

Glu Phe Ser Lys Met Glu Ile Leu Leu Phe Val His His Phe Val Lys
    450                 455                 460

Thr Phe Ser Ser Tyr Thr Pro Val Asp Pro Asp Glu Lys Ile Ser Gly
465                 470                 475                 480

Asp Pro Leu Pro Pro Leu Pro Ser Lys Gly Phe Ser Ile Lys Leu Phe
                485                 490                 495

Pro Glu Thr Ile Val Asn
            500


<210> SEQ ID NO 32
<211> LENGTH: 502
<212> TYPE: PRT
<213> ORGANISM: Artificial Sequence
<220> FEATURE:
<223> OTHER INFORMATION: Modified taxadiene-5a-hydroxylase

<400> SEQUENCE: 32

Met Asp Ala Leu Tyr Lys Ser Thr Val Ala Lys Phe Asn Glu Val Thr
 1               5                  10                  15

Gln Leu Asp Cys Ser Thr Glu Ser Phe Ser Ile Ala Leu Ser Ser Ile
            20                  25                  30

Ala Gly Ile Leu Leu Leu Leu Leu Leu Phe Arg Ser Lys Arg His Ser
        35                  40                  45

Ser Leu Lys Leu Pro Pro Gly Lys Leu Gly Ile Pro Phe Ile Gly Glu
    50                  55                  60

Ser Phe Ile Phe Leu Arg Ala Leu Arg Ser Asn Ser Leu Glu Gln Phe
65                  70                  75                  80

Phe Asp Glu Arg Val Lys Lys Phe Gly Leu Val Phe Lys Thr Ser Leu
                85                  90                  95

Ile Gly His Pro Thr Val Val Leu Cys Gly Pro Ala Gly Asn Arg Leu
            100                 105                 110

Ile Leu Ser Asn Glu Glu Lys Leu Val Gln Met Ser Trp Pro Ala Gln
        115                 120                 125

Phe Met Lys Leu Met Gly Glu Asn Ser Val Ala Thr Arg Arg Gly Glu
    130                 135                 140
```

```
Asp His Ile Val Met Arg Ser Ala Leu Ala Gly Phe Phe Gly Pro Gly
145                 150                 155                 160

Ala Leu Gln Ser Tyr Ile Gly Lys Met Asn Thr Glu Ile Gln Asn His
                165                 170                 175

Ile Asn Glu Lys Trp Lys Gly Lys Asp Glu Val Asn Val Leu Pro Leu
            180                 185                 190

Val Arg Glu Leu Val Phe Asn Ile Ser Ala Ile Leu Phe Phe Asn Ile
        195                 200                 205

Tyr Asp Lys Gln Glu Gln Asp Arg Leu His Lys Leu Leu Glu Thr Ile
    210                 215                 220

Leu Val Gly Ser Phe Ala Leu Pro Ile Asp Leu Pro Gly Phe Gly Phe
225                 230                 235                 240

His Arg Ala Leu Gln Gly Arg Ala Thr Leu Asn Lys Ile Met Leu Ser
                245                 250                 255

Leu Ile Lys Lys Arg Lys Glu Asp Leu Gln Ser Gly Ser Ala Thr Ala
            260                 265                 270

Thr Gln Asp Leu Leu Ser Val Leu Leu Thr Phe Arg Asp Asp Lys Gly
        275                 280                 285

Thr Pro Leu Thr Asn Asp Glu Ile Leu Asp Asn Phe Ser Ser Leu Leu
    290                 295                 300

His Ala Ser Tyr Asp Thr Thr Thr Ser Pro Met Ala Leu Ile Phe Lys
305                 310                 315                 320

Leu Leu Ser Ser Asn Pro Glu Cys Tyr Gln Lys Val Val Gln Glu Gln
                325                 330                 335

Leu Glu Ile Leu Ser Asn Lys Glu Glu Gly Glu Glu Ile Thr Trp Lys
            340                 345                 350

Asp Leu Lys Ala Met Lys Tyr Thr Trp Gln Val Ala Gln Glu Thr Leu
        355                 360                 365

Arg Met Phe Pro Pro Val Phe Gly Thr Phe Arg Lys Ala Ile Thr Asp
    370                 375                 380

Ile Gln Tyr Asp Gly Tyr Thr Ile Pro Lys Gly Trp Lys Leu Leu Trp
385                 390                 395                 400

Thr Thr Tyr Ser Thr His Pro Lys Asp Leu Tyr Phe Ser Glu Pro Glu
                405                 410                 415

Lys Phe Met Pro Ser Arg Phe Asp Gln Glu Gly Lys His Val Ala Pro
            420                 425                 430

Tyr Thr Phe Leu Pro Phe Gly Gly Gly Gln Arg Ser Cys Val Gly Trp
        435                 440                 445

Glu Phe Ser Lys Met Glu Ile Leu Leu Phe Val His His Phe Val Lys
    450                 455                 460

Thr Phe Ser Ser Tyr Thr Pro Val Asp Pro Asp Glu Lys Ile Ser Gly
465                 470                 475                 480

Asp Pro Leu Pro Pro Leu Pro Ser Lys Gly Phe Ser Ile Lys Leu Phe
                485                 490                 495

Pro Glu Thr Ile Val Asn
            500


<210> SEQ ID NO 33
<211> LENGTH: 509
<212> TYPE: PRT
<213> ORGANISM: Arabidopsis thaliana

<400> SEQUENCE: 33

Met Ala Phe Phe Ser Met Ile Ser Ile Leu Leu Gly Phe Val Ile Ser
 1               5                  10                  15
```

```
Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445
```

```
Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505


<210> SEQ ID NO 34
<211> LENGTH: 1896
<212> TYPE: DNA
<213> ORGANISM: Gossypium arboreum

<400> SEQUENCE: 34

ccacttcgca gcaatattat tgcagttcct ggttggctac ctctgagttt tcaacttaaa      60

atttcttggt tttcctcaag aaggaagaag atgttgcaaa tagctttcag ctcgtattca     120

tggctgttga ctgctagcaa ccagaaagat ggaatgttgt tcccagtagc tttgtcattt     180

ttggtagcca tattgggaat ttcactgtgg cacgtatgga ccataaggaa gccaaagaaa     240

gacatcgccc cattaccgcc gggtccccgt gggttgccaa tagtgggata tcttccatat     300

cttggaactg ataatcttca cttggtgttt acagatttgg ctgcagctta cggtcccatc     360

tacaagcttt ggctaggaaa caaattatgc gtagtcatta gctcggcacc actggcgaaa     420

gaagtggttc gtgacaacga catcacattt tctgaaaggg atcctcccgt ttgtgcaaag     480

attattacct ttggcctcaa tgatattgta tttgattctt acagtagtcc agattggaga     540

atgaagagaa aagtgctggt acgtgaaatg cttagccata gtagcattaa agcttgttat     600

ggtctaagga gggaacaagt gcttaaaggc gtacaaaatg ttgctcaaag tgctggcaag     660

ccaattgatt ttggtgaaac ggcattttta acatcaatca atgcgatgat gagcatgctg     720

tggggtggca aacagggagg agagcggaaa ggggccgacg tttggggcca atttcgagat     780

ctcataaccg aactaatggt gatacttgga aaaccaaacg tttctgatat tttcccggtg     840

cttgcaaggt ttgacataca gggattggag aaggaaatga ctaaaatcgt taattctttc     900

gataagcttt tcaactccat gattgaagaa agagagaact ttagcaacaa attgagcaaa     960

gaagatggaa acactgaaac aaaagacttc ttgcagcttc tgttggacct caagcagaag    1020

aacgatagcg gaatatcgat aacaatgaat caagtcaagg ccttgctcat ggacattgtg    1080

gtcggtggaa ctgatacaac atcaaccatg atggaatgga caatggctga actaattgca    1140

aatcctgaag caatgaaaaa ggtgaagcaa gaaatagacg atgttgtcgg ttcggatggc    1200

gccgtcgatg agactcactt gcctaagttg cgctatctag atgctgcagt aaaggagacc    1260

ttccgattgc acccaccgat gccactcctt gtaccccgtt gcccgggcga ctcaagcaac    1320

gttggtggct atagcgtacc aaagggcacc agggtcttct taaacatttg gtgtattcag    1380

agggatccac agctttggga aaatccttta gaattcaagc ctgagaggtt cttgactgat    1440

catgagaagc tcgattattt aggaaacgat tcccggtaca tgccgtttgg ttctggaagg    1500

agaatgtgtg ccggagtatc tctcggtgaa aagatgttgt attcctcctt ggcagcaatg    1560

atccatgctt atgattggaa cttggccgac ggtgaagaaa atgacttgat tggcttattt    1620

ggaattatta tgaagaaaaa gaagccttta attcttgttc ctacaccaag accatcaaat    1680

ctccagcact atatgaagta actttactat tgtatttctt ttataccact ttattgcctc    1740

tttgtcatgt ttaggcaaca attctaagta ataagtttgg ctatatggtg aacaataatg    1800
```

tgtttattat acatcataag caatgagctc ttcccgaccc tagggcaata caatgatact 1860
gtgtattaag tgaaatcaac aaatctttta ttctaa 1896

<210> SEQ ID NO 35
<211> LENGTH: 1677
<212> TYPE: DNA
<213> ORGANISM: Artificial Sequence
<220> FEATURE:
<223> OTHER INFORMATION: Synthetic polynucleotide

<400> SEQUENCE: 35
atgctgcaga ttgctttttc ttcttattct tggctgctga ccgcttctaa ccagaaagac 60
ggcatgctgt tcccggtggc gctgagcttc ctggtggcaa tcctgggcat tagcctgtgg 120
cacgtgtgga ctatccgtaa accgaagaaa gatatcgcac cgctgccacc gggtccgcgt 180
ggcctgccga tcgttggcta cctgccgtat ctgggcaccg acaacctgca cctggtgttc 240
accgacctgg cagccgcgta cggtccgatc tacaaactgt ggctgggcaa taaactgtgc 300
gtagttatct cctctgctcc tctggcgaag gaggtggttc gcgacaacga catcaccttc 360
tccgaacgtg acccaccggt ctgtgctaaa atcatcacct tcggcctgaa cgacatcgta 420
ttcgactcct atagctctcc tgactggcgt atgaaacgta aggttctggt acgcgagatg 480
ctgtcccaca gctccattaa ggcatgctac ggcctgcgtc gcgaacaggt actgaaaggc 540
gtacaaaacg tagcgcagtc cgcgggcaaa ccgatcgatt tcggcgaaac ggccttcctg 600
actagcatca acgctatgat gtccatgctg tggggtggta aacagggcgg cgagcgtaaa 660
ggcgccgacg tatggggcca gtttcgtgac ctgatcaccg aactgatggt gattctgggc 720
aaaccgaacg tcagcgacat cttcccggtt ctggctcgct tcgacatcca gggcctggaa 780
aaagaaatga ccaagatcgt caactctttc gacaaactgt ttaactccat gatcgaagaa 840
cgcgaaaatt tctctaacaa actgagcaaa gaagatggca acaccgaaac taaagatttc 900
ctgcagctgc tgctggacct gaaacaaaag aacgattctg gtatctccat taccatgaac 960
caagtgaaag cgctgctgat ggacattgtt gtgggtggta ctgacaccac ttctaccatg 1020
atggaatgga cgatggcaga actgattgct aatccggaag cgatgaagaa agtgaaacaa 1080
gaaattgatg atgtagtggg ctctgatggt gcggtagacg agacgcacct gcctaagctg 1140
cgttatctgg acgcagccgt gaaagaaacc ttccgtctgc atccgcctat gccgctgctg 1200
gttccacgtt gcccaggcga ttccagcaac gttggtggct atagcgtacc gaagggtacc 1260
cgtgtgttcc tgaatatctg gtgcattcag cgcgacccgc agctgtggga aaacccgctg 1320
gagttcaaac ctgaacgctt cctgaccgac catgaaaagc tggactacct gggcaacgat 1380
tcccgttaca tgccgttcgg ttctggccgt cgtatgtgcg caggcgtctc cctgggcgag 1440
aaaatgctgt actctagcct ggctgccatg atccacgctt acgactggaa cctggcagat 1500
ggtgaagaga acgacctgat cggcctgttc ggcatcatta tgaaaaagaa aaagccgctg 1560
atcctggtgc cgactccgcg tccaagcaac ctgcagcact acatgaaact ggtgccgcgt 1620
ggctctaaag aaaccgctgc tgcaaaattc gaacgtcagc acatggacag ctaataa 1677

<210> SEQ ID NO 36
<211> LENGTH: 717
<212> TYPE: PRT
<213> ORGANISM: Taxus cuspidata

<400> SEQUENCE: 36

Met Gln Ala Asn Ser Asn Thr Val Glu Gly Ala Ser Gln Gly Lys Ser

-continued

```
1               5                   10                  15

Leu Leu Asp Ile Ser Arg Leu Asp His Ile Phe Ala Leu Leu Leu Asn
            20                  25                  30

Gly Lys Gly Gly Asp Leu Gly Ala Met Thr Gly Ser Ala Leu Ile Leu
        35                  40                  45

Thr Glu Asn Ser Gln Asn Leu Met Ile Leu Thr Thr Ala Leu Ala Val
    50                  55                  60

Leu Val Ala Cys Val Phe Phe Phe Val Trp Arg Arg Gly Gly Ser Asp
65                  70                  75                  80

Thr Gln Lys Pro Ala Val Arg Pro Thr Pro Leu Val Lys Glu Glu Asp
                85                  90                  95

Glu Glu Glu Glu Asp Asp Ser Ala Lys Lys Lys Val Thr Ile Phe Phe
            100                 105                 110

Gly Thr Gln Thr Gly Thr Ala Glu Gly Phe Ala Lys Ala Leu Ala Glu
        115                 120                 125

Glu Ala Lys Ala Arg Tyr Glu Lys Ala Val Phe Lys Val Val Asp Leu
    130                 135                 140

Asp Asn Tyr Ala Ala Asp Asp Glu Gln Tyr Glu Glu Lys Leu Lys Lys
145                 150                 155                 160

Glu Lys Leu Ala Phe Phe Met Leu Ala Thr Tyr Gly Asp Gly Glu Pro
                165                 170                 175

Thr Asp Asn Ala Ala Arg Phe Tyr Lys Trp Phe Leu Glu Gly Lys Glu
            180                 185                 190

Arg Glu Pro Trp Leu Ser Asp Leu Thr Tyr Gly Val Phe Gly Leu Gly
        195                 200                 205

Asn Arg Gln Tyr Glu His Phe Asn Lys Val Ala Lys Ala Val Asp Glu
    210                 215                 220

Val Leu Ile Glu Gln Gly Ala Lys Arg Leu Val Pro Val Gly Leu Gly
225                 230                 235                 240

Asp Asp Asp Gln Cys Ile Glu Asp Asp Phe Thr Ala Trp Arg Glu Gln
                245                 250                 255

Val Trp Pro Glu Leu Asp Gln Leu Leu Arg Asp Glu Asp Asp Glu Pro
            260                 265                 270

Thr Ser Ala Thr Pro Tyr Thr Ala Ala Ile Pro Glu Tyr Arg Val Glu
        275                 280                 285

Ile Tyr Asp Ser Val Val Ser Val Tyr Glu Glu Thr His Ala Leu Lys
    290                 295                 300

Gln Asn Gly Gln Ala Val Tyr Asp Ile His His Pro Cys Arg Ser Asn
305                 310                 315                 320

Val Ala Val Arg Arg Glu Leu His Thr Pro Leu Ser Asp Arg Ser Cys
                325                 330                 335

Ile His Leu Glu Phe Asp Ile Ser Asp Thr Gly Leu Ile Tyr Glu Thr
            340                 345                 350

Gly Asp His Val Gly Val His Thr Glu Asn Ser Ile Glu Thr Val Glu
        355                 360                 365

Glu Ala Ala Lys Leu Leu Gly Tyr Gln Leu Asp Thr Ile Phe Ser Val
    370                 375                 380

His Gly Asp Lys Glu Asp Gly Thr Pro Leu Gly Gly Ser Ser Leu Pro
385                 390                 395                 400

Pro Pro Phe Pro Gly Pro Cys Thr Leu Arg Thr Ala Leu Ala Arg Tyr
                405                 410                 415

Ala Asp Leu Leu Asn Pro Pro Arg Lys Ala Ala Phe Leu Ala Leu Ala
            420                 425                 430
```

```
Ala His Ala Ser Asp Pro Ala Glu Ala Glu Arg Leu Lys Phe Leu Ser
        435                 440                 445

Ser Pro Ala Gly Lys Asp Glu Tyr Ser Gln Trp Val Thr Ala Ser Gln
    450                 455                 460

Arg Ser Leu Leu Glu Ile Met Ala Glu Phe Pro Ser Ala Lys Pro Pro
465                 470                 475                 480

Leu Gly Val Phe Phe Ala Ala Ile Ala Pro Arg Leu Gln Pro Arg Tyr
                485                 490                 495

Tyr Ser Ile Ser Ser Ser Pro Arg Phe Ala Pro Ser Arg Ile His Val
            500                 505                 510

Thr Cys Ala Leu Val Tyr Gly Pro Ser Pro Thr Gly Arg Ile His Lys
        515                 520                 525

Gly Val Cys Ser Asn Trp Met Lys Asn Ser Leu Pro Ser Glu Glu Thr
    530                 535                 540

His Asp Cys Ser Trp Ala Pro Val Phe Val Arg Gln Ser Asn Phe Lys
545                 550                 555                 560

Leu Pro Ala Asp Ser Thr Thr Pro Ile Val Met Val Gly Pro Gly Thr
                565                 570                 575

Gly Phe Ala Pro Phe Arg Gly Phe Leu Gln Glu Arg Ala Lys Leu Gln
            580                 585                 590

Glu Ala Gly Glu Lys Leu Gly Pro Ala Val Leu Phe Phe Gly Cys Arg
        595                 600                 605

Asn Arg Gln Met Asp Tyr Ile Tyr Glu Asp Glu Leu Lys Gly Tyr Val
    610                 615                 620

Glu Lys Gly Ile Leu Thr Asn Leu Ile Val Ala Phe Ser Arg Glu Gly
625                 630                 635                 640

Ala Thr Lys Glu Tyr Val Gln His Lys Met Leu Glu Lys Ala Ser Asp
                645                 650                 655

Thr Trp Ser Leu Ile Ala Gln Gly Gly Tyr Leu Tyr Val Cys Gly Asp
            660                 665                 670

Ala Lys Gly Met Ala Arg Asp Val His Arg Thr Leu His Thr Ile Val
        675                 680                 685

Gln Glu Gln Glu Ser Val Asp Ser Ser Lys Ala Glu Phe Leu Val Lys
    690                 695                 700

Lys Leu Gln Met Asp Gly Arg Tyr Leu Arg Asp Ile Trp
705                 710                 715
```

<210> SEQ ID NO 37
<211> LENGTH: 680
<212> TYPE: PRT
<213> ORGANISM: Candida tropicalis

<400> SEQUENCE: 37

```
Met Ala Leu Asp Lys Leu Asp Leu Tyr Val Ile Ile Thr Leu Val Val
 1               5                  10                  15

Ala Ile Ala Ala Tyr Phe Ala Lys Asn Gln Phe Leu Asp Gln Gln Gln
            20                  25                  30

Asp Thr Gly Phe Leu Asn Thr Asp Ser Gly Asp Gly Asn Ser Arg Asp
        35                  40                  45

Ile Leu Gln Ala Leu Lys Lys Asn Asn Lys Asn Thr Leu Leu Leu Phe
    50                  55                  60

Gly Ser Gln Thr Gly Thr Ala Glu Asp Tyr Ala Asn Lys Leu Ser Arg
65                  70                  75                  80

Glu Leu His Ser Arg Phe Gly Leu Lys Thr Met Val Ala Asp Phe Ala
                85                  90                  95
```

```
Asp Tyr Asp Phe Glu Asn Phe Gly Asp Ile Thr Glu Asp Ile Leu Val
            100                 105                 110

Phe Phe Ile Val Ala Thr Tyr Gly Glu Gly Glu Pro Thr Asp Asn Ala
        115                 120                 125

Asp Glu Phe His Thr Trp Leu Thr Glu Glu Ala Asp Thr Leu Ser Thr
    130                 135                 140

Leu Lys Tyr Thr Val Phe Gly Leu Gly Asn Ser Thr Tyr Glu Phe Phe
145                 150                 155                 160

Asn Ala Ile Gly Arg Lys Phe Asp Arg Leu Leu Gly Glu Lys Gly Gly
                165                 170                 175

Asp Arg Phe Ala Glu Tyr Gly Glu Gly Asp Asp Gly Thr Gly Thr Leu
            180                 185                 190

Asp Glu Asp Phe Leu Ala Trp Lys Asp Asn Val Phe Asp Ser Leu Lys
        195                 200                 205

Asn Asp Leu Asn Phe Glu Glu Lys Glu Leu Lys Tyr Glu Pro Asn Val
    210                 215                 220

Lys Leu Thr Glu Arg Asp Asp Leu Ser Gly Asn Asp Pro Asp Val Ser
225                 230                 235                 240

Leu Gly Glu Pro Asn Val Lys Tyr Ile Lys Ser Glu Gly Val Asp Leu
                245                 250                 255

Thr Lys Gly Pro Phe Asp His Thr His Pro Phe Leu Ala Arg Ile Val
            260                 265                 270

Lys Thr Lys Glu Leu Phe Thr Ser Glu Asp Arg His Cys Val His Val
        275                 280                 285

Glu Phe Asp Ile Ser Glu Ser Asn Leu Lys Tyr Thr Thr Gly Asp His
    290                 295                 300

Leu Ala Ile Trp Pro Ser Asn Ser Asp Glu Asn Ile Lys Gln Phe Ala
305                 310                 315                 320

Lys Cys Phe Gly Leu Glu Asp Lys Leu Asp Thr Val Ile Glu Leu Lys
                325                 330                 335

Ala Leu Asp Ser Thr Tyr Ser Ile Pro Phe Pro Asn Pro Ile Thr Tyr
            340                 345                 350

Gly Ala Val Ile Arg His His Leu Glu Ile Ser Gly Pro Val Ser Arg
        355                 360                 365

Gln Phe Phe Leu Ser Ile Ala Gly Phe Ala Pro Asp Glu Glu Thr Lys
    370                 375                 380

Lys Ser Phe Thr Arg Ile Gly Gly Asp Lys Gln Glu Phe Ala Ser Lys
385                 390                 395                 400

Val Thr Arg Arg Lys Phe Asn Ile Ala Asp Ala Leu Leu Phe Ala Ser
                405                 410                 415

Asn Asn Arg Pro Trp Ser Asp Val Pro Phe Glu Phe Leu Ile Glu Asn
            420                 425                 430

Val Gln His Leu Thr Pro Arg Tyr Tyr Ser Ile Ser Ser Ser Ser Leu
        435                 440                 445

Ser Glu Lys Gln Thr Ile Asn Val Thr Ala Val Val Glu Ala Glu Glu
    450                 455                 460

Glu Ala Asp Gly Arg Pro Val Thr Gly Val Val Thr Asn Leu Leu Lys
465                 470                 475                 480

Asn Ile Glu Ile Glu Gln Asn Lys Thr Gly Glu Thr Pro Met Val His
                485                 490                 495

Tyr Asp Leu Asn Gly Pro Arg Gly Lys Phe Ser Lys Phe Arg Leu Pro
            500                 505                 510

Val His Val Arg Arg Ser Asn Phe Lys Leu Pro Lys Asn Ser Thr Thr
        515                 520                 525
```

```
Pro Val Ile Leu Ile Gly Pro Gly Thr Gly Val Ala Pro Leu Arg Gly
    530                 535                 540

Phe Val Arg Glu Arg Val Gln Gln Val Lys Asn Gly Val Asn Val Gly
545                 550                 555                 560

Lys Thr Val Leu Phe Tyr Gly Cys Arg Asn Ser Glu Gln Asp Phe Leu
                565                 570                 575

Tyr Lys Gln Glu Trp Ser Glu Tyr Ala Ser Val Leu Gly Glu Asn Phe
            580                 585                 590

Glu Met Phe Asn Ala Phe Ser Arg Gln Asp Pro Thr Lys Lys Val Tyr
        595                 600                 605

Val Gln Asp Lys Ile Leu Glu Asn Ser Ala Leu Val Asp Glu Leu Leu
    610                 615                 620

Ser Ser Gly Ala Ile Ile Tyr Val Cys Gly Asp Ala Ser Arg Met Ala
625                 630                 635                 640

Arg Asp Val Gln Ala Ala Ile Ala Lys Ile Val Ala Lys Ser Arg Asp
                645                 650                 655

Ile His Glu Asp Lys Ala Ala Glu Leu Val Lys Ser Trp Lys Val Gln
            660                 665                 670

Asn Arg Tyr Gln Glu Asp Val Trp
        675                 680


<210> SEQ ID NO 38
<211> LENGTH: 692
<212> TYPE: PRT
<213> ORGANISM: Arabidopsis thaliana

<400> SEQUENCE: 38

Met Thr Ser Ala Leu Tyr Ala Ser Asp Leu Phe Lys Gln Leu Lys Ser
 1               5                  10                  15

Ile Met Gly Thr Asp Ser Leu Ser Asp Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Asp Gln Ser Ile Glu
    210                 215                 220
```

```
Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
```

```
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690


<210> SEQ ID NO 39
<211> LENGTH: 712
<212> TYPE: PRT
<213> ORGANISM: Arabidopsis thaliana

<400> SEQUENCE: 39

Met Ser Ser Ser Ser Ser Ser Ser Thr Ser Met Ile Asp Leu Met Ala
 1               5                  10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Thr Leu Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
```

```
                325                 330                 335

Phe Asp Ile Ala Gly Ser Gly Leu Thr Met Lys Leu Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Lys Leu Phe Leu Gly
    530                 535                 540

Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710
```

<210> SEQ ID NO 40
<211> LENGTH: 667
<212> TYPE: PRT
<213> ORGANISM: Arabidopsis thaliana

<400> SEQUENCE: 40

Met Leu Ile Glu Asn Arg Gln Phe Ala Met Ile Val Thr Thr Ser Ile
1 5 10 15

Ala Val Leu Ile Gly Cys Ile Val Met Leu Val Trp Arg Arg Ser Gly
20 25 30

Ser Gly Asn Ser Lys Arg Val Glu Pro Leu Lys Pro Leu Val Ile Lys
35 40 45

Pro Arg Glu Glu Glu Ile Asp Asp Gly Arg Lys Lys Val Thr Ile Phe
50 55 60

Phe Gly Thr Gln Thr Gly Thr Ala Glu Gly Phe Ala Lys Ala Leu Gly
65 70 75 80

Glu Glu Ala Lys Ala Arg Tyr Glu Lys Thr Arg Phe Lys Ile Val Asp
85 90 95

Leu Asp Asp Tyr Ala Ala Asp Asp Asp Glu Tyr Glu Glu Lys Leu Lys
100 105 110

Lys Glu Asp Val Ala Phe Phe Phe Leu Ala Thr Tyr Gly Asp Gly Glu
115 120 125

Pro Thr Asp Asn Ala Ala Arg Phe Tyr Lys Trp Phe Thr Glu Gly Asn
130 135 140

Asp Arg Gly Glu Trp Leu Lys Asn Leu Lys Tyr Gly Val Phe Gly Leu
145 150 155 160

Gly Asn Arg Gln Tyr Glu His Phe Asn Lys Val Ala Lys Val Val Asp
165 170 175

Asp Ile Leu Val Glu Gln Gly Ala Gln Arg Leu Val Gln Val Gly Leu
180 185 190

Gly Asp Asp Asp Gln Cys Ile Glu Asp Asp Phe Thr Ala Trp Arg Glu
195 200 205

Ala Leu Trp Pro Glu Leu Asp Thr Ile Leu Arg Glu Glu Gly Asp Thr
210 215 220

Ala Val Ala Thr Pro Tyr Thr Ala Ala Val Leu Glu Tyr Arg Val Ser
225 230 235 240

Ile His Asp Ser Glu Asp Ala Lys Phe Asn Asp Ile Asn Met Ala Asn
245 250 255

Gly Asn Gly Tyr Thr Val Phe Asp Ala Gln His Pro Tyr Lys Ala Asn
260 265 270

Val Ala Val Lys Arg Glu Leu His Thr Pro Glu Ser Asp Arg Ser Cys
275 280 285

Ile His Leu Glu Phe Asp Ile Ala Gly Ser Gly Leu Thr Tyr Glu Thr
290 295 300

Gly Asp His Val Gly Val Leu Cys Asp Asn Leu Ser Glu Thr Val Asp
305 310 315 320

Glu Ala Leu Arg Leu Leu Asp Met Ser Pro Asp Thr Tyr Phe Ser Leu
325 330 335

His Ala Glu Lys Glu Asp Gly Thr Pro Ile Ser Ser Ser Leu Pro Pro
340 345 350

Pro Phe Pro Pro Cys Asn Leu Arg Thr Ala Leu Thr Arg Tyr Ala Cys
355 360 365

Leu Leu Ser Ser Pro Lys Lys Ser Ala Leu Val Ala Leu Ala Ala His
370 375 380

Ala Ser Asp Pro Thr Glu Ala Glu Arg Leu Lys His Leu Ala Ser Pro
385 390 395 400

Ala Gly Lys Asp Glu Tyr Ser Lys Trp Val Val Glu Ser Gln Arg Ser
405 410 415

```
Leu Leu Glu Val Met Ala Glu Phe Pro Ser Ala Lys Pro Pro Leu Gly
            420                 425                 430

Val Phe Phe Ala Gly Val Ala Pro Arg Leu Gln Pro Arg Phe Tyr Ser
        435                 440                 445

Ile Ser Ser Ser Pro Lys Ile Ala Glu Thr Arg Ile His Val Thr Cys
    450                 455                 460

Ala Leu Val Tyr Glu Lys Met Pro Thr Gly Arg Ile His Lys Gly Val
465                 470                 475                 480

Cys Ser Thr Trp Met Lys Asn Ala Val Pro Tyr Glu Lys Ser Glu Asn
                485                 490                 495

Cys Ser Ser Ala Pro Ile Phe Val Arg Gln Ser Asn Phe Lys Leu Pro
            500                 505                 510

Ser Asp Ser Lys Val Pro Ile Ile Met Ile Gly Pro Gly Thr Gly Leu
        515                 520                 525

Ala Pro Phe Arg Gly Phe Leu Gln Glu Arg Leu Ala Leu Val Glu Ser
    530                 535                 540

Gly Val Glu Leu Gly Pro Ser Val Leu Phe Phe Gly Cys Arg Asn Arg
545                 550                 555                 560

Arg Met Asp Phe Ile Tyr Glu Glu Glu Leu Gln Arg Phe Val Glu Ser
                565                 570                 575

Gly Ala Leu Ala Glu Leu Ser Val Ala Phe Ser Arg Glu Gly Pro Thr
            580                 585                 590

Lys Glu Tyr Val Gln His Lys Met Met Asp Lys Ala Ser Asp Ile Trp
        595                 600                 605

Asn Met Ile Ser Gln Gly Ala Tyr Leu Tyr Val Cys Gly Asp Ala Lys
    610                 615                 620

Gly Met Ala Arg Asp Val His Arg Ser Leu His Thr Ile Ala Gln Glu
625                 630                 635                 640

Gln Gly Ser Met Asp Ser Thr Lys Ala Glu Gly Phe Val Lys Asn Leu
                645                 650                 655

Gln Thr Ser Gly Arg Tyr Leu Arg Asp Val Trp
            660                 665


<210> SEQ ID NO 41
<211> LENGTH: 560
<212> TYPE: PRT
<213> ORGANISM: Eschscholzia stolonifera

<400> SEQUENCE: 41

Met Glu Lys Pro Ile Leu Leu Gln Leu Gln Ala Gly Ile Leu Gly Leu
1               5                   10                  15

Leu Ala Leu Ile Cys Phe Leu Tyr Tyr Val Ile Lys Val Ser Leu Ser
            20                  25                  30

Thr Arg Asn Cys Asn Gln Leu Val Lys His Pro Pro Glu Ala Ala Gly
        35                  40                  45

Ser Trp Pro Ile Val Gly His Leu Pro Gln Leu Val Gly Ser Gly Lys
    50                  55                  60

Pro Leu Phe Arg Val Leu Gly Asp Met Ala Asp Lys Phe Gly Pro Ile
65                  70                  75                  80

Phe Met Val Arg Phe Gly Val Tyr Pro Thr Leu Val Val Ser Thr Trp
                85                  90                  95

Glu Met Ala Lys Glu Cys Phe Thr Ser Asn Asp Lys Phe Leu Ala Ser
            100                 105                 110

Arg Pro Pro Ser Ala Ala Ser Ser Tyr Met Thr Tyr Asp His Ala Met
        115                 120                 125
```

```
Phe Gly Phe Ser Phe Tyr Gly Pro Tyr Trp Arg Glu Ile Arg Lys Ile
    130                 135                 140

Ser Thr Leu His Leu Leu Ser His Arg Arg Leu Glu Leu Leu Lys His
145                 150                 155                 160

Val Pro His Thr Glu Ile His Asn Phe Ile Lys Gly Leu Phe Gly Ile
                165                 170                 175

Trp Lys Asp His Gln Lys Gln Gln Gln Pro Thr Gly Arg Glu Asp Arg
            180                 185                 190

Asp Ser Val Met Leu Glu Met Ser Gln Leu Phe Gly Tyr Leu Thr Leu
        195                 200                 205

Asn Val Val Leu Ser Leu Val Val Gly Lys Arg Val Cys Asn Tyr His
    210                 215                 220

Ala Asp Gly His Leu Asp Asp Gly Glu Glu Ala Gly Gln Gly Gln Lys
225                 230                 235                 240

Leu His Gln Thr Ile Thr Asp Phe Phe Lys Leu Ser Gly Val Ser Val
                245                 250                 255

Ala Ser Asp Ala Leu Pro Leu Leu Gly Leu Phe Asp Leu Gly Gly Lys
            260                 265                 270

Lys Glu Ser Met Lys Arg Val Ala Lys Glu Met Asp Phe Phe Ala Glu
        275                 280                 285

Arg Trp Leu Gln Asp Lys Lys Leu Ser Leu Ser Leu Ser Ser Glu Thr
    290                 295                 300

Asn Asn Lys Gln Asn Asp Ala Gly Glu Gly Asp Gly Asp Asp Phe Met
305                 310                 315                 320

Asp Val Leu Met Ser Ile Leu Pro Asp Asp Asp Asp Ser Leu Phe Thr
                325                 330                 335

Lys Tyr Ser Arg Asp Thr Val Ile Lys Ala Thr Ser Leu Ser Met Val
            340                 345                 350

Val Ala Ala Ser Asp Thr Thr Ser Val Ser Leu Thr Trp Ala Leu Ser
        355                 360                 365

Leu Leu Leu Asn Asn Ile Gln Val Leu Arg Lys Ala Gln Asp Glu Leu
    370                 375                 380

Asp Thr Lys Val Gly Arg Asp Arg His Val Glu Glu Lys Asp Ile Asp
385                 390                 395                 400

Asn Leu Val Tyr Leu Gln Ala Ile Val Lys Glu Thr Leu Arg Met Tyr
                405                 410                 415

Pro Ala Gly Pro Leu Ser Val Pro His Glu Ala Ile Glu Asp Cys Asn
            420                 425                 430

Val Gly Gly Tyr His Ile Lys Thr Gly Thr Arg Leu Leu Val Asn Ile
        435                 440                 445

Trp Lys Leu Gln Arg Asp Pro Arg Val Trp Ser Asn Pro Ser Glu Phe
    450                 455                 460

Arg Pro Glu Arg Phe Leu Asp Asn Gln Ser Asn Gly Thr Leu Leu Asp
465                 470                 475                 480

Phe Arg Gly Gln His Phe Glu Tyr Ile Pro Phe Gly Ser Gly Arg Arg
                485                 490                 495

Met Cys Pro Gly Val Asn Phe Ala Thr Leu Ile Leu His Met Thr Leu
            500                 505                 510

Ala Arg Leu Leu Gln Ala Phe Asp Leu Ser Thr Pro Ser Ser Ser Pro
        515                 520                 525

Val Asp Met Thr Glu Gly Ser Gly Leu Thr Met Pro Lys Val Thr Pro
    530                 535                 540

Leu Lys Val Leu Leu Thr Pro Arg Leu Pro Leu Pro Leu Tyr Asp Tyr
545                 550                 555                 560
```

<210> SEQ ID NO 42
<211> LENGTH: 493
<212> TYPE: PRT
<213> ORGANISM: Catharanthus roseus

<400> SEQUENCE: 42

```
Met Asp Tyr Leu Thr Ile Ile Leu Thr Leu Leu Phe Ala Leu Thr Leu
 1               5                  10                  15

Tyr Glu Ala Phe Ser Tyr Leu Ser Arg Arg Thr Lys Asn Leu Pro Pro
            20                  25                  30

Gly Pro Ser Pro Leu Pro Phe Ile Gly Ser Leu His Leu Leu Gly Asp
        35                  40                  45

Gln Pro His Lys Ser Leu Ala Lys Leu Ser Lys Lys His Gly Pro Ile
    50                  55                  60

Met Ser Leu Lys Leu Gly Gln Ile Thr Thr Ile Val Ile Ser Ser Ser
65                  70                  75                  80

Thr Met Ala Lys Glu Val Leu Gln Lys Gln Asp Leu Ala Phe Ser Ser
                85                  90                  95

Arg Ser Val Pro Asn Ala Leu His Ala His Asn Gln Phe Lys Phe Ser
            100                 105                 110

Val Val Trp Leu Pro Val Ala Ser Arg Trp Arg Ser Leu Arg Lys Val
        115                 120                 125

Leu Asn Ser Asn Ile Phe Ser Gly Asn Arg Leu Asp Ala Asn Gln His
    130                 135                 140

Leu Arg Thr Arg Lys Val Gln Glu Leu Ile Ala Tyr Cys Arg Lys Asn
145                 150                 155                 160

Ser Gln Ser Gly Glu Ala Val Asp Val Gly Arg Ala Ala Phe Arg Thr
                165                 170                 175

Ser Leu Asn Leu Leu Ser Asn Leu Ile Phe Ser Lys Asp Leu Thr Asp
            180                 185                 190

Pro Tyr Ser Asp Ser Ala Lys Glu Phe Lys Asp Leu Val Trp Asn Ile
        195                 200                 205

Met Val Glu Ala Gly Lys Pro Asn Leu Val Asp Phe Phe Pro Leu Leu
    210                 215                 220

Glu Lys Val Asp Pro Gln Gly Ile Arg His Arg Met Thr Ile His Phe
225                 230                 235                 240

Gly Glu Val Leu Lys Leu Phe Gly Gly Leu Val Asn Glu Arg Leu Glu
                245                 250                 255

Gln Arg Arg Ser Lys Gly Glu Lys Asn Asp Val Leu Asp Val Leu Leu
            260                 265                 270

Thr Thr Ser Gln Glu Ser Pro Glu Glu Ile Asp Arg Thr His Ile Glu
        275                 280                 285

Arg Met Cys Leu Asp Leu Phe Val Ala Gly Thr Asp Thr Thr Ser Ser
    290                 295                 300

Thr Leu Glu Trp Ala Met Ser Glu Met Leu Lys Asn Pro Asp Lys Met
305                 310                 315                 320

Lys Lys Thr Gln Asp Glu Leu Ala Gln Val Ile Gly Arg Gly Lys Thr
                325                 330                 335

Ile Glu Glu Ser Asp Ile Asn Arg Leu Pro Tyr Leu Arg Cys Val Met
            340                 345                 350

Lys Glu Thr Leu Arg Ile His Pro Pro Val Pro Phe Leu Ile Pro Arg
        355                 360                 365

Lys Val Glu Gln Ser Val Glu Val Cys Gly Tyr Asn Val Pro Lys Gly
    370                 375                 380
```

```
Ser Gln Val Leu Val Asn Ala Trp Ala Ile Gly Arg Asp Glu Thr Val
385                 390                 395                 400

Trp Asp Asp Ala Leu Ala Phe Lys Pro Glu Arg Phe Met Glu Ser Glu
                405                 410                 415

Leu Asp Ile Arg Gly Arg Asp Phe Glu Leu Ile Pro Phe Gly Ala Gly
            420                 425                 430

Arg Arg Ile Cys Pro Gly Leu Pro Leu Ala Leu Arg Thr Val Pro Leu
        435                 440                 445

Met Leu Gly Ser Leu Leu Asn Ser Phe Asn Trp Lys Leu Glu Gly Gly
    450                 455                 460

Met Ala Pro Lys Asp Leu Asp Met Glu Glu Lys Phe Gly Ile Thr Leu
465                 470                 475                 480

Gln Lys Ala His Pro Leu Arg Ala Val Pro Ser Thr Leu
                485                 490


<210> SEQ ID NO 43
<211> LENGTH: 496
<212> TYPE: PRT
<213> ORGANISM: Catharanthus roseus

<400> SEQUENCE: 43

Met Leu Leu Phe Cys Phe Ile Leu Ser Lys Thr Thr Lys Lys Phe Gly
 1               5                  10                  15

Gln Asn Ser Gln Tyr Ser Asn His Asp Glu Leu Pro Pro Gly Pro Pro
            20                  25                  30

Gln Ile Pro Ile Leu Gly Asn Ala His Gln Leu Ser Gly Gly His Thr
        35                  40                  45

His His Ile Leu Arg Asp Leu Ala Lys Lys Tyr Gly Pro Leu Met His
    50                  55                  60

Leu Lys Ile Gly Glu Val Ser Thr Ile Val Ala Ser Ser Pro Gln Ile
65                  70                  75                  80

Ala Glu Glu Ile Phe Arg Thr His Asp Ile Leu Phe Ala Asp Arg Pro
                85                  90                  95

Ser Asn Leu Glu Ser Phe Lys Ile Val Ser Tyr Asp Phe Ser Asp Met
            100                 105                 110

Val Val Ser Pro Tyr Gly Asn Tyr Trp Arg Gln Leu Arg Lys Ile Ser
        115                 120                 125

Met Met Glu Leu Leu Ser Gln Lys Ser Val Gln Ser Phe Arg Ser Ile
    130                 135                 140

Arg Glu Glu Glu Val Leu Asn Phe Ile Lys Ser Ile Gly Ser Lys Glu
145                 150                 155                 160

Gly Thr Arg Ile Asn Leu Ser Lys Glu Ile Ser Leu Leu Ile Tyr Gly
                165                 170                 175

Ile Thr Thr Arg Ala Ala Phe Gly Glu Lys Asn Lys Asn Thr Glu Glu
            180                 185                 190

Phe Ile Arg Leu Leu Asp Gln Leu Thr Lys Ala Val Ala Glu Pro Asn
        195                 200                 205

Ile Ala Asp Met Phe Pro Ser Leu Lys Phe Leu Gln Leu Ile Ser Thr
    210                 215                 220

Ser Lys Tyr Lys Ile Glu Lys Ile His Lys Gln Phe Asp Val Ile Val
225                 230                 235                 240

Glu Thr Ile Leu Lys Gly His Lys Glu Lys Ile Asn Lys Pro Leu Ser
                245                 250                 255

Gln Glu Asn Gly Glu Lys Lys Glu Asp Leu Val Asp Val Leu Leu Asn
            260                 265                 270
```

```
Ile Gln Arg Arg Asn Asp Phe Glu Ala Pro Leu Gly Asp Lys Asn Ile
        275                 280                 285

Lys Ala Ile Ile Phe Asn Ile Phe Ser Ala Gly Thr Glu Thr Ser Ser
    290                 295                 300

Thr Thr Val Asp Trp Ala Met Cys Glu Met Ile Lys Asn Pro Thr Val
305                 310                 315                 320

Met Lys Lys Ala Gln Glu Glu Val Arg Lys Val Phe Asn Glu Glu Gly
                325                 330                 335

Asn Val Asp Glu Thr Lys Leu His Gln Leu Lys Tyr Leu Gln Ala Val
            340                 345                 350

Ile Lys Glu Thr Leu Arg Leu His Pro Pro Val Pro Leu Leu Leu Pro
        355                 360                 365

Arg Glu Cys Arg Glu Gln Cys Lys Ile Lys Gly Tyr Thr Ile Pro Ser
    370                 375                 380

Lys Ser Arg Val Ile Val Asn Ala Trp Ala Ile Gly Arg Asp Pro Asn
385                 390                 395                 400

Tyr Trp Ile Glu Pro Glu Lys Phe Asn Pro Asp Arg Phe Leu Glu Ser
                405                 410                 415

Lys Val Asp Phe Lys Gly Asn Ser Phe Glu Tyr Leu Pro Phe Gly Gly
            420                 425                 430

Gly Arg Arg Ile Cys Pro Gly Ile Thr Phe Ala Leu Ala Asn Ile Glu
        435                 440                 445

Leu Pro Leu Ala Gln Leu Leu Phe His Phe Asp Trp Gln Ser Asn Thr
    450                 455                 460

Glu Lys Leu Asn Met Lys Glu Ser Arg Gly Val Thr Val Arg Arg Glu
465                 470                 475                 480

Asp Asp Leu Tyr Leu Thr Pro Val Asn Phe Ser Ser Ser Ser Pro Ala
                485                 490                 495


<210> SEQ ID NO 44
<211> LENGTH: 505
<212> TYPE: PRT
<213> ORGANISM: Arabidopsis thaliana

<400> SEQUENCE: 44

Met Asp Leu Leu Leu Leu Glu Lys Ser Leu Ile Ala Val Phe Val Ala
 1               5                  10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
        35                  40                  45

Val Gly Asp Asp Leu Asn His Arg Asn Leu Val Asp Tyr Ala Lys Lys
    50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu Leu Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Asn Arg Glu Gly Trp Glu Phe Glu Ala Ala Ser Val Val Glu Asp
145                 150                 155                 160
```

```
Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Arg Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
                245                 250                 255

Phe Val Asp Glu Arg Lys Gln Ile Ala Ser Ser Lys Pro Thr Gly Ser
            260                 265                 270

Glu Gly Leu Lys Cys Ala Ile Asp His Ile Leu Glu Ala Glu Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
                325                 330                 335

Asp Thr Val Leu Gly Pro Gly Val Gln Val Thr Glu Pro Asp Leu His
            340                 345                 350

Lys Leu Pro Tyr Leu Gln Ala Val Val Lys Glu Thr Leu Arg Leu Arg
        355                 360                 365

Met Ala Ile Pro Leu Leu Val Pro His Met Asn Leu His Asp Ala Lys
    370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
                405                 410                 415

Arg Pro Glu Arg Phe Phe Glu Glu Glu Ser His Val Glu Ala Asn Gly
            420                 425                 430

Asn Asp Phe Arg Tyr Val Pro Phe Gly Val Gly Arg Arg Ser Cys Pro
        435                 440                 445

Gly Ile Ile Leu Ala Leu Pro Ile Leu Gly Ile Thr Ile Gly Arg Met
    450                 455                 460

Val Gln Asn Phe Glu Leu Leu Pro Pro Pro Gly Gln Ser Lys Val Asp
465                 470                 475                 480

Thr Ser Glu Lys Gly Gly Gln Phe Ser Leu His Ile Leu Asn His Ser
                485                 490                 495

Ile Ile Val Met Lys Pro Arg Asn Cys
            500                 505


<210> SEQ ID NO 45
<211> LENGTH: 512
<212> TYPE: PRT
<213> ORGANISM: Ocimum basilicum

<400> SEQUENCE: 45

Met Ala Ala Leu Leu Leu Leu Leu Leu Leu Pro Leu Leu Leu Pro Ala
 1               5                  10                  15

Ile Phe Leu Leu His His Leu Tyr Tyr Arg Leu Arg Phe Arg Leu Pro
            20                  25                  30
```

```
Pro Gly Pro Arg Pro Leu Pro Ile Val Gly Asn Leu Tyr Asp Val Lys
        35                  40                  45

Pro Val Arg Phe Arg Cys Phe Ala Asp Trp Ala Gln Ser Tyr Gly Pro
    50                  55                  60

Ile Ile Ser Val Trp Phe Gly Ser Thr Leu Asn Val Ile Val Ser Asn
65                  70                  75                  80

Thr Glu Leu Ala Lys Glu Val Leu Lys Glu Lys Asp Gln Gln Leu Ala
                85                  90                  95

Asp Arg His Arg Ser Arg Ser Ala Ala Lys Phe Ser Arg Asp Gly Gln
            100                 105                 110

Asp Leu Ile Trp Ala Asp Tyr Gly Pro His Tyr Val Lys Val Arg Lys
        115                 120                 125

Val Cys Thr Leu Glu Leu Phe Ser Pro Lys Arg Leu Glu Ala Leu Arg
    130                 135                 140

Pro Ile Arg Glu Asp Glu Val Thr Ala Met Val Glu Ser Ile Tyr His
145                 150                 155                 160

Asp Cys Thr Ala Pro Asp Asn Ala Gly Lys Ser Leu Leu Val Lys Lys
                165                 170                 175

Tyr Leu Gly Ala Val Ala Phe Asn Asn Ile Thr Arg Leu Ala Phe Gly
            180                 185                 190

Lys Arg Phe Val Asn Ser Glu Gly Ile Ile Asp Lys Gln Gly Leu Glu
        195                 200                 205

Phe Lys Ala Ile Val Ser Asn Gly Leu Lys Leu Gly Ala Ser Leu Ala
    210                 215                 220

Met Ala Glu His Ile Pro Ser Leu Arg Trp Met Phe Pro Leu Asp Glu
225                 230                 235                 240

Asp Ala Phe Ala Lys His Gly Ala Arg Arg Asp Gln Leu Thr Arg Glu
                245                 250                 255

Ile Met Glu Glu His Thr Arg Ala Arg Glu Glu Ser Gly Gly Ala Lys
            260                 265                 270

Gln His Phe Phe Asp Ala Leu Leu Thr Leu Lys Asp Lys Tyr Asp Leu
        275                 280                 285

Ser Glu Asp Thr Ile Ile Gly Leu Leu Trp Asp Met Ile Thr Ala Gly
    290                 295                 300

Met Asp Thr Thr Ala Ile Ser Val Glu Trp Ala Met Ala Glu Leu Ile
305                 310                 315                 320

Lys Asn Pro Arg Val Gln Gln Lys Ala Gln Glu Glu Leu Asp Arg Val
                325                 330                 335

Ile Gly Tyr Glu Arg Val Met Thr Glu Leu Asp Phe Ser Asn Leu Pro
            340                 345                 350

Tyr Leu Gln Cys Val Ala Lys Glu Ala Leu Arg Leu His Pro Pro Thr
        355                 360                 365

Pro Leu Met Leu Pro His Arg Ser Asn Ser Asn Val Lys Ile Gly Gly
    370                 375                 380

Tyr Asp Ile Pro Lys Gly Ser Asn Val His Val Asn Val Trp Ala Val
385                 390                 395                 400

Ala Arg Asp Pro Ala Val Trp Lys Asn Pro Cys Glu Phe Arg Pro Glu
                405                 410                 415

Arg Phe Leu Glu Glu Asp Val Asp Met Lys Gly His Asp Phe Arg Leu
            420                 425                 430

Leu Pro Phe Gly Ala Gly Arg Arg Val Cys Pro Gly Ala Gln Leu Gly
        435                 440                 445

Ile Asn Leu Val Thr Ser Met Ile Gly His Leu Leu His His Phe Asn
```

```
    450                 455                 460

Trp Ala Pro Pro Ser Gly Val Ser Ser Asp Glu Leu Asp Met Gly Glu
465                 470                 475                 480

Asn Pro Gly Leu Val Thr Tyr Met Arg Thr Pro Leu Glu Ala Val Pro
                485                 490                 495

Thr Pro Arg Leu Pro Ser Asp Leu Tyr Lys Arg Ile Ala Val Asp Leu
            500                 505                 510


<210> SEQ ID NO 46
<211> LENGTH: 521
<212> TYPE: PRT
<213> ORGANISM: Glycine max

<400> SEQUENCE: 46

Met Leu Leu Glu Leu Ala Leu Gly Leu Phe Val Leu Ala Leu Phe Leu
 1               5                  10                  15

His Leu Arg Pro Thr Pro Ser Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Ser Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Lys Leu Arg Pro Leu Arg Thr Gln Gln Ile Arg Lys Phe Leu
145                 150                 155                 160

Arg Val Met Ala Gln Ser Ala Glu Ala Gln Lys Pro Leu Asp Val Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys Tyr Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Ala Ser Gly Val Phe
            260                 265                 270

Leu Asp Thr Leu Leu Glu Phe Ala Glu Asp Glu Thr Met Glu Ile Lys
        275                 280                 285

Ile Thr Lys Glu Gln Ile Lys Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
```

```
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
    370                 375                 380

Tyr Val Ile Pro Glu Gly Ala Leu Val Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
    450                 455                 460

Ser Leu Ile Gln Cys Phe Asp Leu Gln Val Leu Gly Pro Gln Gly Gln
465                 470                 475                 480

Ile Leu Lys Gly Asp Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520


<210> SEQ ID NO 47
<211> LENGTH: 456
<212> TYPE: PRT
<213> ORGANISM: Streptomyces avermitilis

<400> SEQUENCE: 47

Met Met Ser Gln Ser Thr Ser Ser Ile Pro Glu Ala Pro Gly Ala Trp
 1               5                  10                  15

Pro Val Val Gly His Val Pro Pro Leu Met Arg Gln Pro Leu Glu Phe
            20                  25                  30

Leu Arg Ser Ala Ala Asp His Gly Asp Leu Leu Lys Leu Arg Leu Gly
        35                  40                  45

Pro Lys Thr Ala Tyr Leu Ala Thr His Pro Asp Leu Val Arg Thr Met
    50                  55                  60

Leu Val Ser Ser Gly Ser Gly Asp Phe Thr Arg Ser Lys Gly Ala Gln
65                  70                  75                  80

Gly Ala Ser Arg Phe Ile Gly Pro Ile Leu Val Ala Val Ser Gly Glu
                85                  90                  95

Thr His Arg Arg Gln Arg Arg Arg Met Gln Pro Gly Phe His Arg Gln
            100                 105                 110

Arg Leu Glu Ser Tyr Val Ala Thr Met Ala Ala Ala Ala Gln Glu Thr
        115                 120                 125

Ala Asp Ser Trp Ser Ala Gly Gln Val Val Asp Val Glu Gln Ala Ala
    130                 135                 140

Cys Asp Leu Ser Leu Ala Met Ile Thr Lys Thr Leu Phe Phe Ser Asp
145                 150                 155                 160

Leu Gly Ala Lys Ala Glu Ala Ala Leu Arg Lys Thr Gly His Asp Ile
                165                 170                 175

Leu Lys Val Ala Arg Leu Ser Ala Leu Ala Pro Thr Leu Tyr Glu Val
```

```
            180                 185                 190

Leu Pro Thr Ala Gly Lys Arg Ser Val Gly Arg Thr Ser Ala Thr Ile
        195                 200                 205

Arg Glu Ala Ile Thr Ala Tyr Arg Ala Asp Gly Arg Asp His Gly Asp
    210                 215                 220

Leu Leu Ser Thr Met Leu Arg Ala Thr Asp Ala Glu Gly Ala Ser Met
225                 230                 235                 240

Thr Asp Gln Glu Val His Asp Glu Val Met Gly Ile Ala Val Ala Gly
                245                 250                 255

Ile Gly Gly Pro Ala Ala Ile Thr Ala Trp Ile Phe His Glu Leu Gly
            260                 265                 270

Gln Asn Ala Glu Ile Glu Ser Arg Leu His Ala Glu Leu Asp Thr Val
        275                 280                 285

Leu Gly Gly Arg Leu Pro Thr His Glu Asp Leu Pro Arg Leu Pro Tyr
    290                 295                 300

Thr Gln Asn Leu Val Lys Glu Ala Leu Arg Lys Tyr Pro Gly Trp Val
305                 310                 315                 320

Gly Ser Arg Arg Thr Val Arg Pro Val Arg Leu Gly Gly His Asp Leu
                325                 330                 335

Pro Ala Asp Val Glu Val Met Tyr Ser Ala Tyr Ala Ile Gln Arg Asp
            340                 345                 350

Pro Arg Trp Tyr Pro Glu Pro Glu Arg Leu Asp Pro Gly Arg Trp Glu
        355                 360                 365

Thr Lys Gly Ser Ser Arg Gly Val Pro Lys Gly Ala Trp Val Pro Phe
    370                 375                 380

Ala Leu Gly Thr Tyr Lys Cys Ile Gly Asp Asn Phe Ala Leu Leu Glu
385                 390                 395                 400

Thr Ala Val Thr Val Ala Val Val Ala Ser His Trp Arg Leu His Ala
                405                 410                 415

Leu Pro Gly Asp Glu Val Arg Pro Lys Thr Lys Ala Thr His Val Phe
            420                 425                 430

Pro Asn Arg Leu Arg Met Ile Ala Glu Pro Arg Ser Val Val Arg Leu
        435                 440                 445

Glu Glu Pro Ala Ala Met Gly Ala
    450                 455


<210> SEQ ID NO 48
<211> LENGTH: 401
<212> TYPE: PRT
<213> ORGANISM: Streptomyces bikiniensis

<400> SEQUENCE: 48

Met Gly Leu Pro Leu Thr Ser Thr Lys Thr Ala Pro Val Ser Tyr Pro
 1               5                  10                  15

Phe Gly Arg Pro Glu Gly Leu Asp Leu Asp Glu Ala Tyr Glu Gln Ala
            20                  25                  30

Arg Lys Ser Glu Gly Leu Leu Trp Val His Met Pro Tyr Gly Glu Pro
        35                  40                  45

Gly Trp Leu Val Ser Arg Tyr Asp Asp Ala Arg Phe Val Leu Gly Asp
    50                  55                  60

Arg Arg Phe Ser His Ala Ala Glu Ala Glu Asn Asp Ala Pro Arg Met
65                  70                  75                  80

Arg Glu Leu Arg Thr Pro Asn Gly Ile Ile Gly Met Asp Ala Pro Asp
                85                  90                  95

His Thr Arg Leu Arg Gly Leu Val Thr Lys Ala Phe Thr Pro Arg Arg
```

```
            100                 105                 110

Val Glu Ala Met Arg Pro His Val Arg Arg Met Thr Ala Ser Leu Leu
        115                 120                 125

Arg Asp Met Thr Ala Leu Gly Ser Pro Val Asp Leu Val Asp His Tyr
    130                 135                 140

Ala Val Pro Leu Pro Val Ala Val Ile Cys Gly Leu Leu Gly Val Pro
145                 150                 155                 160

Glu Glu Asp Arg Asp Leu Phe Arg Gly Trp Cys Glu Ile Ala Met Ser
                165                 170                 175

Thr Ser Ser Leu Thr Ala Glu Asp His Val Arg Leu Ala Gly Glu Leu
            180                 185                 190

Thr Gly Tyr Leu Ala Asp Leu Ile Thr Ala Arg Arg Ala Ala Pro Arg
        195                 200                 205

Asp Asp Leu Val Ser Ala Leu Val Glu Ala Arg Asp Ala Gln Gly Arg
    210                 215                 220

Leu Ser Gln Glu Glu Leu Val Asp Leu Ile Val Phe Leu Leu Phe Ala
225                 230                 235                 240

Gly His Glu Thr Thr Ala Ser Gln Ile Ser Asn Phe Val Leu Val Leu
                245                 250                 255

Leu Glu Gln Pro Asp Gln Leu Ala Leu Leu Arg Asp Arg Pro Asp Leu
            260                 265                 270

Leu Asp Asn Ala Val Glu Glu Leu Thr Arg Phe Val Pro Leu Gly Ser
        275                 280                 285

Gln Ala Gly Phe Pro Arg Tyr Ala Thr Glu Asp Val Glu Val Gly Gly
    290                 295                 300

Thr Leu Val Arg Ala Gly Asp Pro Val Leu Val Gln Met Asn Ala Ala
305                 310                 315                 320

Asn Arg Asp Ala Leu Arg Phe Arg Ser Pro Gly Val Leu Asp Ile Thr
                325                 330                 335

Arg Asp Asp Ala Gly Arg His Leu Gly Tyr Gly His Gly Pro His His
            340                 345                 350

Cys Leu Gly Ala Ser Leu Ala Arg Leu Glu Leu Gln Glu Ala Leu Arg
        355                 360                 365

Thr Leu Leu Asp Glu Leu Pro Gly Leu His Leu Ala Gln Pro Val Glu
    370                 375                 380

Trp Lys Thr Glu Met Val Val Arg Gly Pro Arg Thr Met Leu Val Gly
385                 390                 395                 400

Trp
```

<210> SEQ ID NO 49
<211> LENGTH: 1497
<212> TYPE: DNA
<213> ORGANISM: Artemisia annua

<400> SEQUENCE: 49

```
catatgaagt ctattctgaa agcaatggct ctgtctctga ccactagcat cgccctggcg     60

actatcctgc tgtttgtgta caaattcgcg acccgttcta aagcactaaa gaaatctctg    120

ccggaaccgt ggcgtctgcc aatcatcggt cacatgcacc acctgatcgg caccaccccg    180

caccgtggcg tacgcgacct ggcgcgtaag tacggctctc tgatgcatct gcagctgggc    240

gaggtaccta ctatcgtcgt ttcctccccg aagtgggcca aagaaatcct gactacctat    300

gacatcactt tcgccaaccg cccggaaacg ctgaccggcg aaattgtcct gtaccataac    360

acggatgtgg ttctggcccc gtacggtgag tactggcgcc agctgcgcaa aatttgtact    420
```

```
ctggaactgc tgagcgttaa aaaggttaaa tccttccaga gcctgcgtga agaggaatgc    480
tggaacctgg tgcaggagat taaagcgtct ggcagcggtc gtccagttaa cctgtctgag    540
aatgttttta aactgatcgc tactatcctg tctcgcgcgg cattcggtaa aggtatcaaa    600
gatcagaaag aactgaccga aatcgttaag gaaatcctgc gccagactgg tggcttcgac    660
gttgcggaca tcttcccgtc caaaaagttc ctgcaccatc tgtctggcaa acgcgctcgt    720
ctgacctccc tgcgtaagaa aattgataac ctgattgaca acctggtcgc tgagcacact    780
gtgaacacct cttctaaaac caacgaaacc ctgctggacg tactgctgcg cctgaaggac    840
tctgccgaat ttccactgac tagcgacaat atcaaagcaa tcatcctgga catgttcggc    900
gccggtaccg atacgtcctc ttccacgatt gagtgggcta tttccgaact gatcaaatgc    960
ccgaaggcga tggaaaaagt gcaggcggaa ctgcgtaaag cgctgaacgg taaagagaaa   1020
attcatgaag aggacatcca ggaactgtcc tacctgaata tggtaatcaa agaaactctg   1080
cgtctgcatc cgccgctgcc actggttctg ccgcgtgaat gccgtcagcc ggttaacctg   1140
gccggctaca acattccgaa caaaacgaag ctgatcgtca acgttttcgc gatcaaccgc   1200
gatcctgaat actggaaaga cgcggaagcg ttcattccgg aacgctttga gaactcctct   1260
gccaccgtta tgggcgctga atacgagtac ctgccgttcg gtgcgggtcg ccgtatgtgc   1320
ccgggtgctg cactgggcct ggcgaacgtt caactgccac tggcgaacat cctgtaccac   1380
ttcaactgga aactgcctaa cggcgtatct tatgatcaaa tcgacatgac cgaaagctcc   1440
ggcgcgacca tgcagcgtaa aaccgaactg ctgctggttc cgtcctttta acctagg      1497
```

<210> SEQ ID NO 50
<211> LENGTH: 1497
<212> TYPE: DNA
<213> ORGANISM: Artificial Sequence
<220> FEATURE:
<223> OTHER INFORMATION: Modified amorphadiene oxidase nucleic acid

<400> SEQUENCE: 50

```
catatgaagt ctattctgaa agcaatggct ctgtctctga ccactagcat cgccctggcg     60
actatcctgc tgtttgtgta caaattcgcg acccgttcta aaagcactaa gaaatctctg    120
ccggaaccgt ggcgtctgcc aatcatcggt cacatgcacc acctgatcgg caccaccccg    180
caccgtggcg tacgcgacct ggcgcgtaag tacggctctc tgatgcatct gcagctgggc    240
gaggtaccta ctatcgtcgt ttcctccccg aagtgggcca aagaaatcct gactacctat    300
gacatcactt tcgccaaccg cccggaaacg ctgaccggcg aaattgtcct gtaccataac    360
acggatgtgg ttctggcccc gtacggtgag tactggcgcc agctgcgcaa aatttgtact    420
ctggaactgc tgagcgttaa aaaggttaaa tccttccaga gcctgcgtga agaggaatgc    480
tggaacctgg tgcaggagat taaagcgtct ggcagcggtc gtccagttaa cctgtctgag    540
aatgttttta aactgatcgc tactatcctg tctcgcgcgg cattcggtaa aggtatcaaa    600
gatcagaaag aactgaccga aatcgttaag gaaatcctgc gccagactgg tggcttcgac    660
gttgcggaca tcttcccgtc caaaaagttc ctgcaccatc tgtctggcaa acgcgctcgt    720
ctgacctccc tgcgtaagaa aattgataac ctgattgaca acctggtcgc tgagcacact    780
gtgaacacct cttctaaaac caacgaaacc ctgctggacg tactgctgcg cctgaaggac    840
tctgccgaat ttccactgac tagcgacaat atcaaagcaa tcatcctgga catgttcggc    900
gccggtaccg atacgtcctc ttccacgatt gagtgggcta tttccgaact gatcaaatgc    960
ccgaaggcga tggaaaaagt gcaggcggaa ctgcgtaaag cgctgaacgg taaagagaaa   1020
```

```
attcatgaag aggacatcca ggaactgtcc tacctgaata tggtaatcaa agaaactctg   1080

cgtctgcatc cgccgctgcc actggttctg ccgcgtgaat gccgtcagcc ggttaacctg   1140

gccggctaca acattccgaa caaaacgaag ctgatcgtca acgttttcgc gatcaaccgc   1200

gatcctgaat actggaaaga cgcggaagcg ttcattccgg aacgctttga gaactcctct   1260

gccaccgtta tgggcgctga atacgagtac ctgccgttcg gtgcgggtcg ccgtatgtgc   1320

ccgggtgctg cactgggcct ggcgaacgtt caactgccac tggcgaacat cctgtaccac   1380

ttcaactgga aactgcctaa cggcgtatct tatgatcaaa tcgacatgac cgaaagctcc   1440

ggcgcgacca tgcagcgtaa aaccgaactg ctgctggttc cgtcctttta acctagg      1497


<210> SEQ ID NO 51
<211> LENGTH: 1488
<212> TYPE: DNA
<213> ORGANISM: Artificial Sequence
<220> FEATURE:
<223> OTHER INFORMATION: Modified amorphadiene oxidase nucleic acid

<400> SEQUENCE: 51

atgaagtcta ttctgaaagc aatggctctg tctctgacca ctagcatcgc cctggcgact     60

atcctgctgt ttgtgtacaa attcgcgacc cgttctaaaa gcactaagaa atctctgccg    120

gaaccgtggc gtctgccaat catcggtcac atgcaccacc tgatcggcac caccccgcac    180

cgtggcgtac gcgacctggc gcgtaagtac ggctctctga tgcatctgca gctgggcgag    240

gtacctacta tcgtcgtttc ctccccgaag tgggccaaag aaatcctgac tacctatgac    300

atcactttcg ccaaccgccc ggaaacgctg accggcgaaa ttgtcctgta ccataacacg    360

gatgtggttc tggccccgta cggtgagtac tggcgccagc tgcgcaaaat ttgtactctg    420

gaactgctga gcgttaaaaa ggttaaatcc ttccagagcc tgcgtgaaga ggaatgctgg    480

aacctggtgc aggagattaa agcgtctggc agcggtcgtc cagttaacct gtctgagaat    540

gtttttaaac tgatcgctac tatcctgtct cgcgcggcat tcggtaaagg tatcaaagat    600

cagaaagaac tgaccgaaat cgttaaggaa atcctgcgcc agactggtgg cttcgacgtt    660

gcggacatct tcccgtccaa aaagttcctg caccatctgt ctggcaaacg cgctcgtctg    720

acctccctgc gtaagaaaat tgataacctg attgacaacc tggtcgctga gcacactgtg    780

aacacctctt ctaaaaccaa cgaaaccctg ctggacgtac tgctgcgcct gaaggactct    840

gccgaatttc cactgactag cgacaatatc aaagcaatca tcctggacat gttcggcgcc    900

ggtaccgata cgtcctcttc cacgattgag tgggctattt ccgaactgat caaatgcccg    960

aaggcgatgg aaaaagtgca ggcggaactg cgtaaagcgc tgaacggtaa agagaaaatt   1020

catgaagagg acatccagga actgtcctac ctgaatatgg taatcaaaga aactctgcgt   1080

ctgcatccgc cgctgccact ggttctgccg cgtgaatgcc gtcagccggt taacctggcc   1140

ggctacaaca ttccgaacaa aacgaagctg atcgtcaacg ttttcgcgat caaccgcgat   1200

cctgaatact ggaaagacgc ggaagcgttc attccggaac gctttgagaa ctcctctgcc   1260

accgttatgg gcgctgaata cgagtacctg ccgttcggtg cgggtcgccg tatgtgcccg   1320

ggtgctgcac tgggcctggc gaacgttcaa ctgccactgg cgaacatcct gtaccacttc   1380

aactggaaac tgcctaacgg cgtatcttat gatcaaatcg acatgaccga aagctccggc   1440

gcgaccatgc agcgtaaaac cgaactgctg ctggttccgt ccttttaa                1488


<210> SEQ ID NO 52
<211> LENGTH: 495
<212> TYPE: PRT
```

<213> ORGANISM: Artificial Sequence
<220> FEATURE:
<223> OTHER INFORMATION: Modified amorphadiene oxidase

<400> SEQUENCE: 52

```
Met Lys Ser Ile Leu Lys Ala Met Ala Leu Ser Leu Thr Thr Ser Ile
 1               5                  10                  15

Ala Leu Ala Thr Ile Leu Leu Phe Val Tyr Lys Phe Ala Thr Arg Ser
            20                  25                  30

Lys Ser Thr Lys Lys Ser Leu Pro Glu Pro Trp Arg Leu Pro Ile Ile
        35                  40                  45

Gly His Met His His Leu Ile Gly Thr Thr Pro His Arg Gly Val Arg
    50                  55                  60

Asp Leu Ala Arg Lys Tyr Gly Ser Leu Met His Leu Gln Leu Gly Glu
65                  70                  75                  80

Val Pro Thr Ile Val Val Ser Ser Pro Lys Trp Ala Lys Glu Ile Leu
                85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
    210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
            260                 265                 270

Val Leu Leu Arg Leu Lys Asp Ser Ala Glu Phe Pro Leu Thr Ser Asp
        275                 280                 285

Asn Ile Lys Ala Ile Ile Leu Asp Met Phe Gly Ala Gly Thr Asp Thr
    290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                325                 330                 335

Lys Glu Lys Ile His Glu Glu Asp Ile Gln Glu Leu Ser Tyr Leu Asn
            340                 345                 350

Met Val Ile Lys Glu Thr Leu Arg Leu His Pro Pro Leu Pro Leu Val
        355                 360                 365

Leu Pro Arg Glu Cys Arg Gln Pro Val Asn Leu Ala Gly Tyr Asn Ile
    370                 375                 380

Pro Asn Lys Thr Lys Leu Ile Val Asn Val Phe Ala Ile Asn Arg Asp
385                 390                 395                 400
```

Pro Glu Tyr Trp Lys Asp Ala Glu Ala Phe Ile Pro Glu Arg Phe Glu
405 410 415

Asn Ser Ser Ala Thr Val Met Gly Ala Glu Tyr Glu Tyr Leu Pro Phe
420 425 430

Gly Ala Gly Arg Arg Met Cys Pro Gly Ala Ala Leu Gly Leu Ala Asn
435 440 445

Val Gln Leu Pro Leu Ala Asn Ile Leu Tyr His Phe Asn Trp Lys Leu
450 455 460

Pro Asn Gly Val Ser Tyr Asp Gln Ile Asp Met Thr Glu Ser Ser Gly
465 470 475 480

Ala Thr Met Gln Arg Lys Thr Glu Leu Leu Leu Val Pro Ser Phe
485 490 495

<210> SEQ ID NO 53
<211> LENGTH: 3018
<212> TYPE: DNA
<213> ORGANISM: Artificial Sequence
<220> FEATURE:
<223> OTHER INFORMATION: Modified amorphadiene oxidase nucleic acid

<400> SEQUENCE: 53
catatgaccg tacacgacat catcgcaacg tacttcacta aatggtacgt aattgtgccg 60
ctggcactga ttgcgtatcg cgtgctggat tatttctacg cgacccgttc taaaagcact 120
aagaaatctc tgccggaacc gtggcgtctg ccaatcatcg gtcacatgca ccacctgatc 180
ggcaccaccc cgcaccgtgg cgtacgcgac ctggcgcgta agtacggctc tctgatgcat 240
ctgcagctgg gcgaggtacc tactatcgtc gtttcctccc cgaagtgggc caaagaaatc 300
ctgactacct atgacatcac tttcgccaac cgcccggaaa cgctgaccgg cgaaattgtc 360
ctgtaccata acacggatgt ggttctggcc ccgtacggtg agtactggcg ccagctgcgc 420
aaaatttgta ctctggaact gctgagcgtt aaaaaggtta aatccttcca gagcctgcgt 480
gaagaggaat gctggaacct ggtgcaggag attaaagcgt ctggcagcgg tcgtccagtt 540
aacctgtctg agaatgtttt taaactgatc gctactatcc tgtctcgcgc ggcattcggt 600
aaaggtatca aagatcagaa agaactgacc gaaatcgtta aggaaatcct gcgccagact 660
ggtggcttcg acgttgcgga catcttcccg tccaaaaagt tcctgcacca tctgtctggc 720
aaacgcgctc gtctgacctc cctgcgtaag aaaattgata acctgattga caacctggtc 780
gctgagcaca ctgtgaacac ctcttctaaa accaacgaaa ccctgctgga cgtactgctg 840
cgcctgaagg actctgccga atttccactg actagcgaca atatcaaagc aatcatcctg 900
gacatgttcg gcgccggtac cgatacgtcc tcttccacga ttgagtgggc tatttccgaa 960
ctgatcaaat gcccgaaggc gatggaaaaa gtgcaggcgg aactgcgtaa agcgctgaac 1020
ggtaaagaga aaattcatga agaggacatc caggaactgt cctacctgaa tatggtaatc 1080
aaagaaactc tgcgtctgca tccgccgctg ccactggttc tgccgcgtga atgccgtcag 1140
ccggttaacc tggccggcta caacattccg aacaaaacga agctgatcgt caacgttttc 1200
gcgatcaacc gcgatcctga atactggaaa gacgcggaag cgttcattcc ggaacgcttt 1260
gagaactcct ctgccaccgt tatgggcgct gaatacgagt acctgccgtt cggtgcgggt 1320
cgccgtatgt gcccgggtgc tgcactgggc ctggcgaacg ttcaactgcc actggcgaac 1380
atcctgtacc acttcaactg gaaactgcct aacggcgtat cttatgatca aatcgacatg 1440
accgaaagct ccggcgcgac catgcagcgt aaaaccgaac tgctgctggt tccgtccttt 1500
taacctaggc atatgaccgt acacgacatc atcgcaacgt acttcactaa atggtacgta 1560

```
attgtgccgc tggcactgat tgcgtatcgc gtgctggatt atttctacgc gacccgttct   1620
aaaagcacta agaaatctct gccggaaccg tggcgtctgc caatcatcgg tcacatgcac   1680
cacctgatcg gcaccacccc gcaccgtggc gtacgcgacc tggcgcgtaa gtacggctct   1740
ctgatgcatc tgcagctggg cgaggtacct actatcgtcg tttcctcccc gaagtgggcc   1800
aaagaaatcc tgactaccta tgacatcact ttcgccaacc gcccggaaac gctgaccggc   1860
gaaattgtcc tgtaccataa cacggatgtg gttctggccc cgtacggtga gtactggcgc   1920
cagctgcgca aaatttgtac tctggaactg ctgagcgtta aaaaggttaa atccttccag   1980
agcctgcgtg aagaggaatg ctggaacctg gtgcaggaga ttaaagcgtc tggcagcggt   2040
cgtccagtta acctgtctga gaatgttttt aaactgatcg ctactatcct gtctcgcgcg   2100
gcattcggta aaggtatcaa agatcagaaa gaactgaccg aaatcgttaa ggaaatcctg   2160
cgccagactg gtggcttcga cgttgcggac atcttcccgt ccaaaaagtt cctgcaccat   2220
ctgtctggca aacgcgctcg tctgacctcc ctgcgtaaga aaattgataa cctgattgac   2280
aacctggtcg ctgagcacac tgtgaacacc tcttctaaaa ccaacgaaac cctgctggac   2340
gtactgctgc gcctgaagga ctctgccgaa tttccactga ctagcgacaa tatcaaagca   2400
atcatcctgg acatgttcgg cgccggtacc gatacgtcct cttccacgat tgagtgggct   2460
atttccgaac tgatcaaatg cccgaaggcg atggaaaaag tgcaggcgga actgcgtaaa   2520
gcgctgaacg gtaaagagaa aattcatgaa gaggacatcc aggaactgtc ctacctgaat   2580
atggtaatca aagaaactct gcgtctgcat ccgccgctgc cactggttct gccgcgtgaa   2640
tgccgtcagc cggttaacct ggccggctac aacattccga acaaaacgaa gctgatcgtc   2700
aacgttttcg cgatcaaccg cgatcctgaa tactggaaag acgcggaagc gttcattccg   2760
gaacgctttg agaactcctc tgccaccgtt atgggcgctg aatacgagta cctgccgttc   2820
ggtgcgggtc gccgtatgtg cccgggtgct gcactgggcc tggcgaacgt tcaactgcca   2880
ctggcgaaca tcctgtacca cttcaactgg aaactgccta acggcgtatc ttatgatcaa   2940
atcgacatga ccgaaagctc cggcgcgacc atgcagcgta aaaccgaact gctgctggtt   3000
ccgtcctttt aacctagg                                                 3018
```

<210> SEQ ID NO 54
<211> LENGTH: 1500
<212> TYPE: DNA
<213> ORGANISM: Artificial Sequence
<220> FEATURE:
<223> OTHER INFORMATION: Modified amorphadiene oxidase nucleic acid

<400> SEQUENCE: 54

```
atgaccgtac acgacatcat cgcaacgtac ttcactaaat ggtacgtaat tgtgccgctg     60
gcactgattg cgtatcgcgt gctggattat ttctacgcga cccgttctaa aagcactaag    120
aaatctctgc cggaaccgtg gcgtctgcca atcatcggtc acatgcacca cctgatcggc    180
accaccccgc accgtggcgt acgcgacctg gcgcgtaagt acggctctct gatgcatctg    240
cagctgggcg aggtacctac tatcgtcgtt tcctccccga agtgggccaa agaaatcctg    300
actacctatg acatcacttt cgccaaccgc ccggaaacgc tgaccggcga aattgtcctg    360
taccataaca cggatgtggt tctggccccg tacggtgagt actggcgcca gctgcgcaaa    420
atttgtactc tggaactgct gagcgttaaa aaggttaaat ccttccagag cctgcgtgaa    480
gaggaatgct ggaacctggt gcaggagatt aaagcgtctg gcagcggtcg tccagttaac    540
ctgtctgaga atgtttttaa actgatcgct actatcctgt ctcgcgcggc attcggtaaa    600
```

```
ggtatcaaag atcagaaaga actgaccgaa atcgttaagg aaatcctgcg ccagactggt    660

ggcttcgacg ttgcggacat cttcccgtcc aaaaagttcc tgcaccatct gtctggcaaa    720

cgcgctcgtc tgacctccct gcgtaagaaa attgataacc tgattgacaa cctggtcgct    780

gagcacactg tgaacacctc ttctaaaacc aacgaaaccc tgctggacgt actgctgcgc    840

ctgaaggact ctgccgaatt tccactgact agcgacaata tcaaagcaat catcctggac    900

atgttcggcg ccggtaccga tacgtcctct tccacgattg agtgggctat ttccgaactg    960

atcaaatgcc cgaaggcgat ggaaaaagtg caggcggaac tgcgtaaagc gctgaacggt   1020

aaagagaaaa ttcatgaaga ggacatccag gaactgtcct acctgaatat ggtaatcaaa   1080

gaaactctgc gtctgcatcc gccgctgcca ctggttctgc cgcgtgaatg ccgtcagccg   1140

gttaacctgg ccggctacaa cattccgaac aaaacgaagc tgatcgtcaa cgttttcgcg   1200

atcaaccgcg atcctgaata ctggaaagac gcggaagcgt tcattccgga acgctttgag   1260

aactcctctg ccaccgttat gggcgctgaa tacgagtacc tgccgttcgg tgcgggtcgc   1320

cgtatgtgcc cgggtgctgc actgggcctg gcgaacgttc aactgccact ggcgaacatc   1380

ctgtaccact tcaactggaa actgcctaac ggcgtatctt atgatcaaat cgacatgacc   1440

gaaagctccg gcgcgaccat gcagcgtaaa accgaactgc tgctggttcc gtccttttaa   1500
```

```
<210> SEQ ID NO 55
<211> LENGTH: 499
<212> TYPE: PRT
<213> ORGANISM: Artificial Sequence
<220> FEATURE:
<223> OTHER INFORMATION: Modified amorphadiene oxidase

<400> SEQUENCE: 55

Met Thr Val His Asp Ile Ile Ala Thr Tyr Phe Thr Lys Trp Tyr Val
 1               5                  10                  15

Ile Val Pro Leu Ala Leu Ile Ala Tyr Arg Val Leu Asp Tyr Phe Tyr
            20                  25                  30

Ala Thr Arg Ser Lys Ser Thr Lys Lys Ser Leu Pro Glu Pro Trp Arg
        35                  40                  45

Leu Pro Ile Ile Gly His Met His His Leu Ile Gly Thr Thr Pro His
    50                  55                  60

Arg Gly Val Arg Asp Leu Ala Arg Lys Tyr Gly Ser Leu Met His Leu
65                  70                  75                  80

Gln Leu Gly Glu Val Pro Thr Ile Val Val Ser Ser Pro Lys Trp Ala
                85                  90                  95

Lys Glu Ile Leu Thr Thr Tyr Asp Ile Thr Phe Ala Asn Arg Pro Glu
            100                 105                 110

Thr Leu Thr Gly Glu Ile Val Leu Tyr His Asn Thr Asp Val Val Leu
        115                 120                 125

Ala Pro Tyr Gly Glu Tyr Trp Arg Gln Leu Arg Lys Ile Cys Thr Leu
    130                 135                 140

Glu Leu Leu Ser Val Lys Lys Val Lys Ser Phe Gln Ser Leu Arg Glu
145                 150                 155                 160

Glu Glu Cys Trp Asn Leu Val Gln Glu Ile Lys Ala Ser Gly Ser Gly
                165                 170                 175

Arg Pro Val Asn Leu Ser Glu Asn Val Phe Lys Leu Ile Ala Thr Ile
            180                 185                 190

Leu Ser Arg Ala Ala Phe Gly Lys Gly Ile Lys Asp Gln Lys Glu Leu
        195                 200                 205
```

-continued

```
Thr Glu Ile Val Lys Glu Ile Leu Arg Gln Thr Gly Gly Phe Asp Val
    210                 215                 220

Ala Asp Ile Phe Pro Ser Lys Lys Phe Leu His His Leu Ser Gly Lys
225                 230                 235                 240

Arg Ala Arg Leu Thr Ser Leu Arg Lys Lys Ile Asp Asn Leu Ile Asp
                245                 250                 255

Asn Leu Val Ala Glu His Thr Val Asn Thr Ser Ser Lys Thr Asn Glu
            260                 265                 270

Thr Leu Leu Asp Val Leu Leu Arg Leu Lys Asp Ser Ala Glu Phe Pro
        275                 280                 285

Leu Thr Ser Asp Asn Ile Lys Ala Ile Ile Leu Asp Met Phe Gly Ala
    290                 295                 300

Gly Thr Asp Thr Ser Ser Ser Thr Ile Glu Trp Ala Ile Ser Glu Leu
305                 310                 315                 320

Ile Lys Cys Pro Lys Ala Met Glu Lys Val Gln Ala Glu Leu Arg Lys
                325                 330                 335

Ala Leu Asn Gly Lys Glu Lys Ile His Glu Glu Asp Ile Gln Glu Leu
            340                 345                 350

Ser Tyr Leu Asn Met Val Ile Lys Glu Thr Leu Arg Leu His Pro Pro
        355                 360                 365

Leu Pro Leu Val Leu Pro Arg Glu Cys Arg Gln Pro Val Asn Leu Ala
    370                 375                 380

Gly Tyr Asn Ile Pro Asn Lys Thr Lys Leu Ile Val Asn Val Phe Ala
385                 390                 395                 400

Ile Asn Arg Asp Pro Glu Tyr Trp Lys Asp Ala Glu Ala Phe Ile Pro
                405                 410                 415

Glu Arg Phe Glu Asn Ser Ser Ala Thr Val Met Gly Ala Glu Tyr Glu
            420                 425                 430

Tyr Leu Pro Phe Gly Ala Gly Arg Arg Met Cys Pro Gly Ala Ala Leu
        435                 440                 445

Gly Leu Ala Asn Val Gln Leu Pro Leu Ala Asn Ile Leu Tyr His Phe
    450                 455                 460

Asn Trp Lys Leu Pro Asn Gly Val Ser Tyr Asp Gln Ile Asp Met Thr
465                 470                 475                 480

Glu Ser Ser Gly Ala Thr Met Gln Arg Lys Thr Glu Leu Leu Leu Val
                485                 490                 495

Pro Ser Phe


<210> SEQ ID NO 56
<211> LENGTH: 2988
<212> TYPE: DNA
<213> ORGANISM: Artificial Sequence
<220> FEATURE:
<223> OTHER INFORMATION: Modified amorphadiene oxidase

<400> SEQUENCE: 56

catatgatcg aacaactgct ggaatactgg tacgtggttg tgcctgttct gtatattatc      60

aaacagctgc tggcgtacac taaagcgacc cgttctaaaa gcactaagaa atctctgccg     120

gaaccgtggc gtctgccaat catcggtcac atgcaccacc tgatcggcac caccccgcac     180

cgtggcgtac gcgacctggc gcgtaagtac ggctctctga tgcatctgca gctgggcgag     240

gtacctacta tcgtcgtttc ctccccgaag tgggccaaag aaatcctgac tacctatgac     300

atcactttcg ccaaccgccc ggaaacgctg accggcgaaa ttgtcctgta ccataacacg     360

gatgtggttc tggccccgta cggtgagtac tggcgccagc tgcgcaaaat ttgtactctg     420
```

```
gaactgctga gcgttaaaaa ggttaaatcc ttccagagcc tgcgtgaaga ggaatgctgg    480
aacctggtgc aggagattaa agcgtctggc agcggtcgtc cagttaacct gtctgagaat    540
gtttttaaac tgatcgctac tatcctgtct cgcgcggcat tcggtaaagg tatcaaagat    600
cagaaagaac tgaccgaaat cgttaaggaa atcctgcgcc agactggtgg cttcgacgtt    660
gcggacatct tcccgtccaa aaagttcctg caccatctgt ctggcaaacg cgctcgtctg    720
acctccctgc gtaagaaaat tgataacctg attgacaacc tggtcgctga gcacactgtg    780
aacacctctt ctaaaaccaa cgaaaccctg ctggacgtac tgctgcgcct gaaggactct    840
gccgaatttc cactgactag cgacaatatc aaagcaatca tcctggacat gttcggcgcc    900
ggtaccgata cgtcctcttc cacgattgag tgggctattt ccgaactgat caaatgcccg    960
aaggcgatgg aaaaagtgca ggcggaactg cgtaaagcgc tgaacggtaa agagaaaatt   1020
catgaagagg acatccagga actgtcctac ctgaatatgg taatcaaaga aactctgcgt   1080
ctgcatccgc cgctgccact ggttctgccg cgtgaatgcc gtcagccggt taacctggcc   1140
ggctacaaca ttccgaacaa aacgaagctg atcgtcaacg ttttcgcgat caaccgcgat   1200
cctgaatact ggaaagacgc ggaagcgttc attccggaac gctttgagaa ctcctctgcc   1260
accgttatgg gcgctgaata cgagtacctg ccgttcggtg cgggtcgccg tatgtgcccg   1320
ggtgctgcac tgggcctggc gaacgttcaa ctgccactgg cgaacatcct gtaccacttc   1380
aactggaaac tgcctaacgg cgtatcttat gatcaaatcg acatgaccga aagctccggc   1440
gcgaccatgc agcgtaaaac cgaactgctg ctggttccgt ccttttaacc taggcatatg   1500
atcgaacaac tgctggaata ctggtacgtg gttgtgcctg ttctgtatat tatcaaacag   1560
ctgctggcgt acactaaagc gacccgttct aaaagcacta agaaatctct gccggaaccg   1620
tggcgtctgc caatcatcgg tcacatgcac cacctgatcg gcaccacccc gcaccgtggc   1680
gtacgcgacc tggcgcgtaa gtacggctct ctgatgcatc tgcagctggg cgaggtacct   1740
actatcgtcg tttcctcccc gaagtgggcc aaagaaatcc tgactaccta tgacatcact   1800
ttcgccaacc gcccggaaac gctgaccggc gaaattgtcc tgtaccataa cacggatgtg   1860
gttctggccc cgtacggtga gtactggcgc cagctgcgca aaatttgtac tctggaactg   1920
ctgagcgtta aaaaggttaa atccttccag agcctgcgtg aagaggaatg ctggaacctg   1980
gtgcaggaga ttaaagcgtc tggcagcggt cgtccagtta acctgtctga gaatgttttt   2040
aaactgatcg ctactatcct gtctcgcgcg gcattcggta aaggtatcaa agatcagaaa   2100
gaactgaccg aaatcgttaa ggaaatcctg cgccagactg gtggcttcga cgttgcggac   2160
atcttcccgt ccaaaaagtt cctgcaccat ctgtctggca aacgcgctcg tctgacctcc   2220
ctgcgtaaga aaattgataa cctgattgac aacctggtcg ctgagcacac tgtgaacacc   2280
tcttctaaaa ccaacgaaac cctgctggac gtactgctgc gcctgaagga ctctgccgaa   2340
tttccactga ctagcgacaa tatcaaagca atcatcctgg acatgttcgg cgccggtacc   2400
gatacgtcct cttccacgat tgagtgggct atttccgaac tgatcaaatg cccgaaggcg   2460
atggaaaaag tgcaggcgga actgcgtaaa gcgctgaacg gtaaagagaa aattcatgaa   2520
gaggacatcc aggaactgtc ctacctgaat atggtaatca aagaaactct gcgtctgcat   2580
ccgccgctgc cactggttct gccgcgtgaa tgccgtcagc cggttaacct ggccggctac   2640
aacattccga acaaaacgaa gctgatcgtc aacgttttcg cgatcaaccg cgatcctgaa   2700
tactggaaag acgcggaagc gttcattccg gaacgctttg agaactcctc tgccaccgtt   2760
atgggcgctg aatacgagta cctgccgttc ggtgcgggtc gccgtatgtg cccgggtgct   2820
```

```
gcactgggcc tggcgaacgt tcaactgcca ctggcgaaca tcctgtacca cttcaactgg   2880

aaactgccta acggcgtatc ttatgatcaa atcgacatga ccgaaagctc cggcgcgacc   2940

atgcagcgta aaaccgaact gctgctggtt ccgtcctttt aacctagg                2988
```

<210> SEQ ID NO 57
<211> LENGTH: 1485
<212> TYPE: DNA
<213> ORGANISM: Artificial Sequence
<220> FEATURE:
<223> OTHER INFORMATION: Modified amorphadiene oxidase nucleic acid

<400> SEQUENCE: 57

```
atgatcgaac aactgctgga atactggtac gtggttgtgc ctgttctgta tattatcaaa     60

cagctgctgg cgtacactaa agcgacccgt tctaaaagca ctaagaaatc tctgccggaa    120

ccgtggcgtc tgccaatcat cggtcacatg caccacctga tcggcaccac cccgcaccgt    180

ggcgtacgcg acctggcgcg taagtacggc tctctgatgc atctgcagct gggcgaggta    240

cctactatcg tcgtttcctc cccgaagtgg gccaaagaaa tcctgactac ctatgacatc    300

actttcgcca accgcccgga aacgctgacc ggcgaaattg tcctgtacca taacacggat    360

gtggttctgg ccccgtacgg tgagtactgg cgccagctgc gcaaaatttg tactctggaa    420

ctgctgagcg ttaaaaaggt taaatccttc cagagcctgc gtgaagagga atgctggaac    480

ctggtgcagg agattaaagc gtctggcagc ggtcgtccag ttaacctgtc tgagaatgtt    540

tttaaactga tcgctactat cctgtctcgc gcggcattcg gtaaaggtat caaagatcag    600

aaagaactga ccgaaatcgt taaggaaatc ctgcgccaga ctggtggctt cgacgttgcg    660

gacatcttcc cgtccaaaaa gttcctgcac catctgtctg gcaaacgcgc tcgtctgacc    720

tccctgcgta agaaaattga taacctgatt gacaacctgg tcgctgagca cactgtgaac    780

acctcttcta aaaccaacga aaccctgctg gacgtactgc tgcgcctgaa ggactctgcc    840

gaatttccac tgactagcga caatatcaaa gcaatcatcc tggacatgtt cggcgccggt    900

accgatacgt cctcttccac gattgagtgg gctatttccg aactgatcaa atgcccgaag    960

gcgatggaaa aagtgcaggc ggaactgcgt aaagcgctga acggtaaaga gaaaattcat   1020

gaagaggaca tccaggaact gtcctacctg aatatggtaa tcaaagaaac tctgcgtctg   1080

catccgccgc tgccactggt tctgccgcgt gaatgccgtc agccggttaa cctggccggc   1140

tacaacattc cgaacaaaac gaagctgatc gtcaacgttt tcgcgatcaa ccgcgatcct   1200

gaatactgga aagacgcgga agcgttcatt ccggaacgct ttgagaactc ctctgccacc   1260

gttatgggcg ctgaatacga gtacctgccg ttcggtgcgg gtcgccgtat gtgcccgggt   1320

gctgcactgg gcctggcgaa cgttcaactg ccactggcga acatcctgta ccacttcaac   1380

tggaaactgc ctaacggcgt atcttatgat caaatcgaca tgaccgaaag ctccggcgcg   1440

accatgcagc gtaaaaccga actgctgctg gttccgtcct tttaa                   1485
```

<210> SEQ ID NO 58
<211> LENGTH: 494
<212> TYPE: PRT
<213> ORGANISM: Artificial Sequence
<220> FEATURE:
<223> OTHER INFORMATION: Modified amorphadiene oxidase

<400> SEQUENCE: 58

```
Met Ile Glu Gln Leu Leu Glu Tyr Trp Tyr Val Val Val Pro Val Leu
 1               5                  10                  15

Tyr Ile Ile Lys Gln Leu Leu Ala Tyr Thr Lys Ala Thr Arg Ser Lys
```

```
            20                  25                  30

Ser Thr Lys Lys Ser Leu Pro Glu Pro Trp Arg Leu Pro Ile Ile Gly
        35                  40                  45

His Met His His Leu Ile Gly Thr Thr Pro His Arg Gly Val Arg Asp
    50                  55                  60

Leu Ala Arg Lys Tyr Gly Ser Leu Met His Leu Gln Leu Gly Glu Val
65                  70                  75                  80

Pro Thr Ile Val Val Ser Ser Pro Lys Trp Ala Lys Glu Ile Leu Thr
                85                  90                  95

Thr Tyr Asp Ile Thr Phe Ala Asn Arg Pro Glu Thr Leu Thr Gly Glu
            100                 105                 110

Ile Val Leu Tyr His Asn Thr Asp Val Val Leu Ala Pro Tyr Gly Glu
        115                 120                 125

Tyr Trp Arg Gln Leu Arg Lys Ile Cys Thr Leu Glu Leu Leu Ser Val
    130                 135                 140

Lys Lys Val Lys Ser Phe Gln Ser Leu Arg Glu Glu Glu Cys Trp Asn
145                 150                 155                 160

Leu Val Gln Glu Ile Lys Ala Ser Gly Ser Gly Arg Pro Val Asn Leu
                165                 170                 175

Ser Glu Asn Val Phe Lys Leu Ile Ala Thr Ile Leu Ser Arg Ala Ala
            180                 185                 190

Phe Gly Lys Gly Ile Lys Asp Gln Lys Glu Leu Thr Glu Ile Val Lys
        195                 200                 205

Glu Ile Leu Arg Gln Thr Gly Gly Phe Asp Val Ala Asp Ile Phe Pro
    210                 215                 220

Ser Lys Lys Phe Leu His His Leu Ser Gly Lys Arg Ala Arg Leu Thr
225                 230                 235                 240

Ser Leu Arg Lys Lys Ile Asp Asn Leu Ile Asp Asn Leu Val Ala Glu
                245                 250                 255

His Thr Val Asn Thr Ser Ser Lys Thr Asn Glu Thr Leu Leu Asp Val
            260                 265                 270

Leu Leu Arg Leu Lys Asp Ser Ala Glu Phe Pro Leu Thr Ser Asp Asn
        275                 280                 285

Ile Lys Ala Ile Ile Leu Asp Met Phe Gly Ala Gly Thr Asp Thr Ser
    290                 295                 300

Ser Ser Thr Ile Glu Trp Ala Ile Ser Glu Leu Ile Lys Cys Pro Lys
305                 310                 315                 320

Ala Met Glu Lys Val Gln Ala Glu Leu Arg Lys Ala Leu Asn Gly Lys
                325                 330                 335

Glu Lys Ile His Glu Glu Asp Ile Gln Glu Leu Ser Tyr Leu Asn Met
            340                 345                 350

Val Ile Lys Glu Thr Leu Arg Leu His Pro Pro Leu Pro Leu Val Leu
        355                 360                 365

Pro Arg Glu Cys Arg Gln Pro Val Asn Leu Ala Gly Tyr Asn Ile Pro
    370                 375                 380

Asn Lys Thr Lys Leu Ile Val Asn Val Phe Ala Ile Asn Arg Asp Pro
385                 390                 395                 400

Glu Tyr Trp Lys Asp Ala Glu Ala Phe Ile Pro Glu Arg Phe Glu Asn
                405                 410                 415

Ser Ser Ala Thr Val Met Gly Ala Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445
```

```
Gln Leu Pro Leu Ala Asn Ile Leu Tyr His Phe Asn Trp Lys Leu Pro
    450                 455                 460

Asn Gly Val Ser Tyr Asp Gln Ile Asp Met Thr Glu Ser Ser Gly Ala
465                 470                 475                 480

Thr Met Gln Arg Lys Thr Glu Leu Leu Leu Val Pro Ser Phe
                485                 490
```

```
<210> SEQ ID NO 59
<211> LENGTH: 2946
<212> TYPE: DNA
<213> ORGANISM: Artificial Sequence
<220> FEATURE:
<223> OTHER INFORMATION: Modified amorphadiene oxidase nucleic acid

<400> SEQUENCE: 59

catatggctc tgctgctggc tgtcttcctg ggtctgtcct gcctgctgct gctgtccctg      60

tgggcgaccc gttctaaaag cactaagaaa tctctgccgg aaccgtggcg tctgccaatc     120

atcggtcaca tgcaccacct gatcggcacc accccgcacc gtggcgtacg cgacctggcg     180

cgtaagtacg gctctctgat gcatctgcag ctgggcgagg tacctactat cgtcgtttcc     240

tccccgaagt gggccaaaga aatcctgact acctatgaca tcactttcgc caaccgcccg     300

gaaacgctga ccggcgaaat tgtcctgtac cataacacgg atgtggttct ggccccgtac     360

ggtgagtact ggcgccagct gcgcaaaatt tgtactctgg aactgctgag cgttaaaaag     420

gttaaatcct tccagagcct gcgtgaagag gaatgctgga acctggtgca ggagattaaa     480

gcgtctggca gcggtcgtcc agttaacctg tctgagaatg tttttaaact gatcgctact     540

atcctgtctc gcgcggcatt cggtaaaggt atcaaagatc agaaagaact gaccgaaatc     600

gttaaggaaa tcctgcgcca gactggtggc ttcgacgttg cggacatctt cccgtccaaa     660

aagttcctgc accatctgtc tggcaaacgc gctcgtctga cctccctgcg taagaaaatt     720

gataacctga ttgacaacct ggtcgctgag cacactgtga acacctcttc taaaaccaac     780

gaaaccctgc tggacgtact gctgcgcctg aaggactctg ccgaatttcc actgactagc     840

gacaatatca aagcaatcat cctggacatg ttcggcgccg gtaccgatac gtcctcttcc     900

acgattgagt gggctatttc cgaactgatc aaatgcccga aggcgatgga aaaagtgcag     960

gcggaactgc gtaaagcgct gaacggtaaa gagaaaattc atgaagagga catccaggaa    1020

ctgtcctacc tgaatatggt aatcaaagaa actctgcgtc tgcatccgcc gctgccactg    1080

gttctgccgc gtgaatgccg tcagccggtt aacctggccg gctacaacat tccgaacaaa    1140

acgaagctga tcgtcaacgt tttcgcgatc aaccgcgatc ctgaatactg gaaagacgcg    1200

gaagcgttca ttccggaacg ctttgagaac tcctctgcca ccgttatggg cgctgaatac    1260

gagtacctgc cgttcggtgc gggtcgccgt atgtgcccgg gtgctgcact gggcctggcg    1320

aacgttcaac tgccactggc gaacatcctg taccacttca actggaaact gcctaacggc    1380

gtatcttatg atcaaatcga catgaccgaa agctccggcg cgaccatgca gcgtaaaacc    1440

gaactgctgc tggttccgtc cttttgacct aggcatatgg ctctgctgct ggctgtcttc    1500

ctgggtctgt cctgcctgct gctgctgtcc ctgtgggcga cccgttctaa aagcactaag    1560

aaatctctgc cggaaccgtg gcgtctgcca atcatcggtc acatgcacca cctgatcggc    1620

accaccccgc accgtggcgt acgcgacctg gcgcgtaagt acggctctct gatgcatctg    1680

cagctgggcg aggtacctac tatcgtcgtt tcctccccga agtgggccaa agaaatcctg    1740

actacctatg acatcacttt cgccaaccgc ccggaaacgc tgaccggcga aattgtcctg    1800

taccataaca cggatgtggt tctggccccg tacggtgagt actggcgcca gctgcgcaaa    1860
```

atttgtactc tggaactgct gagcgttaaa aaggttaaat ccttccagag cctgcgtgaa 1920
gaggaatgct ggaacctggt gcaggagatt aaagcgtctg gcagcggtcg tccagttaac 1980
ctgtctgaga atgtttttaa actgatcgct actatcctgt ctcgcgcggc attcggtaaa 2040
ggtatcaaag atcagaaaga actgaccgaa atcgttaagg aaatcctgcg ccagactggt 2100
ggcttcgacg ttgcggacat cttcccgtcc aaaaagttcc tgcaccatct gtctggcaaa 2160
cgcgctcgtc tgacctccct gcgtaagaaa attgataacc tgattgacaa cctggtcgct 2220
gagcacactg tgaacacctc ttctaaaacc aacgaaaccc tgctggacgt actgctgcgc 2280
ctgaaggact ctgccgaatt tccactgact agcgacaata tcaaagcaat catcctggac 2340
atgttcggcg ccggtaccga tacgtcctct tccacgattg agtgggctat ttccgaactg 2400
atcaaatgcc cgaaggcgat ggaaaaagtg caggcggaac tgcgtaaagc gctgaacggt 2460
aaagagaaaa ttcatgaaga ggacatccag gaactgtcct acctgaatat ggtaatcaaa 2520
gaaactctgc gtctgcatcc gccgctgcca ctggttctgc cgcgtgaatg ccgtcagccg 2580
gttaacctgg ccggctacaa cattccgaac aaaacgaagc tgatcgtcaa cgttttcgcg 2640
atcaaccgcg atcctgaata ctggaaagac gcggaagcgt tcattccgga acgctttgag 2700
aactcctctg ccaccgttat gggcgctgaa tacgagtacc tgccgttcgg tgcgggtcgc 2760
cgtatgtgcc cgggtgctgc actgggcctg gcgaacgttc aactgccact ggcgaacatc 2820
ctgtaccact tcaactggaa actgcctaac ggcgtatctt atgatcaaat cgacatgacc 2880
gaaagctccg gcgcgaccat gcagcgtaaa accgaactgc tgctggttcc gtccttttaa 2940
cctagg 2946

<210> SEQ ID NO 60
<211> LENGTH: 1464
<212> TYPE: DNA
<213> ORGANISM: Artificial Sequence
<220> FEATURE:
<223> OTHER INFORMATION: Modified amorphadiene oxidase nucleic acid

<400> SEQUENCE: 60
atggctctgc tgctggctgt cttcctgggt ctgtcctgcc tgctgctgct gtccctgtgg 60
gcgacccgtt ctaaaagcac taagaaatct ctgccggaac cgtggcgtct gccaatcatc 120
ggtcacatgc accacctgat cggcaccacc ccgcaccgtg gcgtacgcga cctggcgcgt 180
aagtacggct ctctgatgca tctgcagctg ggcgaggtac ctactatcgt cgtttcctcc 240
ccgaagtggg ccaaagaaat cctgactacc tatgacatca ctttcgccaa ccgcccggaa 300
acgctgaccg gcgaaattgt cctgtaccat aacacggatg tggttctggc cccgtacggt 360
gagtactggc gccagctgcg caaaatttgt actctggaac tgctgagcgt taaaaaggtt 420
aaatccttcc agagcctgcg tgaagaggaa tgctggaacc tggtgcagga gattaaagcg 480
tctggcagcg gtcgtccagt taacctgtct gagaatgttt ttaaactgat cgctactatc 540
ctgtctcgcg cggcattcgg taaaggtatc aaagatcaga aagaactgac cgaaatcgtt 600
aaggaaatcc tgcgccagac tggtggcttc gacgttgcgg acatcttccc gtccaaaaag 660
ttcctgcacc atctgtctgg caaacgcgct cgtctgacct ccctgcgtaa gaaaattgat 720
aacctgattg acaacctggt cgctgagcac actgtgaaca cctcttctaa aaccaacgaa 780
accctgctgg acgtactgct gcgcctgaag gactctgccg aatttccact gactagcgac 840
aatatcaaag caatcatcct ggacatgttc ggcgccggta ccgatacgtc ctcttccacg 900
attgagtggg ctatttccga actgatcaaa tgcccgaagg cgatggaaaa agtgcaggcg 960

```
gaactgcgta aagcgctgaa cggtaaagag aaaattcatg aagaggacat ccaggaactg   1020

tcctacctga atatggtaat caaagaaact ctgcgtctgc atccgccgct gccactggtt   1080

ctgccgcgtg aatgccgtca gccggttaac ctggccggct acaacattcc gaacaaaacg   1140

aagctgatcg tcaacgtttt cgcgatcaac cgcgatcctg aatactggaa agacgcggaa   1200

gcgttcattc cggaacgctt tgagaactcc tctgccaccg ttatgggcgc tgaatacgag   1260

tacctgccgt tcggtgcggg tcgccgtatg tgcccgggtg ctgcactggg cctggcgaac   1320

gttcaactgc cactggcgaa catcctgtac cacttcaact ggaaactgcc taacggcgta   1380

tcttatgatc aaatcgacat gaccgaaagc tccggcgcga ccatgcagcg taaaaccgaa   1440

ctgctgctgg ttccgtcctt ttaa                                           1464
```

<210> SEQ ID NO 61
<211> LENGTH: 487
<212> TYPE: PRT
<213> ORGANISM: Artificial Sequence
<220> FEATURE:
<223> OTHER INFORMATION: Modified amorphadiene oxidase

<400> SEQUENCE: 61

```
Met Ala Leu Leu Leu Ala Val Phe Leu Gly Leu Ser Cys Leu Leu Leu
 1               5                  10                  15

Leu Ser Leu Trp Ala Thr Arg Ser Lys Ser Thr Lys Lys Ser Leu Pro
            20                  25                  30

Glu Pro Trp Arg Leu Pro Ile Ile Gly His Met His His Leu Ile Gly
        35                  40                  45

Thr Thr Pro His Arg Gly Val Arg Asp Leu Ala Arg Lys Tyr Gly Ser
    50                  55                  60

Leu Met His Leu Gln Leu Gly Glu Val Pro Thr Ile Val Val Ser Ser
65                  70                  75                  80

Pro Lys Trp Ala Lys Glu Ile Leu Thr Thr Tyr Asp Ile Thr Phe Ala
                85                  90                  95

Asn Arg Pro Glu Thr Leu Thr Gly Glu Ile Val Leu Tyr His Asn Thr
            100                 105                 110

Asp Val Val Leu Ala Pro Tyr Gly Glu Tyr Trp Arg Gln Leu Arg Lys
        115                 120                 125

Ile Cys Thr Leu Glu Leu Leu Ser Val Lys Lys Val Lys Ser Phe Gln
    130                 135                 140

Ser Leu Arg Glu Glu Glu Cys Trp Asn Leu Val Gln Glu Ile Lys Ala
145                 150                 155                 160

Ser Gly Ser Gly Arg Pro Val Asn Leu Ser Glu Asn Val Phe Lys Leu
                165                 170                 175

Ile Ala Thr Ile Leu Ser Arg Ala Ala Phe Gly Lys Gly Ile Lys Asp
            180                 185                 190

Gln Lys Glu Leu Thr Glu Ile Val Lys Glu Ile Leu Arg Gln Thr Gly
        195                 200                 205

Gly Phe Asp Val Ala Asp Ile Phe Pro Ser Lys Lys Phe Leu His His
    210                 215                 220

Leu Ser Gly Lys Arg Ala Arg Leu Thr Ser Leu Arg Lys Lys Ile Asp
225                 230                 235                 240

Asn Leu Ile Asp Asn Leu Val Ala Glu His Thr Val Asn Thr Ser Ser
                245                 250                 255

Lys Thr Asn Glu Thr Leu Leu Asp Val Leu Leu Arg Leu Lys Asp Ser
            260                 265                 270
```

```
Ala Glu Phe Pro Leu Thr Ser Asp Asn Ile Lys Ala Ile Ile Leu Asp
        275                 280                 285

Met Phe Gly Ala Gly Thr Asp Thr Ser Ser Ser Thr Ile Glu Trp Ala
    290                 295                 300

Ile Ser Glu Leu Ile Lys Cys Pro Lys Ala Met Glu Lys Val Gln Ala
305                 310                 315                 320

Glu Leu Arg Lys Ala Leu Asn Gly Lys Glu Lys Ile His Glu Glu Asp
                325                 330                 335

Ile Gln Glu Leu Ser Tyr Leu Asn Met Val Ile Lys Glu Thr Leu Arg
            340                 345                 350

Leu His Pro Pro Leu Pro Leu Val Leu Pro Arg Glu Cys Arg Gln Pro
        355                 360                 365

Val Asn Leu Ala Gly Tyr Asn Ile Pro Asn Lys Thr Lys Leu Ile Val
    370                 375                 380

Asn Val Phe Ala Ile Asn Arg Asp Pro Glu Tyr Trp Lys Asp Ala Glu
385                 390                 395                 400

Ala Phe Ile Pro Glu Arg Phe Glu Asn Ser Ser Ala Thr Val Met Gly
                405                 410                 415

Ala Glu Tyr Glu Tyr Leu Pro Phe Gly Ala Gly Arg Arg Met Cys Pro
            420                 425                 430

Gly Ala Ala Leu Gly Leu Ala Asn Val Gln Leu Pro Leu Ala Asn Ile
        435                 440                 445

Leu Tyr His Phe Asn Trp Lys Leu Pro Asn Gly Val Ser Tyr Asp Gln
    450                 455                 460

Ile Asp Met Thr Glu Ser Ser Gly Ala Thr Met Gln Arg Lys Thr Glu
465                 470                 475                 480

Leu Leu Leu Val Pro Ser Phe
                485
```

<210> SEQ ID NO 62
<211> LENGTH: 10633
<212> TYPE: DNA
<213> ORGANISM: Artificial Sequence
<220> FEATURE:
<223> OTHER INFORMATION: Recombinant plasmid

<400> SEQUENCE: 62

```
accttcggga gcgcctgaag cccgttctgg acgccctggg gccgttgaat cgggatatgc     60

aggccaaggc cgccgcgatc atcaaggccg tgggcgaaaa gctgctgacg gaacagcggg    120

aagtccagcg ccagaaacag gcccagcgcc agcaggaacg cgggcgcgca catttccccg    180

aaaagtgcca cctgacgtct aagaaaccat tattatcatg acattaacct ataaaaatag    240

gcgtatcacg aggccctttc gtcttcaaga attctcatgt ttgacagctt atcatcgata    300

agctttaatg cggtagttta tcacagttaa attgctaacg cagtcaggca ccgtgtatga    360

aatctaacaa tgcgctcatc gtcatcctcg gcaccgtcac cctggatgct gtaggcatag    420

gcttggttat gccggtactg ccgggcctct tgcgggatat cgtccattcc gacagcatcg    480

ccagtcacta tggcgtgctg ctagcgctat atgcgttgat gcaatttcta tgcgcacccg    540

ttctcggagc actgtccgac cgctttggcc gccgcccagt cctgctcgct tcgctacttg    600

gagccactat cgactacgcg atcatggcga ccacacccgt cctgtggatc ctctacgccg    660

gacgcatcgt ggccggcatc accggcgcca caggtgcggt tgctggcgcc tatatcgccg    720

acatcaccga tggggaagat cgggctcgcc acttcgggct catgagcgct tgtttcggcg    780

tgggtatggt ggcaggcccc gtggccgggg gactgttggg cgccatctcc ttgcatgcac    840
```

-continued

```
cattccttgc ggcggcggtg ctcaacggcc tcaacctact actgggctgc ttcctaatgc    900

aggagtcgca taagggagag cgtcgaccga tgcccttgag agccttcaac ccagtcagct    960

ccttccggtg ggcgcggggc atgactatcg tcgccgcact tatgactgtc ttctttatca   1020

tgcaactcgt aggacaggtg ccggcagcgc tctgggtcat tttcggcgag gaccgctttc   1080

gctggagcgc gacgatgatc ggcctgtcgc ttgcggtatt cggaatcttg cacgccctcg   1140

ctcaagcctt cgtcactggt cccgccacca aacgtttcgg cgagaagcag gccattatcg   1200

ccggcatggc ggccgacgcg ctgggctacg tcttgctggc gttcgcgacg cgaggctgga   1260

tggccttccc cattatgatt cttctcgctt ccggcggcat cgggatgccc gcgttgcagg   1320

ccatgctgtc caggcaggta gatgacgacc atcagggaca gcttcaagga tcgctcgcgg   1380

ctcttaccag cctaacttcg atcactggac cgctgatcgt cacggcgatt tatgccgcct   1440

cggcgagcac atggaacggg ttggcatgga ttgtaggcgc cgccctatac cttgtctgcc   1500

tccccgcgtt gcgtcgcggt gcatggagcc gggccacctc gacctgaatg gaagccggcg   1560

gcacctcgct aacggattca ccactccaag aattggagcc aatcaattct tgcggagaac   1620

tgtgaatgcg caaatgcgcc caatacgcaa accgcctctc cccgcgcgtt ggccgattca   1680

ttaatgcagc tggcacgaca ggtttcccga ctggaaagcg ggcagtgagc gcaacgcaat   1740

taatgtgagt tagctcactc attaggcacc ccaggcttta cactttatgc ttccggctcg   1800

tatgttgtgt ggaattgtga gcggataaca atttcacaca ggaaacagct atgaccatga   1860

ttacgccaag cgcgcaatta accctcacta aagggaacaa aagctgggta ccgggccccc   1920

cctcgaggtc gacggtatcg ataagcttga tatcgaattc ctgcagtagg aggaattaac   1980

catgtcatta ccgttcttaa cttctgcacc gggaaaggtt attatttttg gtgaacactc   2040

tgctgtgtac aacaagcctg ccgtcgctgc tagtgtgtct gcgttgagaa cctacctgct   2100

aataagcgag tcatctgcac cagatactat tgaattggac ttcccggaca ttagctttaa   2160

tcataagtgg tccatcaatg atttcaatgc catcaccgag gatcaagtaa actcccaaaa   2220

attggccaag gctcaacaag ccaccgatgg cttgtctcag gaactcgtta gtcttttgga   2280

tccgttgtta gctcaactat ccgaatcctt ccactaccat gcagcgtttt gtttcctgta   2340

tatgtttgtt tgcctatgcc cccatgccaa gaatattaag ttttctttaa agtctacttt   2400

acccatcggt gctgggttgg gctcaagcgc ctctatttct gtatcactgg ccttagctat   2460

ggcctacttg ggggggttaa taggatctaa tgacttggaa aagctgtcag aaaacgataa   2520

gcatatagtg aatcaatggg ccttcatagg tgaaaagtgt attcacggta ccccttcagg   2580

aatagataac gctgtggcca cttatggtaa tgccctgcta tttgaaaaag actcacataa   2640

tggaacaata aacacaaaca attttaagtt cttagatgat ttcccagcca ttccaatgat   2700

cctaacctat actagaattc caaggtctac aaaagatctt gttgctcgcg ttcgtgtgtt   2760

ggtcaccgag aaatttcctg aagttatgaa gccaattcta gatgccatgg gtgaatgtgc   2820

cctacaaggc ttagagatca tgactaagtt aagtaaatgt aaaggcaccg atgacgaggc   2880

tgtagaaact aataatgaac tgtatgaaca actattggaa ttgataagaa taaatcatgg   2940

actgcttgtc tcaatcggtg tttctcatcc tggattagaa cttattaaaa atctgagcga   3000

tgatttgaga attggctcca caaaacttac cggtgctggt ggcggcggtt gctctttgac   3060

tttgttacga agagacatta ctcaagagca aattgacagc ttcaaaaaga aattgcaaga   3120

tgattttagt tacgagacat ttgaaacaga cttgggtggg actggctgct gtttgttaag   3180

cgcaaaaaat ttgaataaag atcttaaaat caaatcccta gtattccaat tatttgaaaa   3240
```

```
taaaactacc acaaagcaac aaattgacga tctattattg ccaggaaaca cgaatttacc   3300
atggacttca taggaggcag atcaaatgtc agagttgaga gccttcagtg ccccagggaa   3360
agcgttacta gctggtggat atttagtttt agatacaaaa tatgaagcat ttgtagtcgg   3420
attatcggca agaatgcatg ctgtagccca tccttacggt tcattgcaag ggtctgataa   3480
gtttgaagtg cgtgtgaaaa gtaaacaatt taaagatggg gagtggctgt accatataag   3540
tcctaaaagt ggcttcattc ctgtttcgat aggcggatct aagaaccctt tcattgaaaa   3600
agttatcgct aacgtattta gctactttaa acctaacatg gacgactact gcaatagaaa   3660
cttgttcgtt attgatattt tctctgatga tgcctaccat tctcaggagg atagcgttac   3720
cgaacatcgt ggcaacagaa gattgagttt tcattcgcac agaattgaag aagttcccaa   3780
aacagggctg ggctcctcgg caggtttagt cacagtttta actacagctt tggcctcctt   3840
ttttgtatcg gacctggaaa ataatgtaga caaatataga gaagttattc ataatttagc   3900
acaagttgct cattgtcaag ctcagggtaa aattggaagc gggtttgatg tagcggcggc   3960
agcatatgga tctatcagat atagaagatt cccacccgca ttaatctcta atttgccaga   4020
tattggaagt gctacttacg gcagtaaact ggcgcatttg gttgatgaag aagactggaa   4080
tattacgatt aaaagtaacc atttaccttc gggattaact ttatggatgg gcgatattaa   4140
gaatggttca gaaacagtaa aactggtcca gaaggtaaaa aattggtatg attcgcatat   4200
gccagaaagc ttgaaaatat atacagaact cgatcatgca aattctagat ttatggatgg   4260
actatctaaa ctagatcgct tacacgagac tcatgacgat tacagcgatc agatatttga   4320
gtctcttgag aggaatgact gtacctgtca aaagtatcct gaaatcacag aagttagaga   4380
tgcagttgcc acaattagac gttcctttag aaaaataact aaagaatctg gtgccgatat   4440
cgaacctccc gtacaaacta gcttattgga tgattgccag accttaaaag gagttcttac   4500
ttgcttaata cctggtgctg gtggttatga cgccattgca gtgattacta agcaagatgt   4560
tgatcttagg gctcaaaccg ctaatgacaa aagattttct aaggttcaat ggctggatgt   4620
aactcaggct gactggggtg ttaggaaaga aaaagatccg gaaacttatc ttgataaata   4680
ggaggtaata ctcatgaccg tttacacagc atccgttacc gcacccgtca acatcgcaac   4740
ccttaagtat tgggggaaaa gggacacgaa gttgaatctg cccaccaatt cgtccatatc   4800
agtgacttta tcgcaagatg acctcagaac gttgacctct gcggctactg cacctgagtt   4860
tgaacgcgac actttgtggt taaatggaga accacacagc atcgacaatg aaagaactca   4920
aaattgtctg cgcgacctac gccaattaag aaaggaaatg gaatcgaagg acgcctcatt   4980
gcccacatta tctcaatgga aactccacat tgtctccgaa aataactttc ctacagcagc   5040
tggtttagct tcctccgctg ctggctttgc tgcattggtc tctgcaattg ctaagttata   5100
ccaattacca cagtcaactt cagaaatatc tagaatagca agaaaggggt ctggttcagc   5160
ttgtagatcg ttgtttggcg gatacgtggc ctgggaaatg ggaaaagctg aagatggtca   5220
tgattccatg gcagtacaaa tcgcagacag ctctgactgg cctcagatga aagcttgtgt   5280
cctagttgtc agcgatatta aaaaggatgt gagttccact cagggtatgc aattgaccgt   5340
ggcaacctcc gaactattta aagaaagaat tgaacatgtc gtaccaaaga gatttgaagt   5400
catgcgtaaa gccattgttg aaaaagattt cgccaccttt gcaaaggaaa caatgatgga   5460
ttccaactct ttccatgcca catgtttgga ctctttccct ccaatattct acatgaatga   5520
cacttccaag cgtatcatca gttggtgcca caccattaat cagttttacg gagaaacaat   5580
cgttgcatac acgtttgatg caggtccaaa tgctgtgttg tactacttag ctgaaaatga   5640
```

```
gtcgaaactc tttgcattta tctataaatt gtttggctct gttcctggat gggacaagaa   5700
atttactact gagcagcttg aggctttcaa ccatcaattt gaatcatcta actttactgc   5760
acgtgaattg gatcttgagt tgcaaaagga tgttgccaga gtgattttaa ctcaagtcgg   5820
ttcaggccca caagaaacaa acgaatcttt gattgacgca aagactggtc taccaaagga   5880
ataactgcag cccgggagga ggattactat atgcaaacgg aacacgtcat tttattgaat   5940
gcacagggag ttcccacggg tacgctggaa aagtatgccg cacacacggc agacacccgc   6000
ttacatctcg cgttctccag ttggctgttt aatgccaaag gacaattatt agttacccgc   6060
cgcgcactga gcaaaaaagc atggcctggc gtgtggacta actcggtttg tgggcaccca   6120
caactgggag aaagcaacga agacgcagtg atccgccgtt gccgttatga gcttggcgtg   6180
gaaattacgc ctcctgaatc tatctatcct gactttcgct accgcgccac cgatccgagt   6240
ggcattgtgg aaaatgaagt gtgtccggta tttgccgcac gcaccactag tgcgttacag   6300
atcaatgatg atgaagtgat ggattatcaa tggtgtgatt tagcagatgt attacacggt   6360
attgatgcca cgccgtgggc gttcagtccg tggatggtga tgcaggcgac aaatcgcgaa   6420
gccagaaaac gattatctgc atttacccag cttaaataac ccgggggatc cactagttct   6480
agagcggccg ccaccgcgga ggaggaatga gtaatggact ttccgcagca actcgaagcc   6540
tgcgttaagc aggccaacca ggcgctgagc cgttttatcg ccccactgcc ctttcagaac   6600
actcccgtgg tcgaaaccat gcagtatggc gcattattag gtggtaagcg cctgcgacct   6660
ttcctggttt atgccaccgg tcatatgttc ggcgttagca caaacacgct ggacgcaccc   6720
gctgccgccg ttgagtgtat ccacgcttac tcattaattc atgatgattt accggcaatg   6780
gatgatgacg atctgcgtcg cggtttgcca acctgccatg tgaagtttgg cgaagcaaac   6840
gcgattctcg ctggcgacgc tttacaaacg ctggcgttct cgattttaag cgatgccgat   6900
atgccggaag tgtcggaccg cgacagaatt tcgatgattt ctgaactggc gagcgccagt   6960
ggtattgccg gaatgtgcgg tggtcaggca ttagatttag acgcggaagg caaacacgta   7020
cctctggacg cgcttgagcg tattcatcgt cataaaaccg gcgcattgat tcgcgccgcc   7080
gttcgccttg gtgcattaag cgccggagat aaaggacgtc gtgctctgcc ggtactcgac   7140
aagtatgcag agagcatcgg ccttgccttc caggttcagg atgacatcct ggatgtggtg   7200
ggagatactg caacgttggg aaaacgccag ggtgccgacc agcaacttgg taaaagtacc   7260
taccctgcac ttctgggtct tgagcaagcc cggaagaaag cccgggatct gatcgacgat   7320
gcccgtcagt cgctgaaaca actggctgaa cagtcactcg atacctcggc actggaagcg   7380
ctagcggact acatcatcca gcgtaataaa taagagctcc aattcgccct atagtgagtc   7440
gtattacgcg cgctcactgg ccgtcgtttt acaacgtcgt gactgggaaa accctggcgt   7500
tacccaactt aatcgccttg cagcacatcc ccctttcgcc agctggcgta atagcgaaga   7560
ggcccgcacc gatcgccctt cccaacagtt gcgcagcctg aatggcgaat ggaaattgta   7620
agcgttaata ttttgttaaa attcgcgtta aatttttgtt aaatcagctc atttttaac    7680
caataggccg actgcgatga gtggcagggc ggggcgtaat ttttttaagg cagttattgg   7740
tgcccttaaa cgcctggtgc tacgcctgaa taagtgataa taagcggatg aatggcagaa   7800
```

```
attcgaaagc aaattcgacc cggtcgtcgg ttcagggcag ggtcgttaaa tagccgctta   7860
tgtctattgc tggtttaccg gtttattgac taccggaagc agtgtgaccg tgtgcttctc   7920
aaatgcctga ggccagtttg ctcaggctct ccccgtggag gtaataattg acgatatgat   7980
catttattct gcctcccaga gcctgataaa aacggtgaat ccgttagcga ggtgccgccg   8040
gcttccattc aggtcgaggt ggcccggctc catgcaccgc gacgcaacgc ggggaggcag   8100
acaaggtata gggcggcgag gcggctacag ccgatagtct ggaacagcgc acttacgggt   8160
tgctgcgcaa cccaagtgct accggcgcgg cagcgtgacc cgtgtcggcg gctccaacgg   8220
ctcgccatcg tccagaaaac acggctcatc gggcatcggc aggcgctgct gcccgcgccg   8280
ttcccattcc tccgtttcgg tcaaggctgg caggtctggt tccatgcccg gaatgccggg   8340
ctggctgggc ggctcctcgc cggggccggt cggtagttgc tgctcgcccg gatacagggt   8400
cgggatgcgg cgcaggtcgc catgccccaa cagcgattcg tcctggtcgt cgtgatcaac   8460
caccacggcg gcactgaaca ccgacaggcg caactggtcg cggggctggc cccacgccac   8520
gcggtcattg accacgtagg ccgacacggt gccggggccg ttgagcttca cgacggagat   8580
ccagcgctcg gccaccaagt ccttgactgc gtattggacc gtccgcaaag aacgtccgat   8640
gagcttggaa agtgtcttct ggctgaccac cacggcgttc tggtggccca tctgcgccac   8700
gaggtgatgc agcagcattg ccgccgtggg tttcctcgca ataagcccgg cccacgcctc   8760
atgcgctttg cgttccgttt gcacccagtg accgggcttg ttcttggctt gaatgccgat   8820
ttctctggac tgcgtggcca tgcttatctc catgcggtag ggtgccgcac ggttgcggca   8880
ccatgcgcaa tcagctgcaa cttttcggca gcgcgacaac aattatgcgt tgcgtaaaag   8940
tggcagtcaa ttacagattt tctttaacct acgcaatgag ctattgcggg gggtgccgca   9000
atgagctgtt gcgtaccccc ctttttttaag ttgttgattt ttaagtcttt cgcatttcgc   9060
cctatatcta gttctttggt gcccaaagaa gggcacccct gcggggttcc cccacgcctt   9120
cggcgcggct ccccctccgg caaaaagtgg cccctccggg gcttgttgat cgactgcgcg   9180
gccttcggcc ttgcccaagg tggcgctgcc cccttggaac cccgcactc gccgccgtga    9240
ggctcggggg gcaggcgggc gggcttcgcc ttcgactgcc cccactcgca taggcttggg   9300
tcgttccagg cgcgtcaagg ccaagccgct gcgcggtcgc tgcgcgagcc ttgacccgcc   9360
ttccacttgg tgtccaaccg gcaagcgaag cgcgcaggcc gcaggccgga ggcttttccc   9420
cagagaaaat taaaaaaatt gatggggcaa ggccgcaggc cgcgcagttg gagccggtgg   9480
gtatgtggtc gaaggctggg tagccggtgg gcaatccctg tggtcaagct cgtgggcagg   9540
cgcagcctgt ccatcagctt gtccagcagg gttgtccacg ggccgagcga agcgagccag   9600
ccggtggccg ctcgcggcca tcgtccacat atccacgggc tggcaaggga gcgcagcgac   9660
cgcgcagggc gaagcccgga gagcaagccc gtagggcgcc gcagccgccg taggcggtca   9720
cgactttgcg aagcaaagtc tagtgagtat actcaagcat tgagtggccc gccggaggca   9780
ccgccttgcg ctgcccccgt cgagccggtt ggacaccaaa agggaggggc aggcatggcg   9840
gcatacgcga tcatgcgatg caagaagctg gcgaaaatgg gcaacgtggc ggccagtctc   9900
aagcacgcct accgcgagcg cgagacgccc aacgctgacg ccagcaggac gccagagaac   9960
gagcactggg cggccagcag caccgatgaa gcgatgggcc gactgcgcga gttgctgcca   10020
gagaagcggc gcaaggacgc tgtgttggcg gtcgagtacg tcatgacggc cagcccggaa   10080
tggtggaagt cggccagcca agaacagcag gcggcgttct tcgagaaggc gcacaagtgg   10140
ctggcggaca agtacggggc ggatcgcatc gtgacggcca gcatccaccg tgacgaaacc   10200
```

```
agcccgcaca tgaccgcgtt cgtggtgccg ctgacgcagg acggcaggct gtcggccaag  10260

gagttcatcg gcaacaaagc gcagatgacc cgcgaccaga ccacgtttgc ggccgctgtg  10320

gccgatctag ggctgcaacg gggcatcgag ggcagcaagg cacgtcacac gcgcattcag  10380

gcgttctacg aggccctgga gcggccacca gtgggccacg tcaccatcag cccgcaagcg  10440

gtcgagccac gcgcctatgc accgcaggga ttggccgaaa agctgggaat ctcaaagcgc  10500

gttgagacgc cggaagccgt ggccgaccgg ctgacaaaag cggttcggca ggggtatgag  10560

cctgccctac aggccgccgc aggagcgcgt gagatgcgca agaaggccga tcaagcccaa  10620

gagacggccc gag                                                      10633
```

<210> SEQ ID NO 63
<211> LENGTH: 4263
<212> TYPE: DNA
<213> ORGANISM: Artificial Sequence
<220> FEATURE:
<223> OTHER INFORMATION: Recombinant polynucleotide

<400> SEQUENCE: 63

```
cttgatatcg aattcctgca gcccggggat cctctagagt cgactaggag gaatataaaa    60

tgaaaaattg tgtcatcgtc agtgcggtac gtactgctat cggtagtttt aacggttcac   120

tcgcttccac cagcgccatc gacctggggg cgacagtaat taaagccgcc attgaacgtg   180

caaaaatcga ttcacaacac gttgatgaag tgattatggg taacgtgtta caagccgggc   240

tggggcaaaa tccggcgcgt caggcactgt taaaaagcgg gctggcagaa acggtgtgcg   300

gattcacggt caataaagta tgtggttcgg gtcttaaaag tgtggcgctt gccgcccagg   360

ccattcaggc aggtcaggcg cagagcattg tggcgggggg tatggaaaat atgagtttag   420

ccccctactt actcgatgca aaagcacgct ctggttatcg tcttggagac ggacaggttt   480

atgacgtaat cctgcgcgat ggcctgatgt gcgccaccca tggttatcat atggggatta   540

ccgccgaaaa cgtggctaaa gagtacggaa ttacccgtga aatgcaggat gaactggcgc   600

tacattcaca gcgtaaagcg gcagccgcaa ttgagtccgg tgcttttaca gccgaaatcg   660

tcccggtaaa tgttgtcact cgaaagaaaa ccttcgtctt cagtcaagac gaattcccga   720

aagcgaattc aacggctgaa gcgttaggtg cattgcgccc ggccttcgat aaagcaggaa   780

cagtcaccgc tgggaacgcg tctggtatta acgacggtgc tgccgctctg gtgattatgg   840

aagaatctgc ggcgctggca gcaggcctta cccccctggc tcgcattaaa agttatgcca   900

gcggtggcgt gccccccgca ttgatgggta tggggccagt acctgccacg caaaaagcgt   960

tacaactggc ggggctgcaa ctggcggata ttgatctcat tgaggctaat gaagcatttg  1020

ctgcacagtt ccttgccgtt gggaaaaacc tgggctttga ttctgagaaa gtgaatgtca  1080

acggcggggc catcgcgctc gggcatccta tcggtgccag tggtgctcgt attctggtca  1140

cactattaca tgccatgcag gcacgcgata aaacgctggg gctggcaaca ctgtgcattg  1200

gcggcggtca gggaattgcg atggtgattg aacggttgaa ttaaggagga cagctaaatg  1260

aaactctcaa ctaaactttg ttggtgtggt attaaaggaa gacttaggcc gcaaaagcaa  1320

caacaattac acaatacaaa cttgcaaatg actgaactaa aaaaacaaaa gaccgctgaa  1380

caaaaaacca gacctcaaaa tgtcggtatt aaaggtatcc aaatttacat cccaactcaa  1440

tgtgtcaacc aatctgagct agagaaattt gatggcgttt ctcaaggtaa atacacaatt  1500

ggtctgggcc aaaccaacat gtcttttgtc aatgacagag aagatatcta ctcgatgtcc  1560

ctaactgttt tgtctaagtt gatcaagagt tacaacatcg acaccaacaa aattggtaga  1620
```

```
ttagaagtcg gtactgaaac tctgattgac aagtccaagt ctgtcaagtc tgtcttgatg   1680
caattgtttg gtgaaaacac tgacgtcgaa ggtattgaca cgcttaatgc ctgttacggt   1740
ggtaccaacg cgttgttcaa ctctttgaac tggattgaat ctaacgcatg ggatggtaga   1800
gacgccattg tagtttgcgg tgatattgcc atctacgata agggtgccgc aagaccaacc   1860
ggtggtgccg gtactgttgc tatgtggatc ggtcctgatg ctccaattgt atttgactct   1920
gtaagagctt cttacatgga acacgcctac gatttttaca agccagattt caccagcgaa   1980
tatccttacg tcgatggtca tttttcatta acttgttacg tcaaggctct tgatcaagtt   2040
tacaagagtt attccaagaa ggctatttct aaagggttgg ttagcgatcc cgctggttcg   2100
gatgctttga acgttttgaa atatttcgac tacaacgttt tccatgttcc aacctgtaaa   2160
ttggtcacaa aatcatacgg tagattacta tataacgatt tcagagccaa tcctcaattg   2220
ttcccagaag ttgacgccga attagctact cgcgattatg acgaatcttt aaccgataag   2280
aacattgaaa aaacttttgt taatgttgct aagccattcc acaaagagag agttgcccaa   2340
tctttgattg ttccaacaaa cacaggtaac atgtacaccg catctgttta tgccgccttt   2400
gcatctctat taaactatgt tggatctgac gacttacaag gcaagcgtgt tggtttattt   2460
tcttacggtt ccggtttagc tgcatctcta tattcttgca aaattgttgg tgacgtccaa   2520
catattatca aggaattaga tattactaac aaattagcca agagaatcac cgaaactcca   2580
aaggattacg aagctgccat cgaattgaga gaaaatgccc atttgaagaa gaacttcaaa   2640
cctcaaggtt ccattgagca tttgcaaagt ggtgtttact acttgaccaa catcgatgac   2700
aaatttagaa gatcttacga tgttaaaaaa taaggaggat tacactatgg ttttaaccaa   2760
taaaacagtc atttctggat cgaaagtcaa aagtttatca tctgcgcaat cgagctcatc   2820
aggaccttca tcatctagtg aggaagatga ttcccgcgat attgaaagct tggataagaa   2880
aatacgtcct ttagaagaat tagaagcatt attaagtagt ggaaatacaa aacaattgaa   2940
gaacaaagag gtcgctgcct tggttattca cggtaagtta cctttgtacg ctttggagaa   3000
aaaattaggt gatactacga gagcggttgc ggtacgtagg aaggctcttt caattttggc   3060
agaagctcct gtattagcat ctgatcgttt accatataaa aattatgact acgaccgcgt   3120
atttggcgct tgttgtgaaa atgttatagg ttacatgcct ttgcccgttg gtgttatagg   3180
ccccttggtt atcgatggta catcttatca tataccaatg gcaactacag agggttgttt   3240
ggtagcttct gccatgcgtg gctgtaaggc aatcaatgct ggcggtggtg caacaactgt   3300
tttaactaag gatggtatga caagaggccc agtagtccgt ttcccaactt tgaaaagatc   3360
tggtgcctgt aagatatggt tagactcaga agagggacaa aacgcaatta aaaaagcttt   3420
taactctaca tcaagatttg cacgtctgca acatattcaa acttgtctag caggagattt   3480
actcttcatg agatttagaa caactactgg tgacgcaatg ggtatgaata tgatttctaa   3540
aggtgtcgaa tactcattaa agcaaatggt agaagagtat ggctgggaag atatggaggt   3600
tgtctccgtt tctggtaact actgtaccga caaaaaacca gctgccatca actggatcga   3660
aggtcgtggt aagagtgtcg tcgcagaagc tactattcct ggtgatgttg tcagaaaagt   3720
gttaaaaagt gatgtttccg cattggttga gttgaacatt gctaagaatt tggttggatc   3780
tgcaatggct gggtctgttg gtggatttaa cgcacatgca gctaatttag tgacagctgt   3840
tttcttggca ttaggacaag atcctgcaca aaatgttgaa agttccaact gtataacatt   3900
gatgaaagaa gtggacggtg atttgagaat ttccgtatcc atgccatcca tcgaagtagg   3960
taccatcggt ggtggtactg ttctagaacc acaaggtgcc atgttggact tattaggtgt   4020
```

-continued

```
aagaggcccg catgctaccg ctcctggtac caacgcacgt caattagcaa gaatagttgc    4080

ctgtgccgtc ttggcaggtg aattatcctt atgtgctgcc ctagcagccg gccatttggt    4140

tcaaagtcat atgacccaca acaggaaacc tgctgaacca acaaaaccta acaatttgga    4200

cgccactgat ataaatcgtt tgaaagatgg gtccgtcacc tgcattaaat cctaagtcga    4260

cct                                                                  4263
```

NUCLEIC ACIDS ENCODING MODIFIED CYTOCHROME P450 ENZYMES AND METHODS OF USE THEREOF

CROSS-REFERENCE

This application claims the benefit of U.S. Provisional Patent Application No. 60/724,525, filed Oct. 7, 2005, and U.S. Provisional Patent Application No. 60/762,700, filed Jan. 27, 2006, which applications are incorporated herein by reference in their entirety.

FIELD OF THE INVENTION

The present invention is in the field of production of isoprenoid compounds, and in particular host cells that are genetically modified with nucleic acids encoding isoprenoid precursor modifying enzymes.

BACKGROUND OF THE INVENTION

Isoprenoids constitute an extremely large and diverse group of natural products that have a common biosynthetic origin, i.e., a single metabolic precursor, isopentenyl diphosphate (IPP). Isoprenoid compounds are also referred to as "terpenes" or "terpenoids." Over 40,000 isoprenoids have been described. By definition, isoprenoids are made up of so-called isoprene (C5) units. The number of C-atoms present in the isoprenoids is typically divisible by five (C5, C10, C15, C20, C25, C30 and C40), although irregular isoprenoids and polyterpenes have been reported. Important members of the isoprenoids include the carotenoids, sesquiterpenoids, diterpenoids, and hemiterpenes. Carotenoids include, e.g., lycopene, β-carotene, and the like, many of which function as antioxidants. Sesquiterpenoids include, e.g., artemisinin, a compound having anti-malarial activity. Diterpenoids include, e.g., taxol, a cancer chemotherapeutic agent.

Isoprenoids comprise the most numerous and structurally diverse family of natural products. In this family, terpenoids isolated from plants and other natural sources are used as commercial flavor and fragrance compounds as well as antimalarial and anticancer drugs. A majority of the terpenoid compounds in use today are natural products or their derivatives. The source organisms (e.g., trees, marine invertebrates) of many of these natural products are neither amenable to the large-scale cultivation necessary to produce commercially viable quantities nor to genetic manipulation for increased production or derivatization of these compounds. Therefore, the natural products must be produced semi-synthetically from analogs or synthetically using conventional chemical syntheses. Furthermore, many natural products have complex structures, and, as a result, are currently uneconomical or impossible to synthesize. Such natural products must be either extracted from their native sources, such as trees, sponges, corals and marine microbes; or produced synthetically or semi-synthetically from more abundant precursors. Extraction of a natural product from a native source is limited by the availability of the native source; and synthetic or semi-synthetic production of natural products can suffer from low yield and/or high cost. Such production problems and limited availability of the natural source can restrict the commercial and clinical development of such products.

The biosynthesis of isoprenoid natural products in engineered (genetically modified) host cells, e.g., in vitro (e.g., in a fermentation system) or in vivo (e.g., in a genetically modified multi-cellular organism), could tap the unrealized commercial and therapeutic potential of these natural resources and yield less expensive and more widely available fine chemicals and pharmaceuticals. One obstacle to production of isoprenoid or isoprenoid precursor compounds in genetically modified host is efficient production of enzymes that modify the polyprenyl precursors of isoprenoid compounds, or that modify isoprenoid precursors.

One of the most important classes of enzymes in the biochemical transformations of many natural product targets is the cytochrome P450 (P450) superfamily, which takes part in an amazingly wide spectrum of metabolic reactions. In one striking example, P450 s catalyze 8 of the approximately 20 steps in the biosynthesis of taxol from its precursor, geranyl geranyl pyrophosphate.

There is a need in the art for improved isoprenoid-producing or isoprenoid precursor-producing host cells that provide for high-level production of isoprenoid compounds. The present invention addresses this need and provides related advantages.

Literature

U.S. Patent Publication No. 2004/005678; U.S. Patent Publication No. 2003/0148479; Martin et al. (2003) *Nat. Biotech.* 21(7):796-802; Polakowski et al. (1998) *Appl. Microbiol. Biotechnol.* 49: 67-71; Wilding et al. (2000) *J Bacteriol* 182(15): 4319-27; U.S. Patent Publication No. 2004/0194162; Donald et al. (1997) *Appl. Env. Microbiol.* 63:3341-3344; Jackson et al. (2003) *Organ. Lett.* 5:1629-1632; U.S. Patent Publication No. 2004/0072323; U.S. Patent Publication No. 2004/0029239; U.S. Patent Publication No. 2004/0110259; U.S. Patent Publication No. 2004/0063182; U.S. Pat. No. 5,460,949; U.S. Patent Publication No. 2004/0077039; U.S. Pat. No. 6,531,303; U.S. Pat. No. 6,689,593; Hamano et al. (2001) *Biosci. Biotechnol. Biochem.* 65:1627-1635; T. Kuzuyama. (2004) *Biosci. Biotechnol. Biochem.* 68(4): 931-934; T. Kazuhiko. (2004) *Biotechnology Letters.* 26: 1487-1491; Brock et al. (2004) *Eur J. Biochem.* 271: 3227-3241; Choi et al. (1999) *Appl. Environ. Microbio.* 65 4363-4368; Parke et al. (2004) *Appl. Environ. Microbio.* 70: 2974-2983; Subrahmanyam et al. (1998) *J. Bact.* 180: 4596-4602; Murli et al. (2003) *J. Ind. Microbiol. Biotechnol.* 30: 500-509; Starai et al. (2005) *J. Biol. Chem.* 280:26200-26205; and Starai et al. (2004) *J. Mol. Biol.* 340:1005-1012; Jennewein et al. *Chem. Biol.* 2004, 11, 379-387; Sowden et al. *Org. Biomol. Chem.* 2005, 3, 57-64; Luo et al. *Plant J.* 2001, 28, 95-104; Carter et al. *Phytochem.* 2003, 64, 425-433; Craft et al. *Appl. Environ. Microbiol.* 2003, 69, 5983-5991; Barnes et al. *Proc. Natl. Acad. Sci. USA* 1991, 88, 5597-5601; Schoch et al. *Plant Physiol.* 2003, 133, 1198-1208; Roosild et al. *Science* 2005, 307, 1317-1321.

SUMMARY OF THE INVENTION

The present invention provides nucleic acids comprising nucleotide sequences encoding modified cytochrome P450 enzymes; as well as recombinant vectors and host cells comprising the nucleic acids. The present invention further provides methods of producing a functionalized compound in a host cell genetically modified with a nucleic acid comprising nucleotide sequences encoding a modified cytochrome P450 enzyme.

BRIEF DESCRIPTION OF THE DRAWINGS

FIGS. 4A and 4B depict various N-terminal modifications made to CadH (FIG. 4A); and a time course of production of CadOH by genetically modified *E. coli* using various CadH constructs.

FIG. 5 depicts an amino acid sequence of mistic.

FIG. 6 depicts an amino acid sequence of a limonene hydroxylase.

FIG. 7 depicts an amino acid sequence of an aristolochene dihydroxylase.

FIGS. 8A-D depict an amino acid sequence of cadinene hydroxylase with a native transmembrane domain (underlined) (FIG. 8A); cadinene hydroxylase with a heterologous transmembrane domain (bold text) (FIG. 8B); cadinene hydroxylase with a solubilization domain (bold text) (FIG. 8C); and cadinene hydroxylase with a secretion domain and a heterologous transmembrane domain (bold text) (FIG. 8D).

FIGS. 9A and 9B depict amino acid sequences of taxadiene hydroxylases.

FIG. 10 depicts an amino acid sequence of ent-kaurene oxidase.

FIG. 11A depicts a nucleotide sequence encoding cadinene hydroxylase (the start atg is shown in bold); and FIG. 11B depicts a variant nucleotide sequence encoding cadinene hydroxylase, codon optimized for expression in a prokaryote.

FIG. 12A depicts an amino acid sequence of a cytochrome P450 reductase (CPR) from *Taxus cuspidata*; FIG. 12B depicts an amino acid sequence of a CPR from *Candida tropicalis*; FIG. 12C depicts an amino acid sequence of a CPR (ATR1) from *Arabidopsis thaliana*; FIG. 12D depicts an amino acid sequence of a CPR (ATR2) from *Arabidopsis thaliana*; and FIG. 12E depicts a variant ATR2 amino acid which lacks a chloroplast-targeting sequence.

FIGS. 19A-C depict amino acid sequences of various alkaloid pathway intermediate-modifying P450 enzymes.

FIGS. 20A-C depict amino acid sequences of various phenylpropanoid pathway intermediate-modifying P450 enzymes.

FIGS. 21A and 21B depict amino acid sequences of various polyketide pathway intermediate-modifying P450 enzymes.

FIGS. 24A and B depict a nucleotide sequence encoding wild-type AMO.

FIG. 25 depicts an amino acid sequence translation map of the nucleotide sequence depicted in FIG. 24.

FIGS. 26 and 27 depict a nucleotide sequence encoding A13-AMO and the amino acid sequence translation map, respectively.

FIGS. 28 and 29 depict a nucleotide sequence encoding A17-AMO and the amino acid sequence translation map, respectively.

FIGS. 30 and 31 depict a nucleotide sequence encoding bovine-AMO and the amino acid sequence translation map, respectively.

FIGS. 35A and 35B depict nucleotide sequences encoding acetoacetyl-CoA thiolase ("atoB"), HMGS, and truncated HMGR (tHMGR).

FIGS. 36A-D depict the nucleotide sequence of pMBIS.

DEFINITIONS

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, triterpenes, polyterpenes, and diterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid precursor compound is produced. The term "terpene synthase" includes enzymes that catalyze the conversion of a prenyl diphosphate into an isoprenoid or isoprenoid precursor.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway is illustrated schematically in FIG. 17. The "top half" of the mevalonate pathway refers to the enzymes responsible for the conversion of acetyl-CoA to mevalonate through a MEV pathway intermediate.

Figure 18:
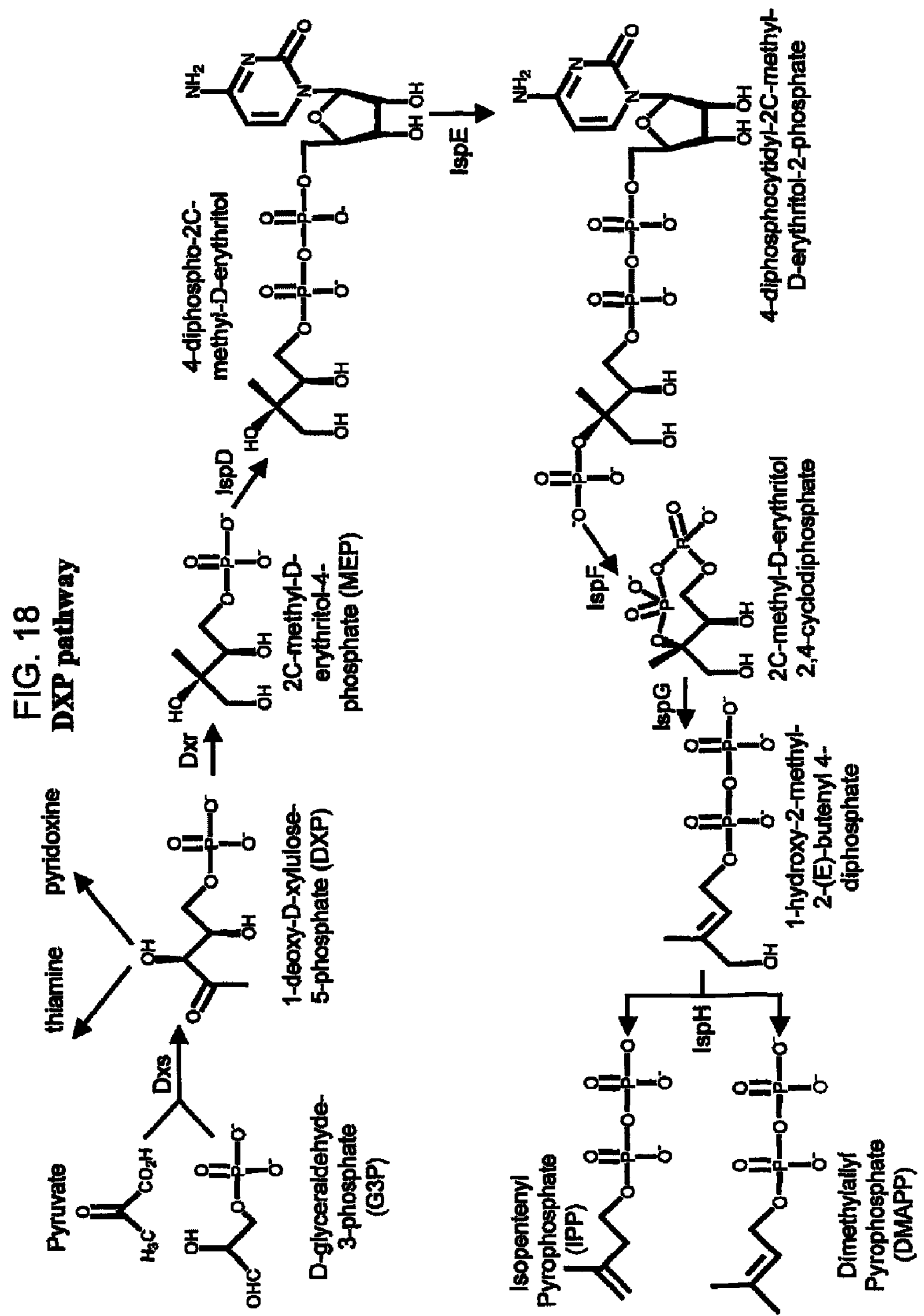
FIG. 18 is a schematic representation of the DXP pathway for the production of IPP and dimethylallyl pyrophosphate (DMAPP).

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reactions depicted schematically in FIG. 18.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, the nucleic acids encoding HMGS, mevalonate kinase, and phosphomevalonate kinase in represent exogenous nucleic acids to *E. coli*. These mevalonate pathway nucleic acids were cloned from *Sacchromyces cerevisiae*. In *S. cerevisiae*, the gene sequences encoding HMGS, MK, and PMK on the chromosome would be "endogenous" nucleic acids.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence that is endogenous to the host microorganism or host cell) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

The term "heterologous polypeptide," as used herein, refers to a polypeptide that is not naturally associated with a given polypeptide. For example, an isoprenoid precursor-modifying enzyme that comprises a "heterologous transmembrane domain" refers to an isoprenoid precursor-modifying enzyme that comprises a transmembrane domain that is not normally associated with (e.g., not normally contiguous with; not normally found in the same polypeptide chain with) the isoprenoid precursor-modifying enzyme in nature. Similarly, an isoprenoid precursor-modifying enzyme that comprises one or more of a "heterologous secretion domain," a "heterologous membrane-inserting polypeptide," and a "heterologous solubilization domain" is an isoprenoid precursor-modifying enzyme that comprises one or more of a secretion domain, a membrane-inserting polypeptide, and a solubilization domain that is not normally associated with (e.g., not normally contiguous with; not normally found in the same polypeptide chain with) the isoprenoid precursor-modifying enzyme in nature.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA: RNA, DNA: RNA, DNA: DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a cytochrome P450 enzyme" includes a plurality of such enzymes and reference to "the cytochrome P450 reductase" includes reference to one or more cytochrome P450 reductase and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides nucleic acids comprising nucleotide sequences encoding modified cytochrome P450 enzymes; as well as recombinant vectors and host cells comprising the nucleic acids. The present invention further provides methods of producing a functionalized compound in a host cell genetically modified with a nucleic acid comprising nucleotide sequences encoding a modified cytochrome P450 enzyme.

The present invention further provides nucleic acids comprising nucleotide sequences encoding isoprenoid precursor-modifying enzymes; as well as recombinant vectors and host cells comprising the nucleic acids. The present invention provides methods of producing an enzymatically active isoprenoid precursor-modifying enzyme in a host cell. The present invention further provides methods of producing an isoprenoid compound in a host cell genetically modified with a nucleic acid comprising nucleotide sequences encoding an isoprenoid precursor-modifying enzyme.

Nucleic Acids, Vectors, and Host Cells

The present invention provides nucleic acids comprising nucleotide sequences encoding modified cytochrome P450 enzymes; as well as recombinant vectors and host cells comprising the nucleic acids. The present invention provides nucleic acids comprising nucleotide sequences encoding isoprenoid precursor-modifying enzymes; as well as recombinant vectors and host cells comprising the nucleic acids.

The term "modified cytochrome P450 enzyme," as used herein, refers to an enzyme that modifies (e.g., "functionalizes") an intermediate in a biosynthetic pathway. A modified cytochrome P450 enzyme encoded by a subject nucleic acid catalyzes one or more of the following reactions: hydroxylation, oxidation, epoxidation, dehydration, dehydrogenation, dehalogenation, isomerization, alcohol oxidation, aldehyde oxidation, dealkylation, and C—C bond cleavage. Such reactions are referred to generically herein as "biosynthetic pathway intermediate modifications." These reactions have been described in, e.g., Sono et al. ((1996) *Chem. Rev.* 96:2841-2887; see, e.g., FIG. 3 of Sono et al. for a schematic representation of such reactions).

In some embodiments, a modified cytochrome P450 enzyme is an isoprenoid precursor-modifying enzyme. The term "isoprenoid precursor-modifying enzyme," used interchangeably herein with "isoprenoid-modifying enzyme," refers to an enzyme that modifies an isoprenoid precursor compound, e.g., with an isoprenoid precursor compound as substrate, the isoprenoid precursor-modifying enzyme catalyzes one or more of the following reactions: hydroxylation, epoxidation, oxidation, dehydration, dehydrogenation, dehalogenation, isomerization, alcohol oxidation, aldehyde oxidation, dealkylation, and C—C bond cleavage. Such reactions are referred to generically herein as "isoprenoid precursor modifications." These reactions have been described in, e.g., Sono et al. ((1996) supra; see, e.g., FIG. 3 of Sono et al. for a schematic representation of such reactions). Isoprenoid precursor-modifying enzymes are in many embodiments cytochrome P450 enzymes. See, e.g., Sono et al. (1996) supra.

Substrates of a Modified Cytochrome P450 Enzyme

As noted above, a substrate of a modified cytochrome P450 enzyme is an intermediate in a biosynthetic pathway. Exemplary intermediates include, but are not limited to, isoprenoid precursors; alkaloid precursors; phenylpropanoid precursors; flavonoid precursors; steroid precursors; polyketide precursors; macrolide precursors; sugar alcohol precursors; phenolic compound precursors; and the like. See, e.g., Hwang et al. ((2003) *Appl. Environ. Microbiol.* 69:2699-2706; Facchini et al. ((2004) *TRENDS Plant Sci.* 9:116.

Biosynthetic pathway products of interest include, but are not limited to, isoprenoid compounds, alkaloid compounds, phenylpropanoid compounds, flavonoid compounds, steroid compounds, polyketide compounds, macrolide compounds, sugar alcohols, phenolic compounds, and the like.

Alkaloid compounds are a large, diverse group of natural products found in about 20% of plant species. They are generally defined by the occurrence of a nitrogen atom in an oxidative state within a heterocyclic ring. Alkaloid compounds include benzylisoquinoline alkaloid compounds, indole alkaloid compounds, isoquinoline alkaloid compounds, and the like. Alkaloid compounds include monocyclic alkaloid compounds, dicyclic alkaloid compounds, tricyclic alkaloid compounds, tetracyclic alkaloid compounds, as well as alkaloid compounds with cage structures. Alkaloid compounds include: 1) Pyridine group: piperine, coniine, trigonelline, arecaidine, guvacine, pilocarpine, cytisine, sparteine, pelletierine; 2) Pyrrolidine group: hygrine, nicotine, cuscohygrine; 3) Tropine group: atropine, cocaine, ecgonine, pelletierine, scopolamine; 4) Quinoline group: quinine, dihydroquinine, quinidine, dihydroquinidine, strychnine, brucine, and the veratrum alkaloids (e.g., veratrine, cevadine); 5) Isoquinoline group: morphine, codeine, thebaine, papaverine, narcotine, narceine, hydrastine, and berberine; 6) Phenethylamine group: methamphetamine, mescaline, ephedrine; 7) Indole group: tryptamines (e.g., dimethyltryptamine, psilocybin, serotonin), ergolines (e.g., ergine, ergotamine, lysergic acid, etc.), and beta-carbolines (e.g., harmine, yohimbine, reserpine, emetine); 8) Purine group: xanthines (e.g., caffeine, theobromine, theophylline); 9) Terpenoid group: aconite alkaloids (e.g., aconitine), and steroids (e.g., solanine, samandarin); 10) Betaine group: (quaternary ammonium compounds: e.g., muscarine, choline, neurine); and 11) Pyrazole group: pyrazole, fomepizole. Exemplary alkaloid compounds are morphine, berberine, vinblastine, vincristine, cocaine, scopolamine, caffeine, nicotine, atropine, papaverine, emetine, quinine, reserpine, codeine, serotonin, etc. See, e.g., Facchini et al. ((2004) *Trends Plant Science* 9:116).

Substrates of Isoprenoid-Modifying Enzymes

The term "isoprenoid precursor compound" is used interchangeably with "isoprenoid precursor substrate" to refer to a compound that is a product of the reaction of a terpene synthase on a polyprenyl diphosphate. The product of action of a terpene synthase (also referred to as a "terpene cyclase") reaction is the so-called "terpene skeleton." In some embodiments, the isoprenoid-modifying enzyme catalyzes the modification of a terpene skeleton, or a downstream product thereof. Thus, in some embodiments, the isoprenoid precursor is a terpene skeleton. Isoprenoid precursor substrates of an isoprenoid precursor-modifying enzyme include monoterpenes, diterpenes, triterpenes, and sesquiterpenes.

Monoterpene substrates of an isoprenoid-modifying enzyme encoded by a subject nucleic acid include, but are not limited to, any monoterpene substrate that yields an oxidation product that is a monoterpene compound or is an intermediate in a biosynthetic pathway that gives rise to a monoterpene compound. Exemplary monoterpene substrates include, but are not limited to, monoterpene substrates that fall into any of the following families: Acyclic monoterpenes, Dimethyloctanes, Menthanes, Irregular Monoterpenoids, Cineols, Camphanes, Isocamphanes, Monocyclic monoterpenes, Pinanes, Fenchanes, Thujanes, Caranes, Ionones, Iridanes, and Cannabanoids. Exemplary monoterpene substrates, intermediates, and products include, but are not limited to, limonene, citranellol, geraniol, menthol, perillyl alcohol, linalool, and thujone.

Diterpene substrates of an isoprenoid-modifying enzyme encoded by a subject nucleic acid include, but are not limited to, any diterpene substrate that yields an oxidation product that is a diterpene compound or is an intermediate in a biosynthetic pathway that gives rise to a diterpene compound. Exemplary diterpene substrates include, but are not limited to, diterpene substrates that fall into any of the following families: Acyclic Diterpenoids, Bicyclic Diterpenoids, Monocyclic Diterpenoids, Labdanes, Clerodanes, Taxanes, Tricyclic Diterpenoids, Tetracyclic Diterpenoids, Kaurenes, Beyerenes, Atiserenes, Aphidicolins, Grayanotoxins, Gibberellins, Macrocyclic Diterpenes, and Elizabethatrianes. Exemplary diterpene substrates, intermediates, and products include, but are not limited to, casbene, eleutherobin, paclitaxel, prostratin, and pseudopterosin.

Triterpene substrates of an isoprenoid-modifying enzyme encoded by a subject nucleic acid include, but are not limited to, any triterpene substrate that yields an oxidation product that is a triterpene compound or is an intermediate in a biosynthetic pathway that gives rise to a triterpene compound. Exemplary triterpene substrates, intermediates, and products include, but are not limited to, arbrusideE, bruceantin, testosterone, progesterone, cortisone, and digitoxin.

Sesquiterpene substrates of an isoprenoid-modifying enzyme encoded by a subject nucleic acid include, but are not limited to, any sesquiterpene substrate that yields an oxidation product that is a sesquiterpene compound or is an intermediate in a biosynthetic pathway that gives rise to a sesquiterpene compound. Exemplary sesquiterpene substrates include, but are not limited to, sesquiterpene substrates that fall into any of the following families: Farnesanes, Monocyclofarnesanes, Monocyclic sesquiterpenes, Bicyclic sesquiterpenes, Bicyclofarnesanes, Bisbolanes, Santalanes, Cupranes, Herbertanes, Gymnomitranes, Trichothecanes, Chamigranes, Carotanes, Acoranes, Antisatins, Cadinanes, Oplopananes, Copaanes, Picrotoxanes, Himachalanes, Longipinanes, Longicyclanes, Caryophyllanes, Modhephanes, Siphiperfolanes, Humulanes, Intergrifolianes, Lippifolianes, Protoilludanes, Illudanes, Hirsutanes, Lactaranes, Sterpuranes, Fomannosanes, Marasmanes, Germacranes, Elemanes, Eudesmanes, Bakkanes, Chilosyphanes, Guaianes, Pseudoguaianes, Tricyclic sesquiterpenes, Patchoulanes, Trixanes, Aromadendranes, Gorgonanes, Nardosinanes, Brasilanes, Pinguisanes, Sesquipinanes, Sesquicamphanes, Thujopsanes, Bicylcohumulanes, Alliacanes, Sterpuranes, Lactaranes, Africanes, Integrifolianes, Protoilludanes, Aristolanes, and Neolemnanes. Exemplary sesquiterpene substrates include, but are not limited to, amorphadiene, alloisolongifolene, (−)-α-trans-bergamotene, (−)-β-elemene, (+)-germacrene A, germacrene B, (+)-γ-gurjunene, (+)-ledene, neointermedeol, (+)-β-selinene, and (+)-valencene.

Modifications

A subject nucleic acid comprises a nucleotide sequence encoding a modified cytochrome P450 enzyme, where the modified cytochrome P450 enzyme encoded by a subject nucleic acid will in many embodiments have a non-native (non-wild-type, or non-naturally occurring, or variant) amino acid sequence. The encoded modified cytochrome P450 enzyme will have one or more amino acid sequence modifications (deletions, additions, insertions, substitutions) that increase the level of activity of the modified cytochrome P450 enzyme in a host cell genetically modified with a subject nucleic acid and/or that increase the level of a given product of a biosynthetic pathway produced by a host cell genetically modified with a subject nucleic acid.

In some embodiments, a subject nucleic acid comprises a nucleotide sequence encoding a modified isoprenoid precursor-modifying enzyme, where the isoprenoid precursor-modifying enzyme encoded by a subject nucleic acid will in many embodiments have a non-native (non-wild-type, or non-naturally occurring, or variant) amino acid sequence. The encoded isoprenoid precursor-modifying enzyme will have one or more amino acid sequence modifications (deletions, additions, insertions, substitutions) that increase the level of activity of the isoprenoid precursor-modifying enzyme in a host cell genetically modified with a subject nucleic acid and/or that increase the level of a given isoprenoid compound produced by a host cell genetically modified with a subject nucleic acid. The encoded isoprenoid precursor-modifying enzyme will in some embodiments include one or more of the following modifications relative to a wild-type isoprenoid precursor-modifying enzyme: a) substitution of a native transmembrane domain with a non-native transmembrane domain; b) replacement of the native transmembrane domain with a secretion signal domain; c) replacement of the native transmembrane domain with a solubilization domain; d) replacement of the native transmembrane domain with membrane insertion domain; e) truncation of the native transmembrane domain; and f) a change in the amino acid sequence of the native transmembrane domain.

In many embodiments, a subject nucleic acid comprises, in order from 5' to 3' and in operable linkage, a nucleotide sequence encoding a first domain selected from a transmembrane domain, a secretion domain, a solubilization domain, and a membrane-inserting protein; and a nucleotide sequence encoding the catalytic domain of a modified P450 enzyme (e.g., an isoprenoid precursor-modifying enzyme), where the first domain is heterologous to the catalytic domain. In some embodiments, the first domain comprises both a secretion signal and a transmembrane domain.

Non-Native Transmembrane Domain

In some embodiments, the encoded modified cytochrome P450 enzyme (e.g., an isoprenoid precursor-modifying enzyme) will comprise a non-native (e.g., a heterologous) transmembrane domain. Suitable non-native transmembrane domains will generally be selected from transmembrane domains that are functional in a given host cell. In some embodiments, the non-native transmembrane domain is one that is functional in a prokaryotic host cell. In other embodiments, the non-native transmembrane domain is one that is functional in a eukaryotic host cell.

For example, for expression in *E. coli*, a non-native transmembrane domain will in many embodiments comprise one of the following the amino acid sequences:

```
                                         (SEQ ID NO:1)
NH2-MWLLLIAVFLLTLAYLFWP-COOH;

                                         (SEQ ID NO:2)
NH2-MALLLAVFLGLSCLLLLSLW-COOH;

                                         (SEQ ID NO:3)
NH2-MAILAAIFALVVATATRV-COOH;

                                         (SEQ ID NO:4)
NH2-MDASLLLSVALAVVLIPLSLALLN-COOH;
and

                                         (SEQ ID NO:5)
NH2-MIEQLLEYWYVVVPVLYIIKQLLAYTK-COOH.
```

Secretion Signal

In some embodiments, the encoded modified cytochrome P450 enzyme (e.g., an isoprenoid precursor-modifying enzyme) will comprise a non-native amino acid sequence that provides for secretion of the fusion protein from the cell. Those skilled in the art are aware of such secretion signal sequences. Secretion signals that are suitable for use in bacteria include, but are not limited to, the secretion signal of Braun's lipoprotein of *E. coli, S. marcescens, E. amylosora, M. morganii*, and *P. mirabilis*, the TraT protein of *E. coli* and *Salmonella*; the penicillinase (PenP) protein of *B. licheniformis* and *B. cereus* and *S. aureus*; pullulanase proteins of *Klebsiella pneumoniae* and *Kiebsiella aerogenese; E. coli* lipoproteins 1 pp-28, Pal, Rp1A, Rp1B, OsmB, NIpB, and Orl17; chitobiase protein of *V. harseyi*; the β-1,4-endoglucanase protein of *Pseudomonas solanacearum*, the Pal and Pcp proteins of *H. influenzae*; the OprI protein of *P. aeruginosa*; the Ma1 X and AmiA proteins of *S. pneumoniae*; the 34 kda antigen and TpmA protein of *Treponema pallidum*; the P37 protein of *Mycoplasma hyorhinis*; the neutral protease of *Bacillus amyloliquefaciens*; the 17 kda antigen of *Rickettsia rickettsii*; the malE maltose binding protein; the rbsb ribose binding protein; phoA alkaline phosphatase; and the OmpA secretion signal (see, e.g., Tanji et al. (1991) *J Bacteriol.* 173(6):1997-2005). Secretion signal sequences suitable for use in yeast are known in the art, and can be used. See, e.g., U.S. Pat. No. 5,712,113. The rbsB, malE, and phoA secretion signals are discussed in, e.g., Collier (1994) J. Bacteriol. 176:3013.

In some embodiments, e.g., for expression in a prokaryotic host cell such as *E. coli*, a secretion signal will comprise one of the following amino acid sequences:

```
                                         (SEQ ID NO:6)
NH2-MKKTAIAIAVALAGFATVAQA-COOH;

                                         (SEQ ID NO:7)
NH2-MKKTAIAIVVALAGFATVAQA-COOH;

                                         (SEQ ID NO:8)
NH2-MKKTALALAVALAGFATVAQA-COOH;

                                         (SEQ ID NO:9)
NH2-MKIKTGARILALSALTTMMFSASALA-COOH;

                                        (SEQ ID NO:10)
NH2-MNMKKLATLVSAVALSATVSANAMA-COOH;
and

                                        (SEQ ID NO:11)
NH2-MKQSTIALALLPLLFTPVTKA-COOH.
```

In some embodiments, the encoded modified cytochrome P450 enzyme (e.g., an isoprenoid precursor-modifying enzyme) will comprise both a non-native secretion signal sequence and a heterologous transmembrane domain. Any combination of secretion signal sequence and heterologous transmembrane domain can be used.

As one non-limiting example, heterologous domain comprising a non-native secretion signal sequence and a heterologous transmembrane domain will in some embodiments have the following amino acid sequence: $NH_2$-MKKTAIAIAVALAGFATVAQA LLEYWYVVVPVLYIIKQLLAYTK—COOH (SEQ ID NO:12), where the transmembrane domain is underlined, and the secretion signal is N-terminal to the transmembrane domain.

Solubilization Domain

In some embodiments, the encoded modified cytochrome P450 enzyme (e.g., an isoprenoid precursor-modifying enzyme) will comprise a non-native domain that provides for solubilization of the protein.

In some embodiments, a solubilization domain will comprise one or more of the following amino acid sequences:

```
                                        (SEQ ID NO:13)
NH2-EELLKQALQQAQQLLQQAQELAKK-COOH;
and

                                        (SEQ ID NO:14)
NH2-MTVHDIIATYFTKWYVIVPLALIAYRVLDYFY-COOH;

                                        (SEQ ID NO:15)
NH2-GLFGAIAGFIEGGWTGMIDGWYGYGGGKK-COOH;
and

                                        (SEQ ID NO:16)
NH2-MAKKTSSKG-COOH.
```

Membrane Insertion Domain

In some embodiments, the encoded modified cytochrome P450 enzyme (e.g., an isoprenoid precursor-modifying enzyme) will comprise a non-native amino acid sequence that provides for insertion into a membrane. In some embodiments, the encoded modified cytochrome P450 enzyme is a fusion polypeptide that comprises a heterologous fusion partner (e.g., a protein other than a cytochrome P450 enzyme) fused in-frame at either the amino terminus or the carboxyl terminus, where the fusion partner provides for insertion of the fusion protein into a biological membrane.

In some embodiments, the fusion partner is a mistic protein, e.g., a protein comprising the amino acid sequence depicted in FIG. 5 (GenBank Accession No. AY874162). A nucleotide sequence encoding the mistic protein is also provided under GenBank Accession No. AY874162. Other polypeptides that provide for insertion into a biological membrane are known in the art and are discussed in, e.g., PsbW Woolhead et al. (*J. Biol. Chem.* 276 (18): 14607), describing PsbW; and Kuhn (FEMS Microbiology Reviews 17 (1992 i) 285), describing M12 procoat protein and Pf3 procoat protein.

Cytochrome P450 Enzymes

The encoded isoprenoid precursor-modifying enzyme will in many embodiments be a cytochrome P450 enzyme. The encoded cytochrome P450 enzyme will carry out one or more of the following reactions: hydroxylation, epoxidation, oxidation, dehydration, dehydrogenation, dehalogenation, isomerization, alcohol oxidation, aldehyde oxidation, dealkylation, and C—C bond cleavage. Such reactions are referred to generically herein as "biosynthetic pathway intermediate modifications" or, in particular embodiments, "isoprenoid precursor modifications." These reactions have been described in, e.g., Sono et al. ((1996) supra; see, e.g., FIG. 3 of Sono et al. for a schematic representation of such reactions). As discussed above, the encoded modified cytochrome P450 enzyme (e.g., isoprenoid precursor-modifying enzyme) will in many embodiments be a cytochrome P450 monooxygenase, a cytochrome P450 hydroxylase, a cytochrome P450 epoxidase, or a cytochrome P450 dehydrogenase. A wide variety of cytochrome P450 monooxygenases, hydroxylases, epoxidases, and dehydrogenases (generically referred to herein as "P450 enzymes") are known in the art, and the amino acid sequence of any known P450 enzyme, or a variant thereof, can be modified according to the instant invention.

Suitable sources of nucleic acids comprising a nucleotide sequence encoding a cytochrome P450 enzyme include, but are not limited to, a cell or organism of any of the six kingdoms, e.g., Bacteria (e.g., Eubacteria); Archaebacteria; Protista; Fungi; Plantae; and Animalia. Suitable sources of exogenous nucleic acids include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e. g, Apicomplexa, Myxozoa, Microsporidia), and ciliates (e.g., Paramecium). Suitable sources of exogenous nucleic acids include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable sources of exogenous nucleic acids include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sources of exogenous nucleic acids include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms) p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., suitable sources include cells from organisms that include, but are not limited to, a protozoan, a plant, a fungus, an alga, a yeast, a reptile, an amphibian, a mammal, a marine microorganism, a marine invertebrate, an arthropod, an isopod, an insect, an arachnid, an archaebacterium, and a *eubacterium.*

Suitable prokaryotic sources include bacteria (e.g., Eubacteria) and archaebacteria. Suitable archaebacteria sources include a methanogen, an extreme halophile, an extreme thermophile, and the like. Suitable archaebacteria sources include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Meth anobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota. Suitable eubacteria sources include, but are not limited to, any member of Hydrogenobacteria, Thermotogales, Green nonsulfphur bacteria, Denococcus Group, Cyanobacteria, Purple bacteria, Planctomyces, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

In some embodiments, a P450 enzyme-encoding nucleic acid will be isolated from a tissue taken from an organism; from a particular cell or group of cells isolated from an organism; etc. For example, where the organism is a plant, the nucleic acid will in some embodiments be isolated from the xylem, the phloem, the cambium layer, leaves, roots, etc. Where the organism is an animal, the nucleic acid will in some embodiments be isolated from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some embodiments, a subject nucleic acid comprises a nucleotide sequence encoding a P450 enzyme that differs from a wild-type or naturally-occurring nucleotide sequence encoding a P450 enzyme, e.g., a subject nucleic acid comprises a nucleotide sequence encoding a variant P450 enzyme. In some embodiments, a variant P450 differs in amino acid sequence by one amino acid, two amino acids, three amino acids, four amino acids, five amino acids, six amino acids, seven amino acids, eight amino acids, nine amino acids, or amino acids, or more, compared to the amino acid sequence of a naturally-occurring parent P450 enzyme. In some embodiments, a variant P450 enzyme differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, or from about 50 amino acids to about 60 amino acids, or more, compared to the amino acid sequence of a naturally-occurring parent P450 enzyme.

In many embodiments, as discussed above, the encoded modified cytochrome P450 enzyme comprises a modification of the N-terminus of a parent (e.g., wild-type, or naturally-occurring, or native), e.g., a modification of the transmembrane domain and/or amino acid sequences N-terminal to the transmembrane domain. In some embodiments, the encoded modified cytochrome P450 enzyme will further include one or more amino acid sequence modifications in the catalytic portion of the enzyme, compared to the amino acid sequence of a wild-type cytochrome P450 enzyme.

A nucleic acid comprising a nucleotide sequence encoding a variant (e.g., modified) P450 enzyme is a synthetic nucleic acid. In some embodiments, a synthetic nucleic acid comprising a nucleotide sequence encoding a variant P450 enzyme is one that hybridizes under suitable hybridization conditions to a nucleic acid comprising a nucleotide sequence encoding naturally-occurring P450 enzyme. In some embodiments, a synthetic nucleic acid comprising a nucleotide sequence encoding a variant P450 enzyme is one that hybridizes under stringent hybridization conditions to a nucleic acid comprising a nucleotide sequence encoding a naturally-occurring P450 enzyme. In some embodiments, a synthetic nucleic acid comprising a nucleotide sequence encoding a variant P450 enzyme comprises a variant P450 enzyme-encoding nucleotide sequence that has less than about 95% nucleotide sequence identity to a naturally-occurring P450 enzyme-encoding nucleotide sequence, e.g., the variant P450 enzyme-encoding nucleotide sequence has no more than from about 90% to about 95%, from about 85% to about 90%, from about 80% to about 85%, from about 75% to about 80%, from about 70% to about 75%, from about 65% to about 70%, from about 60% to about 65%, from about 55% to about 60%, or from about 50% to about 55% nucleotide sequence identity to a naturally-occurring P450 enzyme-encoding nucleotide sequence.

In some embodiments, the nucleotide sequence encoding a variant P450 enzyme encodes a P450 enzyme that has from about 50% to about 55%, from about 55% to about 60%, from about 60% to about 65%, from about 65% to about 70%, from about 70% to about 75%, from about 75% to about 80%, from about 80% to about 85%, from about 85% to about 90%, or from about 90% to about 95% amino acid sequence identity to the amino acid sequence of a naturally-occurring P450 enzyme. Amino acid sequences of a number of P450 enzymes are known in the art.

Suitable P450 enzymes that can be modified and encoded by a nucleotide sequence included in a subject nucleic acid include, but are not limited to: a limonene-6-hydroxylase (see, e.g., FIG. 6; and GenBank Accession Nos. AY281025 and AF124815); 5-epi-aristolochene dihydroxylase (see, e.g., FIG. 7; and GenBank Accession No. AF368376); 6-cadinene-8-hydroxylase (see, e.g., FIG. 8A; and GenBank Accession No. AF332974); taxadiene-5α-hydroxylase (see, e.g., FIGS. 9A and 9B; and GenBank Accession Nos. AY289209, AY959320, and AY364469); ent-kaurene oxidase (see, e.g., FIG. 10; and GenBank Accession No. AF047719; see, e.g., Helliwell et al. (1998) Proc. Natl. Acad. Sci. USA 95:9019-9024).

Figure 22:
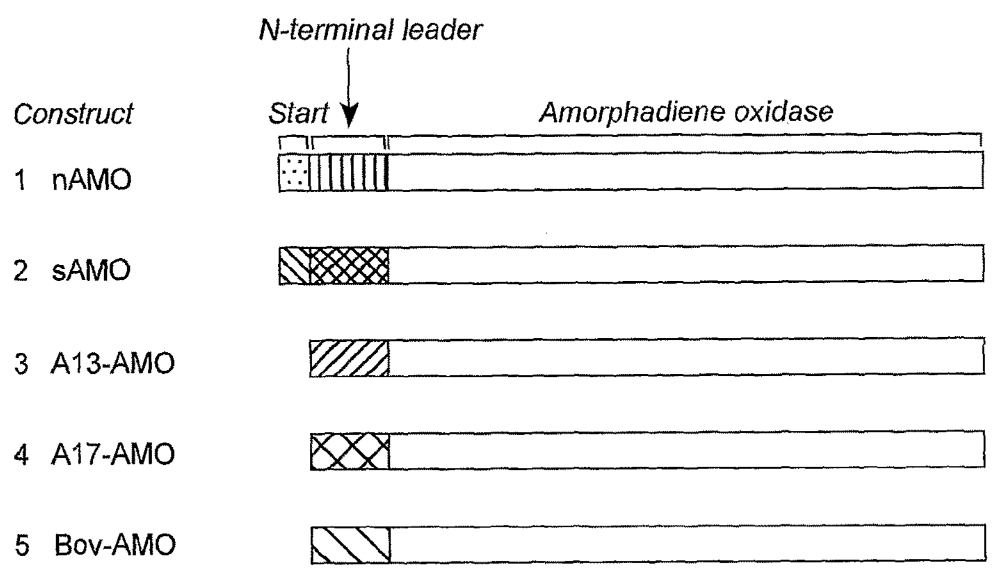
FIG. 22 depicts schematically various amorphadiene oxidase (AMO) constructs. (1) nAMO, native AMO sequence as isolated from *Artemisia annua;* 2) sAMO, synthetic AMO gene codon-optimized for expression in *E. coli;* 3) A13-AMO, synthetic AMO gene with wild-type transmembrane replaced with the A13 N-terminal sequence from *C. tropicalis;* 4) A17-AMO, synthetic AMO gene with wild-type transmembrane replaced with the A17 N-terminal sequence from *C. tropicalis;* 5) Bov-AMO, synthetic AMO gene with wild-type transmembrane replaced with the bovine microsomal N-terminal sequence.

FIGS. 8B-D depict exemplary P450 variants. FIG. 8B depicts cadinene hydroxylase with a heterologous transmembrane domain; FIG. 8C depicts cadinene hydroxylase with a solubilization domain; and FIG. 8C depicts cadinene hydroxylase with a secretion domain and a heterologous transmembrane domain. FIG. 22 depicts further exemplary P450 variants, including amorphadiene oxidase with various N-terminal sequences.

Alkaloid pathway intermediate-modifying cytochrome P450 enzymes are known in the art. See, e.g., Facchini et al. (2004) supra; Pauli and Kutchan ((1998) *Plant J.* 13:793-801; Collu et al. ((2001) *FEBS Lett.* 508:215-220; Schroder et al. ((1999) *FEBS Lett.* 458:97-102. See also FIGS. 19A-C.

Phenylpropanoid pathway intermediate-modifying cytochrome P450 enzymes are known in the art. See, e.g., Mizutani et al. ((1997) *Plant Physiol.* 113:755-763; and Gang et al. ((2002) *Plant Physiol.* 130:1536-1544. See also FIGS. 20A-C.

Exemplary polyketide pathway intermediate-modifying cytochrome P450 enzymes are depicted in FIGS. 21A and 211B. See also Ikeda et al. ((1999) *Proc. Natl. Acad. Sci. USA* 96:9509-9514; and Ward et al. ((2004) *Antimicrob. Agents Chemother.* 48:4703-4712.

The encoded modified cytochrome P450 enzyme (e.g., isoprenoid precursor-modifying enzyme) is enzymatically active, e.g., the modified cytochrome P450 enzyme (e.g., isoprenoid precursor-modifying enzyme) exhibits one or more of the following activities: a) modification of a biosynthetic pathway intermediate by one or more of: oxidation, hydroxylation, epoxidation, dehydration, dehydrogenation, dehalogenation, isomerization, alcohol oxidation, aldehyde oxidation, dealkylation, or C—C bond cleavage; b) modification of an isoprenoid precursor by one or more of: oxidation, hydroxylation, epoxidation, dehydration, dehydrogenation, dehalogenation, isomerization, alcohol oxidation, aldehyde oxidation, dealkylation, or C—C bond cleavage. Whether a subject nucleic acid encodes an enzymatically active cytochrome P450 enzyme is readily determined by detecting a product of the reaction of the P450 enzyme on a substrate and/or detecting a downstream product of the reaction of the P450 enzyme on a substrate. For example, whether a subject nucleic acid encodes an enzymatically active terpene oxidase, or a terpene hydroxylase, can be readily ascertained using standard assays for these enzymatic activities, using the appropriate substrate. Products of the enzymatic modification are generally analyzed by gas chromatography-mass spectrometry. For example, whether a subject nucleic acid encodes a sesquiterpene oxidase, or a sesquiterpene hydroxylase, can be readily ascertained using standard assays for these enzymatic activities. See, e.g., U.S. Patent Publication No. 20050019882.

In some embodiments, a nucleotide sequence encoding a modified cytochrome P450 enzyme (e.g., a modified isoprenoid precursor-modifying enzyme) is modified to reflect the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22): 7055-7074; Eyre-Walker (1996) *Mol. Biol. Evol.* 13(6):864-872. See also Nakamura et al. (2000) *Nucleic Acids Res.* 28(1):292. As one non-limiting example, FIG. 11A depicts a wild-type nucleotide sequence encoding cadinene hydroxylase (atg start codon shown in bold); and FIG. 11B depicts a codon-optimized variant of the sequence depicted in FIG. 11A, where the codons are optimized for expression in a prokaryote such as *E. coli.*

Cytochrome P450 Reductase

NADPH-cytochrome P450 oxidoreductase (CPR, EC 1.6.2.4) is the redox partner of many P450-monooxygenases. In some embodiments, a subject nucleic acid further comprises a nucleotide sequence encoding a cytochrome P450 reductase (CPR). A subject nucleic acid comprising a nucleotide sequence encoding a CPR is referred to as "a CPR nucleic acid." A CPR encoded by a subject CPR nucleic acid transfers electrons from NADPH to cytochrome P450. For example, in some embodiments, a CPR encoded by a subject CPR nucleic acid transfers electrons from NADPH to an isoprenoid-modifying enzyme, e.g., a sesquiterpene oxidase, encoded by a subject isoprenoid-modifying enzyme-encoding nucleic acid.

In some embodiments, a subject nucleic acid comprises a nucleotide sequence encoding both a modified cytochrome P450 enzyme (e.g., a modified isoprenoid precursor-modifying enzyme) and a CPR. In some embodiments, a subject nucleic acid comprises a nucleotide sequence encoding a fusion protein that comprises an amino acid sequence of modified cytochrome P450 enzyme (e.g., a modified isoprenoid precursor-modifying enzyme) that exhibits isoprenoid precursor modification activity, as described above, fused to a CPR polypeptide. In some embodiments, the encoded fusion protein is of the formula $NH_2$-A-X—B—COOH, where A is the modified cytochrome P450 enzyme, X is an optional linker, and B is the CPR polypeptide. In some embodiments, the encoded fission protein is of the formula $NH_2$-A-X—B—COOH, where A is the CPR polypeptide, X is an optional linker, and B is the modified cytochrome P450 enzyme.

The linker peptide may have any of a variety of amino acid sequences. Proteins can be joined by a spacer peptide, generally of a flexible nature, although other chemical linkages are not excluded. The linker may be a cleavable linker. Suitable linker sequences will generally be peptides of between about 5 and about 50 amino acids in length, or between about 6 and about 25 amino acids in length. Peptide linkers with a degree of flexibility will generally be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use according to the present invention.

Suitable linker peptides frequently include amino acid sequences rich in alanine and proline residues, which are known to impart flexibility to a protein structure. Exemplary linkers have a combination of glycine, alanine, proline and methionine residues, such as AAAGGM (SEQ ID NO:17); AAAGGMPPAAAGGM (SEQ ID NO:18); AAAGGM (SEQ ID NO:19); and PPAAAGGM (SEQ ID NO:20). Other exemplary linker peptides include IEGR (SEQ ID NO:21); and GGKGGK (SEQ ID NO:22). However, any flexible linker generally between about 5 and about 50 amino acids in length may be used. Linkers may have virtually any sequence that results in a generally flexible peptide, including alanine-proline rich sequences of the type exemplified above.

In some embodiments, a subject nucleic acid comprises a nucleotide sequence encoding a CPR polypeptide that has at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% amino acid sequence identity to a known or naturally-occurring CPR polypeptide.

CPR polypeptides, as well as nucleic acids encoding the CPR polypeptides, are known in the art, and any CPR-encoding nucleic acid, or a variant thereof, can be used in the instant invention. Suitable CPR-encoding nucleic acids include nucleic acids encoding CPR found in plants. Suitable CPR-encoding nucleic acids include nucleic acids encoding CPR found in fungi. Examples of suitable CPR-encoding nucleic acids include: GenBank Accession No. AJ303373 (*Triticum aestivum* CPR); GenBank Accession No. AY959320 (*Taxus chinensis* CPR); GenBank Accession No. AY532374 (*Ammi majus* CPR); GenBank Accession No. AG211221 (*Oryza sativa* CPR); and GenBank Accession No. AF024635 (*Petroselinum crispum* CPR); *Candida tropicalis* cytochrome P450 reductase (GenBank Accession No. M35199); *Arabidopsis thaliana* cytochrome P450 reductase ATR1 (GenBank Accession No. 66016); and *Arabidopsis thaliana* cytochrome P450 reductase ATR2 (GenBank Accession No. X66017); and putidaredoxin reductase and putidaredoxin (GenBank Accession No. J05406).

In some embodiments, a subject nucleic acid comprises a nucleotide sequence that encodes a CPR polypeptide that is specific for a given P450 enzyme. As one non-limiting example, a subject nucleic acid comprises a nucleotide sequence that encodes *Taxus cuspidata* CPR (FIG. 12A; GenBank AY571340). As another non-limiting example, a subject nucleic acid comprises a nucleotide sequence that encodes *Candida tropicalis* CPR (FIG. 12B). In other embodiments, a subject nucleic acid comprises a nucleotide sequence that encodes a CPR polypeptide that can serve as a redox partner for two or more different P450 enzymes. One such CPR is depicted in FIG. 12C (*Arabidopsis thaliana* cytochrome P450 reductase ATR1). Another such CPR is depicted in FIG. 12D (*Arabidopsis thaliana* cytochrome P450 reductase ATR2). Also suitable is a modified or variant ATR2, e.g., as depicted in FIG. 12D, which variant ATR2 lacks a chloroplast-targeting sequence.

The encoded CPR will in some embodiments comprise a heterologous amino acid sequence or a variant amino acid sequence (e.g., substitutions, deletions, insertions, additions). In some embodiments, the encoded CPR will in some embodiments include one or more of the following modifications relative to a wild-type CPR: a) substitution of a native transmembrane domain with a non-native transmembrane domain; b) replacement of the native transmembrane domain with a secretion signal domain; c) replacement of the native transmembrane domain with a solubilization domain; d) replacement of the native transmembrane domain with membrane insertion domain; e) truncation of the native transmembrane domain; and f) a change in the amino acid sequence of the native transmembrane domain.

In some embodiments, a nucleotide sequence encoding a CPR polypeptide is modified to reflect the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Constructs

The present invention further provides recombinant vectors ("constructs") comprising a subject nucleic acid. In some embodiments, a subject recombinant vector provides for amplification of a subject nucleic acid. In some embodiments, a subject recombinant vector provides for production of an encoded modified cytochrome P450 enzyme (e.g., an isoprenoid-modifying enzyme), or an encoded CPR, in a eukaryotic cell, in a prokaryotic cell, or in a cell-free transcription/translation system. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli*, yeast, and plant cells).

In some embodiments, a subject recombinant vector comprises a subject modified cytochrome P450-encoding nucleic acid and a subject CPR-encoding nucleic acid. In some of these embodiments, a subject recombinant vector is an expression vector that provides for production of both the encoded modified cytochrome P450 enzyme (e.g., modified isoprenoid-modifying enzyme) and the encoded CPR in a eukaryotic cell, in a prokaryotic cell, or in a cell-free transcription/translation system.

Certain types of vectors allow the expression cassettes of the present invention to be amplified. Other types of vectors are necessary for efficient introduction of subject nucleic acid to cells and their stable expression once introduced. Any vector capable of accepting a subject nucleic acid is contemplated as a suitable recombinant vector for the purposes of the invention. The vector may be any circular or linear length of DNA that either integrates into the host genome or is maintained in episomal form. Vectors may require additional manipulation or particular conditions to be efficiently incorporated into a host cell (e.g., many expression plasmids), or can be part of a self-integrating, cell specific system (e.g., a recombinant virus). The vector is in some embodiments functional in a prokaryotic cell, where such vectors function to propagate the recombinant vector and/or provide for expression of a subject nucleic acid. The vector is in some embodiments functional in a eukaryotic cell, where the vector will in many embodiments be an expression vector.

Numerous suitable expression vectors are known to those of skill in the art, and many are commercially available. The following vectors are provided by way of example; for bacterial host cells: pBluescript (Stratagene, San Diego, Calif.), pQE vectors (Qiagen), pBluescript plasmids, pNH vectors, lambda-ZAP vectors (Stratagene); pTrc (Amann et al., Gene, 69:301-315 (1988)); pTrc99a, pKK223-3, pDR540, and pRIT2 T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell. In particular embodiments, the plasmid vector pSP19 g10L is used for expression in a prokaryotic host cell. In other particular embodiments, the plasmid vector pCWori is used for expression in a prokaryotic host cell. See, e.g., Barnes ((1996) *Methods Enzymol.* 272:1-14) for a description of pSP19 g10L and pCWori.

In many embodiments, a subject nucleic acid comprises a nucleotide sequence encoding an isoprenoid-modifying enzyme, where the isoprenoid-modifying enzyme-encoding nucleotide sequence is operably linked to one or more transcriptional and/or translational control elements. In many embodiments, a subject nucleic acid comprises a nucleotide sequence encoding a CPR, where the CPR-encoding nucleotide sequence is operably linked to one or more transcriptional and/or translational control elements.

In some embodiments, as noted above, a subject recombinant vector comprises a subject modified cytochrome P450 enzyme-encoding nucleic acid and a subject CPR-encoding nucleic acid. In some of these embodiments, the modified cytochrome P450 enzyme-encoding nucleotide sequence and the CPR-encoding nucleotide sequence are operably linked to different transcriptional control elements. In other embodiments, the modified cytochrome P450 enzyme-encoding nucleotide sequence and the CPR-encoding nucleotide sequence are operably linked to the same transcriptional control element(s). In some embodiments, the modified cytochrome P450 enzyme-encoding nucleotide sequence and the CPR-encoding nucleotide sequence are both operably linked to the same inducible promoter. In some embodiments, the modified cytochrome P450 enzyme-encoding nucleotide sequence and the CPR-encoding nucleotide sequence are both operably linked to the same constitutive promoter.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.,* 1991: 173(1): 86-93; Alpuche-Aranda et al., PNAS, 1992; 89(21): 10079-83), a nirB promoter (Harbome et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma 70 promoter, e.g., a consensus sigma 70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PH05 promoter, a CUP1 promoter, a GAL7 promoter, a MET25 promoter, a MET3 promoter, and the like. Selection of the appropriate vector and promoter is well within the level of ordinary skill in the art. The expression vector may also contain a ribosome binding site for translation initiation and a transcription terminator. The expression vector may also include appropriate sequences for amplifying expression.

A subject recombinant vector will in many embodiments contain one or more selectable marker genes to provide a phenotypic trait for selection of transformed host cells. Suitable selectable markers include, but are not limited to, dihydrofolate reductase, neomycin resistance for eukaryotic cell culture; and tetracycline or ampicillin resistance in prokaryotic host cells such as *E. coli.*

Generally, recombinant expression vectors will include origins of replication and selectable markers permitting transformation of the host cell, e.g., the ampicillin resistance gene of *E. coli*, the *S. cerevisiae* TRP 1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In many embodiments, a nucleotide sequence encoding a modified cytochrome P450 enzyme (e.g., a modified isoprenoid modifying enzyme) is operably linked to an inducible promoter. In many embodiments, a nucleotide sequence encoding a CPR is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., PBAD (see, e.g., Guzman et al. (1995) *J. Bacteriol.* 177:4121-4130); a xylose-inducible promoter, e.g., Pxy1 (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N. Y., Vol. 153, pp. 516-544; Glover, 1986, DNA Cloning, Vol. II, IRL Press, Wash., D. C., Ch. 3; and Bitter, 1987, Heterologous Gene Expression in Yeast, Methods in Enzymology, Eds. Berger & Kimmel, Acad. Press, N. Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D. C.). Alternatively, vectors may be used which promote integration of foreign DNA sequences into the yeast chromosome.

In some embodiments, a subject nucleic acid or a subject vector comprises a promoter or other regulatory element(s) for expression in a plant cell. Non-limiting examples of suitable constitutive promoters that are functional in a plant cell is the cauliflower mosaic virus 35 S promoter, a tandem 35 S promoter (Kay et al., *Science* 236:1299 (1987)), a cauliflower mosaic virus 19 S promoter, a nopaline synthase gene promoter (Singer et al., *Plant Mol. Biol.* 14:433 (1990); An, *Plant Physiol.* 81:86 (1986), an octopine synthase gene promoter, and a ubiquitin promoter. Suitable inducible promoters that are functional in a plant cell include, but are not limited to, a phenylalanine ammonia-lyase gene promoter, a chalcone synthase gene promoter, a pathogenesis-related protein gene promoter, a copper-inducible regulatory element (Mett et al., *Proc. Natl. Acad. Sci. USA* 90:4567-4571 (1993); Furst et al., Cell 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992); a nitrate-inducible promoter derived from the spinach nitrite reductase gene (Back et al., *Plant Mol. Biol.* 17:9 (1991)); a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)); a light-responsive regulatory element as described in U.S. Patent Publication No. 20040038400; a salicylic acid inducible regulatory elements (Uknes et al., *Plant Cell* 5:159-169 (1993); Bi et al., *Plant J.* 8:235-245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991).

Plant tissue-selective regulatory elements also can be included in a subject nucleic acid or a subject vector. Suitable tissue-selective regulatory elements, which can be used to ectopically express a nucleic acid in a single tissue or in a limited number of tissues, include, but are not limited to, a xylem-selective regulatory element, a tracheid-selective regulatory element, a fiber-selective regulatory element, a trichome-selective regulatory element (see, e.g., Wang et al. (2002) *J. Exp. Botany* 53:1891-1897), a glandular trichome-selective regulatory element, and the like.

Vectors that are suitable for use in plant cells are known in the art, and any such vector can be used to introduce a subject nucleic acid into a plant host cell. Suitable vectors include, e.g., a Ti plasmid of *Agrobacterium tumefaciens* or an $Ri_1$ plasmid of *A. rhizogenes*. The Ti or $Ri_1$ plasmid is transmitted to plant cells on infection by *Agrobacterium* and is stably integrated into the plant genome. J. Schell, *Science,* 237: 1176-83 (1987). Also suitable for use is a plant artificial chromosome, as described in, e.g., U.S. Pat. No. 6,900,012.

Compositions

The present invention further provides compositions comprising a subject nucleic acid.

The present invention further provides compositions comprising a subject recombinant vector. Compositions comprising a subject nucleic acid or a subject expression vector will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]-methyl-3-aminopropanesulfonic acid (TAPS), etc.; a solubilizing agent; a detergent, e.g., a non-ionic detergent such as Tween-20, etc.; a nuclease inhibitor; and the like. In some embodiments, a subject nucleic acid or a subject recombinant vector is lyophilized.

Host Cells

The present invention provides genetically modified host cells, e.g., host cells that have been genetically modified with a subject nucleic acid or a subject recombinant vector. In many embodiments, a subject genetically modified host cell is an in vitro host cell. In other embodiments, a subject genetically modified host cell is an in vivo host cell. In other embodiments, a subject genetically modified host cell is part of a multicellular organism.

Host cells are in many embodiments unicellular organisms, or are grown in in vitro culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a eukaryotic cell other than a plant cell.

In other embodiments, the host cell is a plant cell. Plant cells include cells of monocotyledons ("monocots") and dicotyledons ("dicots").

In other embodiments, the host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270: 299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli.*

To generate a subject genetically modified host cell, a subject nucleic acid comprising nucleotide sequences encoding a modified cytochrome P450 enzyme (e.g., a modified isoprenoid-modifying enzyme) is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In some embodiments, a subject genetically modified host cell is a plant cell. A subject genetically modified plant cell is useful for producing a selected isoprenoid compound in in vitro plant cell culture. Guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

Genetically Modified Host Cells

In some embodiments, a subject genetically modified host cell comprises a subject expression vector, where the subject expression vector comprises a nucleotide sequence encoding a modified cytochrome P450 enzyme. In some embodiments, a subject genetically modified host cell comprises a subject expression vector, where the subject expression vector comprises a nucleotide sequence encoding a modified isoprenoid precursor-modifying enzyme.

In some embodiments, a subject genetically modified host cell comprises a first subject expression vector, where the first subject expression vector comprises a subject nucleic acid comprising a nucleotide sequence encoding a modified cytochrome P450 enzyme; and further comprises a second subject expression vector, where the second subject expression vector comprises a subject nucleic acid comprising a nucleotide sequence encoding a CPR. In other embodiments, a subject genetically modified host cell comprises a subject expression vector, wherein the subject expression vector comprises a subject nucleic acid comprising a nucleotide sequence encoding a modified cytochrome P450 enzyme and a subject nucleic acid comprising a nucleotide sequence encoding a CPR. In other embodiments, a subject genetically modified host cell comprises a subject expression vector, where the subject expression vector comprises a subject nucleic acid comprising a nucleotide sequence encoding a fusion polypeptide (e.g. a polypeptide that includes a modified cytochrome P450 enzyme and a CPR).

In some embodiments, a subject genetically modified host cell comprises a first expression vector, where the first expression vector comprises subject nucleic acid comprising a nucleotide sequence encoding a modified cytochrome P450 enzyme; and further comprises a second expression vector, where the second expression vector comprises a nucleotide sequence encoding a CPR. In other embodiments, a subject genetically modified host cell comprises a subject expression vector, wherein the subject expression vector comprises a subject nucleic acid comprising a nucleotide sequence encoding a modified cytochrome P450 enzyme and a nucleotide sequence encoding a CPR.

In some embodiments, a subject genetically modified host cell is further genetically modified to include one or more nucleic acids comprising nucleotide sequences encoding one or more enzymes that give rise to a substrate for a cytochrome P450 enzyme. Examples of such enzymes include, but are not limited to terpene synthases; prenyl transferases; isopentenyl diphosphate isomerase; one or more enzymes in a mevalonate pathway; and one or more enzymes in a DXP pathway. In some embodiments, a subject genetically modified host cell is further genetically modified to include one or more nucleic acids comprising nucleotide sequences encoding one, two, three, four, five, six, seven, or eight, or more of: a terpene synthase, a prenyl transferase, an IPP isomerase, an acetoacetyl-CoA thiolase, an HMGS, an HMGR, an MK, a PMK, and an MPD. In some embodiments, e.g., where a subject genetically modified host cell is further genetically modified to include one or more nucleic acids comprising nucleotide sequences encoding two or more of a terpene synthase, a prenyl transferase, an IPP isomerase, an acetoacetyl-CoA thiolase, an HMGS, an HMGR, an MK, a PMK, and an MPD, the nucleotide sequences are present in at least two operons, e.g., two separate operons, three separate operons, or four separate operons.

Terpene Synthases

In some embodiments, a subject genetically modified host cell is further genetically modified to include a nucleic acid comprising a nucleotide sequence encoding a terpene synthase. In some embodiments, the terpene synthase is one that modifies FPP to generate a sesquiterpene. In other embodiments, the terpene synthase is one that modifies GPP to generate a monoterpene. In other embodiments, the terpene synthase is one that modifies GGPP to generate a diterpene. The terpene synthase acts on a polyprenyl diphosphate substrate, modifying the polyprenyl diphosphate substrate by cyclizing, rearranging, or coupling the substrate, yielding an isoprenoid precursor (e.g., limonene, amorphadiene, taxadiene, etc.), which isoprenoid precursor is the substrate for an isoprenoid precursor-modifying enzyme(s). By action of the terpene synthase on a polyprenyl diphosphate substrate, the substrate for an isoprenoid-precursor-modifying enzyme is produced.

Nucleotide sequences encoding terpene synthases are known in the art, and any known terpene synthase-encoding nucleotide sequence can be used to genetically modify a host cell. For example, the following terpene synthase-encoding nucleotide sequences, followed by their GenBank accession numbers and the organisms in which they were identified, are known and can be used: (−)-germacrene D synthase mRNA (AY438099; *Populus balsamifera* subsp. *trichocarpa* x *Populus deltoids*); E, E-alpha-farnesene synthase mRNA (AY640154; *Cucumis sativus*); 1,8-cineole synthase mRNA (AY691947; *Arabidopsis thaliana*); terpene synthase 5 (TPS5) mRNA (AY518314; *Zea mays*); terpene synthase 4 (TPS4) mRNA (AY518312; *Zea mays*); myrcene/ocimene synthase (TPS10) (At2 g24210) mRNA (NM__127982; *Arabidopsis thaliana*); geraniol synthase (GES) mRNA (AY362553; *Ocimum basilicum*); pinene synthase mRNA (AY237645; *Picea sitchensis*); myrcene synthase 1 e20 mRNA (AY195609; *Antirrhinum majus*); (E)-β-ocimene synthase (0 e23) mRNA (AY195607; *Antirrhinum majus*); E-β-ocimene synthase mRNA (AY151086; *Antirrhinum majus*); terpene synthase mRNA (AF497-492; *Arabidopsis thaliana*); (−)-camphene synthase (AG6.5) mRNA (U87910; *Abies grandis*); (−)-4 S-limonene synthase gene (e.g., genomic sequence) (AF326518; *Abies grandis*); delta-selinene synthase gene (AF326513; *Abies grandis*); amorpha-4,11-diene synthase mRNA (AJ251751; *Artemisia annua*); E-α-bisabolene synthase mRNA (AF006195; *Abies grandis*); gamma-humulene synthase mRNA (U92267; *Abies grandis*); δ-selinene synthase miRNA (U92266; *Abies grandis*); pinene synthase (AG3.18) mRNA (U87909; *Abies grandis*); myrcene synthase (AG2.2) mRNA (U87908; *Abies grandis*); etc.

Mevalonate Pathway

In some embodiments, a subject genetically modified host cell is a host cell that does not normally synthesize isopentenyl pyrophosphate (IPP) or mevalonate via a mevalonate pathway. The mevalonate pathway comprises: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway enzymes required for production of IPP vary, depending on the culture conditions.

As noted above, in some embodiments, a subject genetically modified host cell is a host cell that does not normally synthesize isopentenyl pyrophosphate (IPP) or mevalonate via a mevalonate pathway. In some of these embodiments, the host cell is genetically modified with a subject expression vector comprising a subject nucleic acid encoding an isoprenoid-modifying enzyme; and the host cell is genetically modified with one or more heterologous nucleic acids comprising nucleotide sequences encoding acetoacetyl-CoA thiolase, hydroxymethylglutaryl-CoA synthase (HMGS), hydroxymethylglutaryl-CoA reductase (HMGR), mevalonate kinase (MK), phosphomevalonate kinase (PMK), and mevalonate pyrophosphate decarboxylase (MPD) (and optionally also IPP isomerase). In many of these embodiments, the host cell is genetically modified with an expression vector comprising a nucleotide sequence encoding a CPR. In some of these embodiments, the host cell is genetically modified with a subject expression vector comprising a subject nucleic acid encoding an isoprenoid-modifying enzyme; and the host cell is genetically modified with one or more heterologous nucleic acids comprising nucleotide sequences encoding MK, PMK, MPD (and optionally also IPP isomerase). In many of these embodiments, the host cell is genetically modified with an expression vector comprising a nucleotide sequence encoding a CPR.

In some embodiments, a subject genetically modified host cell is a host cell that does not normally synthesize IPP or mevalonate via a mevalonate pathway; the host cell is genetically modified with a subject expression vector comprising a subject nucleic acid encoding an isoprenoid-modifying enzyme; and the host cell is genetically modified with one or more heterologous nucleic acids comprising nucleotide sequences encoding acetoacetyl-CoA thiolase, HMGS, HMGR, MK, PMK, MPD, IPP isomerase, and a prenyl transferase. In many of these embodiments, the host cell is genetically modified with an expression vector comprising a nucleotide sequence encoding a CPR. In some embodiments, a subject genetically modified host cell is a host cell that does not normally synthesize IPP or mevalonate via a mevalonate pathway; the host cell is genetically modified with a subject expression vector comprising a subject nucleic acid encoding an isoprenoid-modifying enzyme; and the host cell is genetically modified with one or more heterologous nucleic acids comprising nucleotide sequences encoding MK, PMK, MPD, IPP isomerase, and a prenyl transferase. In many of these embodiments, the host cell is genetically modified with an expression vector comprising a nucleotide sequence encoding a CPR.

In some embodiments, a subject genetically modified host cell is one that normally synthesizes IPP or mevalonate via a mevalonate pathway, e.g., the host cell is one that comprises an endogenous mevalonate pathway. In some of these embodiments, the host cell is a yeast cell. In some of these embodiments, the host cell is *Saccharomyces cerevisiae*.

In some embodiments, a subject genetically modified host cell is further genetically modified with one or more nucleic acids that comprise nucleotide sequences encoding a dehydrogenase or dehydrogenases, which dehydrogenase further modifies an isoprenoid compound. The encoded dehydrogenase may be one that is naturally found in a prokaryotic cell or a eukaryotic cell, or may be a variant of such a dehydrogenase. In some embodiments, the present invention provides isolated nucleic acids comprising nucleotide sequences encoding such dehydrogenases.

Mevalonate Pathway Nucleic Acids

Nucleotide sequences encoding MEV pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC__000913 REGION: 2324131.2325315; *E. coli*), (D49362; *Paracoccus denitrificans*), and (L20428; *Saccharomyces cerevisiae*); HMGS: (NC__001145. complement 19061.20536; *Saccharomyces cerevisiae*), (X96617; *Saccharomyces cerevisiae*), (X83882; *Arabidopsis thaliana*), (AB037907; *Kitasatospora griseola*), and (BT007302;

*Homo sapiens*); HMGR: (NM_206548; *Drosophila melanogaster*), (NM_204485; *Gallus gallus*), (ABO15627; *Streptomyces* sp. KO-3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315.713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087.3031635; *E. coli*), and (AF082326; *Haematococcus pluvialis*).

In some embodiments, the HMGR coding region encodes a truncated form of HMGR ("tHMGR") that lacks the transmembrane domain of wild-type HMGR. The transmembrane domain of HMGR contains the regulatory portions of the enzyme and has no catalytic activity.

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Prenyl Transferases

In some embodiments, a subject genetically modified host cell is genetically modified to include a nucleic acid comprising a nucleotide sequence encoding an isoprenoid-modifying enzyme; and in some embodiments is also genetically modified to include one or more nucleic acids comprising a nucleotide sequence(s) encoding one or more mevalonate pathway enzymes, as described above; and a nucleic acid comprising a nucleotide sequence that encodes a prenyl transferase.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 2 isoprene units to about 6000 isoprene units or more, e.g., 2 isoprene units (Geranyl Pyrophosphate synthase), 3 isoprene units (Farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase, 10 isoprene units (decaprenyl pyrophosphate synthase), from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a subject genetically modified host cell. Nucleotide sequences encoding prenyl transferases are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000) *Biochim. Biophys. Acta* 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4 g17190) mRNA (GenBank Accession No. NM_202836); *Ginkgo biloba* geranylgeranyl diphosphate synthase (ggpps) mRNA (GenBank Accession No. AY371321); *Arabidopsis thaliana* geranylgeranyl pyrophosphate synthase (GGPS1)/GGPP synthetase/farnesyltranstransferase (At4 g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095); etc.

Codon Usage

In some embodiments, a nucleotide sequence used to generate a subject genetically modified host cell is modified such that the nucleotide sequence reflects the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Additional Genetic Modifications

In some embodiments, a subject genetically modified host cell is further genetically modified to is one that is genetically modified to include one or more nucleic acids comprising a nucleotide sequence(s) that encode a modified cytochrome P450 enzyme (e.g, a modified isoprenoid-modifying enzyme); and that is further genetically modified to achieve enhanced heme production, and/or to achieve enhanced production of a terpene biosynthetic pathway intermediate, and/or that is further genetically modified such that an endogenous terpene biosynthetic pathway gene is functionally disabled. The term "functionally disabled," as used herein in the context of an endogenous terpene biosynthetic pathway gene, refers to a genetic modification of a terpene biosynthetic pathway gene, which modification results in production of a gene product encoded by the gene that is produced at below normal levels, and/or is non-functional.

Enhanced Heme Production

In some embodiments, a subject genetically modified host cell comprises one or more additional genetic modifications that provide for enhanced heme production, e.g., to achieve an at least about 10%, at least about 15%, at least about 20%, at least about 25%, at least about 30%, at least about 40%, at least about 50%, at least about 60%, at least about 70%, at least about 80%, at least about 90%, at least about 2-fold, at least about 2.5-fold, at least about 5-fold, at least about 10-fold, at least about 15-fold, at least about 20-fold, or at least about 25-fold, or greater, increase in heme production, compared to a host cell that does not comprise the one or more additional genetic modifications.

Figure 13:
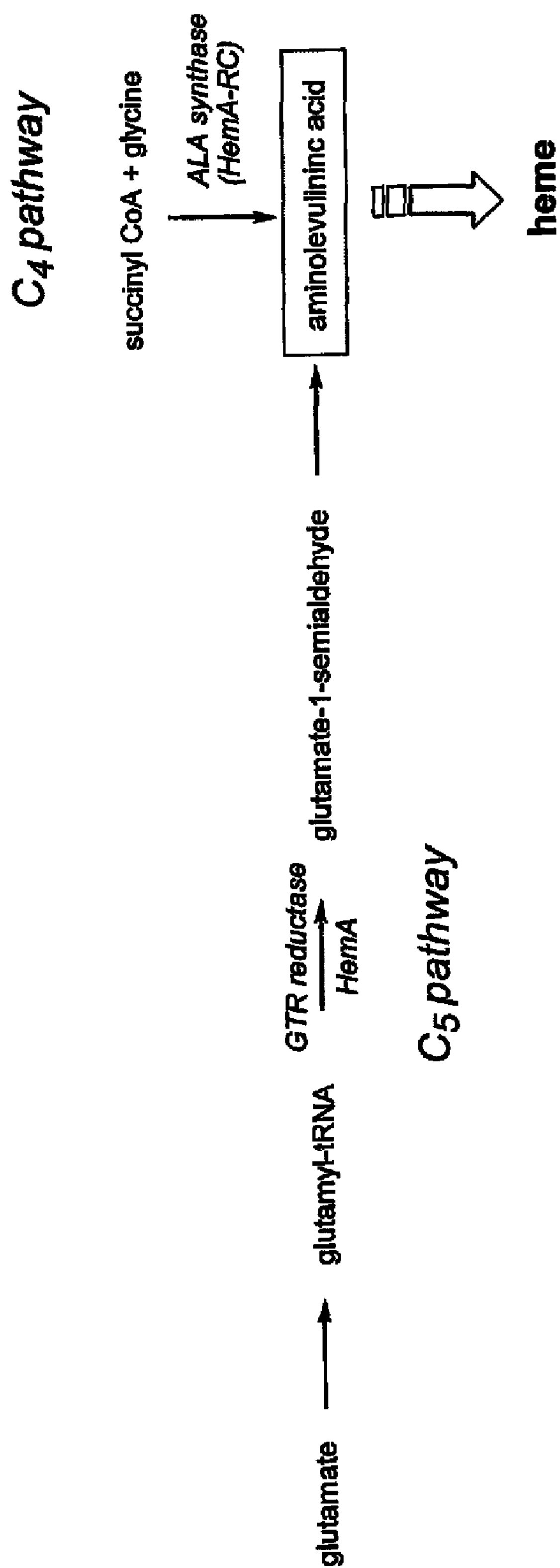
FIG. 13 depicts schematically two heme biosynthetic pathways.

The limiting step in heme production in a cell is the biosynthesis of aminolevulinic acid (ALA). As depicted in FIG. 13, there are two distinct pathways for ALA biosynthesis involving either a $C_4$ pathway or $C_5$ pathway. In some embodiments, a subject genetically modified host cell is further genetically modified to overexpress glutamyl-tRNA reductase (GTR reductase). In some embodiments, a subject genetically modified host cell is further genetically modified to produce a level of GTR reductase activity that is at least about 10%, at least about 15%, at least about 20%, at least about 25%, at least about 30%, at least about 40%, at least about 50%, at least about 60%, at least about 70%, at least about 80%, at least about 90%, at least about 2-fold, at least about 2.5-fold, at least about 5-fold, at least about 10-fold, at least about 15-fold, at least about 20-fold, or at least about 25-fold, or greater, higher than the level of GTR reductase activity produced in a control host cell.

Increasing the level of GTR reductase activity in a cell is achieved in a number of ways, including, but not limited to: 1) increasing the promoter strength of the promoter to which the GTR reductase coding region is operably linked; 2) increasing the copy number of the plasmid comprising a nucleotide sequence encoding GTR reductase; 3) increasing the stability of a GTR reductase mRNA (where an "GTR reductase mRNA" is an mRNA comprising a nucleotide sequence encoding GTR reductase); 4) modifying the codon usage of GTR reductase such that the level of translation of the GTR reductase mRNA is increased; 5) increasing the enzyme stability of GTR reductase; 6) increasing the specific activity (units activity per unit protein) of GTR reductase; and 7) reducing negative feedback regulation of GTR reductase.

In some embodiments, a genetic modification that results in increased level of GTR reductase is a genetic modification that reduces the negative feedback regulation of GTR reductase. Reduction of the negative feedback regulation of GTR reductase is in some embodiments reduced by insertion of a positively-charged KK sequence at or near the N-terminus.

In some embodiments, a subject genetically modified host cell is further genetically modified to overexpress ALA synthase. In some embodiments, a subject genetically modified host cell is further genetically modified to produce a level of ALA synthase that is at least about 10%, at least about 15%, at least about 20%, at least about 25%, at least about 30%, at least about 40%, at least about 50%, at least about 60%, at least about 70%, at least about 80%, at least about 90%, at least about 2-fold, at least about 2.5-fold, at least about 5-fold, at least about 10-fold, at least about 15-fold, at least about 20-fold, or at least about 25-fold, or greater, higher than the level of ALA synthase activity produced in a control host cell.

Increasing the level of ALA synthase activity in a cell is achieved in a number of ways, including, but not limited to: 1) increasing the promoter strength of the promoter to which the ALA synthase coding region is operably linked; 2) increasing the copy number of the plasmid comprising a nucleotide sequence encoding ALA synthase; 3) increasing the stability of an ALA synthase mRNA (where an "ALA synthase mRNA" is an mRNA comprising a nucleotide sequence encoding ALA synthase); 4) modifying the codon usage of ALA synthase such that the level of translation of the ALA synthase mRNA is increased; 5) increasing the enzyme stability of ALA synthase; and 6) increasing the specific activity (units activity per unit protein) of ALA synthase.

Enhanced Production of an Endogenous Terpene Biosynthetic Pathway Intermediate

Genetic modifications that enhance production of an endogenous terpene biosynthetic pathway intermediate include, but are not limited to, genetic modifications that result in a reduced level and/or activity of a phosphotransacetylase in the host cell. The intracellular concentration of a terpene biosynthetic pathway intermediate is enhanced by increasing the intracellular concentration of acetyl-CoA. *E. coli* secretes a significant fraction of intracellular acetyl-CoA in the form of acetate into the medium. Deleting the gene encoding phosphotransacetylase, pta, the first enzyme responsible for transforming acetyl-CoA into acetate, reduces acetate secretion. Genetic modifications that reduce the level and/or activity of phosphotransacetylase in a prokaryotic host cell are particularly useful where the genetically modified host cell is one that is genetically modified with a nucleic acid comprising nucleotide sequences encoding one or more MEV pathway gene products.

In some embodiments, a genetic modification that results in a reduced level of phosphotransacetylase in a prokaryotic host cell is a genetic mutation that functionally disables the prokaryotic host cell's endogenous pta gene encoding the phosphotransacetylase. The pta gene can be functionally disabled in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional in converting acetyl-CoA to acetate; deletion or mutation of one or more control elements that control expression of the pta gene such that the gene product is not made; and the like.

In some embodiments, the endogenous pta gene of a genetically modified host cell is deleted. Any method for deleting a gene can be used. One non-limiting example of a method for deleting a pta gene is by use of the λRed recombination system. Datsenko and Wanner (2000) *Proc Natl Acad Sci USA* 97 (12): p. 6640-5. The pta gene will in some embodiments be deleted from a host cell (e.g., *E. coli*) that is genetically modified with a nucleic acid comprising nucleotide sequences encoding MK, PMK, MPD, and IDI. The pta gene will in some embodiments be deleted from a host cell (e.g., *E. coli*) that is genetically modified with a nucleic acid comprising nucleotide sequences encoding MK, PMK, MPD, and IPP. The pta gene will in some embodiments be deleted from a host cell (e.g., *E. coli*) that is genetically modified with a nucleic acid comprising nucleotide sequences encoding MK, PMK, MPD, IPP, and a prenyl transferase.

Functionally Disabled DXP Pathway

In some embodiments, a subject genetically modified host cell is one that is genetically modified to include one or more nucleic acids comprising a nucleotide sequence(s) that encode MEV biosynthetic pathway gene product(s); and that is further genetically modified such that an endogenous DXP biosynthetic pathway gene is functionally disabled. In other embodiments, a subject genetically modified host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, where subject genetically modified host cell is a prokaryotic host cell that is genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2 C-methyl-D-erythritol 2,4-cyclodiphosphate synthase, and 1-hydroxy-2-methyl-2-(E)-butenyl 4-diphosphate synthase.

An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

In other embodiments, where subject genetically modified host cell is a prokaryotic host cell that is genetically modified with nucleic acid(s) comprising nucleotide sequences encoding one or more DXP pathway gene products, the host cell will be further genetically modified such that one or more endogenous MEV pathway genes is functionally disabled. Endogenous MEV pathway genes that can be functionally disabled include one or more of the genes encoding any of the following MEV gene products: HMGS, HMGR, MK, PMK, MPD, and IDI. An endogenous MEV pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

Compositions Comprising a Subject Genetically Modified Host Cell

The present invention further provides compositions comprising a subject genetically modified host cell. A subject composition comprises a subject genetically modified host cell, and will in some embodiments comprise one or more further components, which components are selected based in part on the intended use of the genetically modified host cell. Suitable components include, but are not limited to, salts; buffers; stabilizers; protease-inhibiting agents; nuclease-inhibiting agents; cell membrane- and/or cell wall-preserving compounds, e.g., glycerol, dimethylsulfoxide, etc.; nutritional media appropriate to the cell; and the like. In some embodiments, the cells are lyophilized.

Transgenic Plants

In some embodiments, a subject nucleic acid or a subject expression vector (e.g., a subject modified cytochrome P450 enzyme nucleic acid or a subject expression vector comprising a modified cytochrome P450 enzyme nucleic acid) is used as a transgene to generate a transgenic plant that produces the encoded modified cytochrome P450 enzyme. Thus, the present invention further provides a transgenic plant (or a plant part, seed, tissue, etc.), which plant comprises a transgene comprising a subject nucleic acid comprising a nucleotide sequence encoding a modified cytochrome P450 enzyme, as described above. In some embodiments, the genome of the transgenic plant comprises a subject nucleic acid. In some embodiments, the transgenic plant is homozygous for the genetic modification. In some embodiments, the transgenic plant is heterozygous for the genetic modification.

In some embodiments, a subject transgenic plant produces a transgene-encoded modified cytochrome P450 and produces a product of the modified cytochrome P450 in an amount that is at least about 50%, at least about 2-fold, at least about 5-fold, at least about 10-fold, at least about 25-fold, at least about 50-fold, or at least about 100-fold, or higher, than the amount of the product produced by a control plant, e.g., a non-transgenic plant (a plant that does not include the transgene encoding the polypeptide) of the same species.

In some embodiments, a subject transgenic plant is a transgenic version of a control, non-transgenic plant that normally produces an isoprenoid compound that is generated by, or is a downstream product of, a transgene-encoded modified isoprenoid precursor-modifying enzyme; where the transgenic plant produces the isoprenoid compound in an amount that is at least about 50%, at least about 2-fold, at least about 5-fold, at least about 10-fold, at least about 25-fold, at least about 50-fold, or at least about 100-fold, or higher, than the amount of the isoprenoid compound produced by the control plant, e.g., a non-transgenic plant (a plant that does not include the transgene encoding the polypeptide) of the same species.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or, preferably, binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo'Alto, Calif.). Methods of coculturing *Agrobacterium* with cultured plant cells or wounded tissue such as leaf tissue, root explants, hypocotyledons, stem pieces or tubers, for example, also are well known in the art. See., e.g., Glick and Thompson, (eds.), *Methods in Plant Molecular Biology and Biotechnology*, Boca Raton, Fla.: CRC Press (1993).

*Agrobacterium*-mediated transformation is useful for producing a variety of transgenic vascular plants (Wang et al., supra, 1995) including at least one species of Eucalyptus and forage legumes such as alfalfa (lucerne); birdsfoot trefoil, white clover, *Stylosanthes, Lotononis bainessii* and sainfoin.

Microprojectile-mediated transformation also can be used to produce a subject transgenic plant. This method, first described by Klein et al. (*Nature* 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A subject nucleic acid may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-962) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice. Other examples include *Artemisia annua*, or other plants known to produce isoprenoid compounds of interest.

Also provided by the subject invention are transformed plant cells, tissues, seeds, plants, and products that contain the transformed plant cells. A feature of the subject transformed cells, and tissues and products that include the same is the presence of a subject nucleic acid integrated into the genome, and production by plant cells of a modified cytochrome P450 enzyme. Recombinant plant cells of the present invention are useful as populations of recombinant cells, or as a tissue, seed, whole plant, stem, fruit, leaf, root, flower, stem, tuber, grain, animal feed, a field of plants, and the like.

Also provided by the subject invention is reproductive material of a subject transgenic plant, where reproductive material includes seeds, progeny plants and clonal material.

Methods of Producing a Product of a Biosynthetic Pathway

The present invention provides methods of producing a biosynthetic pathway product. The methods generally involve culturing a subject genetically modified host cell in a suitable medium. A subject genetically modified host cell is one that has been is genetically modified with a nucleic acid comprising a nucleotide sequence encoding a modified cytochrome P450 enzyme operably linked to a domain selected from a transmembrane domain, a secretion domain, a solubilization domain, and a membrane-inserting protein, to produce a modified cytochrome P450 enzyme. In the presence of a biosynthetic pathway intermediate, production of the modified cytochrome P450 enzyme results in enzymatic modification of the intermediate and production of a biosynthetic pathway product. In other embodiments, the methods generally involve maintaining a subject transgenic plant under conditions that favor production of the encoded modified cytochrome P450 enzyme. Production of the modified cytochrome P450 enzyme results in production of the biosynthetic pathway product. Typically, the method is carried out in vitro (e.g., in a living cell cultured in vitro), although in vivo production of a biosynthetic pathway product is also contemplated. In some of these embodiments, the host cell is a eukaryotic cell, e.g., a yeast cell. In other embodiments, the host cell is a prokaryotic cell. In some of these embodiments, the host cell is a plant cell. In some embodiments, the method is carried out in a subject transgenic plant.

A subject genetically modified host cell provides for enhanced production of a biosynthetic pathway product, compared to a control, parent host cell. Thus, e.g., production of a biosynthetic pathway product is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the level of the product produced in a control parent host cell. A control parent host cell does not comprise the genetic modification(s) present in the genetically modified host cell.

In some embodiments, a subject genetically modified host cell provides for enhanced production of a biosynthetic pathway product, compared to a control host cell. Thus, e.g., production of a biosynthetic pathway product is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the level of the product produced in a control host cell. In some of these embodiments, the control host cell does not comprise the genetic modification(s) present in the genetically modified host cell, e.g., the isoprenoid modifying enzyme-encoding nucleic acid (e.g., the cytochrome P450 enzyme-encoding nucleic acid) in the control host cell is operably linked to one or more of a native transmembrane domain, a native secretion domain, a native solubilization domain, and a native membrane-insertion polypeptide, while the genetically modified host cell comprises an isoprenoid modifying enzyme-encoding nucleic acid operably linked to one or more of a non-native (e.g., heterologous) transmembrane domain, a non-native secretion domain, a non-native solubilization domain, and a non-native membrane-insertion domain. As one example, where the genetically modified host cell comprises an isoprenoid modifying enzyme-encoding nucleic acid operably linked to a non-native isoprenoid modifying enzyme-encoding nucleic acid, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a heterologous secretion signal domain, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a heterologous solubilization domain, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a heterologous membrane insertion domain, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a variant transmembrane domain (e.g., a truncation of the native transmembrane domain; a transmembrane domain comprising a change in amino acid sequence compared to the amino acid sequence of the native transmembrane domain), a suitable control host cell comprises the isoprenoid modifying enzyme-encoding nucleic acid operably linked to a native transmembrane domain.

The present invention provides methods of producing an isoprenoid compound. The methods generally involve culturing a subject genetically modified host cell in a suitable medium, where the subject genetically modified host cell is one that has been is genetically modified with a nucleic acid comprising a nucleotide sequence encoding an isoprenoid precursor-modifying enzyme operably linked to a domain selected from a transmembrane domain, a secretion domain, a solubilization domain, and a membrane-inserting protein, to produce an isoprenoid precursor-modifying enzyme. In the presence of an isoprenoid precursor compound, production of the isoprenoid precursor-modifying enzyme results in enzymatic modification of the isoprenoid precursor and production of the isoprenoid compound. In other embodiments, the methods generally involve maintaining a subject transgenic plant under conditions that favor production of the encoded isoprenoid precursor-modifying enzyme. Production of the isoprenoid precursor-modifying enzyme results in production of the isoprenoid compound. For example, in some embodiments, the methods generally involve culturing a genetically modified host cell in a suitable medium, wherein said host cell is genetically modified with a subject nucleic acid comprising a nucleotide sequence encoding a terpene modifying enzyme, e.g., a terpene oxidase, a terpene hydroxylase, etc. Production of the terpene oxidase results in production of the isoprenoid compound. Typically, the method is carried out in vitro (e.g., in a living cell cultured in vitro), although in vivo production of an isoprenoid compound is also contemplated. In some of these embodiments, the host cell is a eukaryotic cell, e.g., a yeast cell. In other embodiments, the host cell is a prokaryotic cell. In some of these embodiments, the host cell is a plant cell. In some embodiments, the method is carried out in a subject transgenic plant.

A subject genetically modified host cell provides for enhanced production of an isoprenoid compound, compared to a control, parent host cell. Thus, e.g., production of an isoprenoid or isoprenoid precursor is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to a control parent host cell. A control parent host cell does not comprise the genetic modification(s) present in the genetically modified host cell.

In some embodiments, a subject genetically modified host cell provides for enhanced production of an isoprenoid compound, compared to a control host cell. Thus, e.g., production of an isoprenoid or isoprenoid precursor is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to a control host cell. In some of these embodiments, the control host cell does not comprise the genetic modification(s) present in the genetically modified host cell, e.g., the isoprenoid modifying enzyme-encoding nucleic acid (e.g., the cytochrome P450 enzyme-encoding nucleic acid) in the control host cell is operably linked to one or more of a native transmembrane domain, a native secretion domain, a native solubilization domain, and a native membrane-insertion polypeptide, while the genetically modified host cell comprises an isoprenoid modifying enzyme-encoding nucleic acid operably linked to one or more of a non-native (e.g., heterologous) transmembrane domain, a non-native secretion domain, a non-native solubilization domain, and a non-native membrane-insertion domain. As one example, where the genetically modified host cell comprises an isoprenoid modifying enzyme-encoding nucleic acid operably linked to a non-native isoprenoid modifying enzyme-encoding nucleic acid, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a heterologous secretion signal domain, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a heterologous solubilization domain, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a heterologous membrane insertion domain, a suitable control host cell comprises the isoprenoid modifying enzyme-encoding nucleic acid operably linked to a native transmembrane domain. As another example, where the genetically modified host cell comprises an isoprenoid modifying enzyme-encoding nucleic acid operably linked to a variant transmembrane domain (e.g., a truncation of the native transmembrane domain; a transmembrane domain comprising a change in amino acid sequence compared to the amino acid sequence of the native transmembrane domain), a suitable control host cell comprises the isoprenoid modifying enzyme-encoding nucleic acid operably linked to a native transmembrane domain.

Thus, in some embodiments, a subject genetically modified host cell produces, on a per cell basis, a level of an isoprenoid compound that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the level of the isoprenoid compound produced in a control host cell not comprises the one or more genetic modifications that the genetically modified host cell comprises. Growth of genetically modified host cells is readily determined using well-known methods, e.g., optical density (OD) measurement at about 600 nm ($OD_{600}$) of liquid cultures of bacteria; colony size; growth rate; and the like.

In some embodiments, a subject genetically modified host cell produces an isoprenoid compound in a recoverable amount of at least about 1 mg/L, at least about 5 mg/L, at least about 10 mg/L, at least about 15 mg/L, at least about 20 mg/L, at least about 25 mg/L, at least about 30 mg/L, at least about 35 mg/L, at least about 40 mg/L, at least about 50 mg/L, at least about 75 mg/L, at least about 100 mg/L, at least about 125 mg/L, at least about 150 mg/L, at least about 200 mg/L, at least about 300 mg/L, at least about 500 mg/L, at least about 1000 mg/L, or at least about 5000 mg/L.

In some embodiments, a subject genetically modified host cell produces an isoprenoid compound in a recoverable amount of from about 1 mg/L to about 5000 mg/L, e.g., from about 1 mg/L to about 2 mg/L, from about 2 mg/L to about 5 mg/L, from about 5 mg/L to about 10 mg/L, from about 10 mg/L to about 15 mg/L, from about 15 mg/L to about 20 mg/L, from about 20 mg/L to about 25 mg/L, from about 25 mg/L to about 50 mg/L, from about 50 mg/L to about 75 mg/L, from about 75 mg/L to about 100 mg/L, from about 100 mg/L to about 150 mg/L, from about 150 mg/L to about 200 mg/L, from about 200 mg/L to about 250 mg/L, from about 250 mg/L to about 300 mg/L, from about 300 mg/L to about 350 mg/L, from about 350 mg/L to about 400 mg/L, from about 400 mg/L to about 450 mg/L, from about 450 mg/L to about 500 mg/L, from about 500 mg/L to about 1000 mg/L, from about 1000 mg/L to about 2000 mg/L, from about 2000 mg/L to about 3000 mg/L, from about 3000 mg/L to about 4000 mg/L, or from about 4000 mg/L to about 5000 mg/L. The produced isoprenoids can be recovered from the medium or from the host cell, e.g., from the culture medium or from a cell lysate or a fraction of a cell lysate. The recovery methods may vary, depending on a variety of factors, e.g., the nature of the specific isoprenoids that are produced.

Figure 14:
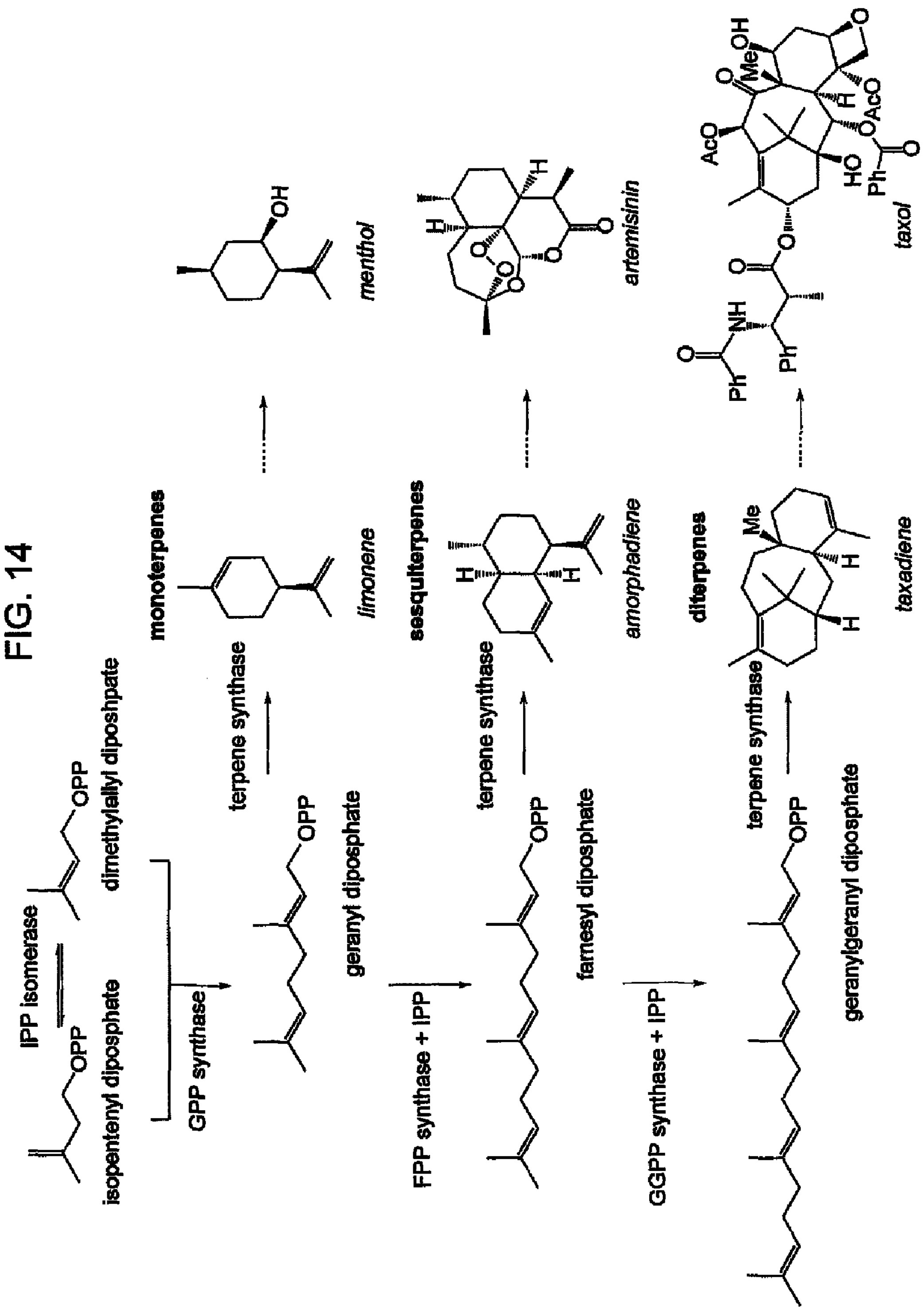
FIG. 14 depicts schematically the biosynthesis of exemplary isoprenoid products taxol, artemisinin, and menthol.
Figure 15:
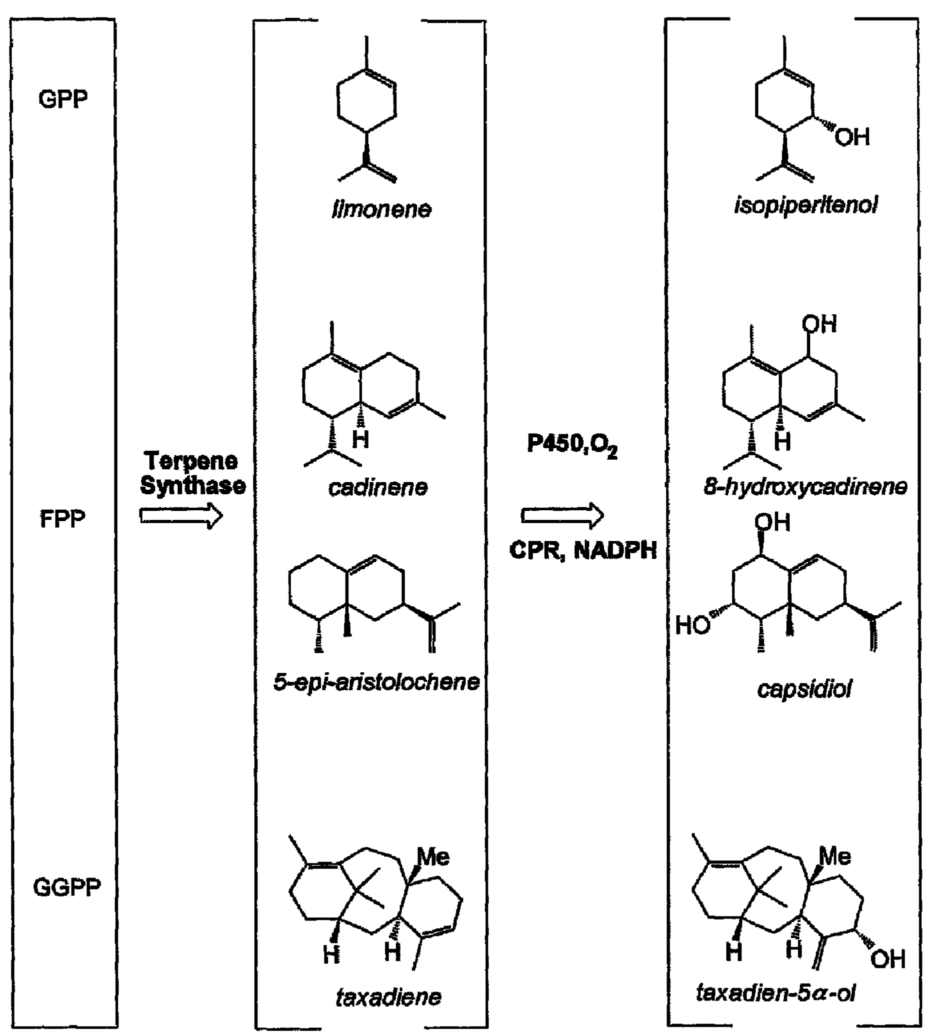
FIG. 15 depicts schematically the reaction scheme for production of exemplary isoprenoid compounds.

FIGS. 14 and 15 depict schematically the biosynthesis of exemplary isoprenoid products. Conversion of linear polyprenyl diphosphates is catalyzed by terpene synthases; and the products of the conversion are the substrates of an isoprenoid precursor-modifying enzyme (e.g., a P450 enzyme). Specific functionalization then takes place by reaction of the carbon skeleton of the precursor, catalyzed by a P450 and its redox partner, a CPR.

In some embodiments, the genetically modified host cell is further genetically modified with a nucleic acid comprising a nucleotide sequence encoding a terpene synthase, which may be a heterologous terpene synthase (e.g., a terpene synthase not normally produced in the host cell). Thus, e.g., the host cell is in some embodiments, genetically modified with one or more nucleic acids comprising nucleotide sequences encoding a terpene synthase and an isoprenoid-modifying enzyme (e.g., a sesquiterpene oxidase). Culturing such a host cell in a suitable culture medium provides for production of the terpene synthase and the isoprenoid-modifying enzyme (e.g., a sesquiterpene oxidase). For example, the terpene synthase modifies a farnesyl pyrophosphate to generate a sesquiterpene substrate for said sesquiterpene oxidase.

In some embodiments, the host cell is further genetically modified with a nucleic acid comprising a nucleotide sequence encoding a cytochrome P450 reductase (CPR). A wide variety of nucleotide sequences of CPR are known, and any known CPR-encoding nucleic acid can be used, as long as the encoded CPR exhibits activity in transferring electrons from NADPH. In some embodiments, the CPR-encoding nucleic acid encodes a CPR that transfers electrons from NADPH to an isoprenoid-modifying enzyme, e.g., a sesquiterpene oxidase, encoded by a subject isoprenoid-modifying enzyme-encoding nucleic acid.

Figure 16:
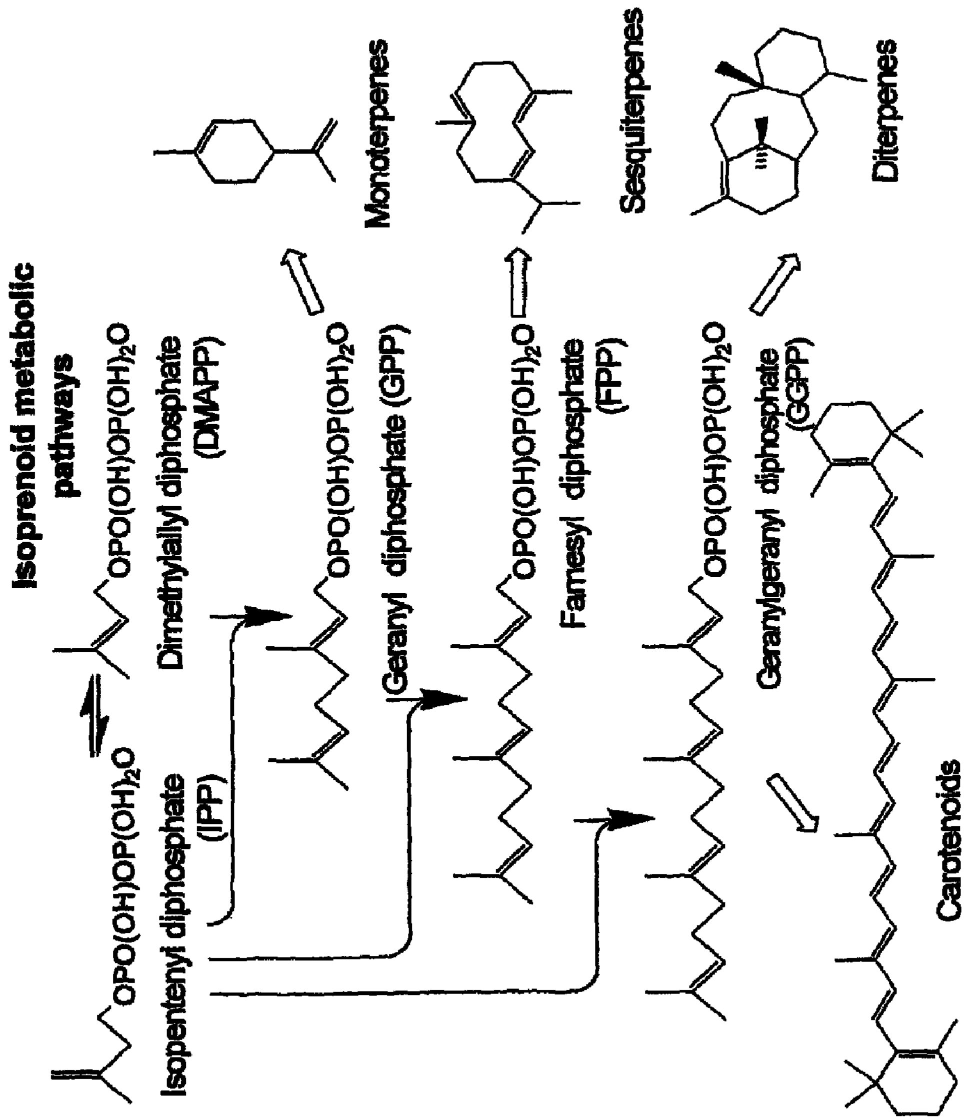
FIG. 16 is a schematic representation of isoprenoid metabolic pathways that result in the production of the isoprenoid biosynthetic pathway intermediates polyprenyl diphosphates geranyl diphosphate (GPP), farnesyl diphosphate (FPP), and geranylgeranyl diphosphate (GGPPP), from isopentenyl diphosphate (IPP) and dimethylallyl diphosphate (DMAPP).
Figure 17:
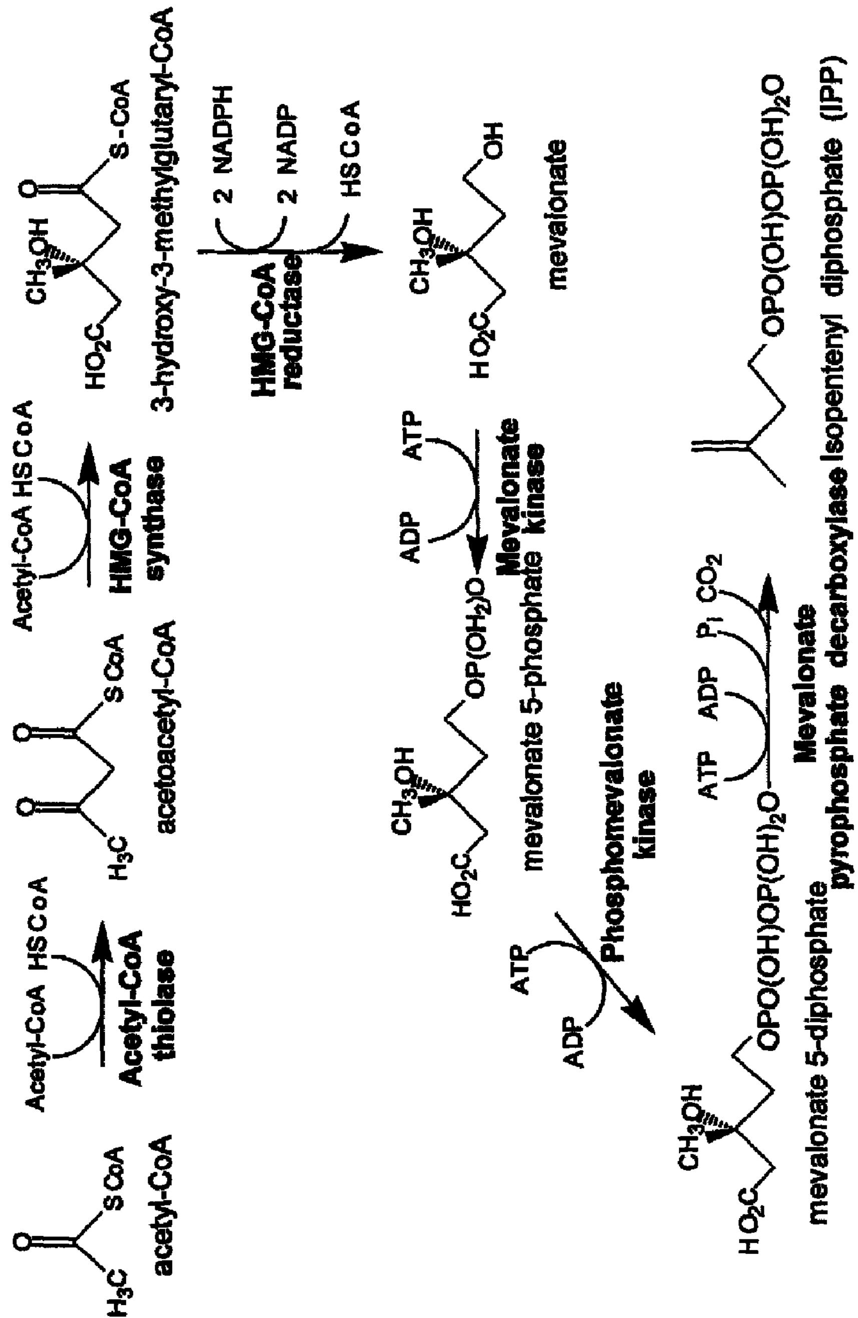
FIG. 17 is a schematic representation of the mevalonate (MEV) pathway for the production of IPP.

In some embodiments, a host cell is further genetically modified to produce a prenyl transferase and/or one or more enzymes in a biosynthetic pathway to produce isopentenyl pyrophosphate. Cells typically use one of two pathways to generate isoprenoids or isoprenoid precursors (e.g., IPP, polyprenyl diphosphates, etc.). FIGS. 16-18 serve to illustrate the pathways used by cells to generate isoprenoid compounds, or precursors such as polyprenyl diphosphates.

FIG. 16 depicts isoprenoid pathways involving modification of isopentenyl diphosphate (IPP) and/or its isomer dimethylallyl diphosphate (DMAPP) by prenyl transferases to generate the polyprenyl diphosphates geranyl diphosphate (GPP), farnesyl diphosphate (FPP), and geranylgeranyl diphosphate (GGPP). GPP and FPP are further modified by terpene synthases to generate monoterpenes and sesquiterpenes, respectively; and GGPP is further modified by terpene synthases to generate diterpenes and carotenoids. IPP and DMAPP are generated by one of two pathways: the mevalonate (MEV) pathway and the 1-deoxy-D-xylulose-5-phosphate (DXP) pathway.

FIG. 17 depicts schematically the MEV pathway, where acetyl CoA is converted via a series of reactions to IPP.

FIG. 18 depicts schematically the DXP pathway, in which pyruvate and D-glyceraldehyde-3-phosphate are converted via a series of reactions to IPP and DMAPP. Eukaryotic cells other than plant cells use the MEV isoprenoid pathway exclusively to convert acetyl-coenzyme A (acetyl-CoA) to IPP, which is subsequently isomerized to DMAPP. Plants use both the MEV and the mevalonate-independent, or DXP pathways for isoprenoid synthesis. Prokaryotes, with some exceptions, use the DXP pathway to produce IPP and DMAPP separately through a branch point.

Depending on the culture medium in which the host cell is cultured, and depending on whether the host cell synthesizes IPP via a DXP pathway or via a mevalonate pathway, the host cell will in some embodiments include further genetic modifications. For example, in some embodiments, the host cell is one that does not have an endogenous mevalonate pathway, e.g., the host cell is one that does not normally synthesize IPP or mevalonate via a mevalonate pathway. For example, in some embodiments, the host cell is one that does not normally synthesize IPP via a mevalonate pathway, and the host cell is genetically modified with one or more nucleic acids comprising nucleotide sequences encoding two or more enzymes in the mevalonate pathway, an IPP isomerase, a prenyltransferase, a terpene synthase, and an isoprenoid-modifying enzyme (e.g., an isoprenoid-modifying enzyme encoded by a subject nucleic acid). Culturing such a host cell provides for production of the mevalonate pathway enzymes, the IPP isomerase, the prenyltransferase, the terpene synthase, and the isoprenoid-modifying enzyme (e.g., a sesquiterpene oxidase). Production of the mevalonate pathway enzymes, the IPP isomerase, the prenyltransferase, the terpene synthase, and the isoprenoid-modifying enzyme (e.g., a sesquiterpene oxidase) results in production of an isoprenoid compound. In many embodiments, the prenyltransferase is an FPP synthase, which generates a sesquiterpene substrate for a sesquiterpene oxidase encoded by a subject nucleic acid; and production of the sesquiterpene oxidase results in oxidation of the sesquiterpene substrate in the host cell. Any nucleic acids encoding the mevalonate pathway enzymes, the IPP isomerase, the prenyltransferase, and the terpene synthase are suitable for use. For example, suitable nucleic acids are described in, e.g., Martin et al. (2003) supra.

In some of the above-described embodiments, where the host cell is genetically modified with one or more nucleic acids comprising nucleotide sequences encoding two or more mevalonate pathway enzymes, the two or more mevalonate pathway enzymes include MK, PMK, and MPD, and the host cell is cultured in medium that includes mevalonate. In other embodiments, the two or more mevalonate pathway enzymes include acetoacetyl CoA thiolase, HMGS, HMGR, MK, PMK, and MPD.

In some embodiments, the host cell is one that does not normally synthesize IPP via mevalonate pathway, the host cell is genetically modified as described above, and the host cell further comprises a functionally disabled DXP pathway.

A subject method is useful for production of a variety of isoprenoid compounds, including, but not limited to, artemisinic acid (e.g., where the sesquiterpene substrate is amorpha-4,11-diene), alloisolongifolene alcohol (e.g., where the substrate is alloisolongifolene), (E)-trans-bergamota-2,12-dien-14-ol (e.g., where the substrate is (−)-α-trans-bergamotene), (−)-elema-1,3,11(13)-trien-12-ol (e.g., where the substrate is (−)-β-elemene), germacra-1(10),4,11(13)-trien-12-ol (e.g., where the substrate is (+)-germacrene A), germacrene B alcohol (e.g., where the substrate is germacrene B), 5,11(13)-guaiadiene-12-ol (e.g., where the substrate is (+)-γ-gurjunene), ledene alcohol (e.g., where the substrate is (+)-ledene), 4β-H-eudesm-11(13)-ene-4,12-diol (e.g., where the substrate is neointermedeol), (+)-β-costol (e.g., where the substrate is (+)-β-selinene, and the like; and further derivatives of any of the foregoing.

A subject genetically modified host cell is in many embodiments cultured in vitro in a suitable medium and at a suitable temperature. The temperature at which the cells are cultured is generally from about 18° C. to about 40° C., e.g., from about 18° C. to about 20° C., from about 20° C. to about 25° C., from about 25° C. to about 30° C., from about 30° C. to about 35° C., or from about 35° C. to about 40° C. (e.g., at about 37° C.).

In some embodiments, a subject genetically modified host cell is cultured in a suitable medium (e.g., Luria-Bertoni broth, optionally supplemented with one or more additional agents, such as an inducer (e.g., where the isoprenoid-modifying enzyme-encoding nucleotide sequence is under the control of an inducible promoter), etc.); and the culture medium is overlaid with an organic solvent, e.g. dodecane, forming an organic layer. The isoprenoid compound produced by the genetically modified host cell partitions into the organic layer, from which it can be purified. In some embodiments, where the isoprenoid-modifying enzyme-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid compound will be separated from other products which may be present in the organic layer. Separation of the isoprenoid compound from other products that may be present in the organic layer is readily achieved using, e.g., standard chromatographic techniques.

In some embodiments, an isoprenoid compound synthesized by a subject method is further chemically modified in a cell-free reaction. For example, in some embodiments, artemisinic acid is isolated from culture medium and/or a cell lysate, and the artemisinic acid is further chemically modified in a cell-free reaction to generate artemisinin.

In some embodiments, the isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an isoprenoid compound refers to an isoprenoid compound that is free from other isoprenoid compounds, macromolecules, contaminants, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s);

kb, kilobase(s); bp, base pair(s); nt, nucleotide(s); i.m., intramuscular (ly); i.p., intraperitoneal (ly); s.c., subcutaneous (ly); and the like.

Example 1

Production of 8-hydroxy-δ-cadinene in *Escherichia coli*

Figure 1:
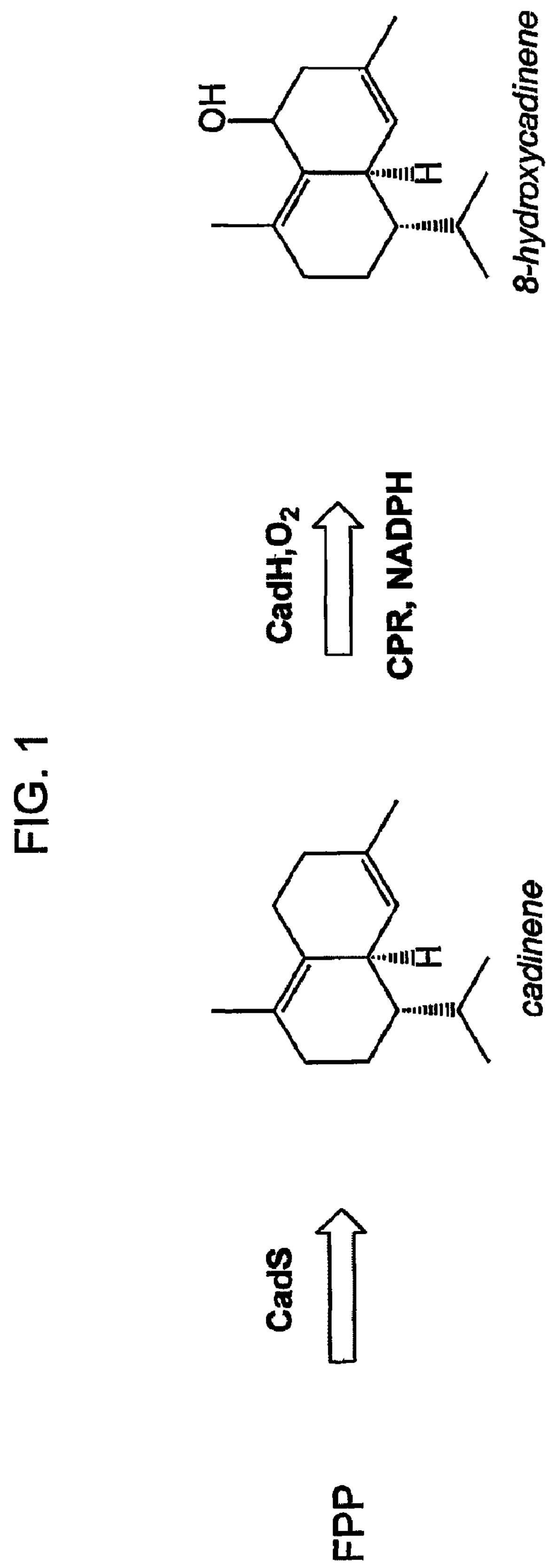
FIG. 1 schematically depicts biosynthesis of 8-hydroxy-δ-cadinene in *E. coli.*

This example describes production of an in vivo-produced substrate at high levels (up to 30 mg $L^{-1}$) using the native P450 participating in the biosynthetic pathway. δ-Cadinene-8-hydroxylase (CadH) is a plant-derived membrane-bound P450 which hydroxylates the sesquiterpene, δ-cadinene (cad), to 8-hydroxy-δ-cadinene (CadOH) in the biosynthesis of gossypol, a plant defense compound. Biosynthesis of CadOH in *E. coli* is depicted schematically in FIG. 1. Substrate (Cad) is produced from endogenous farnesyl pyrophosphate (FPP) in *E. coli* by terpene synthase CadS. Cad is further hydroxylated to product (CadOH) by the action of CadH along with its redox partner (CPR).

The CadH expression vector includes both the CadH gene as well as the gene encoding a cytochrome P450 reductase (CPR) redox partner from *Candida tropicalis*. This construct was co-transformed into *E. coli* along with a compatible expression vector for δ-cadinene synthase (CadS), thereby providing the substrate for CadH. This strain was grown in rich media and induced in the presence of heme supplements for 48 h at 20° C. before extracting the media with organic solvent. The results, depicted in FIG. 2, show a clearly detectable amount of CadOH (~100 μg $L^{-1}$) produced in this system measured by GC-MS (gas chromatography-mass spectrometry.

Figure 2:
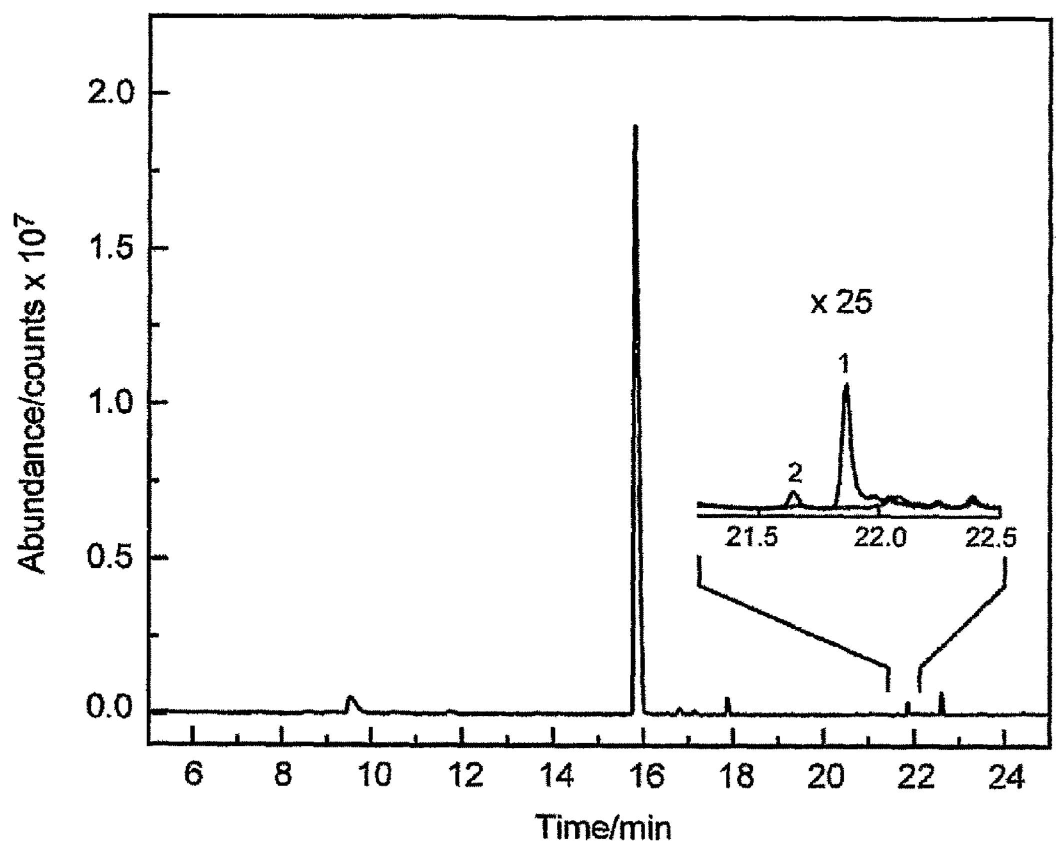
FIG. 2 depicts gas chromatography-mass spectrometry (GC-MS) trace of organic layer extracted from *E. coli* expressing CadOH biosynthetic pathway.

FIG. 2. GC-MS trace of organic layer extracted from *E. coli* expressing CadOH biosynthetic pathway. Inset shows blow-up of the region showing CadOH (peak 1) and the putative ketone species (peak 2). Upper line corresponds to samples expressing CadS, CadH, and CPR while the lower line corresponds to the negative controls expressing CadS and CPR only, without CadH.

In addition, a small amount of a putative ketone product ($[M^{+}]$: m/z=218) was also observed (FIG. 2 inset, upper line, peak 2), meaning that multiple turnovers by the same enzyme may be possible. The negative control plasmid, containing the CPR only and not CadH, exhibited no product peak in the GC-MS trace (FIG. 2 inset, lower line). The mass spectrum of the CadOH produced in vivo by *E. coli* using this system and the literature spectrum of CadOH are very similar [4]. Previous attempts to use native P450 s for in vivo production of functionalized natural products in a similar family of compounds were unsuccessful and pointed to problems of substrate accessibility.

Figure 3:
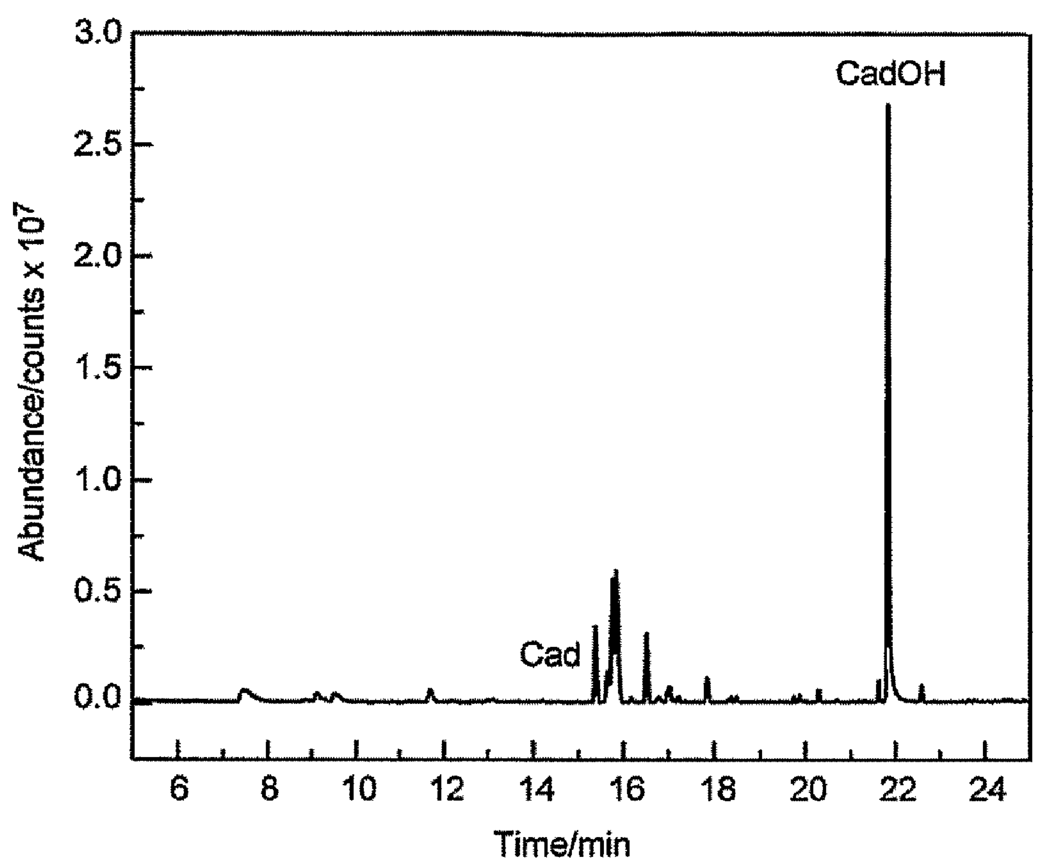
FIG. 3 depicts a GC-MS trace of the organic layer extracted from mevalonate-fed *E. coli* expressing CadOH biosynthetic pathway as well as a portion of the mevalonate pathway (pMBIS).

Production of CadOH was significantly increased by increasing the amount of FPP produced in *E. coli* using the pMBIS plasmid, which allows *E. coli* to produce FPP from mevalonate [6]. The nucleotide sequence of pMBIS is depicted in FIGS. 36A-D (SEQ ID NO:62). pMBIS is also described in U.S. Patent Publications Nos. 2003/0148479; and 2004/0005678; and comprises nucleotide sequences encoding mevalonate kinase, phosphomevalonate kinase, mevalonate pyrophosphate decarboxylase, IPP isomerase, and FPP synthase. In these studies, *E. coli* was transformed with three expression plasmids: (1) pMBIS, (2) CadS, and (3) CadH/CPR. 20 mM mevalonate was added upon induction. Addition of pMBIS increased production of CadOH production 74 fold increase compared to that produced by cells with no pMBIS (FIG. 3). Again, the negative control (no CadH) showed no product formation. These results indicate that P450 turnover may be limited by substrate production in vivo (e.g., in a living cell in in vitro culture). These cells may also be grown in a mixed aqueous/organic media; the strain was grown and induced in the presence of a dodecane overlay without significantly altering productivity for CadOH (~2-fold less).

FIG. 3. GC-MS trace of organic layer extracted from mevalonate-fed *E. coli* expressing CadOH biosynthetic pathway as well as pMBIS. Cad and CadOH are indicated on the trace.

It was further shown that productivity is increased by engineering the P450 without losing product specificity. In vivo production with the native gene (nCadH) vs. a synthetic gene (sCadH) with codon usage optimized for expression in *E. coli* was compared (FIG. 4B). This comparison indicates that the synthetic gene performs slightly better than the native gene.

The wild-type N-terminal transmembrane domain (TM) was replaced with sequences that are known to function in *E. coli* (FIG. 4A). Among the N-terminal sequences tested were two P450 N-terminal leaders derived from *C. tropicalis*-CYP52 A13 (A13) which contains no predicted TM domain and CYP52 A17 (A17) which does contain a TM domain [7]—as well as a bovine microsomal leader (bovine) [8].

The wild-type TM domain was removed entirely (truncated), and was replaced with a secretion tag (OmpA), solubilization domain (PD1) [9], or a membrane-inserting protein (mistic) [10]. The bovine-CadH outperformed the wild-type CadH by approximately 2-fold, producing ~30 mg $L^{-1}$ (FIG. 4B).

References

1. M. Sono, M. P. Roach, E. D. Coulter, and J. H. Dawson, *Chem. Rev.* 1996, 96, 2841-2887.
2. S. Jennewein, R. M. Long, R. M. Williams, and R. Croteau, *Chem. Biol.* 2004, 11, 379-387.
3. R. J. Sowden, S. Yasmin, N. H. Rees, S. G. Bell and L.-L. Wong, *Org. Biomol. Chem.* 2005, 3, 57-64.
4. P. Luo, Y.-H. Wang, G.-D. Wang, M. Essenberg, and X.-Y. Chen, *Plant J.* 2001, 28, 95-104.
5. O. A. Carter, R. J. Peters, and R. Croteau, *Phytochem.* 2003, 64, 425-433.
6. V. J. J. Martin, D. J. Pitera, S. T. Withers, J. D. Newman, and J. D. Keasling, *Nature Biotech.* 2003, 21, 796-801
7. D. L. Craft, K. M. Madduri, M. Eshoo, and C. R. Wilson, *Appl. Environ. Microbiol.* 2003, 69, 5983-5991.
8. H. J. Barnes, M. P. Arlotto, and M. R. Waterman, *Proc. Natl. Acad. Sci. USA* 1991, 88, 5597-5601.
9. G. A. Schock, R. Attias, M. Belghazi, P. M. Dansette, and D. Werck-Reichart, *Plant Physiol.* 2003, 133, 1198-1208.
10. T. P. Roosild, J. Greenwald, M. Vega, S. Castronovo, R. Riek, and S. Choe *Science* 2005, 307, 1317-1321.

Example 2

Oxidation of Amorphadiene by Amorphadiene Oxidase (AMO)

This example describes the in vivo (e.g., in a living cell in in vitro cell culture) oxidation of amorphadiene by amorphadiene oxidase (AMO), also called CYP71AV1, isolated from *Artemisia annua*. Various constructs comprising a nucleotide sequence encoding AMO were generated and tested in order to optimize the yield of oxidized product. FIG. 22 schematically depicts the various AMO constructs. (1) nAMO, native AMO sequence as isolated from *A. annua*. (2) sAMO, synthetic AMO gene codon-optimized for expression in *E. coli*.

(3) A13-AMO, synthetic AMO gene with wild-type transmembrane replaced with the A13 N-terminal sequence from *C. tropicalis*. (4) A17-AMO, synthetic AMO gene with wild-type transmembrane replaced with the A17 N-terminal sequence from *C. tropicalis*. (5) Bov-AMO, synthetic AMO gene with wild-type transmembrane replaced with the bovine microsomal N-terminal sequence. Nucleotide and amino acid sequences of various constructs are depicted in FIGS. 24-31.

Figure 23A:
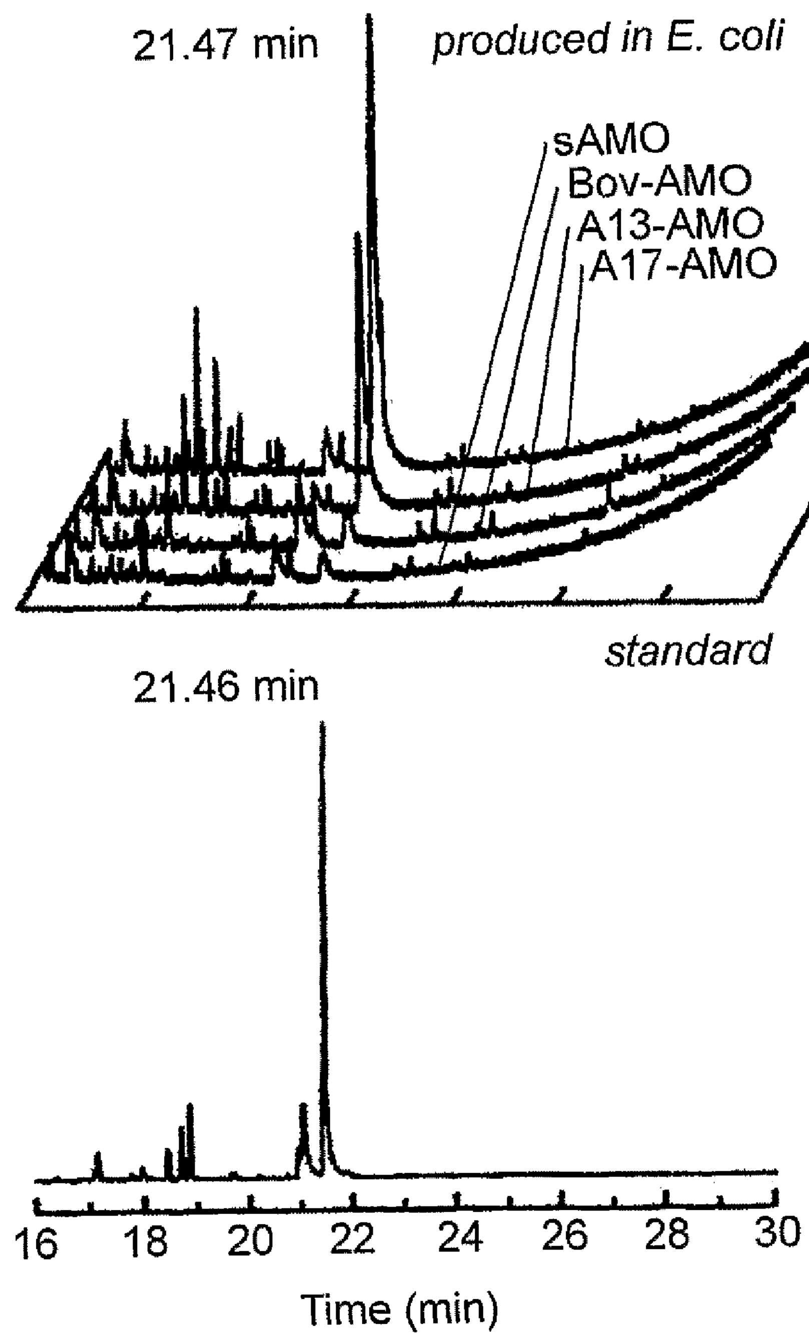
FIGS. 23A and B depict oxidation of amorphadiene in *E. coli* by various AMO constructs.

The various AMO constructs were co-expressed with: a) a CPR; b) amorphadiene synthase (ADS); and c) plasmid pMBIS. In the presence of mevalonate, amorphadiene was observed to be oxidized at the C-12 position to the corresponding alcohol. FIG. 23A shows the relative amount of artemisinic alcohol produced in vivo. Comparison to an authentic standard of artemisinic alcohol confirms the identity of the product (FIG. 23A, bottom panel and FIG. 23B).

Figure 23B:
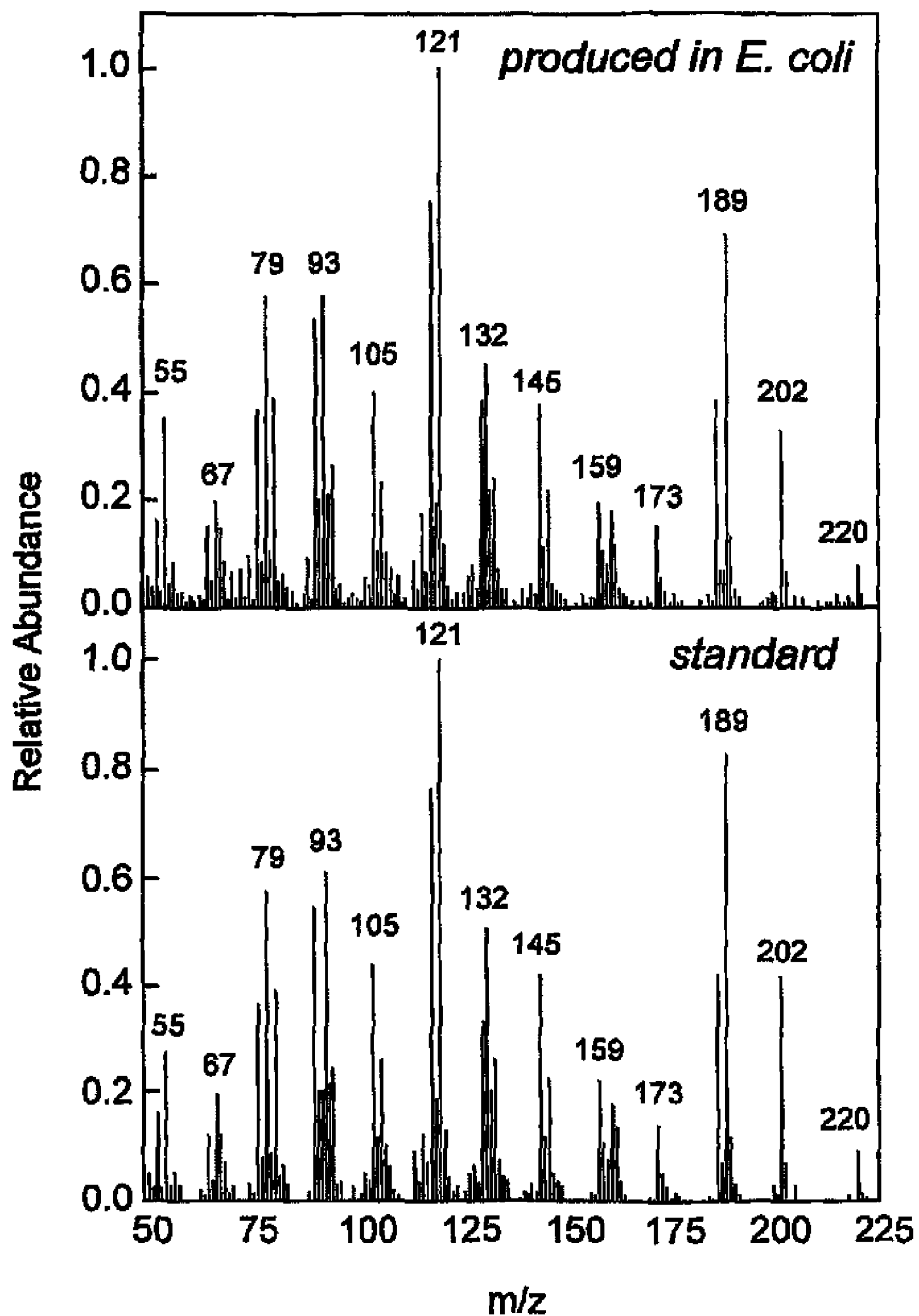

FIGS. 23A and 23B. In vivo oxidation of amorphadiene in *E. coli* by various AMO constructs. (A) GC-MS trace showing production of artemisinic alcohol produced in *E. coli* (top panel) by sAMO, A13-AMO, A17-AMO, and bov-AMO, compared to the authentic standard (bottom panel). (B) EI-MS of the artemisinic alcohol produced in *E. coli* (top panel) compared to the authentic standard (bottom panel).

Example 3

Substrate Oxidation in Cells Expressing the Full Mevalonate Pathway

Figure 32:
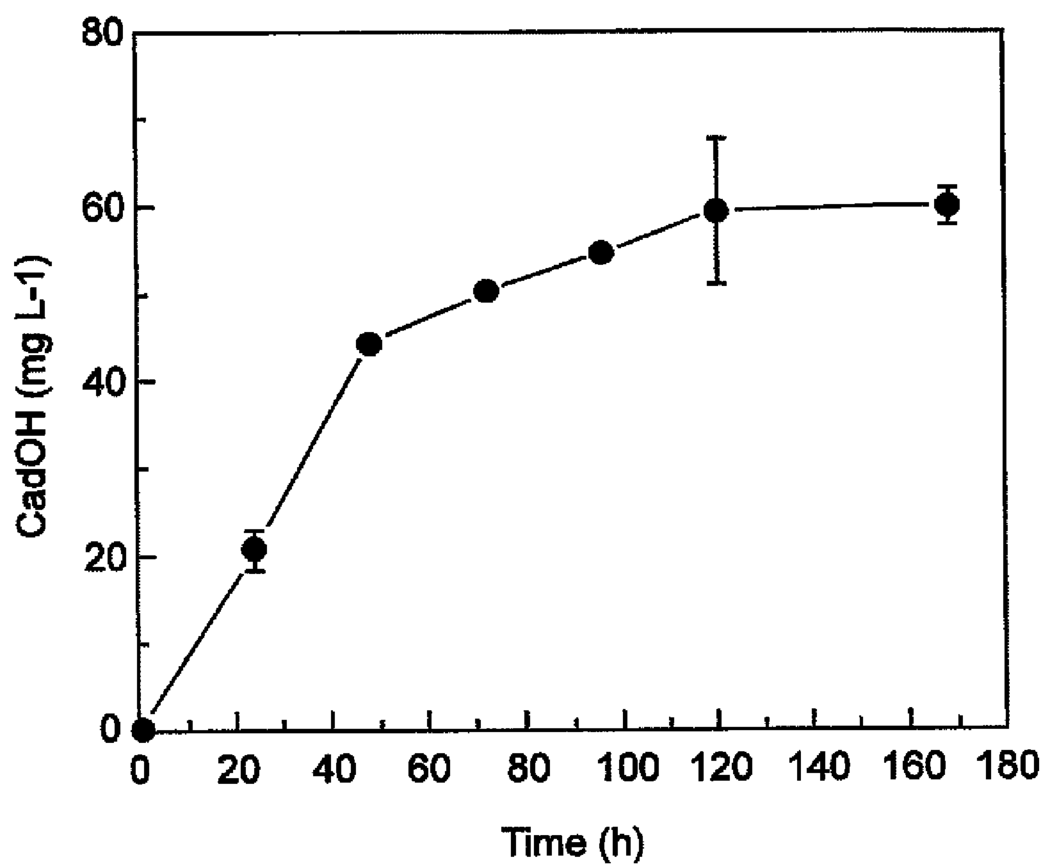
FIG. 32 depicts production of CadOH in *E. coli* containing the fall mevalonate pathway in addition to an expression vector comprising nucleotide sequences encoding CadOH, CPR, and CadS.

Substrate oxidation was also carried out in cells expressing the full mevalonate pathway from acetyl-CoA. The following example for CadOH production utilized 3 plasmids: (1) pMevT containing AtoB, HMGR, and HMGS, (2) pMBIS (containing nucleotide sequences encoding MK, PMK, PMD, IDI (IPP isomerase), and IspA (FPP synthase)), and (3) an expression vector containing CadH, CPR, and CadS. The cells were cultured at 20° C. in TB glycerol with the addition of the heme supplement, δ-aminolevulinic acid. The cells produced CadOH up to titers of 60 mg/L. The data are shown in FIG. 32.

Figure 33:
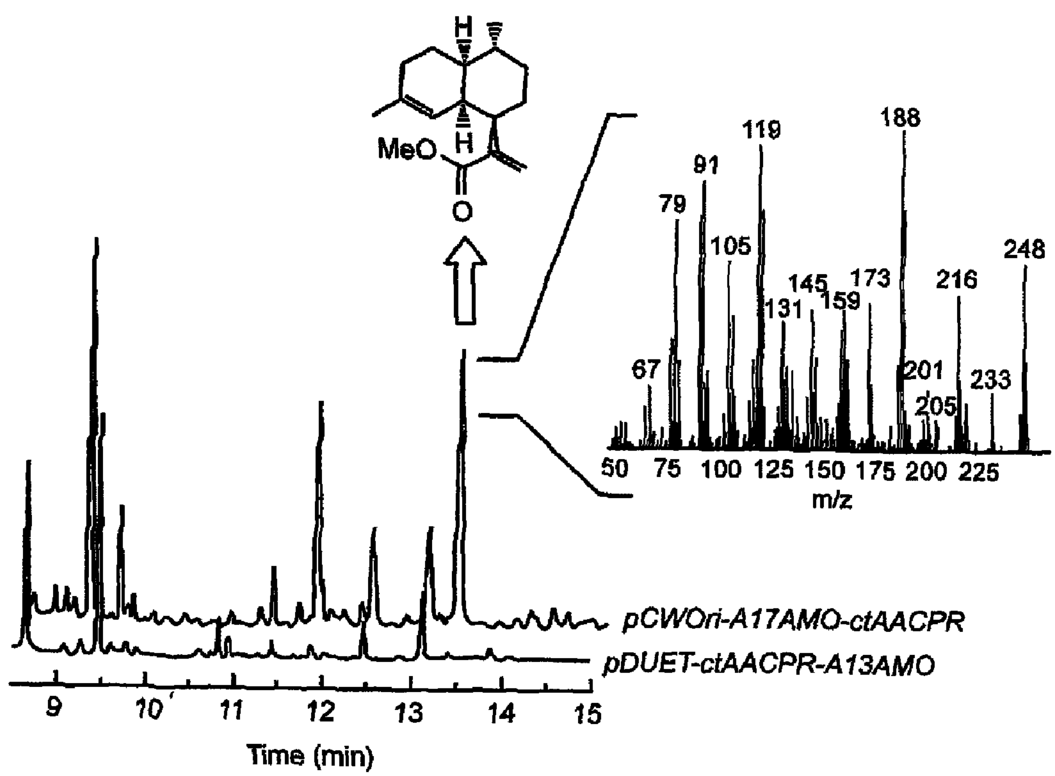
FIG. 33 depicts a GC-MS chromatograph and spectrum showing comparative production of artemisinic acid in *E. coli* expressing the full amorphadiene pathway and either the pDUET-ctAACPR-A13 AMO plasmid or the pCWori-A17 AMO-ctAACPR plasmid.
Figure 34:
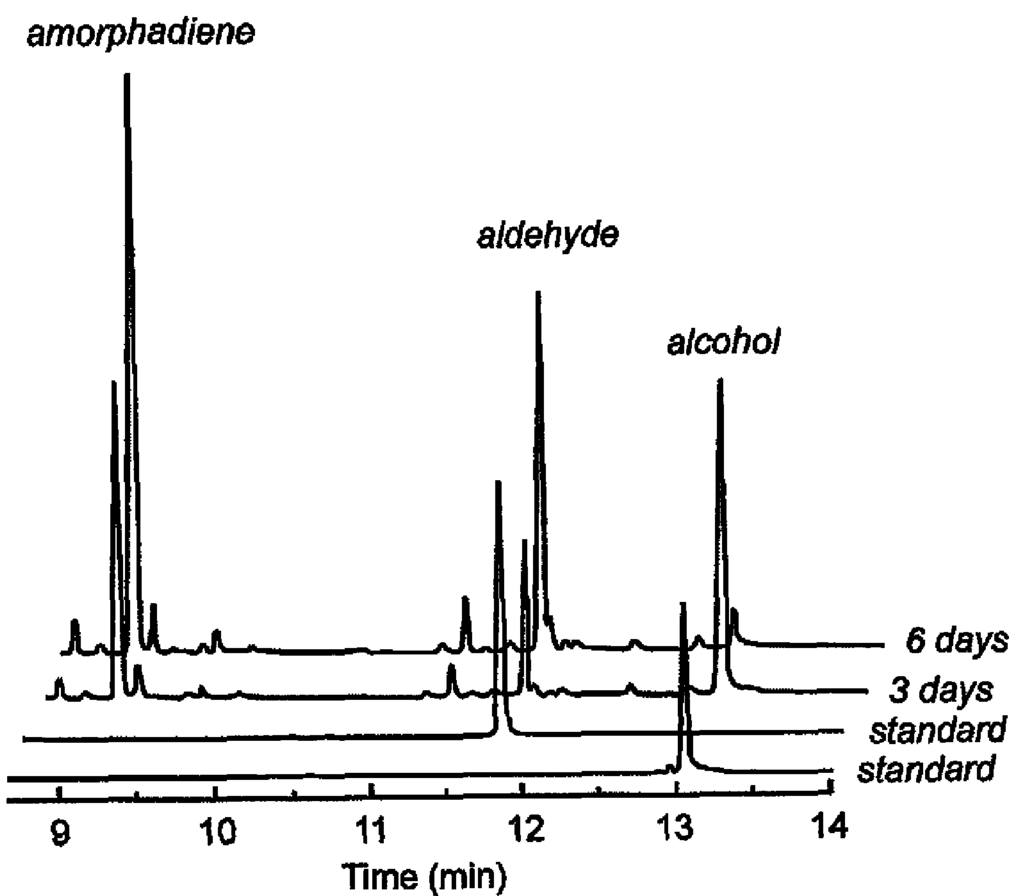
FIG. 34 depicts GC-MS chromatographs showing oxidation of artemisinic alcohol to artemisinic aldehyde in *E. coli* genetically modified with nucleic acids encoding mevalonate pathway enzymes and amorphadiene synthase, and with the pCWori-A17 AMO-ctAACPR plasmid.

In a second example, artemisinic acid was produced using 2 plasmids: (1) an expression vector containing nucleotide sequences encoding the MevT (AtoB, HMGR, and HMGS) (see FIGS. 35A and B), MBIS (MK, PMK, PMD, IDI, and IspA), and ADS operons and (2) an expression vector containing nucleotide sequences encoding AMO and a CPR redox partner from *A. annua* (AACPR). After culturing the *E. coli* cells at 20° C. in TB glycerol with the addition of the heme supplement, trace amounts of artemisinic acid were observed using a T7 promoter-based vector (FIG. 33). After changing the vector to pCWOri, AMO could be used for the 3-step oxidation of amorphadiene to produce artemisinic acid in *E. coli* at titers of 20 mg/L (FIG. 33). In addition, stepwise oxidation of the alcohol to the aldehyde was observed with the aldehyde produced at titers of 40-80 mg/L (FIG. 34).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of producing 8-hydroxy-delta cadinene in a genetically modified host cell, the method comprising:

culturing the genetically modified host cell in a suitable medium, wherein said host cell is genetically modified with:

a) a nucleic acid comprising a nucleotide sequence encoding cytochrome P450 enzyme wherein the cytochrome P450 enzyme is δ-cadinene-8-hydroxylase operably linked to a heterologous domain selected from a heterologous transmembrane domain, a heterologous secretion domain, a heterologous solubilization domain, and a heterologous membrane-inserting protein, to produce an enzymatically active, modified δ-cadinene-8-hydroxylase;

b) a nucleic acid comprising a nucleotide sequence encoding a cytochrome P450 reductase comprising the amino acid sequence set forth in SEQ ID NO:37;

c) a nucleic acid comprising a nucleotide sequence encoding a cadinene synthase; and d) one or more heterologous nucleic acids comprising nucleotide sequences encoding mevalonate pathway enzymes, wherein the mevalonate pathway enzymes include:

i) a mevalonate kinase;

ii) a phosphomevalonate kinase; and iii) a mevalonate pyrophosphate decarboxylase, wherein production of said enzymes in said genetically modified host cell results in production of 8-hydroxy-delta cadinene in an amount of at least 10 mg per liter.

2. The method of claim 1, wherein said host cell is a eukaryotic host cell.

3. The method of claim 2, wherein said host cell is a yeast cell.

4. The method of claim 1, wherein said host cell is a prokaryotic cell.

5. The method of claim 1, wherein said host cell is one that does not normally synthesize isopentenyl pyrophosphate (IPP) via a mevalonate pathway.

6. The method of claim 1, wherein the host cell is cultured in the presence of mevalonate.

7. The method of claim 1, wherein said mevalonate pathway enzymes further comprise acetoacetyl-CoA thiolase, hydroxymethylglutaryl-CoA synthase, and hydroxymethylglutaryl-CoA reductase.

8. The method of claim 1, wherein said cytochrome P450 enzyme-encoding nucleotide sequence is operably linked to an inducible promoter.

9. The method of claim 1, further comprising isolating the 8-hydroxy-delta cadinene.

10. The method of claim 1, wherein the genetically modified host cell is further genetically modified with a nucleic acid comprising a nucleotide sequence encoding a heterologous isopentenyl diphosphate isomerase.

11. The method of claim 1, wherein the genetically modified host cell is further genetically modified with a nucleic acid comprising a nucleotide sequence encoding a heterologous farnesyl diphosphate synthase.

12. The method of claim 4, wherein said host cell is *Escherichia coli*.

13. The method of claim 1, wherein the modified δ-cadinene-8-hydroxylase comprises an amino acid sequence selected from SEQ ID NOs:28-30.

* * * * *